US012637471B2

(12) United States Patent
Linnanen et al.

(10) Patent No.: US 12,637,471 B2
(45) Date of Patent: May 26, 2026

(54) HETEROCYCLIC COMPOUNDS, COMPOSITIONS, METHODS OF PREPARATION AND USES THEREOF

(71) Applicant: Organon R&D Finland Ltd, Turku (FI)

(72) Inventors: Tero Linnanen, Naantali (FI); Leena Hirvelä, Turku (FI); Kaisa Illikainen, Turku (FI); Marjo Hakola, Turku (FI); Sanna Niinivehmas, Littoinen (FI); Olli Pentikäinen, Lieto (FI); Camilla Stjernschantz, Turku (FI)

(73) Assignee: ORGANON R&D FINLAND LTD., Turku (FI)

( * ) Notice: Subject to any disclaimer, the term of this patent is extended or adjusted under 35 U.S.C. 154(b) by 378 days.

(21) Appl. No.: 18/558,860

(22) PCT Filed: May 5, 2022

(86) PCT No.: PCT/FI2022/050301
§ 371 (c)(1),
(2) Date: Nov. 3, 2023

(87) PCT Pub. No.: WO2022/234193
PCT Pub. Date: Nov. 10, 2022

(65) Prior Publication Data
US 2024/0254131 A1 Aug. 1, 2024

(30) Foreign Application Priority Data
May 7, 2021 (FI) ..................................... 20215545

(51) Int. Cl.

| | |
|---|---|
| ***C07D 211/70*** | (2006.01) |
| ***A61K 31/4535*** | (2006.01) |
| ***A61K 31/4545*** | (2006.01) |
| ***A61K 31/497*** | (2006.01) |
| ***A61K 31/4985*** | (2006.01) |
| ***A61K 31/5377*** | (2006.01) |
| ***A61P 35/00*** | (2006.01) |
| ***C07D 211/72*** | (2006.01) |
| ***C07D 401/06*** | (2006.01) |
| ***C07D 401/14*** | (2006.01) |
| ***C07D 405/12*** | (2006.01) |
| ***C07D 409/06*** | (2006.01) |
| ***C07D 409/14*** | (2006.01) |
| ***C07D 413/06*** | (2006.01) |

(Continued)

(52) U.S. Cl.
CPC ........ *C07D 487/04* (2013.01); *A61K 31/4535* (2013.01); *A61K 31/4545* (2013.01); *A61K 31/497* (2013.01); *A61K 31/4985* (2013.01); *C07D 211/70* (2013.01); *C07D 401/06* (2013.01); *C07D 401/14* (2013.01); *C07D 409/06* (2013.01); *C07D 409/14* (2013.01); *C07D 495/04* (2013.01); *C07D 498/04* (2013.01); *C07D 498/18* (2013.01)

(58) Field of Classification Search
CPC .. C07D 487/04; C07D 211/70; C07D 401/06; C07D 401/14; C07D 409/06; C07D 409/14; C07D 495/04; C07D 498/04; C07D 498/18; C07D 211/72; C07D 405/12; C07D 417/06; C07D 471/04; C07D 513/00; C07D 413/06; A61K 31/4535; A61K 31/4545; A61K 31/497; A61K 31/4985; A61K 31/5377; A61P 35/00
See application file for complete search history.

(56) References Cited

U.S. PATENT DOCUMENTS

| | | | |
|---|---|---|---|
| 2006/0122197 | A1 | 6/2006 | Yao et al. |
| 2010/0256189 | A1 | 10/2010 | Kakefuda |

FOREIGN PATENT DOCUMENTS

| | | | |
|---|---|---|---|
| EP | 0441226 | A1 | 8/1991 |
| EP | 3421483 | A1 | 1/2019 |

(Continued)

OTHER PUBLICATIONS

Carceller et al., (Pyridylcyanomethyl)piperazines as Orally Active PAF Antagonists, J. Med. Chem., 35, pp. 4118-4134 (Year: 1992).*

(Continued)

*Primary Examiner* — Jeffrey S Lundgren
*Assistant Examiner* — Alexander K. Showalter
(74) *Attorney, Agent, or Firm* — Barnes & Thornburg LLP; Ryan L. Marshall

(57) ABSTRACT

The present invention relates to compounds of formula (I)

(I)

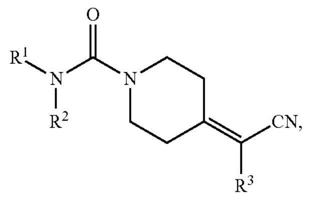

to salts, solvates and solvates of salts thereof, and to pharmaceutical compositions comprising these compounds as active ingredients. The invention further relates to their use as aldo-keto reductase family 1 C3 (AKR1C3), also known as 17β-hydroxysteroid dehydrogenase type 5 (17β-HSD5, HSD17B5) and prostaglandin (PG) F2α synthase, inhibitors. The invention further relates to methods for their preparation, and to uses of said compounds.

20 Claims, No Drawings

(51) Int. Cl.

| | |
|---|---|
| ***C07D 417/06*** | (2006.01) |
| ***C07D 471/04*** | (2006.01) |
| ***C07D 487/04*** | (2006.01) |
| ***C07D 495/04*** | (2006.01) |
| ***C07D 498/04*** | (2006.01) |
| ***C07D 498/18*** | (2006.01) |
| ***C07D 513/00*** | (2006.01) |

(56) References Cited

FOREIGN PATENT DOCUMENTS

| | | | |
|---|---|---|---|
| EP | 3438109 | A1 | 2/2019 |
| WO | 2006136606 | A2 | 12/2006 |
| WO | 2008000950 | A2 | 1/2008 |
| WO | 2018002220 | A1 | 1/2018 |
| WO | 2019002015 | A1 | 1/2019 |
| WO | 2019002571 | A1 | 1/2019 |
| WO | 2019180185 | A1 | 9/2019 |
| WO | 2021005586 | A1 | 1/2021 |

OTHER PUBLICATIONS

CAS Registry No. 1856781-24-2, obtained from STN (Year: 2016).*

Barnard, Monique, et al. "11-Oxygenated androgen precursors are the preferred substrates for aldo-keto reductase 1C3 (AKR1C3): implications for castration resistant prostate cancer." The Journal of steroid biochemistry and molecular biology 183 (2018): 192-201.

Bortolozzi, Roberta, et al. "AKR1C enzymes sustain therapy resistance in paediatric T-ALL." British Journal of Cancer 118.7 (2018): 985-994.

Bukum, Neslihan, et al. "Buparlisib is a novel inhibitor of daunorubicin reduction mediated by aldo-keto reductase 1C3." Chemico-biological interactions 302 (2019): 101-107.

Byrns M et al., "Aldo-Keto Reductase 1C3 Expression in MCF-7 Cells Reveals Roles in Steroid Hormone and Prostaglandin Metabolism that may Explain its Over-Expression in Breast Cancer", J. Steroid Biochem. Mol. Biol. 118 (2010) 177-187.

Byrns M. et al., "An Indomethacin Analogue, N-(4-Chlorobenzoyl)-melatonin, is a Selective Inhibitor of Aldo-keto Reductase 1C3 (Type 2 3α-HSD, Type 5 17β-HSD, and Prostaglandin F Synthase), a Potential Target for the Treatment of Hormone Dependent and Hormone Independent Malignancies" Biochem. Pharmacol. 2008, 75 (2), 484-493.

Evans, Kathryn, et al. "OBI-3424, a novel AKR1C3-activated prodrug, exhibits potent efficacy against preclinical models of T-ALL." Clinical Cancer Research 25.14 (2019): 4493-4503.

Flanagan, Jack U., et al. "Morpholylureas are a new class of potent and selective inhibitors of the type 5 17-β-hydroxysteroid dehydrogenase (AKR1C3)." Bioorganic & Medicinal Chemistry 22.3 (2014): 967-977.

Gao X. et al. "Functional silencing of HSD17B2 in prostate cancer promotes disease progression" Clin. Cancer Res. 2019, 25, 1291-301.

Hendriks, Christine MM, et al. "Pentafluorosulfanyl-containing flufenamic acid analogs: Syntheses, properties and biological activities." Bioorganic & medicinal chemistry letters 25.20 (2015): 4437-4440.

Hofman, Jakub, et al. "Anthracycline resistance mediated by reductive metabolism in cancer cells: the role of aldo-keto reductase 1C3." Toxicology and applied pharmacology 278.3 (2014): 238-248.

Ko, Hyun-Kyung, et al. "Loss of an androgen-inactivating and isoform-specific HSD17B4 splice form enables emergence of castration-resistant prostate cancer." Cell reports 22.3 (2018): 809-819.

Komoto, Junichi, et al. "Prostaglandin F2α formation from prostaglandin H2 by prostaglandin F synthase (PGFS): crystal structure of PGFS containing bimatoprost." Biochemistry 45.7 (2006): 1987-1996.

Penning, Trevor M. "AKR1C3 (type 5 17β-hydroxysteroid dehydrogenase/prostaglandin F synthase): Roles in malignancy and endocrine disorders." Molecular and cellular endocrinology 489 (2019): 82-91.

Penning, Trevor M., et al. "Aldo-keto reductase (AKR) 1C3: role in prostate disease and the development of specific inhibitors." Molecular and cellular endocrinology 248.1-2 (2006): 182-191.

Penning, Trevor M., et al. "Pre-receptor regulation of the androgen receptor." Molecular and cellular endocrinology 281.1-2 (2008): 1-8.

Rižner, Tea Lanišnik, and Trevor M. Penning. "Role of aldo-keto reductase family 1 (AKR1) enzymes in human steroid metabolism." Steroids 79 (2014): 49-63.

Schiffer, Lina, et al. "Peripheral blood mononuclear cells preferentially activate 11-oxygenated androgens." European Journal of Endocrinology 2021) 184, 357-367.

Storbeck KH et al. "11b-Hydroxydihydrotestosterone and 11-ketodihydrotestosterone, novel C19 steroids with androgenic activity: A putative role in castration resistant prostate cancer?", Mol. Cell Endocrinol. 2013; 377: 135-46.

Suzuki-Yamamoto, Toshiko, et al. "cDNA cloning, expression and characterization of human prostaglandin F synthase." FEBS letters 462.3 (1999): 335-340.

Yang et al, "Overview of AKR1C3: Inhibitor Achievements and Disease Insights" J. Med. Chem. 2020, 63, 20, 11305-11329.

Yepuru, Muralimohan, et al. "Steroidogenic enzyme AKR1C3 is a novel androgen receptor-selective coactivator that promotes prostate cancer growth." Clinical Cancer Research 19.20 (2013): 5613-5625.

Zhao, Yining, et al. "In vitro inhibition of AKR1Cs by sulphonylureas and the structural basis." Chemico-Biological Interactions 240 (2015): 310-315.

Zhong, Ting, et al. "Aldo-keto reductase 1C3 (AKR1C3) is associated with the doxorubicin resistance in human breast cancer via PTEN loss." Biomedicine & Pharmacotherapy 69 (2015): 317-325.

International Search Report dated Aug. 1, 2022, prepared in International Application No. PCT/FI2022/050301.

* cited by examiner

HETEROCYCLIC COMPOUNDS, COMPOSITIONS, METHODS OF PREPARATION AND USES THEREOF

CROSS-REFERENCE TO RELATED APPLICATIONS

This application is a National Stage application of International Application No. PCT/FI2022/050301, filed May 5, 2022. This application also claims priority under 35 U.S.C. § 119 to Finnish Patent Application No. 20215545, filed May 7, 2021.

FIELD OF THE INVENTION

The present invention relates to a novel class of aldo-keto reductase family 1 C3 (AKR1C3), also known as 17β-hydroxysteroid dehydrogenase type 5 (17β-HSD5, HSD17B5) and prostaglandin (PG) F2α synthase inhibitors, to salts, solvates and solvates of salts thereof, and to pharmaceutical compositions comprising these compounds as active ingredients. The invention further relates to methods for their preparation, and to methods of use thereof.

BACKGROUND OF THE INVENTION

Aldo-keto reductase family 1 member C3 (AKR1C3) is also known as 17β-hydroxysteroid dehydrogenase type 5 (17β-HSD5, HSD17B5) and prostaglandin (PG) F2α synthase. AKR1C3 is a member of the aldo-keto reductase 1C (AKR1C) subfamily of the aldo-keto reductase (AKR) superfamily of enzymes, which contains >190 members. The human AKR1C subfamily consists of four isoforms (AKR1C1, -C2, -C3, and -C4) that are phase I metabolic enzymes and depend on nicotinamide adenine dinucleotide phosphate (NADPH) in reducing 3-keto-, 17-keto-, and 20-ketosteroids. Also AKR1C3 reduce carbonyl groups in steroid hormones to the corresponding alcohols and therefore play an important role in the metabolism, activation, and deactivation of androgens, estrogens, progesterones and prostaglandins.

AKR1C3 shares high sequence homology (>86%) with AKR1C1, -C2, and -C4. Even though the structures of the isoforms are similar, the isomers are distributed differently, and they show different biological functions. AKR1C3 shows endocrine organ expression (including liver, GI-tract, prostate, testes, adrenal gland, uterus, breast, lung, kidney, bladder, ovary, adipose tissue, and brain).

In more detail, AKR1C3 can catalyse the conversion of estrone (weak estrogen) to estradiol (potent estrogen), the conversion of progesterone (strong anti-estrogenic activity) to 20-α-hydroxyprogesterone (weak antiestrogenic activity), the conversion of dehydroepiandrosterone (DHEA, weak androgen) to androstenediol (a precursor to testosterone), the conversion of androstenedione (weak androgen) to testosterone (potent androgen), the conversion of 5α-androstanedione (5α-dione, weak androgen) to DHT (potent androgen), the conversion of androsterone to 17β-dihydroandrosterone (Penning et al. *Mol. Cell. Endocrinol.* 2006, 248 (1-2), 182-191; Rižner T L, Penning T M. *Steroids* 2014; 79: 49-63). In addition, AKR1C3 has enzymatic activity for 11-keto forms of androgens and therefore capable of the conversion of 11-ketoandrostenedione (weak androgen) to 11-ketotestosterone (potent androgen), the conversion of 11-keto-5α-androstanedione to 11-keto-5α-dihydrotestosterone, the conversion of 11-ketoandrosterone to 11-keto-3α-androstanediol (Barnarda M. et al. *J. Steroid Biochem. Mol. Biol.* 2018; 183: 192-201; Schiffer L et al. *Eur. J. Endocrinol.* 2021; 184: 357-67; Storbeck K H et al. *Mol. Cell Endocrinol.* 2013; 377: 135-46). The AKR1C3 is also capable of the conversion of $PGH_2$ to $PGF_{2\alpha}$ and $PGD_2$ to 11β-$PGF_2$, both of which are known to stimulate inflammation and proliferation (Byrns M. et al., *Biochem. Pharmacol.* 2008, 75 (2), 484-493; Byrns M et al. *J. Steroid Biochem. Mol. Biol.* 118 (2010) 177-187; Penning T M. *Mol. Cell Endocrin.* 2019; 489; 82-91; Suzuki-Yamamoto T. et al. *FEBS Lett.* 462 (1999) 335-340; Komoto J et al. *Biochemistry* 45 (7) (2006) 1987-1996). Therefore, inhibition of AKR1C3 activity may reduce the level of end products as described above and as a result, AKR1C3 mediates the regulation of ligands for androgen, estrogen, progesterone, and prostaglandin receptors.

In addition, AKR1C3 has also been shown to metabolize a wide range of carbonyl compounds and xenobiotics. AKR1C3 as a carbonyl reductase can mediate the inactivation and resistance of anthracyclines (Bukum N. et al. *Chem.-Biol. Interact.* 2019, 302, 101-107; Zhong et al. *Biomed. Pharmacother.* 2015, 69, 317-325; Hofman J. et al. *Toxicol. Appl. Pharmacol.* 2014, 278 (3), 238-248), and AKR1C3 as a nitroreductase can induce the activation of nitrogen mustard anticancer drugs (PR-104A (Bortolozzi R. et al. *Br. J. Cancer* 2018, 118 (7), 985-994) and OBI-3424/TH3424 (Evans K. et al. *Clin. Cancer Res.* 2019, 25 (14), 4493-4503).

There is an existing need in the art for new compounds that inhibit AKR1C3. As described above, AKR1C3 mediates the regulation of ligands for androgen, estrogen, progesterone, and prostaglandin receptors and therefore, inhibition of AKR1C3 activity can reduce the level of these end products and as a result such AKR1C3 inhibitors are suitable for treating and/or preventing diseases and disorders associated with altered levels of androgens, estrogens, progesterones and/or prostaglandins.

AKR1C3 inhibitors have been previously published. Among the most potent inhibitors published is GTx-560, a pyridine derivative, which inhibits AKR1C3 with an $IC_{50}$-value of 0.035±0.002 μM (*Clin. Cancer Res.* 2013, 19, 20; 5613-5625). A flufenamic acid analogue with an AKR1C3 $IC_{50}$-value of 35 nM was published in Heindriks et al., *Bioorg. Med. Chem. Lett.* 2015, 25 (20), 4437-4440. Furthermore, patent application EP 3421483A1 discloses AKR1C3 inhibitors that are steroidal 17-beta heteroaryl compounds. One of the disclosed compounds is BAY-1128688, which was included in a phase II clinical trial for the treatment of endometriosis, however, it raised bilirubin levels of patients and the trial was terminated.

In addition, morpholylureas have been disclosed as AKRIC3 inhibitors; e.g. the morpholylurea compound SN34037 has an $IC_{50}$-value of 0.11 μM (Flanagan et al., *Bioorg. Med. Chem.* 2014, 22 (3), 967-977). Furthermore, among sulphonylurea compounds published, Glimepiride (GLM) shows an AKR1C3 $IC_{50}$-value of 0.85 μM (Zhao Y. et al., *Chem.-Biol. Interact.* 2015, 240, 310-315). Many AKR1C3 inhibitors are shown to inhibit other AKR enzymes and COX enzymes (Yang et al, *J. Med. Chem.* 2020, 63, 20, 11305-11329).

Due to counteracting biological functions of some close relative enzymes in the aldo-keto reductase (AKR) or hydroxysteroid (17β) dehydrogenase (HSD17B) enzyme families, it is beneficial to develop AKR1C3 inhibitors inhibiting selectively AKR1C3 over other AKRs or HSD17Bs. For example, in the prostate, AKR1C2 plays important role in the inactivation of 5α-dihydrotestosterone. While AKR1C2 inhibition in prostate cancer can promote proliferative signalling in the prostate, treatment of prostate carcinoma can be achieved by AKR1C3 inhibition. Therefore, isomer selective AKR1C3 inhibitors are needed (Penning T M et al. *Mol. Cell Endocrinol.* 2008, 281, 1-8). On the other hand, type 2 17β-hydroxysteroid dehydrogenase (HSD17B2) drives steroid metabolism opposite direction to AKR1C3 and converts potent steroids like estradiol, testosterone and 5α-dihydrotestrosterone to their less active forms estrone, androstenedione and 5α-androstanedione, respectively (Gao X. et al. *Clin. Cancer Res.* 2019, 25, 1291-301; Ko H. et al. *Cell Rep.* 2018, 22, 809-819). Due to its wide and abundant expression in number of various estrogen and androgen target tissues, such as uterus, placenta, liver and the gastrointestinal and urinary tracts, it has been suggested that type 2 enzyme protects tissues from excessive steroid actions. Therefore, it is important to have selective AKR1C3 inhibitors.

BRIEF DESCRIPTION OF THE INVENTION

An object of the present invention is to provide compounds useful in treating or preventing diseases and disorders associated with altered levels of androgens, estrogens, progesterones and/or prostaglandins, and/or treatable by inhibition of AKR1C3 enzyme. It is further an object of the present invention to provide compounds that selectively inhibit the AKR1C3 enzyme over the AKR1C2 enzyme. The objects of the invention are achieved by a compound which is characterized by what is stated in the independent claims. The preferred embodiments of the invention are disclosed in the dependent claims. The embodiments, examples and features, if any, described in this specification that do not fall under the scope of the independent claims are to be interpreted as examples useful for understanding various embodiments of the invention.

In one aspect, an embodiment of the present disclosure provides novel compounds of formula (I)

(I)

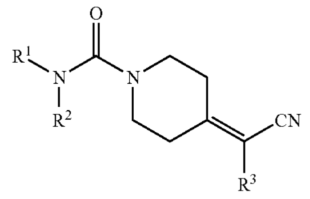

or a salt, solvate or solvate of a salt thereof, wherein $R^1$, $R^2$, and $R^3$ are as defined in the claims.

In another aspect, an embodiment of the present disclosure provides a method for the preparation of a compounds of formula (I), or a salt, solvate or solvate of a salt thereof.

In another aspect, an embodiment of the present disclosure provides pharmaceutical compositions comprising an effective amount of one or more compounds of formula (I), or a salt, solvate or solvate of a salt thereof, together with one or more pharmaceutically acceptable excipient(s).

In another aspect, an embodiment of the present disclosure provides compounds of formula (I) for use as a medicament.

In another aspect, an embodiment of the present disclosure provides compounds of formula (I) for use in treatment or prevention of a disease or disorder selected from the group consisting of polycystic ovary syndrome, endometriosis, uterine leiomyoma, uterine bleeding disorders, dysmenorrhoea, hyperandrogenism, chronic obstructive pulmonary disease (COPD), lung cancer, non-small-cell lung cancer, prostate cancer including castration-resistant prostate cancer, prostate hyperplasia, breast cancer, invasive breast ductal carcinoma, triple negative breast cancer, endometrial carcinoma, renal cell carcinoma, bladder carcinoma, pancreatic adenocarcinoma, acute myeloid leukemia, T-Cell acute lymphoblastic leukemia, melanoma, non-Hodgkins lymphoma, acne, seborrhoea, hair loss, premature sexual maturity, obesity, and inflammation-related pain.

DETAILED DESCRIPTION OF THE INVENTION

The present invention provides a compound of formula (I)

(I)

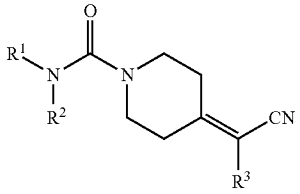

or a salt, solvate or solvate of a salt thereof, wherein $R^1$, $R^2$, and $R^3$ are as defined in the claims. The invention is based on the surprising realization and finding that novel compounds of formula (I) inhibit the AKR1C3 enzyme. A further surprising realization and advantage of the current invention is that compounds of formula (I) inhibit selectively AKR1C3 over other aldo-keto reductases or hydroxysteroid (17β) dehydrogenases (HSD17Bs) enzymes like AKR1C2 and HSD17B2 (17β-HSD2). Therefore, an advantage of the invention is that novel compounds of formula (I) do not, or to less extent, cause biological effects due to inhibition of AKR1C2. A further surprising realization and advantage of the current invention is that compounds of formula (I) do not, or to less extent, cause biological effects due to HSD17B2 inhibition.

The following embodiments are exemplary. Although the specification may refer to "an", "one", or "some" embodiment(s) in several locations, this does not necessarily mean that each such reference is to the same embodiment(s), or that the feature only applies to a single embodiment. Single features of different embodiments may also be combined to provide other embodiments. Furthermore, words "comprising", "comprises", "containing" and "including" should be understood as not limiting the described embodiments to consist of only those features that have been mentioned and such embodiments may contain also features/structures that have not been specifically mentioned.

In one aspect, an embodiment of the present disclosure provides novel compounds of formula (I)

(I)

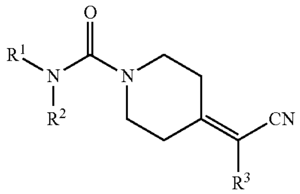

wherein $R^1$ is a group selected from $C_{1-6}$-alkyl, $C_{1-6}$-haloalkyl, $C_{1-6}$-perhaloalkyl, $(CH_2)_mOR'$, $(CH_2)_mN(R')_2$, 6- to 13-membered aryl, 5- to 11-membered heteroaryl, 3- to 12-membered cycloalkyl, and 3- to 10-membered heterocyclyl, and said group being optionally substituted with one to six substituent(s) each independently selected from $R^{11}$;

$R^2$ is a group selected from $C_{1-6}$-alkyl, $C_{1-6}$-haloalkyl, $C_{1-6}$-perhaloalkyl, $(CH_2)_mOR'$, $(CH_2)_mN(R')_2$, 6- to 13-membered aryl, 5- to 11-membered heteroaryl, 3- to 12-membered cycloalkyl, and 3- to 10-membered heterocyclyl, and said group being optionally substituted with one to six substituent(s) each independently selected from $R^{12}$;

or $R^1$ and $R^2$, together with the ring nitrogen atom they are attached to, form a 4- to 11-membered unsaturated or aromatic heterocycle or a 4- to 10-membered saturated or partially unsaturated heterocycle, and said heterocycle being optionally substituted with one to six substituent(s) each independently selected from $R^{13}$;

$R^3$ is a group selected from 6- to 13-membered aryl, 5- to 11-membered heteroaryl, 3- to 12-membered cycloalkyl, and 3- to 10-membered heterocyclyl, and said group being optionally substituted with one to six substituent(s) each independently selected from $R^{31}$;

$R^{11}$ is selected from halogen, CN, $C_{1-6}$-alkyl, $C_{1-6}$-alkoxy, $C_{1-6}$-(per)haloalkyl, $C_{1-6}$-(per)haloalkoxy, OR', oxo, $(OCH_2)_nOR'$, SR', $NO_2$, $N(R')_2$, $(CH_2)_nN(R')_2$, $(CH_2)_nOR'$, CH(XR')R', $CO_2R'$, $C(O)N(R')_2$, C(O)NR'C(O)R", NR'COR", C(=NH)R", C(=N—OR')R", C(O)R", NR'C(O)NR", $NR'SO_2R"$, $SO_2NHSO_2R"$, and $SO_2N(R')_2$ and being optionally substituted with one or more substituents each independently selected from the group consisting of R', OR', $N(R')_2$;

$R^{12}$ is selected from halogen, CN, $C_{1-6}$-alkyl, $C_{1-6}$-alkoxy, $C_{1-6}$-(per)haloalkyl, $C_{1-6}$-(per)haloalkoxy, OR', oxo, $(OCH_2)_nOR'$, SR', $NO_2$, $N(R')_2$, $(CH_2)_nN(R')_2$, $(CH_2)_nOR'$, CH(XR')R', $CO_2R'$, $C(O)N(R')_2$, NHCOR", C(=NH)R", C(=N—OR')R", C(O)R", and $SO_2N(R')_2$ and being optionally substituted with one or more substituents each independently selected from the group consisting of R', OR', $N(R')_2$;

$R^{13}$ is selected from halogen, CN, $C_{1-6}$-alkyl, $C_{1-6}$-alkoxy, $C_{1-6}$-(per)haloalkyl, $C_{1-6}$-(per)haloalkoxy, OR', oxo, $(OCH_2)_nOR'$, SR', $NO_2$, $N(R')_2$, $(CH_2)_nN(R')_2$, $(CH_2)_nOR'$, CH(XR')R', $CO_2R'$, $C(O)N(R')_2$, C(O)NR'C(O)R", NR'C(O)R", C(=NH)R", C(=N—OR')R", C(O)R", NR'C(O)NR", $NR'SO_2R"$, $SO_2NHSO_2R"$, and $SO_2N(R')_2$ and being optionally substituted with one or more substituents each independently selected from the group consisting of R', OR', $N(R')_2$;

$R^{31}$ is selected from halogen, CN, $C_{1-6}$-alkyl, $C_{1-6}$-alkoxy, $C_{1-6}$-(per)haloalkyl, $C_{1-6}$-(per)haloalkoxy, OR', oxo, $(OCH_2)_nOR'$, SR', $NO_2$, $N(R')_2$, $(CH_2)_nN(R')_2$, $(CH_2)_nOR'$, $CO_2R'$, $C(O)N(R')_2$, C(O)NR'C(O)R", NR'C(O)R", C(=NH)R", C(=N—$OR^1$H)R", C(O)R", NR'C(O)NR", $NR'SO_2R"$, $SO_2NHSO_2R"$, and $SO_2N(R')_2$ and being optionally substituted with one or more substituents each independently selected from the group consisting of R', OR', $N(R')_2$;

each R' is independently selected from H, $C_{1-6}$-alkyl, $C_{1-6}$-haloalkyl, and $C_{1-6}$-perhaloalkyl, or when part of any $N(R')_2$ both R's, together with the nitrogen they are attached to, may form a 3- to 6-membered aliphatic or aromatic heterocyclic ring comprising 1 to 4 heteroatoms each independently selected from N, S, and O;

each R" is independently selected from $C_{1-6}$-alkyl, $C_{1-6}$-haloalkyl, and $C_{1-6}$-perhaloalkyl;

X is O or S;

m is 0-6; and n is 1-6; or a salt, solvate or solvate of a salt thereof.

The term "$C_{1-6}$-alkyl" as used herein and hereafter, as such or as part of haloalkyl, perhaloalkyl or alkoxy group, is an aliphatic linear, branched or cyclic, especially linear or branched, hydrocarbon group having the indicated number of carbon atoms; for example $C_{1-6}$-alkyl has 1 to 6 carbon atoms in the alkyl moiety and thus, for example, $C_{1-3}$-alkyl includes methyl, ethyl, n-propyl, isopropyl, and $C_{1-6}$-alkyl additionally includes branched and straight chain n-butyl, sec-butyl, isobutyl, tert-butyl, pentyl and hexyl. The said hydrocarbon group having suitably 1 to 6, preferably 1 to 3, carbon atoms in the alkyl moiety. Examples of aliphatic cyclic hydrocarbon groups include, but are not limited to, cyclopropyl, and cyclohexyl.

The term "haloalkyl" as used herein and hereafter refers to any of the above alkyl groups where one or more hydrogen atoms are replaced by halogen(s): in particular I, Br, F or Cl. Examples of haloalkyl groups include without limitation chloromethyl, fluoromethyl, $—CH_2CF_3$.

The term "perhaloalkyl" is understood to refer to an alkyl group, in which all the hydrogen atoms are replaced by halogen atoms. Preferred examples include trifluoromethyl ($—CF_3$) and trichloromethyl ($—CCl_3$).

The term "(per)haloalkyl" as used herein and hereafter refers to a haloalkyl or a perhaloalkyl.

The term "halogen" as used herein and hereafter by itself or as part of other groups refers to the Group VIIa elements and includes F, Cl, Br and I.

The term "aryl" used herein and hereafter refers to mono- and polycyclic aromatic hydrocarbons that have the indicated number of ring atoms, e.g. "6- to 13-membered aryl" refers to an aryl with 6 to 13 ring atoms. Examples of aryls include, but are not limited to, phenyl, naphtalenyl, and fluorenyl. The aryl may be substituted with one to six, preferably one or two, substituents as denoted, in particular one, at any suitable ring atom. Preferred substituents include, but are not limited to, halogen, in particular F and Cl, cyano, methyl, ethyl, acetyl, trifluoromethyl, hydroxy, methoxy, $OCF_3$, $CH_2OH$, $CH_2OCH_3$, $CH_2CH_2OH$, $CH_2CH_2CH_2OH$, $OCH_2CH_3$, 1-hydroxyethyl, $SO_2NH_2$, and acetyl.

The term "heteroaryl" used herein and hereafter refers to mono-, bi-, tri- and tetracyclic aromatic rings having one or more heteroatom(s) as ring atom(s), while the remaining ring atoms are carbon atoms. Therefore, e.g. "5- to 11-membered heteroaryl" refers to a mono-, and bicyclic heteroaryls having in total 5 to 11 ring atoms of which one or more ring atom(s) is/are heteroatom(s) and the remaining ring atoms are carbon atoms. Preferably, the heteroaryl has 1 to 6 heteroatoms, more preferably 1 to 4 heteroatoms, as ring atoms, while the remaining ring atoms are carbon atoms, where the said heteroatoms include at least the heteroatom(s) denoted in the same context and optionally one or more further heteroatom(s). Each heteroatom is independently selected form N, O, S, P, Si, and Se, preferably from N, O and S, unless denoted otherwise. The heteroaryl group need only have some degree of aromatic character. Examples of monocyclic heteroaryls include, but are not limited to, pyrrolyl, pyrazolyl, furyl, thienyl, triazolyl, furazanyl, oxadiazolyl, thiadiazolyl, tetrazolyl, imidazolyl, pyridinyl, pyrazinyl, pyrimidinyl, pyridazinyl, triazinyl, and tetrazinyl. Examples of bicyclic heteroaryls include indolyl, 1H- and 2H-indazolyl, indolinyl, isoindolinyl, quinolinyl, benzimidazolyl, benzoazepinyl, benzothiazolyl, 4,5-dihydro-7H-isoxazolo[3,4-c]pyridinyl, 6,7-dihydro-4H-isoxazolo[4,3-c]pyridinyl, 6,7-dihydro-4H-[1,2,3]triazolo[1,5-a]pyrazinyl, 1,4,6,7-tetrahydroimidazo[4,5-c]pyridinyl, 1,4,6,7-tetrahydropyrazolo[4,3-c]pyridinyl, 5,6-dihydro-8H-[1,2,4]triazolo[1,5-a]pyrazinyl, 5,6-dihydro-8H-imidazo[1,5-a]pyrazinyl, 3,4-dihydro-1H-pyrrolo[1,2-a]pyrazinyl, 2,3-dihydropyrrolo[2,3-b]pyridinyl, 6,7-dihydro-4H-thieno[3,2-c]pyridinyl, and other bicyclic heteroaryls resulting from the fusion of a monocyclic heteroaryl and an aromatic ring, same or another monocyclic aromatic heterocycle, or a saturated or partly unsaturated cyclic or heterocyclic group. Examples of tricyclic heteroaryls include carbazolyl, acridinyl, and other tricyclic heteroaryls resulting from the fusion of a mono- or bicyclic heteroaryl and an aromatic ring, same or another bicyclic aromatic heterocycle, or a saturated or partly unsaturated cyclic or heterocyclic group. The heteroaryl may be substituted with one to six, preferably one or two, substituents as denoted, in particular one, at any suitable ring atom, including N. Preferred substituents include, but are not limited to, halogen, in particular F and Cl, cyano, methyl, ethyl, acetyl, trifluoromethyl, hydroxy, methoxy, $OCF_3$, $CH_2OH$, $CH_2OCH_3$, $CH_2CH_2OH$, $CH_2CH_2CH_2OH$, $OCH_2CH_3$, 1-hydroxyethyl, $SO_2NH_2$, and acetyl.

The term "cycloalkyl" as used herein and hereafter refers to saturated or partly unsaturated mono-, bi-, tri- and tetracyclic cycloalkyl groups having the indicated number of ring atoms. "3- to 12-membered cycloalkyls" include, but are not limited to, cyclopropyl, cyclobutyl, cyclopentyl, cyclohexyl, cycloheptyl, cyclohexene, trans-cyclooctene, cyclooctyne, bicyclo[2.2.1]heptyl, bicyclo[2.2.1]heptenyl, and bicyclo[4.4.0]decanyl. It is to be understood that the cycloalkyl can be a spirocyclic, fused bicyclic or a bridged bicyclic cycloalkyl. The cycloalkyl may be substituted with one to six, preferably one or two, substituents as denoted, in particular one, at any suitable ring atom. Preferred substituents include, but are not limited to, halogen, in particular F and Cl, cyano, methyl, ethyl, acetyl, trifluoromethyl, hydroxy, methoxy, $OCF_3$, $CH_2OH$, $CH_2OCH_3$, $CH_2CH_2OH$, $CH_2CH_2CH_2OH$, $OCH_2CH_3$, 1-hydroxyethyl, $SO_2NH_2$, and acetyl.

The term "heterocyclyl" used herein and refers to saturated or partly unsaturated mono-, bi-, tri- and tetracyclic rings having one or more heteroatom(s) as ring atom(s), while the remaining ring atoms are carbon atoms. Therefore, e.g. "3- to 10-membered heterocyclyl" refers to saturated or partly unsaturated mono, bi-, and tri-cyclic rings having in total 3 to 10 ring atoms of which one or more ring atom(s) is/are heteroatom(s) and the remaining ring atoms are carbon atoms. Preferably, the heterocyclyl has 1 to 6 heteroatoms, more preferably 1 to 4 heteroatoms, as ring atoms, while the remaining ring atoms are carbon atoms, where the said heteroatoms include at least the heteroatom(s) denoted in the same context and optionally one or more further heteroatom(s). Each heteroatom is independently selected from N, S, O, P, Si and Se, preferably from N, O and S, unless denoted otherwise. Examples of heterocyclyls include, but are not limited to, 1,4-diazabicyclo[2.2.2]octanyl, 3-oxa-8-azabicyclo[3.2.1]octanyl, azetidinyl, 2-azabicyclo[2.2.1]heptanyl, pyrrolidinyl, tetrahydrofuranyl, imidazolidinyl, pyrazolidinyl, piperidinyl, tetrahydropyranyl, tetrahydrothiopyranyl, piperazinyl, 2,5-diketopiperazine, piperazinedione, morpholinyl, thiomorpholinyl, dioxanyl, oxiranyl, dithianyl, dithiazolyl, oxazinyl, thiazinyl, diozinyl, dithiinyl, thiopyranyl, pyranyl, and tetrazolyl. It is to be understood that the heterocycle can be a spirocyclic, fused bicyclic or a bridged bicyclic heterocycle. The heterocyclyl may be substituted with one to six, preferably one or two, substituents as denoted, in particular one, at any suitable ring atom, including N. Preferred substituents include, but are not limited to, halogen, in particular F and Cl, cyano, methyl, ethyl, acetyl, trifluoromethyl, hydroxy, methoxy, $OCF_3$, $CH_2OH$, $CH_2OCH_3$, $CH_2CH_2OH$, $CH_2CH_2CH_2OH$, $OCH_2CH_3$, 1-hydroxyethyl, $SO_2NH_2$, and acetyl.

"Optional" or "optionally" denotes that the subsequently described event or circumstance may but need not occur, and that the description includes instances where the event or circumstance occurs and instances in which it does not.

The term "optionally substituted" as used herein and hereafter denotes that the group it refers to is either unsubstituted or substituted independently with one to six, preferably 1, 2, 3 or 4, substituent(s) attached at any available atom to produce a stable compound. E.g. phenyl may be substituted once with a denoted substituent attached to o-, m- or p-position of the phenyl ring. In general, "substituted" refers to a substituent (group) as defined herein and hereafter in which one or more bonds to a hydrogen atom contained therein are replaced by a bond to a non-hydrogen atom unless otherwise denoted.

The term "unsaturated or aromatic heterocycle" refers to unsaturated or aromatic mono-, bi-, tri- and tetracyclic rings having one or more heteroatom(s) as ring atom(s), while the remaining ring atoms are carbon atoms. Therefore, e.g. "4- to 11-membered unsaturated or aromatic heterocycle" refers to unsaturated or aromatic mono-, bi-, and tricyclic rings having in total 4 to 11 ring atoms of which one or more ring atom(s) is/are heteroatom(s) and the remaining ring atoms are carbon atoms. Preferably the unsaturated or aromatic heterocycle has 1 to 6 heteroatoms as ring atoms, more preferably 1 to 4 heteroatoms, each independently selected from the group consisting of N, S, and O, while the remaining ring atoms are carbon atoms. It is to be understood that the unsaturated or aromatic heterocycle can be a spirocyclic, fused bicyclic or a bridged bicyclic heterocycle. Furthermore, it is to be understood that when $R^1$ and $R^2$, together with the ring nitrogen atom they are attached to, form a unsaturated or aromatic heterocycle, e.g. a 9-membered unsaturated or aromatic heterocycle, it is enough that at least one of the cyclic rings of said 9-membered unsaturated or aromatic heterocycle is unsaturated or aromatic; a representative example of such $R^1$ and $R^2$, together with the ring nitrogen atom they are attached to, form a unsaturated or aromatic heterocycle is indolinyl, which consist of a 6-membered benzene ring fused to a 5-membered pyrrolidinyl. Therefore, the nitrogen to which $R^1$ and $R^2$ are attached to, together with the $R^1$ and $R^2$ may form a saturated or partially unsaturated heterocycle, which is fused with a unsaturated or aromatic ring and is therefore considered an unsaturated or aromatic heterocycle. Examples of unsaturated or aromatic heterocycles include, but are not limited to, pyrrolyl, pyrazolyl, furyl, thienyl, triazolyl, furazanyl, 1,2,3-, 1,2,4-, 1,2,5- and 1,3,4-oxadiazolyl, 1,2,3-, 1,2,4-, 1,2,5-, and 1,3,4-thiadiazolyl, tetrazolyl, imidazolyl, pyridinyl, pyrazinyl, pyrimidinyl, pyridazinyl, triazinyl, tetrazinyl, 1H- and 2H-indazolyl, indolinyl, isoindolinyl, quinolinyl, benzimidazolyl, benzoazepinyl, benzothiazolyl, 4,5-dihydro-7H-isoxazolo[3,4-c]pyridinyl, 6,7-dihydro-4H-isoxazolo[4,3-c]pyridinyl, 6,7-dihydro-4H-[1,2,3]triazolo[1,5-a]pyrazinyl, 1,4,6,7-tetrahydroimidazo[4,5-c]pyridinyl, 1,4,6,7-tetrahydropyrazolo[4,3-c]pyridinyl, 5,6-dihydro-8H-[1,2,4]triazolo

[1,5-a]pyrazinyl, 5,6-dihydro-8H-imidazo[1,5-a]pyrazinyl, 3,4-dihydro-1H-pyrrolo[1,2-a]pyrazinyl, 2,3-dihydropyrrolo[2,3-b]pyridinyl, 6,7-dihydro-4H-thieno[3,2-c]pyridinyl, 5,6-dihydro-8H-[1,2,4]triazolo[4,3-a]pyrazinyl, and other unsaturated or aromatic heterocycles resulting from the fusion of a saturated or partly unsaturated heterocyclyl and an aromatic ring, same or another unsaturated or aromatic heterocycle, or a saturated or partly unsaturated heterocycle. Preferably, the unsaturated or aromatic heterocycle is selected from indolin-1-yl, isoindolin-2-yl, 4,5-dihydro-7H-isoxazolo[3,4-c]pyridin-6-yl, 6,7-dihydro-4H-isoxazolo[4,3-c]pyridin-5-yl, 6,7-dihydro-4H-[1,2,3]triazolo[1,5-a]pyrazin-5-yl, 3-oxa-8-azabicyclo[3.2.1]octan-8-yl, azetidin-1-yl, 1,4,6,7-tetrahydroimidazo[4,5-c]pyridin-5-yl, 1,4,6,7-tetrahydropyrazolo[4,3-c]pyridin-5-yl, 5,6-dihydro-8H-[1,2,4]triazolo[1,5-a]pyrazin-7-yl, 5,6-dihydro-8H-imidazo[1,5-a]pyrazin-7-yl), 3,4-dihydro-1H-pyrrolo[1,2-a]pyrazin-2-yl, 2,3-dihydropyrrolo[2,3-b]pyridin-1-yl, 2-azabicyclo[2.2.1]heptan-2-yl, 6,7-dihydro-4H-thieno[3,2-c]pyridin-5-yl, and 5,6-dihydro-8H-[1,2,4]triazolo[4,3-a]pyrazin-7-yl. The heterocycle may be substituted with one to six, preferably one or two, substituents as denoted, in particular one, at any suitable ring atom, including N. Preferred substituents include, but are not limited to, halogen, in particular F and Cl, cyano, methyl, ethyl, acetyl, trifluoromethyl, hydroxy, methoxy, $OCF_3$, $CH_2OH$, $CH_2OCH_3$, $CH_2CH_2OH$, $CH_2CH_2CH_2OH$, $OCH_2CH_3$, 1-hydroxyethyl, $SO_2NH_2$, and acetyl.

The term "saturated or partially unsaturated heterocycle" refers to saturated or partly unsaturated mono-, bi-, tri- and tetracyclic rings having one or more heteroatom(s) as ring atom(s), while the remaining ring atoms are carbon atoms. Therefore, e.g. "4- to 10-membered saturated or partly unsaturated heterocycle" refers to saturated or partly unsaturated mono-, bi-, and tricyclic rings having in total 4 to 10 ring atoms of which one or more ring atom(s) is/are heteroatom(s) and the remaining ring atoms are carbon atoms. Preferably the saturated or partly unsaturated heterocycle has 1 to 6 heteroatoms as ring atoms, more preferably 1 to 4 heteroatoms, each independently selected from the group consisting of N, S, and O, while the remaining ring atoms are carbon atoms. It is to be understood that the saturated or partially unsaturated heterocycle can be a spirocyclic, fused bicyclic or a bridged bicyclic heterocycle. Examples of saturated or partially unsaturated heterocycles include, but are not limited to, 1,4-diazabicyclo[2.2.2]octanyl, 3-oxa-8-azabicyclo[3.2.1]octanyl, azetidinyl, 2-azabicyclo[2.2.1]heptanyl, pyrrolidinyl, tetrahydrofuranyl, imidazolidinyl, pyrazolidinyl, piperidinyl, tetrahydropyranyl, tetrahydrothiopyranyl, piperazinyl, 2,5-diketopiperazine, piperazinedione, morpholinyl, thiomorpholinyl, dioxanyl, oxiranyl, dithianyl, dithiazolyl, oxazinyl, thiazinyl, diozinyl, dithiinyl, thiopyranyl, pyranyl, 2-oxa-7-azaspiro[3.5]nonan-7-yl, tetrazolyl, and other saturated or partially unsaturated heterocycles resulting from the fusion of a saturated or partially unsaturated heterocycle and an aromatic ring, unsaturated or aromatic heterocycle, or a same or another saturated or partially unsaturated heterocycle. The heterocycle may be substituted with one to six, preferably one or two, substituents as denoted, in particular one, at any suitable ring atom, including N. Preferred substituents include, but are not limited to, halogen, in particular F and Cl, cyano, methyl, ethyl, acetyl, trifluoromethyl, hydroxy, methoxy, $OCF_3$, $CH_2OH$, $CH_2OCH_3$, $CH_2CH_2OH$, $CH_2CH_2CH_2OH$, $OCH_2CH_3$, 1-hydroxyethyl, $SO_2NH_2$, and acetyl.

The term "$C_{1-6}$-alkoxy" as used herein and hereafter refers to a —O—($C_{1-6}$-alkyl) group where the "$C_{1-6}$-alkyl" has the above-defined meaning. Examples of preferred alkoxy groups include, but are not limited to, methoxy, ethoxy, and isopropyloxy.

The term "$C_{1-6}$-(per)haloalkoxy" as used herein and hereafter refers to a —O—($C_{1-6}$-(per)haloalkyl) group where the "$C_{1-6}$-(per)haloalkyl" has the above-defined meaning. Examples of preferred alkoxy groups include, but are not limited to, trifluoromethoxy, 2,2,2-trichloromethoxy, and 1,1,1,3,3,3-hexafluoro-isopropoxy.

The term "oxo" as used herein and hereafter refers to a substituent oxygen atom bonded to another atom by a double or single bond. Example of a functional group with an oxo include, but is not limited to, carbonyl group (C═O).

The term "3- to 6-membered aliphatic or aromatic heterocyclic ring comprising 1 to 4 heteroatoms each independently selected from N, S, and O" as used herein and hereafter refers to a monocyclic ring which is saturated, partially unsaturated, unsaturated or aromatic with 3 to 6 ring atoms that may or may not comprise one or more double bond between the ring atoms and said monocyclic ring comprises 1 to 4 heteroatom(s) each independently selected from the group consisting of N, S, and O, while the remaining ring atoms are carbon atoms. It may be substituted with one to four substituent(s) at any suitable ring atom, including N. Preferred substituents groups include, but are not limited to halogen, in particular fluoro, CN, methoxy, hydroxy, amino, and methyl. Examples of heterocyclic rings include, but are not limited to, aziridinyl, azetidinyl, 1,3-diazetidinyl, pyrazolidinyl, imidazolidinyl, imidazolyl, piperidinyl, dihydrothiazolyl, piperazinyl, pyrrolidinyl, thiomorpholinyl, dioxide of thiomorpholinyl, and methoxymethylpyrrolidinyl.

The term "salt" as used herein and hereafter refers to salts which are known to be non-toxic and are physiologically and/or pharmaceutically acceptable salts. Typically, these are acid addition salts or base addition salts of the referred compounds of the invention. Also encompassed are salts which are not themselves suitable for pharmaceutical applications but can be used, for example, for isolation or purification of the inventive compounds.

The expression "acid addition salt" includes any non-toxic organic and inorganic acid addition salts that that the compounds of the invention can form. Illustrative inorganic acids, which form suitable acid addition salts, include, but are not limited to, hydrogen chloride, hydrogen bromide, sulphuric and phosphoric acids. Illustrative organic acids, which form suitable acid addition salts, include, but are not limited to, formic acid, acetic acid, trifluoroacetic acid, lactic acid, malonic acid, succinic acid, glutaric acid, fumaric acid, malic acid, tartaric acid, citric acid, ascorbic acid, maleic acid, benzoic acid, phenylacetic acid, cinnamic acid, methane sulfonic acid, ethane sulfonic acid, toluene sulfonic acid, benzene sulfonic acid, naphthalene disulfonic acid, salicylic acid, and the like. These salts also include salts useful for the chiral resolution of racemates.

The expression "base addition salt" includes any non-toxic base addition salts that the compounds of the invention can form. Suitable base addition salts include, but are not limited to, those derived from inorganic bases such as aluminum, ammonium, calcium, copper, iron, lithium, magnesium, manganese, potassium, sodium, and zinc salts, in particular sodium and ammonium salts. Examples of organic base addition salts include, but are not limited to, salts of trialkylamines, such as triethyl amine, trimethyl amine, ethyldiisopropylamine, other salts of organic amines such as methylamine, dimethylamine, trimethylamine, ethylamine, monoethanolamine, diethanolamine, triethanolamine, dicyclohexylamine, dimethylaminoethanol, procaine, dibenzylamine, N-methylmorpholine, morpholine, arginine, lysine, ethylenediamine and N-methylpiperidine, and the like, and choline salts.

The term "solvate" as used herein and hereafter refers to those forms of the compounds which, in the solid or liquid state, form a complex by coordination with solvent molecules. Examples of solvates include, but are not limited to, hydrates, alcoholates, and the like. Hydrates are a specific form of the solvates in which the coordination is with water. Preferred solvates in the context of the present invention are hydrates.

Where the inventive compounds can occur in tautomeric forms, the present invention encompasses all the tautomeric forms.

Where the inventive compounds can occur in stereomeric forms, the present invention encompasses all the diastereomeric and enantiomeric forms.

Additionally, or alternatively, in embodiments of the present invention is provided a compound of formula (I), wherein $R^3$ is a group selected from 6-membered aryl and 5- to 9-membered heteroaryl, wherein the heteroaryl comprises 1 to 3 heteroatom(s), each independently selected from the group consisting of N, O, and S, and said group being optionally substituted with one to three substituent(s) each independently selected from $R^{31}$;

$R^{31}$ is as previously defined; or a salt, solvate or solvate of a salt thereof. Preferably, the heteroaryl has 1, 2, or 3 heteroatom(s) as ring atoms, while the remaining ring atoms are carbon atoms, each heteroatom independently selected from the group consisting of N, O, and S.

Additionally, or alternatively, in embodiments of the present invention is provided a compound of formula (I), wherein $R^1$ is a group selected from $C_{1-6}$-alkyl, 5- to 9-membered heteroaryl, and 5- to 7-membered heterocyclyl, and said group being optionally substituted with one to three substituent(s) each independently selected from $R^{11}$; and $R^2$ is a group selected from $C_{1-6}$-alkyl, 5- to 9-membered heteroaryl, and 5- to 7-membered heterocyclyl, and said group being optionally substituted with one to three substituent(s) each independently selected from $R^{12}$;

$R^{11}$ and $R^{12}$ are as previously defined; or a salt, solvate or solvate of a salt thereof.

Additionally, or alternatively, in embodiments of the present invention is provided a compound of formula (I), wherein $R^1$ and $R^2$, together with the ring nitrogen atom to which they are attached, form a 5 to 9-membered aromatic heterocycle or a 4- to 9-membered saturated heterocycle, wherein the heterocycle optionally comprises 1 to 4 further heteroatom(s) each independently selected from the group consisting of N, O, and S, and said heterocycle being optionally substituted with one to four substituent(s) each independently selected from $R^{13}$;

$R^{13}$ is as previously defined; or a salt, solvate or solvate of a salt thereof. Preferably, the heterocycle has 1 nitrogen atom and further 0 to 4 heteroatom(s) as ring atoms, while the remaining ring atoms are carbon atoms, each further heteroatom independently selected from the group consisting of N, O, and S, and said heterocycle being optionally substituted with one or two substituent(s), each independently selected from $R^{13}$; wherein $R^{13}$ is as previously defined.

Additionally, or alternatively, in embodiments of the present invention is provided a compound of formula (I), wherein $R^3$ is a group selected from phenyl, pyridinyl, thienyl, and 1H-indazolyl, and said group being optionally substituted with one or two substituent(s) each independently selected from $R^{31}$;

$R^{31}$ is as previously defined; or a salt, solvate or solvate of a salt thereof. Preferably, $R^3$ is a group selected from phenyl, pyridin-2-yl, thien-2-yl, 1H-indazol-4-yl, 1H-indazol-3-yl, 1H-indazol-6-yl, 1H-indazol-5-yl, and 1H-indazol-7-yl, and said group being optionally substituted with one or two substituent(s) each independently selected from $R^{31}$. More preferably, $R^3$ is a group selected from phenyl, pyridine-2-yl, thien-2-yl, 1-acetyl-1H-indazol-4-yl, 5-fluoro-1H-indazol-3-yl, and 1-methyl-1H-indazol-7-yl, and said group being optionally substituted with one or two substituent(s) each independently selected from $R^{31}$; wherein $R^{31}$ is as previously defined.

Additionally, or alternatively, in embodiments of the present invention is provided a compound of formula (I), wherein $R^{31}$ is selected from halogen, $C_{1-3}$-alkyl, $C_{1-3}$-(per)haloalkyl, $C_{1-3}$-(per)haloalkoxy, and $C(O)C_{1-6}$-alkyl; or a salt, solvate or solvate of a salt thereof. Preferably, $R^{31}$ is selected from F, Cl, methyl, $CF_3$, $OCF_3$, and $C(O)CH_3$.

Additionally, or alternatively, in embodiments of the present invention is provided a compound of formula (I), wherein $R^1$ is a group selected from methyl, ethyl, and tetrahydropyranyl;

$R^2$ is a group selected from methyl, ethyl, and tetrahydropyranyl; or a salt, solvate or solvate of a salt thereof.

Additionally, or alternatively, in embodiments of the present invention is provided a compound of formula (I), wherein $R^1$ and $R^2$, together with the ring nitrogen atom to which they are attached, form an aromatic heterocycle or a saturated heterocycle selected from piperidinyl, piperazinyl, morpholinyl, pyrrolidinyl, indolinyl, isoindolinyl, 4,5-dihydro-7H-isoxazolo[3,4-c]pyridinyl, 6,7-dihydro-4H-isoxazolo[4,3-c]pyridinyl, 6,7-dihydro-4H-[1,2,3]triazolo[1,5-a]pyrazinyl, 3-oxa-8-azabicyclo[3.2.1]octanyl, azetidinyl, 1,4,6,7-tetrahydroimidazo[4,5-c]pyridinyl, 1,4,6,7-tetrahydropyrazolo[4,3-c]pyridinyl, 5,6-dihydro-8H-[1,2,4]triazolo[1,5-a]pyrazinyl, 5,6-dihydro-8H-imidazo[1,5-a]pyrazinyl, 3,4-dihydro-1H-pyrrolo[1,2-a]pyrazinyl, 2,3-dihydro-pyrrolo[2,3-b]pyridinyl, 2-azabicyclo[2.2.1]heptanyl, 6,7-dihydro-4H-thieno[3,2-c]pyridinyl, thiomorpholinyl, octahydrocyclopenta[c]pyrrolyl, N-methyl-N-(oxetan-3-yl), 4-hydroxyazepanyl, 5-fluoroindolinyl, 2-methylpiperidinyl, 4-isopropoxypiperidinyl, 4-propoxypiperidinyl, and 5,6-dihydro-8H-[1,2,4]triazolo[4,3-a]pyrazinyl, and said heterocycle being optionally substituted with one or two substituent(s) each independently selected from $R^{13}$;

$R^{13}$ is as previously defined; or a salt, solvate or solvate of a salt thereof.

Additionally, or alternatively, in embodiments of the present invention is provided a compound of formula (I), wherein $R^{13}$ is selected from CN, $C_{1-3}$-(per)haloalkyl, OR', $(CH_2)_n$OR', CH(OH)$C_{1-6}$-alkyl, C(O)R", and $SO_2N(R')_2$;

each R' is independently selected from H, and $C_{1-6}$-alkyl;

each R" is independently selected from $C_{1-6}$-alkyl;

n is 1-3; or a salt, solvate or solvate of a salt thereof. Preferably, $R^{13}$ is selected from CN, $CF_3$, OH, methoxy, ethoxy, $(CH_2)_n$OH, $CH_2$OMe, CH(OH)$C_{1-6}$-alkyl, C(O)$CH_3$, and $SO_2NH_2$; and n is 1-3.

In embodiments of the present invention is provided a compound of formula (I), wherein the compound has formula (Ia)

(Ia)

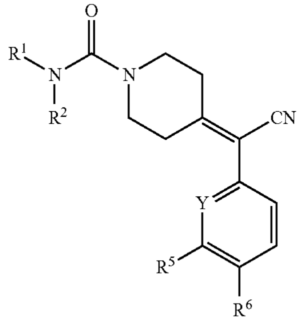

wherein

Y is N or C—$R^4$, wherein $R^4$ is H or F;

$R^5$ is H, Cl or F;

or

Y is C—$R^4$, and $R^4$ and $R^5$, together with the carbon atoms they are attached to, form a 5-membered aromatic heterocycle;

$R^6$ is F, Cl, or H;

or

Y is N or C—$R^4$, wherein $R^4$ is H or F;

$R^5$ and $R^6$, together with the carbon atoms they are attached to, form a 5-membered aromatic heterocycle; and $R^1$ and $R^2$ are as previously defined; or a salt, solvate or solvate of a salt thereof.

Additionally, or alternatively, in embodiments of the present invention is provided a compound of formula (I) or (Ia), wherein $R^1$ and $R^2$, together with the ring nitrogen atom to which they are attached, form an aromatic heterocycle or a saturated heterocycle selected from piperidin 1-yl, piperazin-1-yl, morpholin-4-yl, pyrrolidin-1-yl, indolin-1-yl, isoindolin-2-yl, 4,5-dihydro-7H-isoxazolo[3,4-c]pyridin-6-yl, 6,7-dihydro-4H-isoxazolo[4,3-c]pyridin-5-yl, 6,7-dihydro-4H-[1,2,3]triazolo[1,5-a]pyrazin-5-yl, 3-oxa-8-azabicyclo[3.2.1]octan-8-yl, azetidin-1-yl, 1,4,6,7-tetrahydroimidazo[4,5-c]pyridin-5-yl, 1,4,6,7-tetrahydropyrazolo[4,3-c]pyridin-5-yl, 5,6-dihydro-8H-[1,2,4]triazolo[1,5-a]pyrazin-7-yl, 5,6-dihydro-8H-imidazo[1,5-a]pyrazin-7-yl, 3,4-dihydro-1H-pyrrolo[1,2-a]pyrazin-2-yl, 2,3-dihydropyrrolo[2,3-b]pyridin-1-yl, 2-azabicyclo[2.2.1]heptan-2-yl, and 6,7-dihydro-4H-thieno[3,2-c]pyridin-5-yl, and 5,6-dihydro-8H-[1,2,4]triazolo[4,3-a]pyrazin-7-yl, and said heterocycle being optionally substituted with one or two substituent(s) each independently selected from $R^{13}$;

$R^{13}$ is selected from CN, $C_{1-3}$-(per)haloalkyl, OR', $(CH_2)_n$OR', CH(OH)$C_{1-6}$-alkyl, C(O)R", and $SO_2N(R')_2$;

each R' is independently selected from H, and $C_{1-6}$-alkyl;

each R" is independently selected from $C_{1-6}$-alkyl; or a salt, solvate or solvate of a salt thereof.

Additionally, or alternatively, in embodiments of the present invention is provided a compound of formula (I) or (Ia), wherein $R^{13}$ is selected from CN, $CF_3$, OH, methoxy, ethoxy, $(CH_2)_n$OH, $CH_2$OMe, CH(OH)$C_{1-6}$-alkyl, C(O)$CH_3$, and $SO_2NH_2$; and n is 1-3; or a salt, solvate or solvate of a salt thereof.

In embodiments of the present invention is provided a compound of formula (I), wherein the compound has formula (Ib) or (Ic)

(Ib)

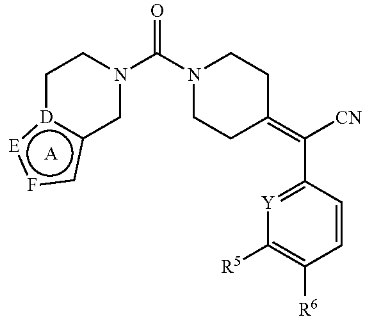

(Ic)

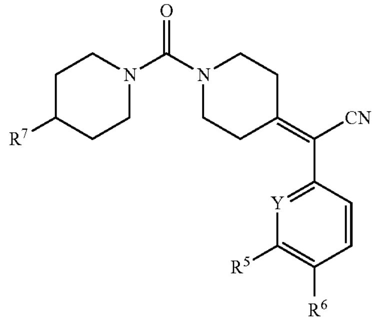

wherein

D is C or N;

E is N, NH, or CH;

F is O or N;

Y is N or C—$R^4$, wherein $R^4$ is H or F;

$R^5$ is H, Cl, or F;

or

Y is C—$R^4$, and $R^4$ and $R^5$, together with the carbon atoms they are attached to, form a 5-membered aromatic heterocycle;

$R^6$ is F, Cl, or H;

or

Y is N or C—$R^4$, wherein $R^4$ is H or F;

$R^5$ and $R^6$, together with the carbon atoms they are attached to, form a 5-membered aromatic heterocycle; and $R^7$ is OH or $CH_2$OH; or a salt, solvate or solvate of a salt thereof.

The ring A in formula (Ib) is a 5-membered aromatic heterocyclic ring having at least one nitrogen atom as ring atom and further one or two heteroatom(s) as ring atom(s), wherein the further one or two heteroatom(s) is/are each independently selected from the group consisting of N and O, while the remaining ring atoms are carbon atoms. Examples of ring A include, but are not limited to, the bivalent radicals of imidazole, pyrazole, triazolyl and isoxazole.

In embodiments of the present invention is provided a compound of formula (I), wherein the compound has formula (Ia), (Ib), or (Ic), wherein Y is C—$R^4$, and $R^4$ and $R^5$, together with the carbon atoms they are attached to, form a pyrazole group;

$R^6$ is F, Cl, or H;

or

Y is N or C—$R^4$, wherein $R^4$ is H or F;

$R^5$ and $R^6$, together with the carbon atoms they are attached to, form a pyrazole group; and $R^1$, $R^2$, D, E, F, and $R^7$ are as previously defined; or a salt, solvate or solvate of a salt thereof.

In embodiments of the present invention is provided a compound of formula (I), wherein the compound has formula (Ib), wherein ring A is

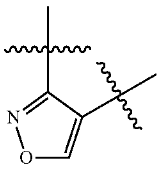
,
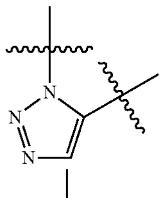
,
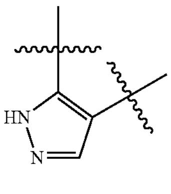
or
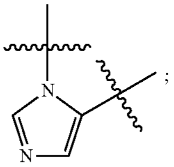
;

or a salt, solvate or solvate of a salt thereof.

Additionally, or alternatively,

Y is CH;

$R^5$ is H and $R^6$ is F or Cl, preferably Cl. Alternatively, both $R^5$ and $R^6$ are F. Alternatively, Y is CF;

$R^5$ is H and $R^6$ is F or Cl.

In embodiments of the present invention is provided a compound of formula (I), wherein the compound has formula (Ic), wherein $R^7$ is OH or $CH_2OH$;

Y is CH;

$R^5$ is H and $R^6$ is F or Cl, preferably Cl; or a salt, solvate or solvate of a salt thereof. Alternatively, both $R^5$ and $R^6$ are F. Alternatively, Y is CF;

$R^5$ is H and $R^6$ is F or C1.

In embodiments of the present disclosure is provided a compound of formula (I), wherein the compound is selected from the compounds presented in Table 1.

In embodiments of the present disclosure is provided a compound of formula (I), wherein the compound is selected from the group consisting of:

2-(4-fluorophenyl)-2-(1-(4-hydroxypiperidine-1-carbonyl) piperidin-4-ylidene)acetonitrile (4);

2-(4-fluorophenyl)-2-(1-(4,5,6,7-tetrahydroisoxazolo[4,3-c] pyridine-5-carbonyl)piperidin-4-ylidene)acetonitrile (12);

2-(4-fluorophenyl)-2-(1-(4,5,6,7-tetrahydro-[1,2,3]triazolo [1,5-a]pyrazine-5-carbonyl)piperidin-4-ylidene)acetonitrile (13);

2-(4-chlorophenyl)-2-(1-(4-hydroxypiperidine-1-carbonyl) piperidin-4-ylidene)acetonitrile (18);

2-(4-fluorophenyl)-2-(1-(4,5,6,7-tetrahydro-1H-pyrazolo[4,3-c]pyridine-5-carbonyl)piperidin-4-ylidene)acetonitrile (25);

2-(3,4-difluorophenyl)-2-(1-(4-hydroxypiperidine-1-carbonyl)piperidin-4-ylidene)acetonitrile (41);

2-(2,4-difluorophenyl)-2-(1-(4-hydroxypiperidine-1-carbonyl)piperidin-4-ylidene)acetonitrile (42);

2-(3,4-difluorophenyl)-2-(1-(4,5,6,7-tetrahydro-1H-pyrazolo[4,3-c]pyridine-5-carbonyl)piperidin-4-ylidene)acetonitrile (43);

2-(3,4-difluorophenyl)-2-(1-(5,6,7,8-tetrahydroimidazo[1,5-a]pyrazine-7-carbonyl)piperidin-4-ylidene)acetonitrile (44);

2-(1-(4-hydroxypiperidine-1-carbonyl)piperidin-4-ylidene)-2-(1H-indazol-4-yl)acetonitrile (48);

2-(5-chloropyridin-2-yl)-2-(1-(4,5,6,7-tetrahydro-1H-pyrazolo[4,3-c]pyridine-5-carbonyl)piperidin-4-ylidene)acetonitrile (67);

2-(4-chlorophenyl)-2-(1-(4-(hydroxymethyl)piperidine-1-carbonyl)piperidin-4-ylidene)acetonitrile (74);

2-(3-chlorophenyl)-2-(1-(4-hydroxypiperidine-1-carbonyl) piperidin-4-ylidene)acetonitrile (80);

2-(5-fluoropyridin-2-yl)-2-(1-(4,5,6,7-tetrahydroisoxazolo [4,3-c]pyridine-5-carbonyl)piperidin-4-ylidene)acetonitrile (84);

1-(4-((3-chlorophenyl)(cyano)methylene)piperidine-1-carbonyl)piperidine-4-sulfonamide (99);

2-(4-chlorophenyl)-2-(1-(4,5,6,7-tetrahydro-1H-pyrazolo[4,3-c]pyridine-5-carbonyl)piperidin-4-ylidene)acetonitrile (113);

2-(1-(4-(hydroxymethyl)piperidine-1-carbonyl)piperidin-4-ylidene)-2-(1-methyl-1H-indazol-7-yl)acetonitrile (118);

2-(1H-indazol-4-yl)-2-(1-(4,5,6,7-tetrahydroisoxazolo[4,3-c]pyridine-5-carbonyl)piperidin-4-ylidene)acetonitrile (138);

2-(3-chlorophenyl)-2-(1-(4-(2-hydroxyethyl)piperidine-1-carbonyl)piperidin-4-ylidene)acetonitrile (140);

2-(4-chlorophenyl)-2-(1-(4,5,6,7-tetrahydroisoxazolo[4,3-c] pyridine-5-carbonyl)piperidin-4-ylidene)acetonitrile (141);

2-(1H-indazol-4-yl)-2-(1-(4-methoxypiperidine-1-carbonyl) piperidin-4-ylidene)acetonitrile (144);

2-(1H-indazol-4-yl)-2-(1-(4-(trifluoromethyl)piperidine-1-carbonyl)piperidin-4-ylidene)acetonitrile (145);

2-(1-(3-oxa-8-azabicyclo[3.2.1]octane-8-carbonyl)piperidin-4-ylidene)-2-(3-chlorophenyl)acetonitrile (156);

2-(5-chloropyridin-2-yl)-2-(1-(4,5,6,7-tetrahydroisoxazolo [4,3-c]pyridine-5-carbonyl)piperidin-4-ylidene)acetonitrile (161); or a salt, solvate or solvate of a salt thereof.

In another aspect, an embodiment of the present disclosure provides a method for the preparation of a compound of formula (I), or a salt, solvate or solvate of a salt thereof, comprising the steps:

reacting a compound of formula (II)

(II)

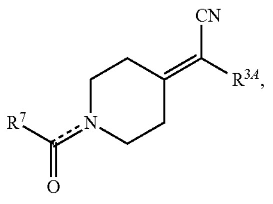

wherein the dotted line represents an optional bond, $R^7$ is a leaving group A or absent when the dotted line represents a bond, and $R^{3A}$ is $R^3$ as defined for compound of formula (I) or a leaving group B, with a compound of formula (III)

(III)

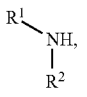

or hydrogen halide thereof, wherein $R^1$ and $R^2$ are as defined for compound of formula (I);

or reacting a compound of formula (IV)

(IV)

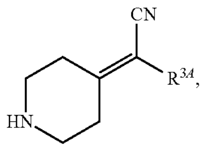

or hydrogen halide thereof, wherein $R^{3A}$ is $R^3$ as defined for compound of formula (I) or a leaving group B, with a compound of formula (V)

(V)

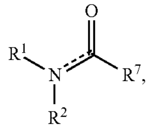

wherein the dotted line represents an optional bond, $R^7$ is a leaving group A or absent when the dotted line represents a bond, and $R^1$ and $R^2$ are as defined for compound of formula (I);

optionally in the presence of a base, to obtain a compound of formula (I)

(I)

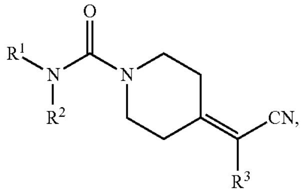

wherein $R^1$, $R^2$, and $R^3$ are as defined for compound of formula (I); or $R^1$ and $R^2$ are as defined for compound of formula (I), and $R^3$ is the leaving group B;

and optionally, provided that $R^3$ is the leaving group B, reacting the obtained compound of formula (I) with a compound of formula (VII)

(VII)

wherein $R^{3B}$ is $R^3$ as defined for compound of formula (I),

Z is a leaving group C or $B(R^8)_2$, wherein $R^8$ is OH, $OC_{1-6}$-alkyl, or both $R^8$, together with the ring boron atom they are attached to, form a cyclic boronic ester, in the presence of a base and a coupling agent, to obtain a compound of formula (I), wherein $R^1$, $R^2$, and $R^3$ are as defined for compound of formula (I);

and optionally converting the compound of formula (I) to a salt, solvate or solvate of a salt thereof. Preferably, the leaving group A is selected from the group consisting of imidazol-1-yl, 3-methylimidazol-3-ium-1-yl iodide, Cl, I, and Br; the leaving group B is selected from the group consisting of Br and I; and the leaving group C is selected from the group consisting of Br or I.

The term "leaving group" as used herein and hereafter refers to a group of a compound that promotes a reaction to occur and/or has a positive influence of the overall reaction rate and/or have a directing effect on positional isomer of the products that are formed. Said leaving group may or may not be part of the formed product, i.e. it is to be understood that the leaving group may be present in the product, or the leaving group may be part of a product, in e.g. $S_N2$, $S_N1$, cross-coupling, and addition-elimination reactions. A compound disclosed herein may have one or more leaving group (s) that may be the same or different. Examples of leaving groups include, but are not limited to, sulfonyls such as phenylsulfonyl, tosyl (Ts), mesyl, and trifyl; halogen (fluoride, chloride, bromide, iodide), (substituted) amino groups, amides, esters, hydroxy, alkoxy, acyloxy, thiol, alkyl, (per)haloalkyl, (per)haloalkoxy, photolabile groups, leaving groups formed from boronic acids and (cyclic) boronic esters in cross-coupling reactions, imidazol-1-yl, 3-methylimidazol-3-ium-1-yl halide, such as iodide, and the like.

The term "hydrogen halide" as used herein and hereafter refers to hydrogen fluoride, -chloride, -bromide, and -iodide.

The term "base" as used herein and hereafter refers to organic and inorganic bases such as aluminum, ammonium, calcium, copper, iron, lithium, magnesium, manganese, caesium, potassium, sodium, and zinc, and acetates, hydroxides, alkoxides, phosphates, and carbonates thereof. Examples of inorganic bases include, but are not limited to, $K_2CO_3$, KOtBu, KOAc, $Cs_2CO_3$, $K_3PO_4$, and NaOH. Examples of organic bases include, but are not limited to, triethyl amine, trimethyl amine, ethyldiisopropylamine, methylamine, dimethylamine, trimethylamine, ethylamine, monoethanolamine, diethanolamine, triethanolamine, dicyclohexylamine, dimethylaminoethanol, procaine, dibenzylamine, N-methylmorpholine, morpholine, arginine, lysine, ethylenediamine and N-methylpiperidine, and the like.

The term "cyclic boronic ester" as used herein and hereafter refers to mono- and bicyclic heterocycles having one boron and two oxygens as ring atoms, while the remaining ring atoms are carbon atoms. Preferably the cyclic boronic ester is a 5 to 7 membered monocyclic heterocycle, such as a dioxaborolane or dioxaborinane. Examples of cyclic boronic esters are esters formed between a boronic acid and an alcohol such as, but not limited to, pinacol, and trimethylene glycol.

The term "coupling agent" as used herein and hereafter refers to a substance or compound added to a reaction to cause a chemical reaction. Said coupling agent may be an activating agent and may or may not be a catalyst. It is to be understood that said coupling agent may or may not be consumed in the reaction. Examples of coupling agents include, but are not limited to, palladium(0) complexes such as tetrakis(triphenylphosphine)palladium(0) ($Pd(PPh_3)_4$), tris(dibenzylideneacetone)dipalladium(0) ($Pd_2(dba)_3$); and palladium(II) complexes such as palladium(II) acetate, [1,1'-bis(di-tert-butylphosphino)ferrocene]-dichloropalladium(II) ($PdCl_2(dtbpf)$), and [1,1'-is(diphenylphosphino)ferrocene] dichloropalladium(II), complex with dichloromethane ($Pd(dppf)Cl_2 \cdot DCM$), and the like.

In embodiments of the present disclosure is provided a method for the preparation of a compound of formula (I), or a salt, solvate or solvate of a salt thereof, comprising the steps:

reacting a compound of formula (II)

(II)

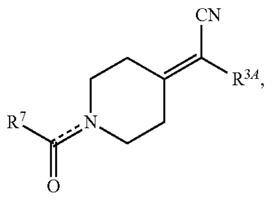

wherein $R^7$ is a leaving group A selected from the group consisting of imidazol-1-yl, 3-methylimidazol-3-ium-1-yl iodide, Cl, I, and Br, and $R^{3A}$ is $R^3$ as defined for compound of formula (I), with a compound of formula (III)

(III)

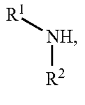

or hydrogen halide thereof, preferably hydrogen chloride thereof, wherein $R^1$ and $R^2$ are as defined for compound of formula (I);

in the presence of a base, preferably triethylamine, to obtain a compound of formula (I), wherein $R^1$, $R^2$, and $R^3$ are as defined for compound of formula (I);

and optionally converting the compound of formula (I) to a salt, solvate or solvate of a salt thereof.

In embodiments of the present disclosure is provided a method for the preparation of a compound of formula (I), or a salt, solvate or solvate of a salt thereof, comprising the steps:

reacting a compound of formula (II)

(II)

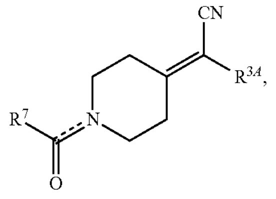

wherein $R^7$ is a leaving group A selected from the group consisting of imidazol-1-yl, 3-methylimidazol-3-ium-1-yl iodide, Cl, I, and Br, and $R^{3A}$ is a leaving group B selected from the group consisting of Br and I, with a compound of formula (III)

(III)

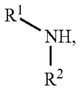

or hydrogen halide thereof, preferably hydrogen chloride thereof, wherein $R^1$ and $R^2$ are as defined for compound of formula (I);

in the presence of a base, preferably triethylamine, to obtain a compound of formula (I)

(I)

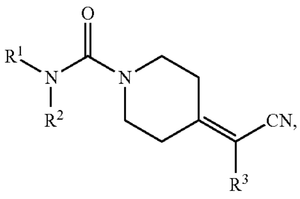

wherein $R^1$ and $R^2$ are as defined for compound of formula (I), and $R^3$ is the leaving group B;

and reacting the obtained compound of formula (I) with a compound of formula (VII)

(VII)

wherein $R^{3B}$ is $R^3$ as defined for compound of formula (I),

Z is a leaving group C, preferably Br or I, or $B(R^8)_2$, wherein $R^8$ is OH, $OC_{1-6}$-alkyl, or both $R^8$, together with the ring boron atom they are attached to, form a cyclic boronic ester, in the presence of a base, preferably $Cs_2CO_3$, and a coupling agent, preferably $Pd(dppf)Cl_2$, to obtain a compound of formula (I), wherein $R^1$, $R^2$, and $R^3$ are as defined for compound of formula (I);

and optionally converting the compound of formula (I) to a salt, solvate or solvate of a salt thereof.

In embodiments of the present disclosure is provided a method for the preparation of a compound of formula (I), or a salt, solvate or solvate of a salt thereof, comprising the steps:

reacting a compound of formula (IV)

(IV)

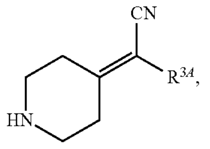

or hydrogen halide thereof, wherein $R^{3A}$ is $R^3$ as defined for compound of formula (I), with a compound of formula (V)

(V)

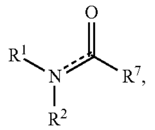

wherein the dotted line represents an optional bond, $R^7$ is a leaving group A selected from the group consisting of imidazol-1-yl, 3-methylimidazol-3-ium-1-yl iodide, Cl, I, and Br, and $R^1$ and $R^2$ are as defined for compound of formula (I);

optionally in the presence of a base, to obtain a compound of formula (I)

(I)

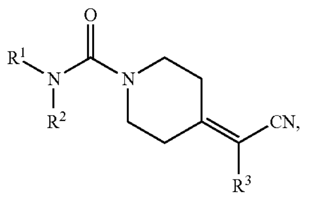

wherein $R^1$, $R^2$, and $R^3$ are as defined for compound of formula (I);

and optionally converting the compound of formula (I) to a salt, solvate or solvate of a salt thereof.

In embodiments of the present disclosure is provided a method for the preparation of a compound of formula (I), or a salt, solvate or solvate of a salt thereof, comprising the steps:

reacting a compound of formula (IV)

(IV)

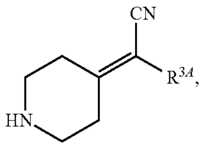

or hydrogen halide thereof, wherein $R^{3A}$ is a leaving group B selected from the group consisting of Br and I, with a compound of formula (V)

(V)

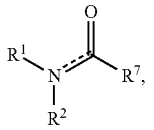

wherein the dotted line represents an optional bond, $R^7$ is a leaving group A selected from the group consisting of imidazol-1-yl, 3-methylimidazol-3-ium-1-yl iodide, Cl, I, and Br, and $R^1$ and $R^2$ are as defined for compound of formula (I);

optionally in the presence of a base, to obtain a compound of formula (I)

(I)

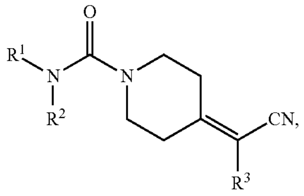

wherein $R^1$ and $R^2$ are as defined for compound of formula (I), and $R^3$ is the leaving group B;

and reacting the obtained compound of formula (I) with a compound of formula (VII)

(VII)

wherein $R^{3B}$ is $R^3$ as defined for compound of formula (I),

Z is a leaving group C, preferably Br or I, or $B(R^8)_2$, wherein $R^8$ is OH, $OC_{1-6}$-alkyl, or both $R^8$, together with the ring boron atom they are attached to, form a cyclic boronic ester, in the presence of a base and a coupling agent, to obtain a compound of formula (I), wherein $R^1$, $R^2$, and $R^3$ are as defined for compound of formula (I);

and optionally converting the compound of formula (I) to a salt, solvate or solvate of a salt thereof.

In another aspect, an embodiment of the present disclosure provides a pharmaceutical composition comprising an effective amount of one or more compounds of formula (I), a salt, solvate or solvate of a salt thereof, together with one or more pharmaceutically acceptable excipient(s).

Pharmaceutical compositions of the present invention may be administered in an effective amount within a wide dosage range and can cover any effective amount, preferably the dosage range is of about 0.1 μg/kg to about 300 mg/kg, more preferably between 1.0 μg/kg to 10 mg/kg of body weight per day. Compounds of the present invention may be administered in a single daily dose, or the total daily dosage may be administered in divided doses of two, three or four times daily.

The term "effective amount" refers to an amount of a composition or a pharmaceutical composition that confers a therapeutic effect on the treated subject. The therapeutic effect may be objective (i.e. measurable by some test or marker) or subjective (i.e. subject gives an indication of or feels an effect). Such treatment need not necessarily completely ameliorate the disorder, condition, or disease. Further, such treatment or prevention can be used in conjunction with other traditional treatments for reducing the disorder, condition, or disease known to those skilled in the art. The effective amount will typically be determined by a physician, and depend on the disorder, condition, or disease to be treated, the chosen route of administration, the actual compound administered, the age, gender, weight, and response of the individual patient, the severity of the patient's symptoms, and like. For example, less than the minimum amount described above may be sufficient in some cases, while the upper limit mentioned must be exceeded in other cases.

Skilled artisans possess the knowledge and skill in the art to enable them to select suitable pharmaceutically acceptable excipients in appropriate amounts for use in the invention. In addition, there are a number of resources that are available to the skilled artisan which describe pharmaceutically acceptable excipients and may be useful in selecting suitable pharmaceutically acceptable excipients. Suitable pharmaceutically acceptable excipients include, but are not limited to, the following types of excipients: diluents (for example starches, mannitol), fillers (for example lactose, microcrystalline cellulose or calcium hydrogen phosphate), binders (for example pre-gelatised corn starch, polyvinylpyrrolidone or methylcellulose), additives (for example magnesium stearate, talc, silica), disintegrants (for example potato starch), lubricants (for example sodium lauryl sulphate), glidants (for example fumed silica, talc, magnesium carbonate), granulating agents (for example water, ethanol), coating agents (for example hydroxypropyl methylcellulose, gelatin, waxes, shellac, plastics, plant fibers), wetting agents (for example sorbitan monopalmitate, poloxamer 407), solvents (for example water), co-solvents (for example ethanol, propylene glycol), suspending agents (for example sorbitol, cellulose derivatives, edible hydrogenated fats), emulsifiers (for example lecithin or acacia), sweeteners (for example sucrose), flavoring agents (for example cherry, lime), flavor masking agents (for example vanilla, citrus), coloring agents (for example titanium oxide), anti-caking agents (for example silicon dioxide), humectants (for example glycerine, sorbitol), chelating agents (for example EDTA salts, histidine, aspartic acid), plasticizers (for example tributyl citrate, diethyl phthalate), viscosity increasing agents (for example methylcellulose), antioxidants (for example (ascorbic acid, cysteine), preservatives (for example methyl or propyl p-hydroxybenzoates, sorbic acid or ascorbic acid), stabilizers (for example polysorbate 20 & 80, poloxamer 407), surfactants (for example polyethylene glycol, polysorbate 80), and buffering agents (for example sodium and potassium phosphates, citrate, acetate, carbonate or glycine buffers de-pending on the targeted pH-range). Excipients and/or auxiliaries may facilitate processing of the active agent(s) into preparations that can be used pharmaceutically. The skilled artisan will appreciate that certain pharmaceutically acceptable excipients may serve more than one function and may serve alternative functions depending on how much of the excipient is present in the pharmaceutical composition and what other ingredients are present in the pharmaceutical composition.

Pharmaceutical compositions of the invention are most preferably used alone or in combination i.e. administered simultaneously, separately or sequentially with one or more further active ingredients, e.g. pharmaceutically active compounds or biologic products. The amounts of the pharmaceutical composition(s) of the invention, particularly a pharmaceutical composition comprising a compound of formula (I), or a salt, solvate or solvate of a salt thereof, and the further active ingredient(s) and the relative timings of administration will be selected in order to achieve the desired combined therapeutic effect. Pharmaceutical compositions of the invention may be administered by various routes, for example, oral, parenteral, subcutaneous, intravenous, intraarticular, intrathecal, intramuscular, intraperitoneal, topical, lingual, sublingual, and by intradermal injections, and via dermal, transdermal, rectal, buccal, oromucosal, nasal, ocular routes and via inhalation and via implant or stent.

Pharmaceutical compositions may be formulated into suitable pharmaceutical formulations; suitable administration forms include, for example, solutions, dispersions, suspensions, powders, capsules, tablets, pills, controlled release capsules, controlled release tablets, controlled release pills, suppositories, vaginal capsules, creams, vaginal rings and stents. In addition, or alternatively, to pharmaceutically acceptable excipient(s) and/or further active ingredients(s), the pharmaceutical formulations of the pharmaceutical compositions may contain one or more suitable pharmaceutically acceptable carrier(s).

The term "pharmaceutically acceptable carrier(s)" as used herein and hereafter refers to substrates comprised in pharmaceutical compositions for drug delivery, which serves to improve the selectivity, effectiveness, and/or safety of drug administration. Examples of pharmaceutically acceptable carriers include, but are not limited to, pharmaceutically acceptable excipients, liposomes, (polymeric) micelles, microspheres, nanoparticles, and protein-drug conjugates.

The pharmaceutical compositions of the invention are prepared using techniques and methods known to those skilled in the art. Pharmaceutical compositions of the invention include, but are not limited to, for parenteral and topical administration that include, but are not limited to, sterile aqueous or non-aqueous solvents, suspensions and emulsions. Examples of non-aqueous solvents are propylene glycol, polyethylene glycol, vegetable oil, fish oil, and injectable organic esters. Aqueous carriers include, but are not limited to, water, water-alcohol solutions, including saline and buffered medial parenteral vehicles including sodium chloride solution, Ringer's dextrose solution, dextrose plus sodium chloride solution, Ringer's solution containing lactose, or fixed oils. Intravenous vehicles include, but are not limited to, fluid and nutrient replenishers, electrolyte replenishers, such as those based on Ringer's dextrose and the like. Aqueous pharmaceutical compositions according to the invention may comprise suitable buffer agents, such as sodium and potassium phosphates, citrate, acetate, carbonate or glycine buffers depending on the targeted pH-range. The use of sodium chloride as a tonicity adjuster is also useful. Pharmaceutical compositions may include other excipients, such as stabilizing agents or preservatives. Useful stabilizing excipients include surfactants (polysorbate 20 & 80, poloxamer 407), polymers (polyethylene glycols, povidones), carbohydrates (sucrose, mannitol, glucose, lactose), alcohols (sorbitol, glycerol propylene glycol, ethylene glycol), suitable proteins (albumin), suitable amino acids (glycine, glutamic acid), fatty acids (ethanolamine), antioxidants (ascorbic acid, cysteine etc.), chelating agents (EDTA salts, histidine, aspartic acid) or metal ions (Ca, Ni, Mg, Mn). Among useful preservative agents are benzyl alcohol, chlorbutanol, benzalkonium chloride and possibly parabens. The pharmaceutical composition according to the present invention may be provided in concentrated form or in form of a powder to be reconstituted on demand. In such cases formulations of powder for solution for injection/infusion excipients mentioned above may be used. In case of lyophilizing, certain cryoprotectants are preferred, including polymers (povidones, polyethylene glycol, dextran), sugars (sucrose, glucose, lactose), amino acids (glycine, arginine, glutamic acid) and albumin. If solution for reconstitution is added to the packaging, it may consist e.g. of pure water for injection or sodium chloride solution or dextrose or glucose solutions.

Additionally, or alternatively, to pharmaceutically acceptable excipient(s) and/or pharmaceutically acceptable carrier(s), pharmaceutical compositions of the present disclosure comprise an effective amount of one or more compounds of formula (I), or a salt, solvate or solvate of a salt thereof, in combination with one or more further active ingredient(s). Therefore, in embodiments, pharmaceutical compositions comprise an effective amount of one or more compounds of formula (I), a salt, solvate or solvate of a salt thereof, together with one or more pharmaceutically acceptable excipient(s) and/or one or more pharmaceutically acceptable carrier(s) and/or one or more other active ingredient(s), or any combination thereof.

In embodiments of the present invention is provided a pharmaceutical composition comprising one or more compounds of formula (I), a salt, solvate or solvate of a salt thereof, together with one or more pharmaceutically acceptable excipient(s) in combination with one or more further active ingredients, wherein the one or more further active ingredients are each independently selected from an antihyperproliferative, cytostatic and cytotoxic substance.

In one aspect of the present invention is provided a compound of formula (I), or a salt, solvate or solvate of a salt thereof, for use in the treatment or prevention of a disease or disorder selected from the group consisting of polycystic ovary syndrome, endometriosis, uterine leiomyoma, uterine bleeding disorders, dysmenorrhoea, hyperandrogenism, chronic obstructive pulmonary disease (COPD), lung cancer, non-small-cell lung cancer, prostate cancer including castration-resistant prostate cancer, prostate hyperplasia, breast cancer, invasive breast ductal carcinoma, triple negative breast cancer, endometrial carcinoma, renal cell carcinoma, bladder carcinoma, pancreatic adenocarcinoma, acute myeloid leukemia, T-Cell acute lymphoblastic leukemia, melanoma, non-Hodgkins lymphoma, acne, seborrhoea, hair loss, premature sexual maturity, obesity, and inflammation-related pain. Preferably, the treatment or prevention of a disease or disorder require the inhibition of AKR1C3 enzyme.

The term "treatment" or "treating" as used herein and hereafter includes alleviating, ameliorating, attenuating, elimination, inhibition, retardation, checking, attenuating, restricting, reducing, suppressing, repelling, curing or healing of a disease, a condition, a disorder, an injury or a health problem, or the development, the course or the progression of such states and/or the symptoms of such states. The term "therapy" is understood here to be synonymous with the term "treatment".

The terms "prevention", "prophylaxis" or "preclusion" are used synonymously in the context of the present invention and refer to the avoidance or reduction of the risk of contracting, experiencing, suffering from or having a disease, a condition, a disorder, an injury or a health problem, or a development or advancement of such states and/or the symptoms of such states.

The treatment or prevention of a disease, a condition, a disorder, an injury or a health problem may be partial or complete.

The terms "administering" or "administered" to a subject or patient includes dispensing, delivering or applying the composition or pharmaceutical composition to the subject by any suitable route for delivery of the composition or pharmaceutical composition to a site in the body where desired.

In embodiments of the present invention is provided a compound of formula (I), or a salt, solvate or solvate of a salt thereof, for use in treatment or prevention of disease or disorder requiring the inhibition of AKR1C3 enzyme.

In embodiments of the present invention is provided a compound of formula (I), or a salt, solvate or solvate of a salt thereof, for use in treatment or prevention of a steroid hormone or prostaglandin dependent malign or benign disease or disorder. Preferably, the steroid hormone is selected from the group consisting of androgens, estrogen, and progesterones.

In one aspect of the present invention is provided a method for treating or preventing a disease or disorder selected from the group consisting of polycystic ovary syndrome, endometriosis, uterine leiomyoma, uterine bleeding disorders, dysmenorrhoea, hyperandrogenism, chronic obstructive pulmonary disease (COPD), lung cancer, non-small-cell lung cancer, prostate cancer including castration-resistant prostate cancer, prostate hyperplasia, breast cancer, invasive breast ductal carcinoma, triple negative breast cancer, endometrial carcinoma, renal cell carcinoma, bladder carcinoma, pancreatic adenocarcinoma, acute myeloid leukemia, T-Cell acute lymphoblastic leukemia, melanoma, non-Hodgkins lymphoma, acne, seborrhoea, hair loss, premature sexual maturity, obesity, and inflammation-related pain.

In embodiments is provided a method for treating or preventing a steroid hormone or prostaglandin dependent malign or benign disease or disorder, comprising administering a compound of formula (I), or a salt, solvate or solvate of a salt thereof, to a patient in need thereof.

In embodiments is provided a method for treating or preventing a steroid hormone or prostaglandin dependent malign or benign disease or disorder, comprising administering a compound of formula (I), or a salt, solvate or solvate of a salt thereof, to a patient in need thereof, wherein the disease or disorder is selected from the group consisting of polycystic ovary syndrome, endometriosis, uterine leiomyoma, uterine bleeding disorders, dysmenorrhoea, hyperandrogenism, chronic obstructive pulmonary disease (COPD), lung cancer, non-small-cell lung cancer, prostate cancer including castration-resistant prostate cancer, prostate hyperplasia, breast cancer, invasive breast ductal carcinoma, triple negative breast cancer, endometrial carcinoma, renal cell carcinoma, bladder carcinoma, pancreatic adenocarcinoma, acute myeloid leukemia, T-Cell acute lymphoblastic leukemia, melanoma, non-Hodgkins lymphoma, acne, seborrhoea, hair loss, premature sexual maturity, obesity, and inflammation-related pain.

In another aspect of the present invention is provided a use of one or more compounds of formula (I) for the manufacture of a medicament for use in treatment or prevention of disease or disorder selected from the group consisting of polycystic ovary syndrome, endometriosis, uterine leiomyoma, uterine bleeding disorders, dysmenorrhoea, hyperandrogenism, chronic obstructive pulmonary disease (COPD), lung cancer, non-small-cell lung cancer, prostate cancer including castration-resistant prostate cancer, prostate hyperplasia, breast cancer, invasive breast ductal carcinoma, triple negative breast cancer, endometrial carcinoma, renal cell carcinoma, bladder carcinoma, pancreatic adenocarcinoma, acute myeloid leukemia, T-Cell acute lymphoblastic leukemia, melanoma, non-Hodgkins lymphoma, acne, seborrhoea, hair loss, premature sexual maturity, obesity, and inflammation-related pain.

In embodiments is provided use of one or more compounds of formula (I) for the manufacture of a medicament for use in treatment or prevention of a steroid hormone or prostaglandin dependent malign or benign disease or disorder.

In embodiments is provided use of one or more compounds of formula (I) for the manufacture of a medicament for use in treatment or prevention of a steroid hormone or prostaglandin dependent malign or benign disease or disorder selected from the group consisting of polycystic ovary syndrome, endometriosis, uterine leiomyoma, uterine bleeding disorders, dysmenorrhoea, hyperandrogenism, chronic obstructive pulmonary disease (COPD), lung cancer, non-small-cell lung cancer, prostate cancer including castration-resistant prostate cancer, prostate hyperplasia, breast cancer, invasive breast ductal carcinoma, triple negative breast cancer, endometrial carcinoma, renal cell carcinoma, bladder carcinoma, pancreatic adenocarcinoma, acute myeloid leukemia, T-Cell acute lymphoblastic leukemia, melanoma, non-Hodgkins lymphoma, acne, seborrhoea, hair loss, premature sexual maturity, obesity, and inflammation-related pain.

Furthermore, compounds of formula (I) may be used as synthesis intermediates for the preparation of other compounds, in particular of other pharmaceutically active compositions, which are obtainable from compounds of formula (I) and, for example by introduction of substituents or modification of functional moieties.

The compounds and pharmaceutical compositions of the invention may also be useful in medical devices and medical kits.

EXAMPLES OF THE INVENTION

Representative examples of compounds of formula (I), (Ia), (Ib), and (Ic) are compounds 1-173 shown in Table 1.

TABLE 1

Compound 1

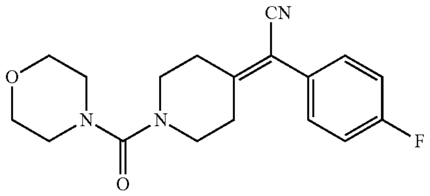 [SMILES: N#CC(=C1CCN(C(=O)N2CCOCC2)CC1)c1ccc(F)cc1]

TABLE 1-continued

Compound 2

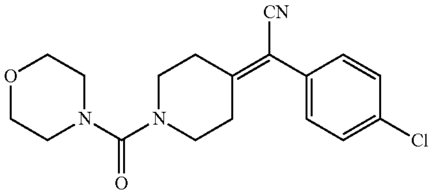 [SMILES: N#CC(=C1CCN(C(=O)N2CCOCC2)CC1)c1ccc(Cl)cc1]

Compound 3

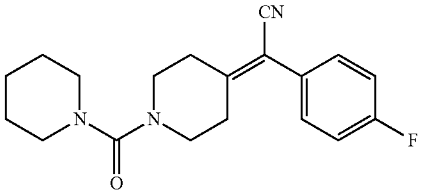 [SMILES: N#CC(=C1CCN(C(=O)N2CCCCC2)CC1)c1ccc(F)cc1]

Compound 4

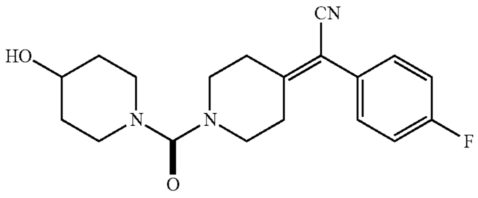 [SMILES: N#CC(=C1CCN([C@@H](O)N2CCC(O)CC2)CC1)c1ccc(F)cc1]

Compound 5

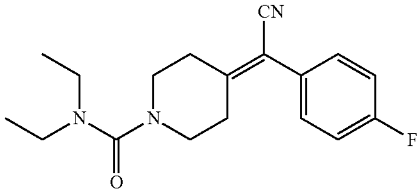 [SMILES: CCN(CC)C(=O)N1CCC(=C(C#N)c2ccc(F)cc2)CC1]

Compound 6

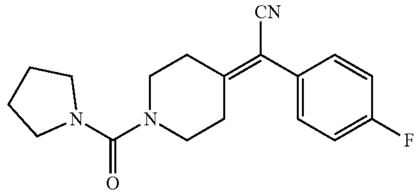 [SMILES: N#CC(=C1CCN(C(=O)N2CCCC2)CC1)c1ccc(F)cc1]

Compound 7

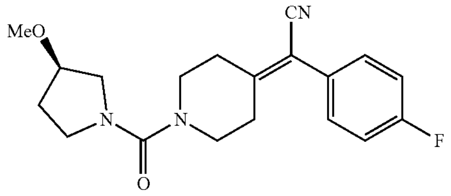 [SMILES: CO[C@@H]1CCN(C(=O)N2CCC(=C(C#N)c3ccc(F)cc3)CC2)C1]

TABLE 1-continued
Compound 8
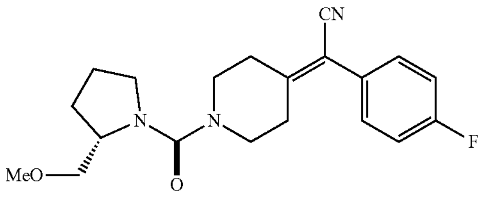 [SMILES: COC[C@@H]1CCCN1[C@H](O)N1CCC(=C(C#N)c2ccc(F)cc2)CC1]
Compound 9
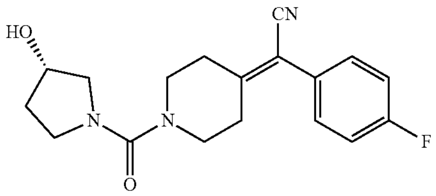 [SMILES: N#CC(=C1CCN(C(=O)N2CC[C@H](O)C2)CC1)c1ccc(F)cc1]
Compound 10
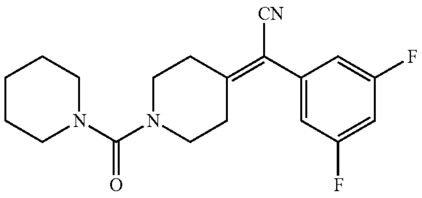 [SMILES: N#CC(=C1CCN(C(=O)N2CCCCC2)CC1)c1cc(F)cc(F)c1]
Compound 11
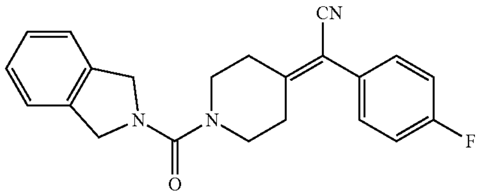 [SMILES: N#CC(=C1CCN(C(=O)N2Cc3ccccc3C2)CC1)c1ccc(F)cc1]
Compound 12
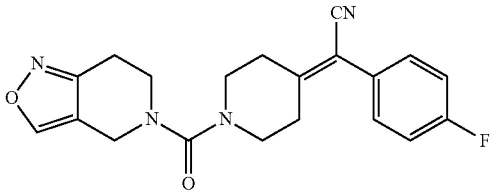 [SMILES: N#CC(=C1CCN(C(=O)N2CCc3nocc3C2)CC1)c1ccc(F)cc1]
Compound 13
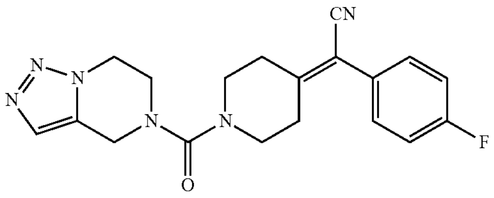 [SMILES: N#CC(=C1CCN(C(=O)N2CCn3nncc3C2)CC1)c1ccc(F)cc1]
TABLE 1-continued
Compound 14
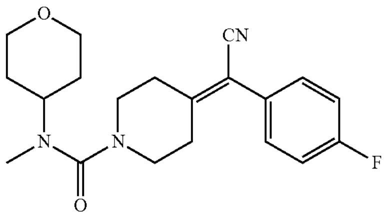 [SMILES: CN(C(=O)N1CCC(=C(C#N)c2ccc(F)cc2)CC1)C1CCOCC1]
Compound 15
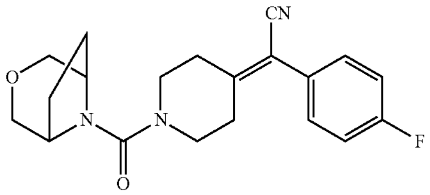 [SMILES: N#CC(=C1CCN(C(=O)N2C3CCC2COC3)CC1)c1ccc(F)cc1]
Compound 16
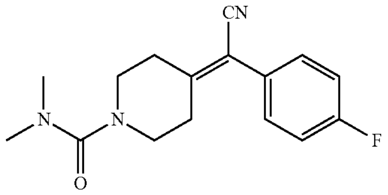 [SMILES: CN(C)C(=O)N1CCC(=C(C#N)c2ccc(F)cc2)CC1]
Compound 17
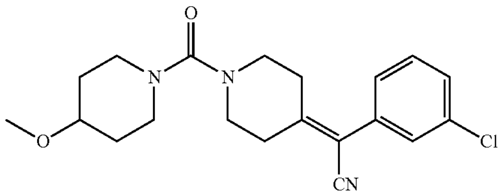 [SMILES: COC1CCN(C(=O)N2CCC(=C(C#N)c3cccc(Cl)c3)CC2)CC1]
Compound 18
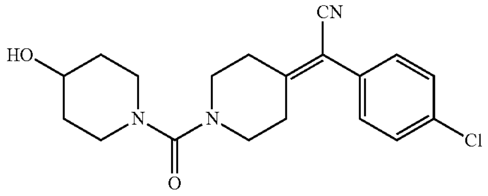 [SMILES: N#CC(=C1CCN(C(=O)N2CCC(O)CC2)CC1)c1ccc(Cl)cc1]
Compound 19
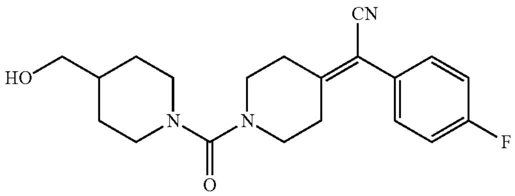 [SMILES: N#CC(=C1CCN(C(=O)N2CCC(CO)CC2)CC1)c1ccc(F)cc1]

TABLE 1-continued
Compound 20
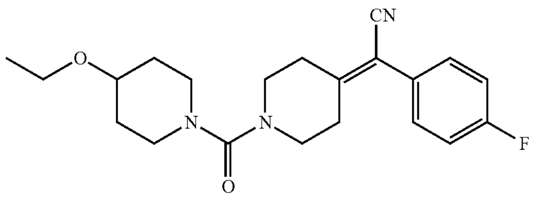 [SMILES: CCOC1CCN(C(=O)N2CCC(=C(C#N)c3ccc(F)cc3)CC2)CC1]
Compound 21
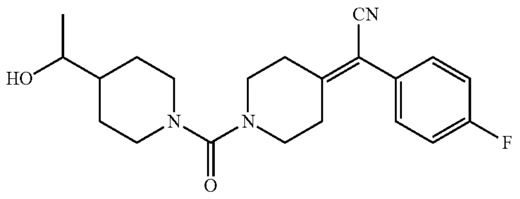 [SMILES: CC(O)C1CCN(C(=O)N2CCC(=C(C#N)c3ccc(F)cc3)CC2)CC1]
Compound 22
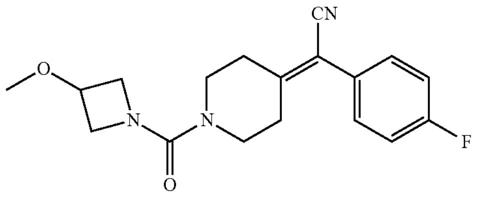 [SMILES: COC1CN(C(=O)N2CCC(=C(C#N)c3ccc(F)cc3)CC2)C1]
Compound 23
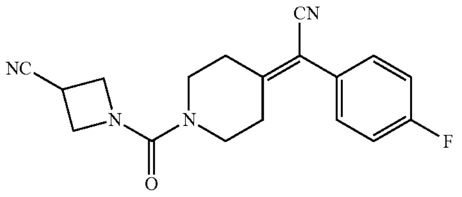 [SMILES: N#CC(=C1CCN(C(=O)N2CC(C#N)C2)CC1)c1ccc(F)cc1]
Compound 24
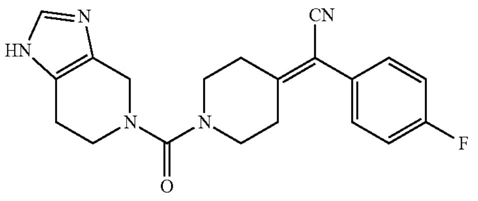 [SMILES: N#CC(=C1CCN(C(=O)N2CCc3[nH]cnc3C2)CC1)c1ccc(F)cc1]
Compound 25
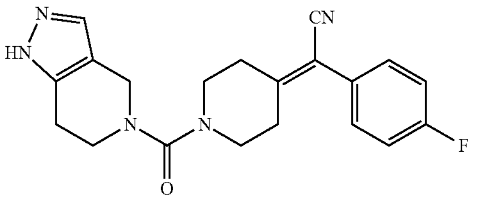 [SMILES: N#CC(=C1CCN(C(=O)N2CCc3[nH]ncc3C2)CC1)c1ccc(F)cc1]
TABLE 1-continued
Compound 26
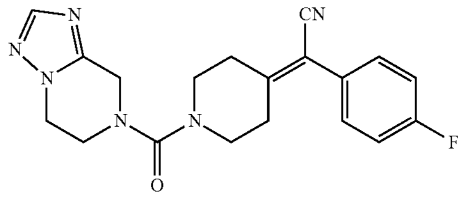 [SMILES: N#CC(=C1CCN(C(=O)N2CCn3ncnc3C2)CC1)c1ccc(F)cc1]
Compound 27
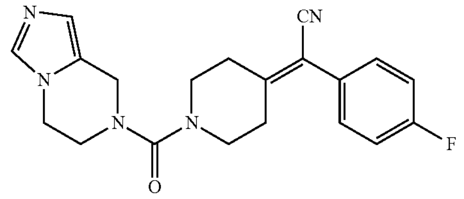 [SMILES: N#CC(=C1CCN(C(=O)N2CCn3cncc3C2)CC1)c1ccc(F)cc1]
Compound 28
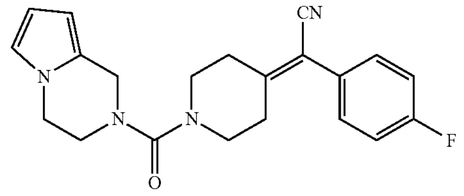 [SMILES: N#CC(=C1CCN(C(=O)N2CCn3cccc3C2)CC1)c1ccc(F)cc1]
Compound 29
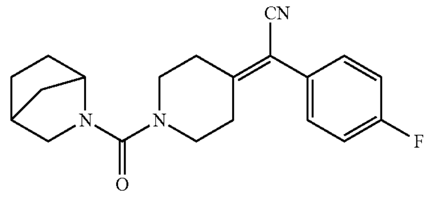 [SMILES: N#CC(=C1CCN(C(=O)N2CC3CCC2C3)CC1)c1ccc(F)cc1]
Compound 30
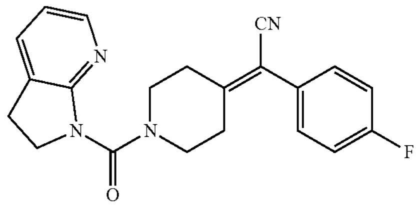 [SMILES: N#CC(=C1CCN(C(=O)N2CCc3cccnc32)CC1)c1ccc(F)cc1]
Compound 31
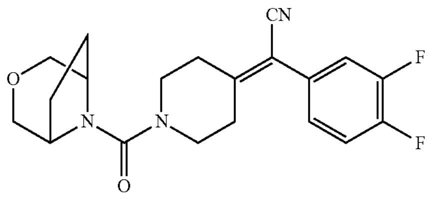 [SMILES: N#CC(=C1CCN(C(=O)N2C3CCC2COC3)CC1)c1ccc(F)c(F)c1]

TABLE 1-continued
Compound 32
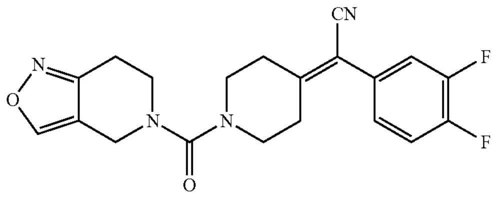 [SMILES: N#CC(=C1CCN(C(=O)N2CCc3nocc3C2)CC1)c1ccc(F)c(F)c1]
Compound 33
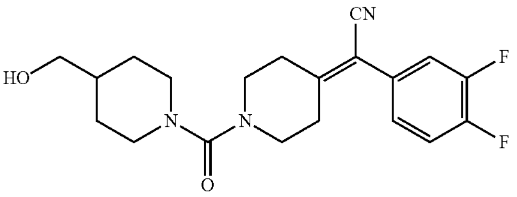 [SMILES: N#CC(=C1CCN(C(=O)N2CCC(CO)CC2)CC1)c1ccc(F)c(F)c1]
Compound 34
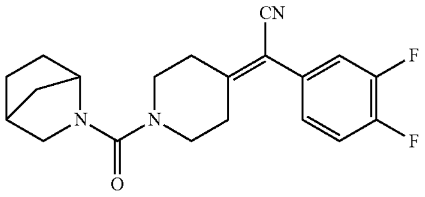 [SMILES: N#CC(=C1CCN(C(=O)N2CC3CCC2C3)CC1)c1ccc(F)c(F)c1]
Compound 35
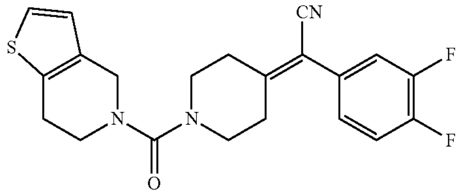 [SMILES: N#CC(=C1CCN(C(=O)N2CCc3sccc3C2)CC1)c1ccc(F)c(F)c1]
Compound 36
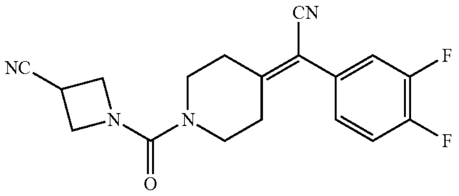 [SMILES: N#CC(=C1CCN(C(=O)N2CC(C#N)C2)CC1)c1ccc(F)c(F)c1]
Compound 37
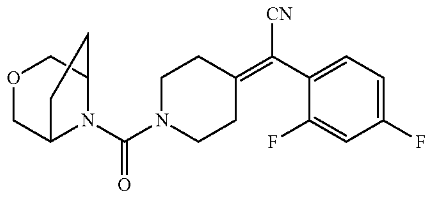 [SMILES: N#CC(=C1CCN(C(=O)N2C3CCC2COC3)CC1)c1ccc(F)cc1F]
TABLE 1-continued
Compound 38
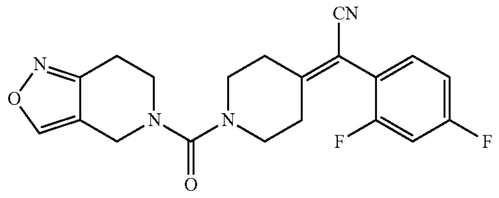 [SMILES: N#CC(=C1CCN(C(=O)N2CCc3nocc3C2)CC1)c1ccc(F)cc1F]
Compound 39
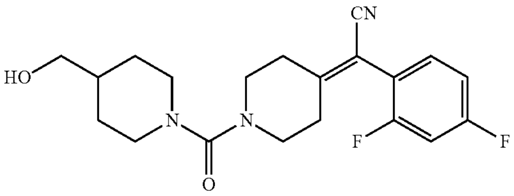 [SMILES: N#CC(=C1CCN(C(=O)N2CCC(CO)CC2)CC1)c1ccc(F)cc1F]
Compound 40
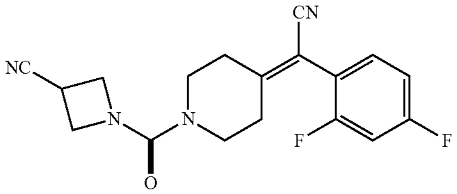
Compound 41
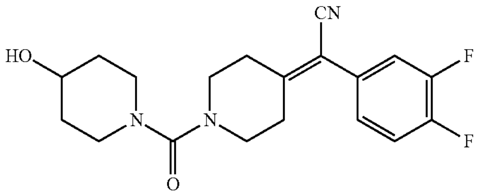 [SMILES: N#CC(=C1CCN(C(=O)N2CCC(O)CC2)CC1)c1ccc(F)c(F)c1]
Compound 42
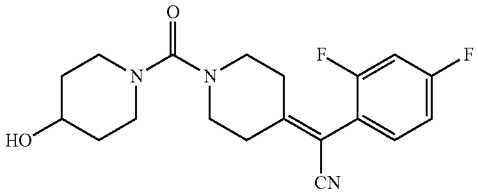 [SMILES: N#CC(=C1CCN(C(=O)N2CCC(O)CC2)CC1)c1ccc(F)cc1F]
Compound 43
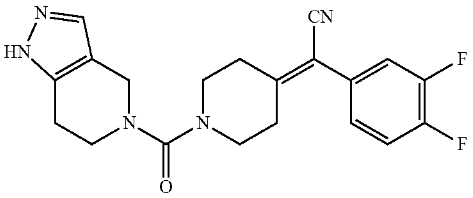 [SMILES: N#CC(=C1CCN(C(=O)N2CCc3[nH]ncc3C2)CC1)c1ccc(F)c(F)c1]

TABLE 1-continued
Compound 44
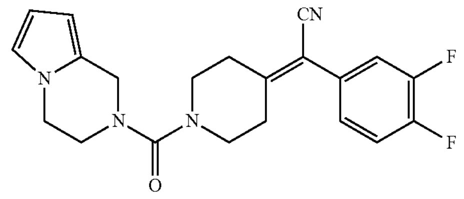 [SMILES: N#CC(=C1CCN(C(=O)N2CCn3cccc3C2)CC1)c1ccc(F)c(F)c1]
Compound 45
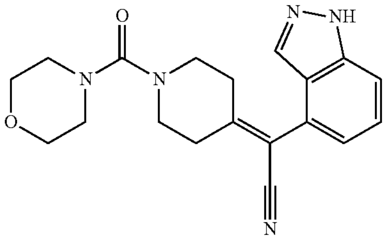 [SMILES: N#CC(=C1CCN(C(=O)N2CCOCC2)CC1)c1cccc2[nH]ncc12]
Compound 46
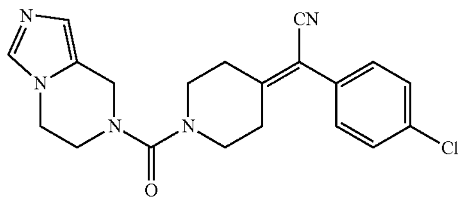 [SMILES: N#CC(=C1CCN(C(=O)N2CCn3cncc3C2)CC1)c1ccc(Cl)cc1]
Compound 47
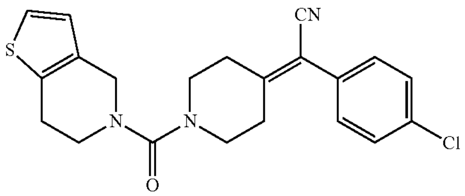 [SMILES: N#CC(=C1CCN(C(=O)N2CCc3sccc3C2)CC1)c1ccc(Cl)cc1]
Compound 48
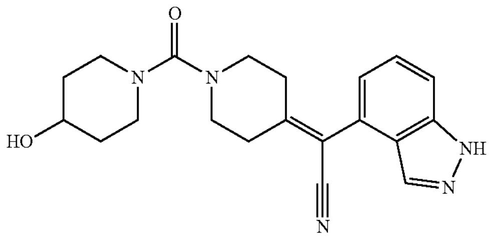 [SMILES: N#CC(=C1CCN(C(=O)N2CCC(O)CC2)CC1)c1cccc2[nH]ncc12]
Compound 49
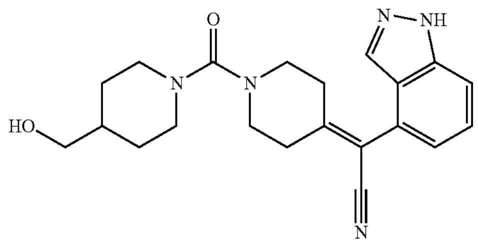 [SMILES: N#CC(=C1CCN(C(=O)N2CCC(CO)CC2)CC1)c1cccc2[nH]ncc12]
TABLE 1-continued
Compound 50
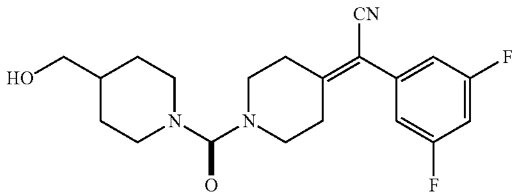
Compound 51
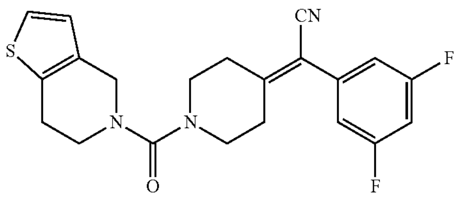 [SMILES: N#CC(=C1CCN(C(=O)N2CCc3sccc3C2)CC1)c1cc(F)cc(F)c1]
Compound 52
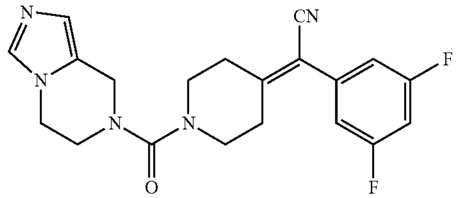 [SMILES: N#CC(=C1CCN(C(=O)N2CCn3cncc3C2)CC1)c1cc(F)cc(F)c1]
Compound 53
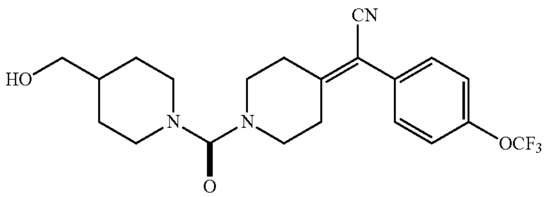 [SMILES: N#CC(=C1CCN([C@@H](O)N2CCC(CO)CC2)CC1)c1ccc(OC(F)(F)F)cc1]
Compound 54
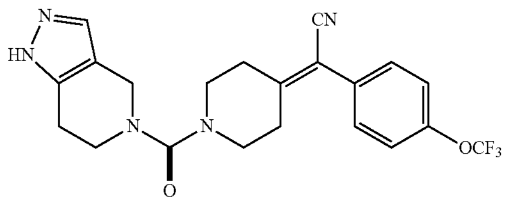 [SMILES: N#CC(=C1CCN([C@@H](O)N2CCc3[nH]ncc3C2)CC1)c1ccc(OC(F)(F)F)cc1]
Compound 55
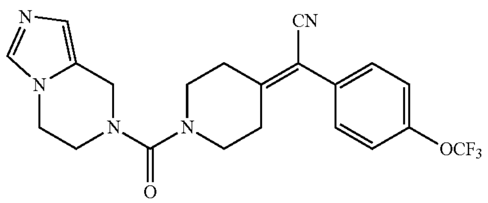 [SMILES: N#CC(=C1CCN(C(=O)N2CCn3cncc3C2)CC1)c1ccc(OC(F)(F)F)cc1]

TABLE 1-continued
Compound 56
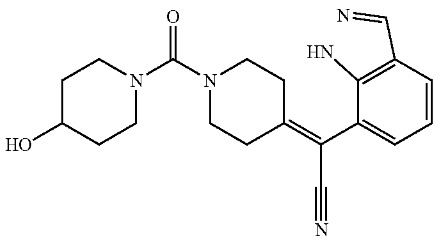 [SMILES: N#CC(=C1CCN(C(=O)N2CCC(O)CC2)CC1)c1cccc(C=N)c1N]
Compound 57
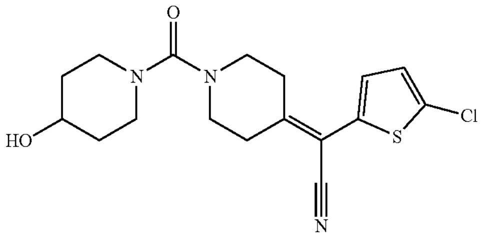 [SMILES: N#CC(=C1CCN(C(=O)N2CCC(O)CC2)CC1)c1ccc(Cl)s1]
Compound 58
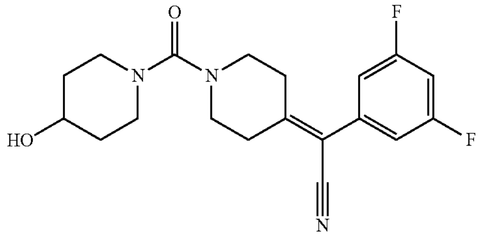 [SMILES: N#CC(=C1CCN(C(=O)N2CCC(O)CC2)CC1)c1cc(F)cc(F)c1]
Compound 59
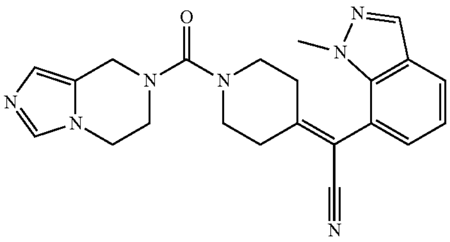 [SMILES: Cn1ncc2cccc(C(C#N)=C3CCN(C(=O)N4CCn5cncc5C4)CC3)c21]
Compound 60
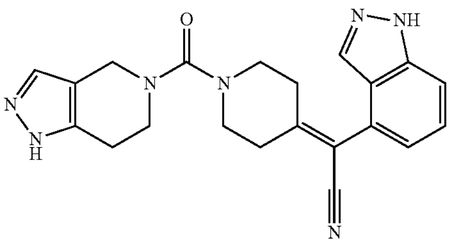 [SMILES: N#CC(=C1CCN(C(=O)N2CCc3[nH]ncc3C2)CC1)c1cccc2[nH]ncc12]
TABLE 1-continued
Compound 61
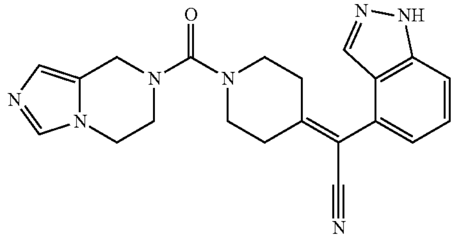 [SMILES: N#CC(=C1CCN(C(=O)N2CCn3cncc3C2)CC1)c1cccc2[nH]ncc12]
Compound 62
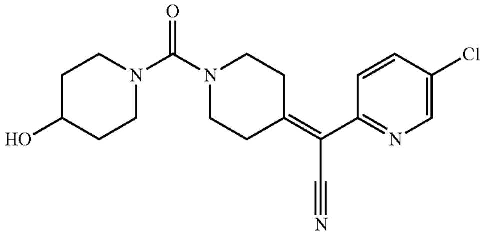 [SMILES: N#CC(=C1CCN(C(=O)N2CCC(O)CC2)CC1)c1ccc(Cl)cn1]
Compound 63
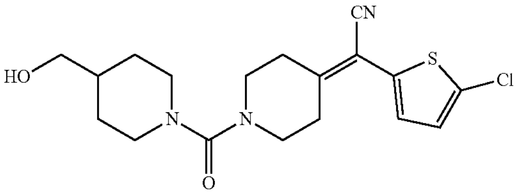 [SMILES: N#CC(=C1CCN(C(=O)N2CCC(CO)CC2)CC1)c1ccc(Cl)s1]
Compound 64
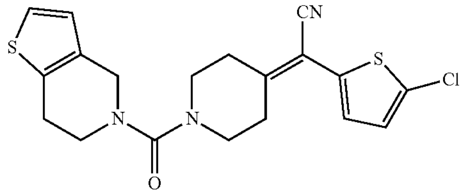 [SMILES: N#CC(=C1CCN(C(=O)N2CCc3sccc3C2)CC1)c1ccc(Cl)s1]
Compound 65
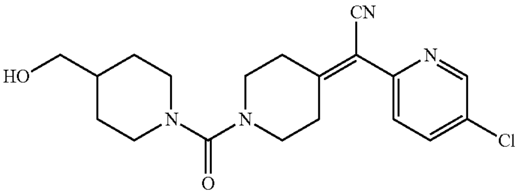 [SMILES: N#CC(=C1CCN(C(=O)N2CCC(CO)CC2)CC1)c1ccc(Cl)cn1]
Compound 66
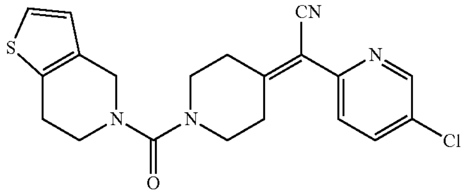 [SMILES: N#CC(=C1CCN(C(=O)N2CCc3sccc3C2)CC1)c1ccc(Cl)cn1]

TABLE 1-continued
Compound 67
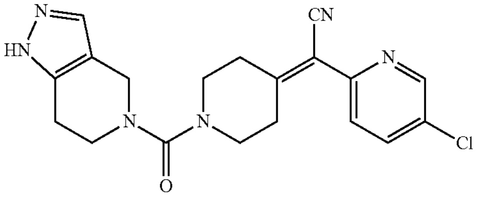 [SMILES: N#CC(=C1CCN(C(=O)N2CCc3[nH]ncc3C2)CC1)c1ccc(Cl)cn1]
Compound 68
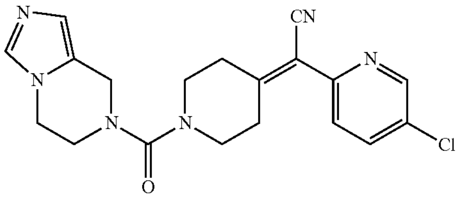 [SMILES: N#CC(=C1CCN(C(=O)N2CCn3cncc3C2)CC1)c1ccc(Cl)cn1]
Compound 69
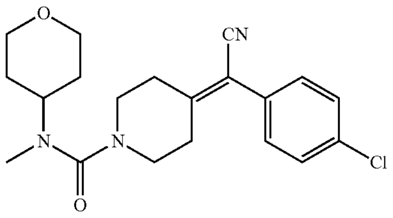 [SMILES: CN(C(=O)N1CCC(=C(C#N)c2ccc(Cl)cc2)CC1)C1CCOCC1]
Compound 70
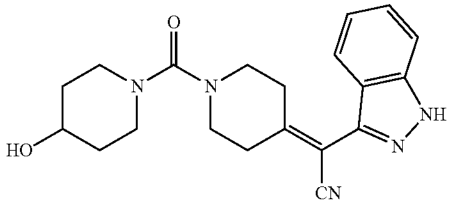 [SMILES: N#CC(=C1CCN(C(=O)N2CCC(O)CC2)CC1)c1n[nH]c2ccccc12]
Compound 71
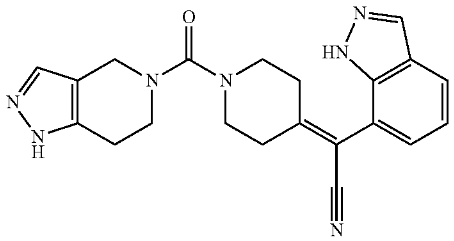 [SMILES: N#CC(=C1CCN(C(=O)N2CCc3[nH]ncc3C2)CC1)c1cccc2cn[nH]c12]
Compound 72
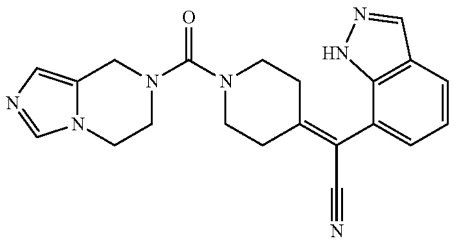 [SMILES: N#CC(=C1CCN(C(=O)N2CCn3cncc3C2)CC1)c1cccc2cn[nH]c12]
TABLE 1-continued
Compound 73
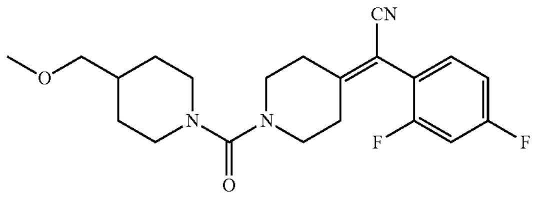 [SMILES: COCC1CCN(C(=O)N2CCC(=C(C#N)c3ccc(F)cc3F)CC2)CC1]
Compound 74
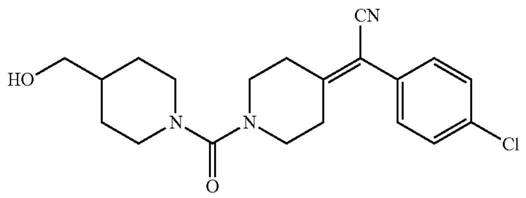 [SMILES: N#CC(=C1CCN(C(=O)N2CCC(CO)CC2)CC1)c1ccc(Cl)cc1]
Compound 75
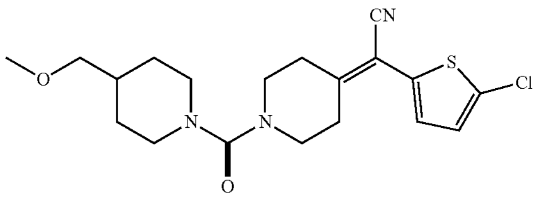
Compound 76
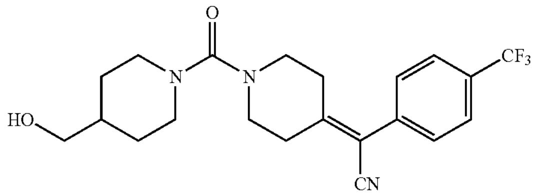 [SMILES: N#CC(=C1CCN(C(=O)N2CCC(CO)CC2)CC1)c1ccc(C(F)(F)F)cc1]
Compound 77
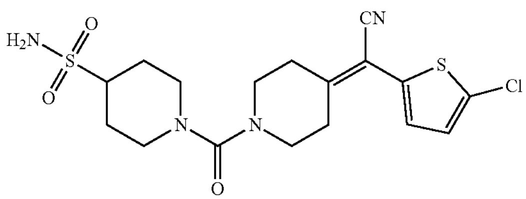 [SMILES: N#CC(=C1CCN(C(=O)N2CCC(S(N)(=O)=O)CC2)CC1)c1ccc(Cl)s1]
Compound 78
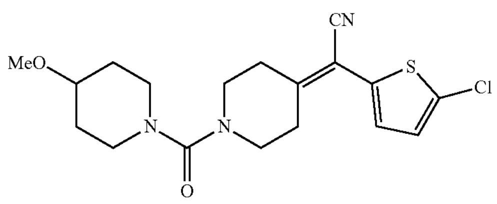 [SMILES: COC1CCN(C(=O)N2CCC(=C(C#N)c3ccc(Cl)s3)CC2)CC1]

TABLE 1-continued
Compound 79
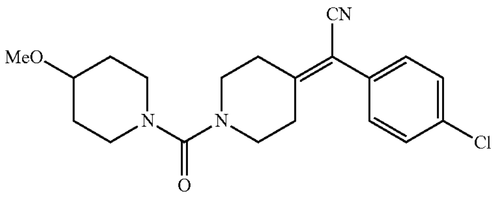 [SMILES: COC1CCN(C(=O)N2CCC(=C(C#N)c3ccc(Cl)cc3)CC2)CC1]
Compound 80
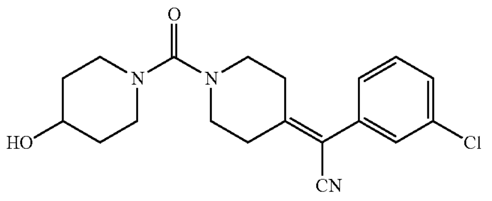 [SMILES: N#CC(=C1CCN(C(=O)N2CCC(O)CC2)CC1)c1cccc(Cl)c1]
Compound 81
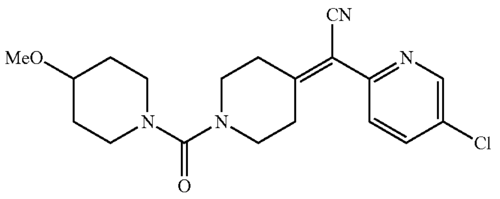 [SMILES: COC1CCN(C(=O)N2CCC(=C(C#N)c3ccc(Cl)cn3)CC2)CC1]
Compound 82
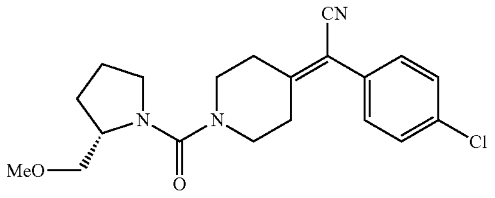 [SMILES: COC[C@@H]1CCCN1C(=O)N1CCC(=C(C#N)c2ccc(Cl)cc2)CC1]
Compound 83
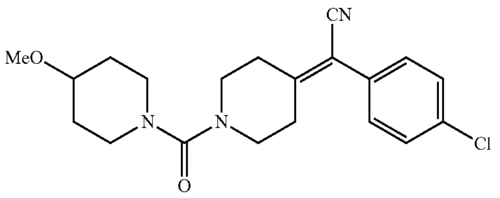 [SMILES: COC1CCN(C(=O)N2CCC(=C(C#N)c3ccc(Cl)cc3)CC2)CC1]
Compound 84
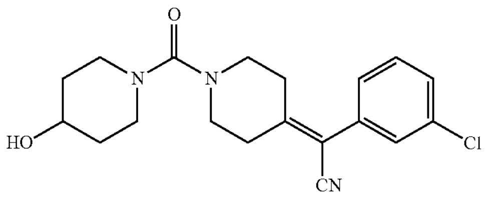 [SMILES: N#CC(=C1CCN(C(=O)N2CCC(O)CC2)CC1)c1cccc(Cl)c1]
TABLE 1-continued
Compound 85
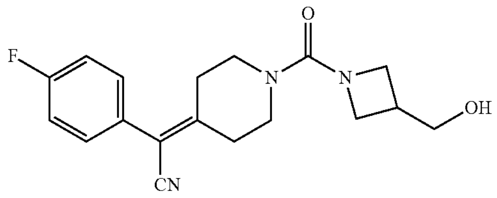 [SMILES: N#CC(=C1CCN(C(=O)N2CC(CO)C2)CC1)c1ccc(F)cc1]
Compound 86
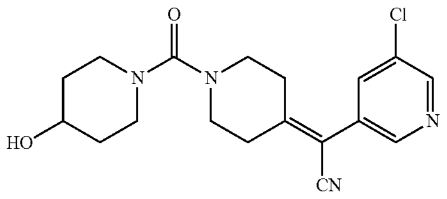 [SMILES: N#CC(=C1CCN(C(=O)N2CCC(O)CC2)CC1)c1cncc(Cl)c1]
Compound 87
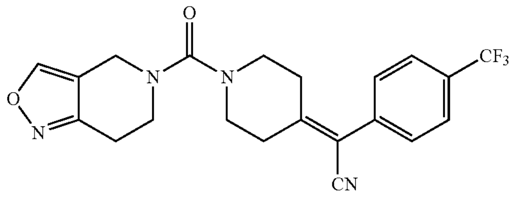 [SMILES: N#CC(=C1CCN(C(=O)N2CCc3nocc3C2)CC1)c1ccc(C(F)(F)F)cc1]
Compound 88
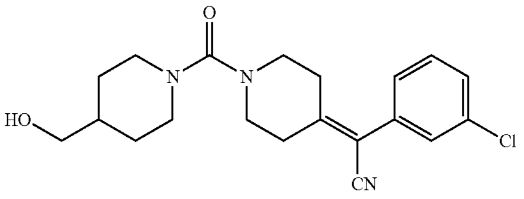 [SMILES: N#CC(=C1CCN(C(=O)N2CCC(CO)CC2)CC1)c1cccc(Cl)c1]
Compound 89
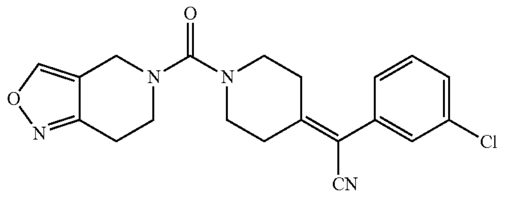 [SMILES: N#CC(=C1CCN(C(=O)N2CCc3nocc3C2)CC1)c1cccc(Cl)c1]
Compound 90
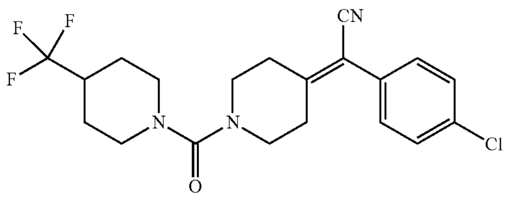 [SMILES: N#CC(=C1CCN(C(=O)N2CCC(C(F)(F)F)CC2)CC1)c1ccc(Cl)cc1]

TABLE 1-continued
Compound 91
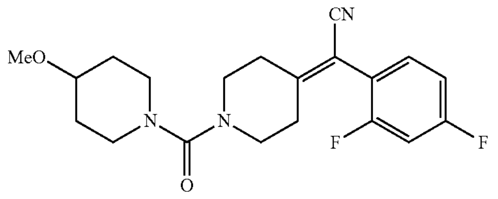 [SMILES: COC1CCN(C(=O)N2CCC(=C(C#N)c3ccc(F)cc3F)CC2)CC1]
Compound 92
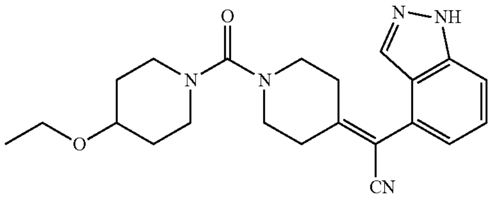 [SMILES: CCOC1CCN(C(=O)N2CCC(=C(C#N)c3cccc4[nH]ncc34)CC2)CC1]
Compound 93
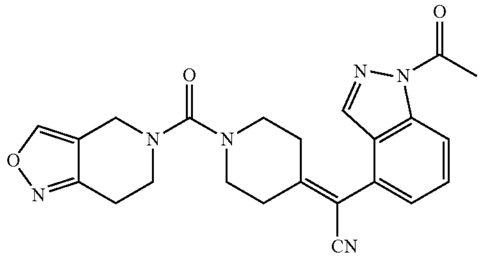 [SMILES: CC(=O)n1ncc2c(C(C#N)=C3CCN(C(=O)N4CCc5nocc5C4)CC3)cccc21]
Compound 94
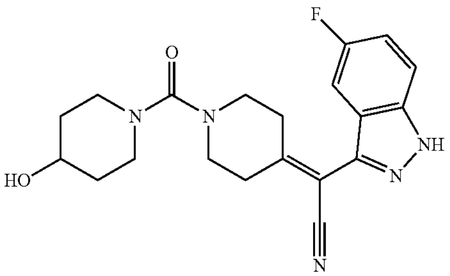 [SMILES: N#CC(=C1CCN(C(=O)N2CCC(O)CC2)CC1)c1n[nH]c2ccc(F)cc12]
Compound 95
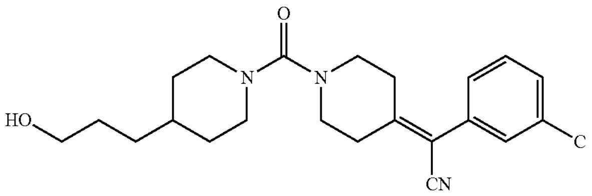 [SMILES: Cc1cccc(C(C#N)=C2CCN(C(=O)N3CCC(CCCO)CC3)CC2)c1]
Compound 96
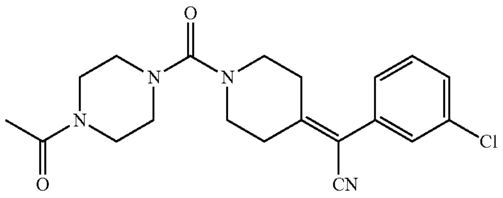 [SMILES: CC(=O)N1CCN(C(=O)N2CCC(=C(C#N)c3cccc(Cl)c3)CC2)CC1]
TABLE 1-continued
Compound 97
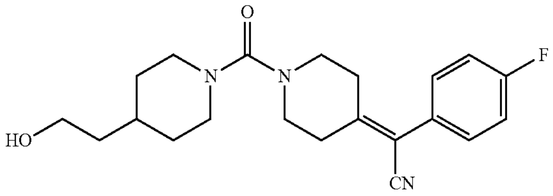 [SMILES: N#CC(=C1CCN(C(=O)N2CCC(CCO)CC2)CC1)c1ccc(F)cc1]
Compound 98
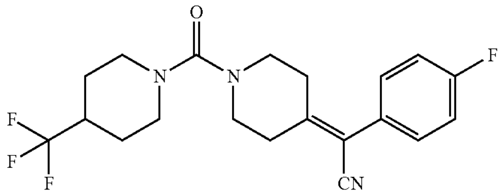 [SMILES: N#CC(=C1CCN(C(=O)N2CCC(C(F)(F)F)CC2)CC1)c1ccc(F)cc1]
Compound 99
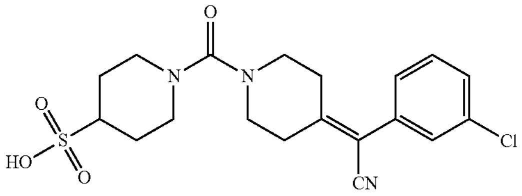 [SMILES: N#CC(=C1CCN(C(=O)N2CCC(S(=O)(=O)O)CC2)CC1)c1cccc(Cl)c1]
Compound 100
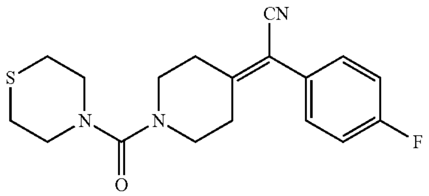 [SMILES: N#CC(=C1CCN(C(=O)N2CCSCC2)CC1)c1ccc(F)cc1]
Compound 101
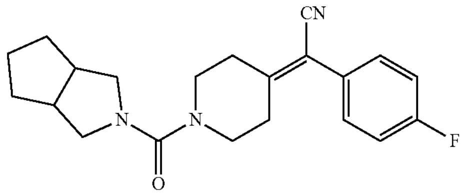 [SMILES: N#CC(=C1CCN(C(=O)N2CC3CCCC3C2)CC1)c1ccc(F)cc1]
Compound 102
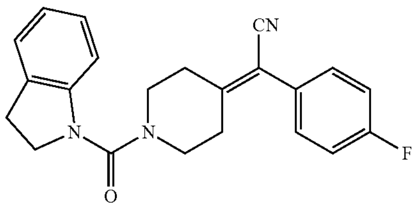 [SMILES: N#CC(=C1CCN(C(=O)N2CCc3ccccc32)CC1)c1ccc(F)cc1]

TABLE 1-continued
Compound 103
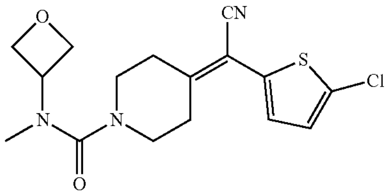 [SMILES: CN(C(=O)N1CCC(=C(C#N)c2ccc(Cl)s2)CC1)C1COC1]
Compound 104
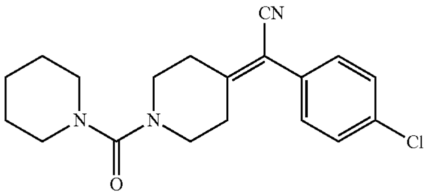 [SMILES: N#CC(=C1CCN(C(=O)N2CCCCC2)CC1)c1ccc(Cl)cc1]
Compound 105
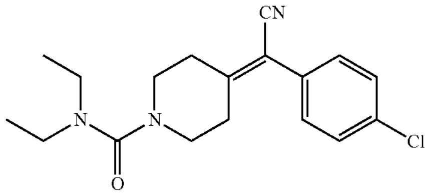 [SMILES: CCN(CC)C(=O)N1CCC(=C(C#N)c2ccc(Cl)cc2)CC1]
Compound 106
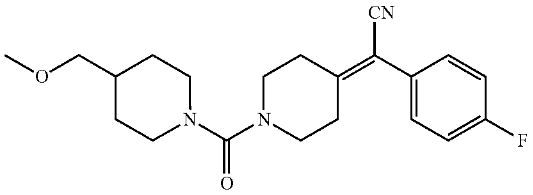 [SMILES: COCC1CCN(C(=O)N2CCC(=C(C#N)c3ccc(F)cc3)CC2)CC1]
Compound 107
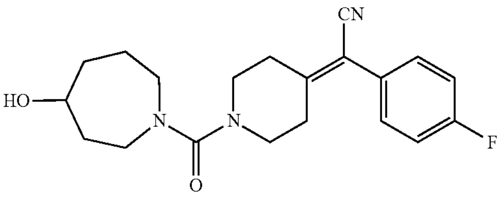 [SMILES: N#CC(=C1CCN(C(=O)N2CCCC(O)CC2)CC1)c1ccc(F)cc1]
Compound 108
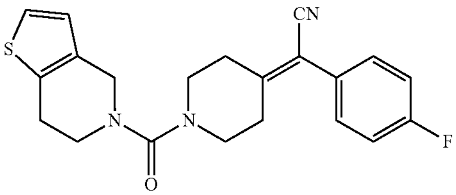 [SMILES: N#CC(=C1CCN(C(=O)N2CCc3sccc3C2)CC1)c1ccc(F)cc1]
TABLE 1-continued
Compound 109
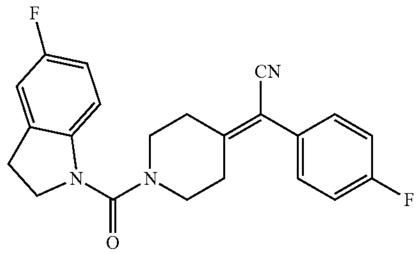 [SMILES: N#CC(=C1CCN(C(=O)N2CCc3cc(F)ccc32)CC1)c1ccc(F)cc1]
Compound 110
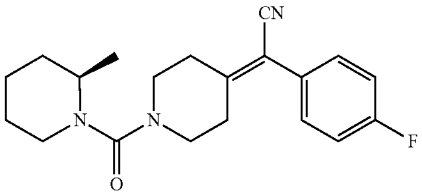 [SMILES: C[C@@H]1CCCCN1C(=O)N1CCC(=C(C#N)c2ccc(F)cc2)CC1]
Compound 111
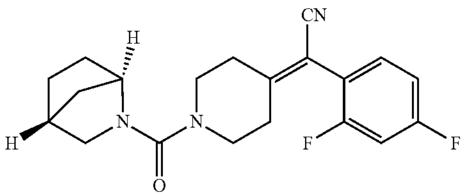 [SMILES: N#CC(=C1CCN(C(=O)N2C[C@@H]3CC[C@@H]2C3)CC1)c1ccc(F)cc1F]
Compound 112
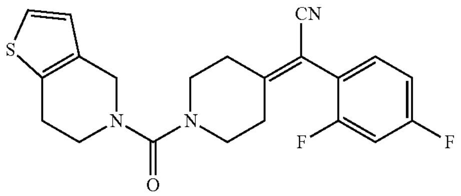 [SMILES: N#CC(=C1CCN(C(=O)N2CCc3sccc3C2)CC1)c1ccc(F)cc1F]
Compound 113
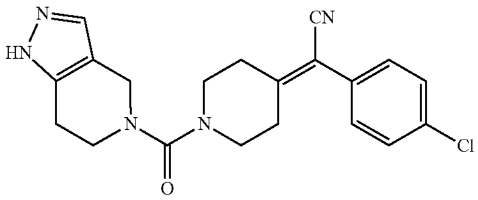 [SMILES: N#CC(=C1CCN(C(=O)N2CCc3[nH]ncc3C2)CC1)c1ccc(Cl)cc1]
Compound 114
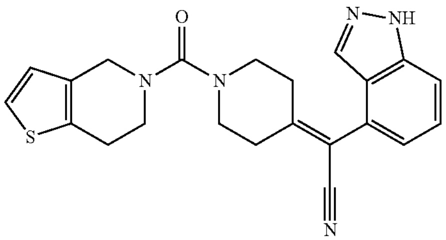 [SMILES: N#CC(=C1CCN(C(=O)N2CCc3sccc3C2)CC1)c1cccc2[nH]ncc12]

TABLE 1-continued
Compound 115
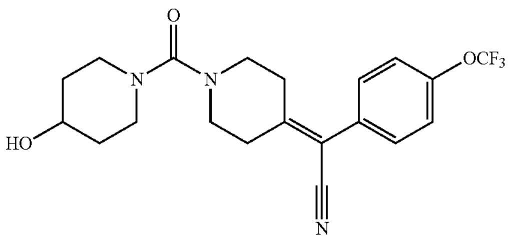 [SMILES: N#CC(=C1CCN(C(=O)N2CCC(O)CC2)CC1)c1ccc(OC(F)(F)F)cc1]
Compound 116
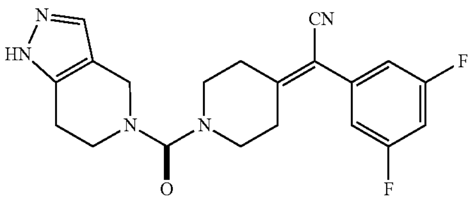
Compound 117
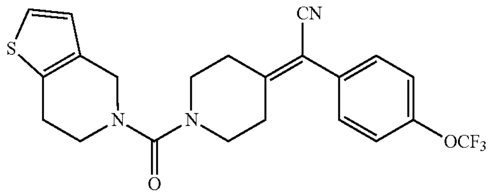 [SMILES: N#CC(=C1CCN(C(=O)N2CCc3sccc3C2)CC1)c1ccc(OC(F)(F)F)cc1]
Compound 118
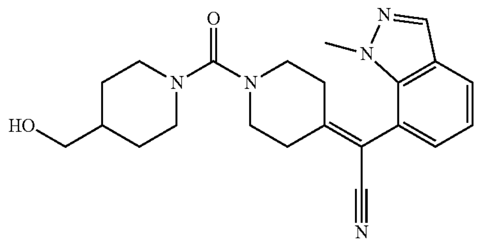 [SMILES: Cn1ncc2cccc(C(C#N)=C3CCN(C(=O)N4CCC(CO)CC4)CC3)c21]
Compound 119
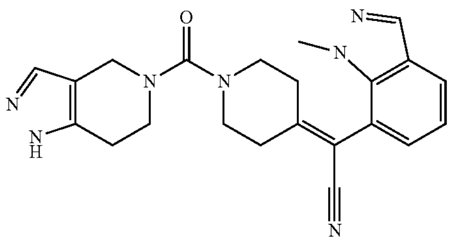 [SMILES: CNc1c(C=N)cccc1C(C#N)=C1CCN(C(=O)N2CCC(N)=C(C=N)C2)CC1]
Compound 120
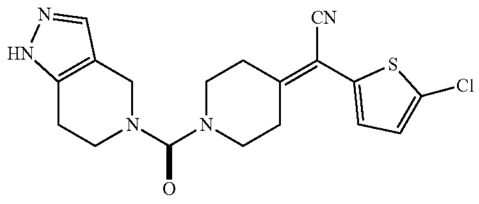 [SMILES: N#CC(=C1CCN([C@@H](O)N2CCc3[nH]ncc3C2)CC1)c1ccc(Cl)s1]
TABLE 1-continued
Compound 121
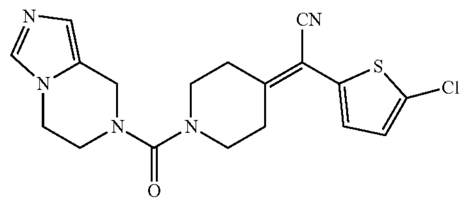 [SMILES: N#CC(=C1CCN(C(=O)N2CCn3cncc3C2)CC1)c1ccc(Cl)s1]
Compound 122
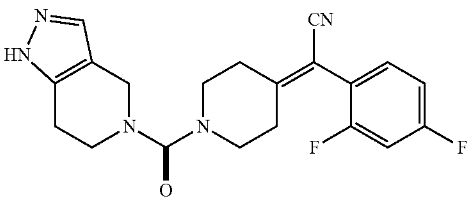 [SMILES: N#CC(=C1CCN([C@@H](O)N2CCc3[nH]ncc3C2)CC1)c1ccc(F)cc1F]
Compound 123
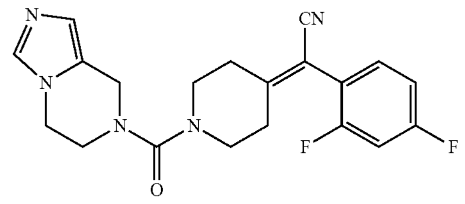 [SMILES: N#CC(=C1CCN(C(=O)N2CCn3cncc3C2)CC1)c1ccc(F)cc1F]
Compound 124
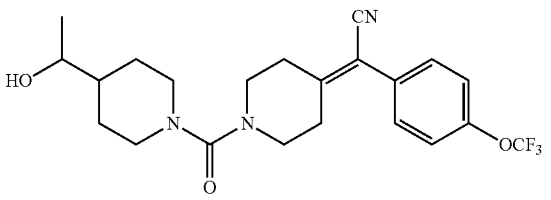 [SMILES: CC(O)C1CCN(C(=O)N2CCC(=C(C#N)c3ccc(OC(F)(F)F)cc3)CC2)CC1]
Compound 125
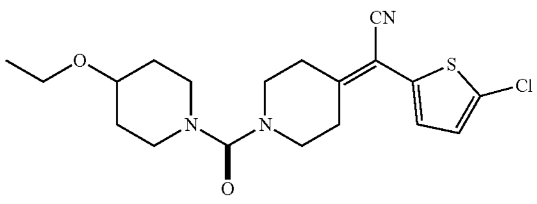
Compound 126
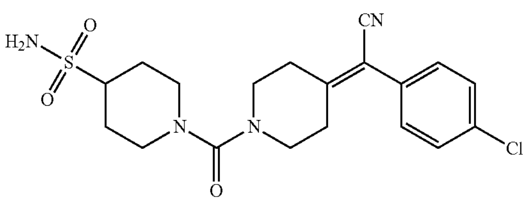 [SMILES: N#CC(=C1CCN(C(=O)N2CCC(S(N)(=O)=O)CC2)CC1)c1ccc(Cl)cc1]

TABLE 1-continued
Compound 127
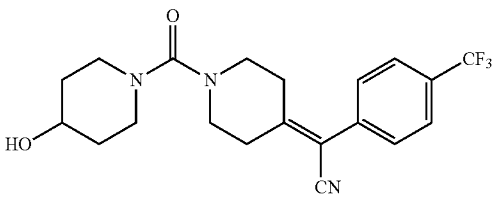 [SMILES: N#CC(=C1CCN(C(=O)N2CCC(O)CC2)CC1)c1ccc(C(F)(F)F)cc1]
Compound 128
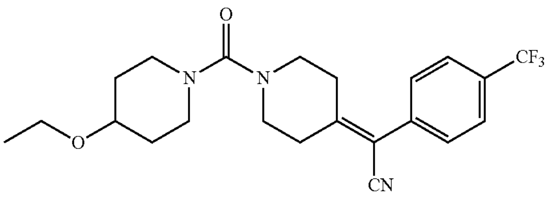 [SMILES: CCOC1CCN(C(=O)N2CCC(=C(C#N)c3ccc(C(F)(F)F)cc3)CC2)CC1]
Compound 129
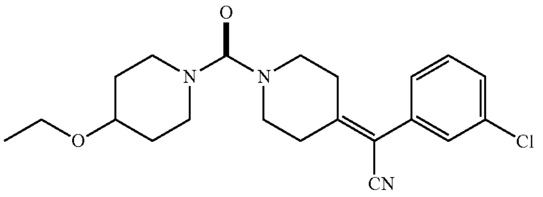 [SMILES: CCOC1CCN([C@@H](O)N2CCC(=C(C#N)c3cccc(Cl)c3)CC2)CC1]
Compound 130
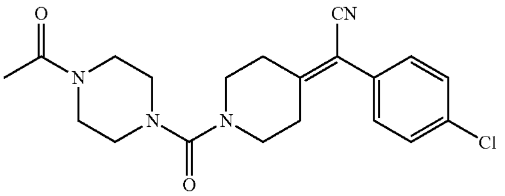 [SMILES: CC(=O)N1CCN(C(=O)N2CCC(=C(C#N)c3ccc(Cl)cc3)CC2)CC1]
Compound 131
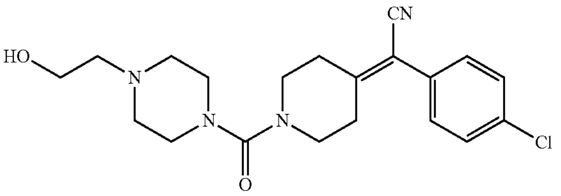 [SMILES: N#CC(=C1CCN(C(=O)N2CCN(CCO)CC2)CC1)c1ccc(Cl)cc1]
Compound 132
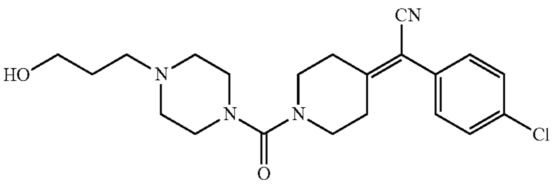
TABLE 1-continued
Compound 133
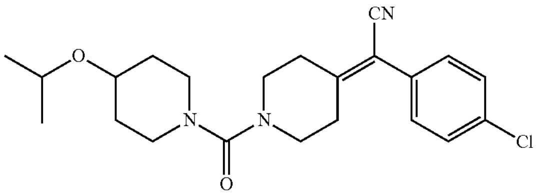 [SMILES: CC(C)OC1CCN(C(=O)N2CCC(=C(C#N)c3ccc(Cl)cc3)CC2)CC1]
Compound 134
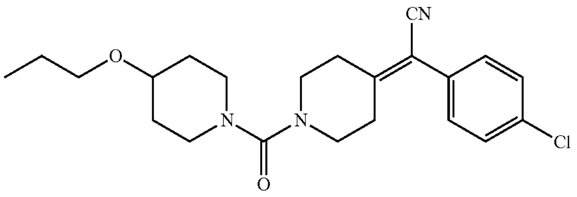 [SMILES: CCCOC1CCN(C(=O)N2CCC(=C(C#N)c3ccc(Cl)cc3)CC2)CC1]
Compound 135
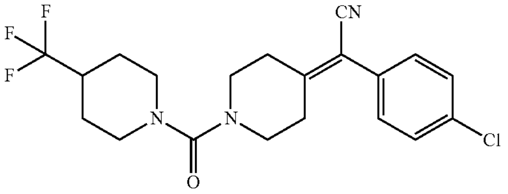 [SMILES: N#CC(=C1CCN(C(=O)N2CCC(C(F)(F)F)CC2)CC1)c1ccc(Cl)cc1]
Compound 136
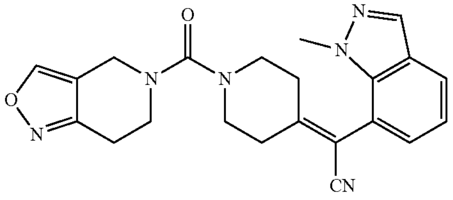 [SMILES: Cn1ncc2cccc(C(C#N)=C3CCN(C(=O)N4CCc5nocc5C4)CC3)c21]
Compound 137
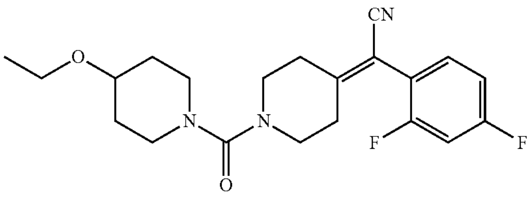 [SMILES: CCOC1CCN(C(=O)N2CCC(=C(C#N)c3ccc(F)cc3F)CC2)CC1]
Compound 138
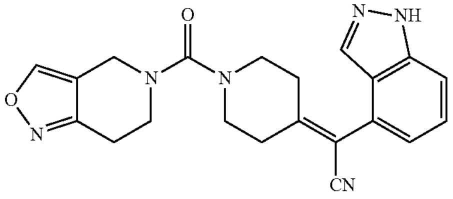 [SMILES: N#CC(=C1CCN(C(=O)N2CCc3nocc3C2)CC1)c1cccc2[nH]ncc12]

TABLE 1-continued
Compound 139
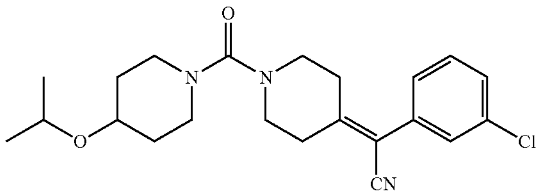 [SMILES: CC(C)OC1CCN(C(=O)N2CCC(=C(C#N)c3cccc(Cl)c3)CC2)CC1]
Compound 140
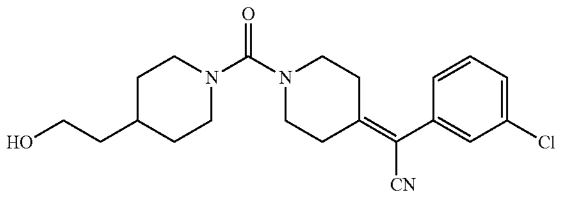 [SMILES: N#CC(=C1CCN(C(=O)N2CCC(CCO)CC2)CC1)c1cccc(Cl)c1]
Compound 141
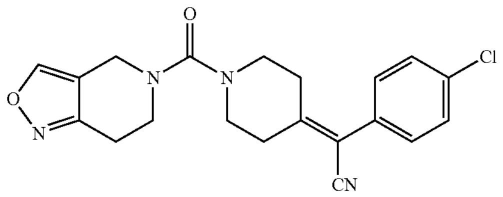 [SMILES: N#CC(=C1CCN(C(=O)N2CCc3nocc3C2)CC1)c1ccc(Cl)cc1]
Compound 142
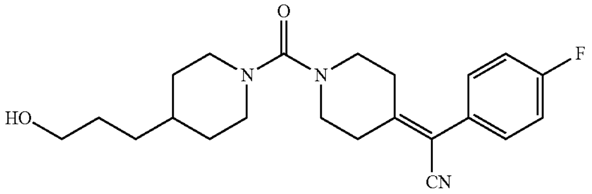 [SMILES: N#CC(=C1CCN(C(=O)N2CCC(CCCO)CC2)CC1)c1ccc(F)cc1]
Compound 143
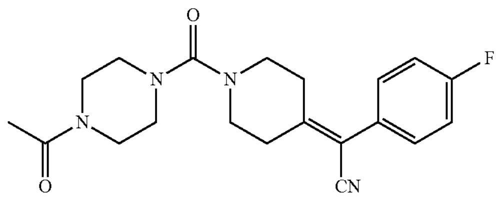 [SMILES: CC(=O)N1CCN(C(=O)N2CCC(=C(C#N)c3ccc(F)cc3)CC2)CC1]
Compound 144
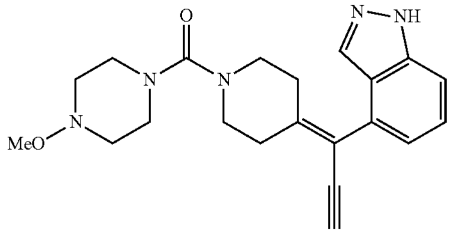 [SMILES: C#CC(=C1CCN(C(=O)N2CCN(OC)CC2)CC1)c1cccc2[nH]ncc12]
TABLE 1-continued
Compound 145
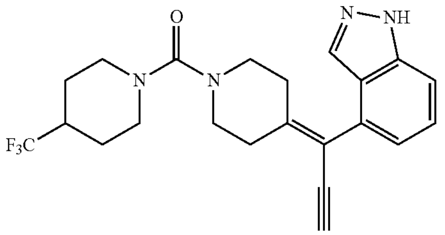 [SMILES: C#CC(=C1CCN(C(=O)N2CCC(C(F)(F)F)CC2)CC1)c1cccc2[nH]ncc12]
Compound 146
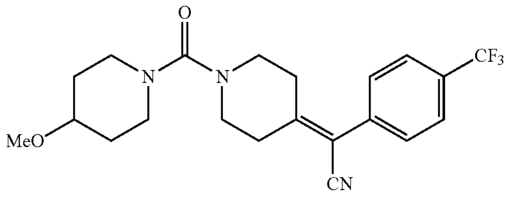 [SMILES: COC1CCN(C(=O)N2CCC(=C(C#N)c3ccc(C(F)(F)F)cc3)CC2)CC1]
Compound 147
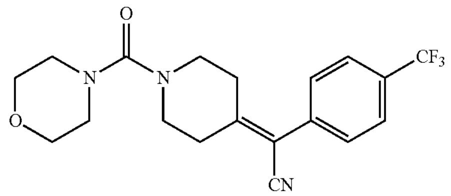 [SMILES: N#CC(=C1CCN(C(=O)N2CCOCC2)CC1)c1ccc(C(F)(F)F)cc1]
Compound 148
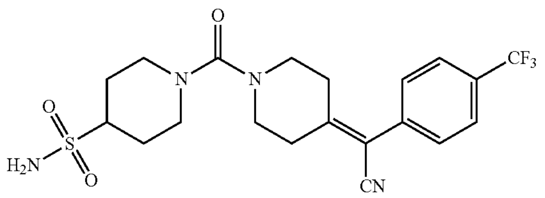 [SMILES: N#CC(=C1CCN(C(=O)N2CCC(S(N)(=O)=O)CC2)CC1)c1ccc(C(F)(F)F)cc1]
Compound 149
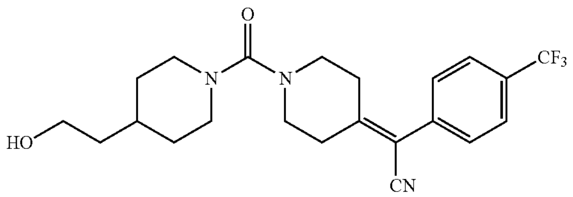 [SMILES: N#CC(=C1CCN(C(=O)N2CCC(CCO)CC2)CC1)c1ccc(C(F)(F)F)cc1]
Compound 150
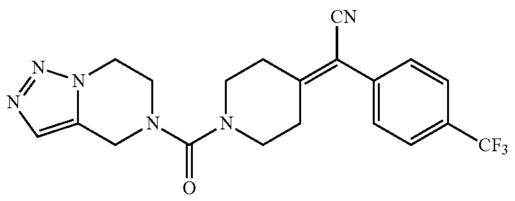 [SMILES: N#CC(=C1CCN(C(=O)N2CCn3nncc3C2)CC1)c1ccc(C(F)(F)F)cc1]

TABLE 1-continued
Compound 151
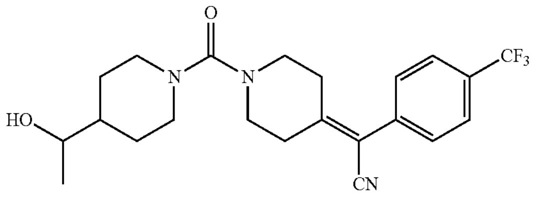 [SMILES: CC(O)C1CCN(C(=O)N2CCC(=C(C#N)c3ccc(C(F)(F)F)cc3)CC2)CC1]
Compound 152
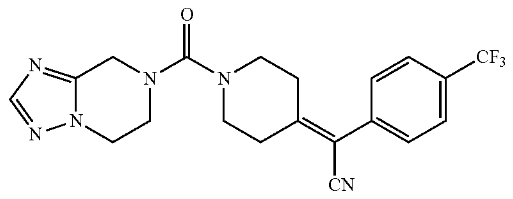 [SMILES: N#CC(=C1CCN(C(=O)N2CCn3ncnc3C2)CC1)c1ccc(C(F)(F)F)cc1]
Compound 153
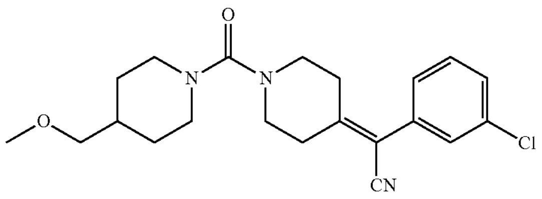 [SMILES: COCC1CCN(C(=O)N2CCC(=C(C#N)c3cccc(Cl)c3)CC2)CC1]
Compound 154
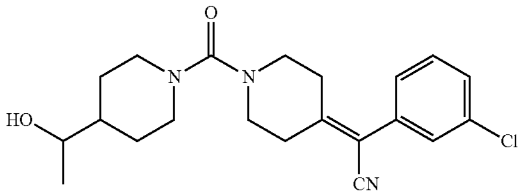
Compound 155
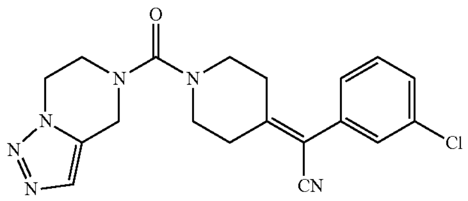 [SMILES: N#CC(=C1CCN(C(=O)N2CCn3nncc3C2)CC1)c1cccc(Cl)c1]
Compound 156
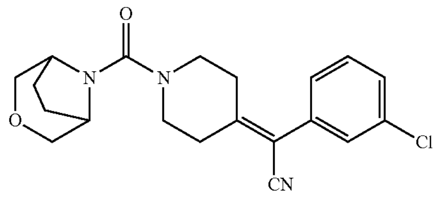 [SMILES: N#CC(=C1CCN(C(=O)N2C3CCC2COC3)CC1)c1cccc(Cl)c1]
TABLE 1-continued
Compound 157
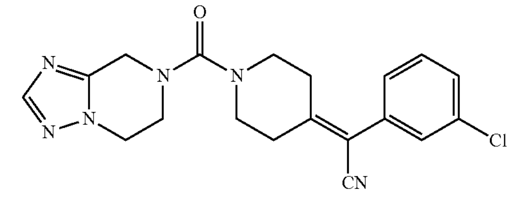 [SMILES: N#CC(=C1CCN(C(=O)N2CCn3ncnc3C2)CC1)c1cccc(Cl)c1]
Compound 158
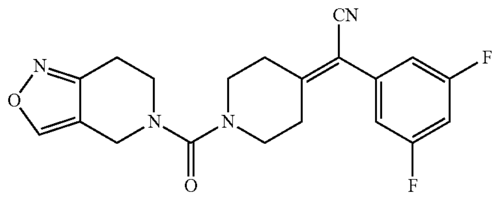 [SMILES: N#CC(=C1CCN(C(=O)N2CCc3nocc3C2)CC1)c1cc(F)cc(F)c1]
Compound 159
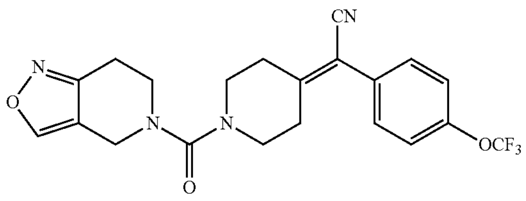 [SMILES: N#CC(=C1CCN(C(=O)N2CCc3nocc3C2)CC1)c1ccc(OC(F)(F)F)cc1]
Compound 160
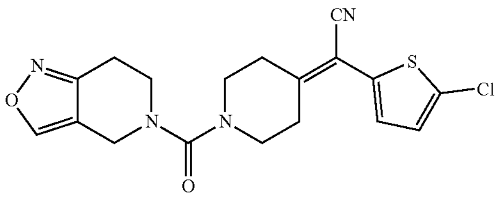 [SMILES: N#CC(=C1CCN(C(=O)N2CCc3nocc3C2)CC1)c1ccc(Cl)s1]
Compound 161
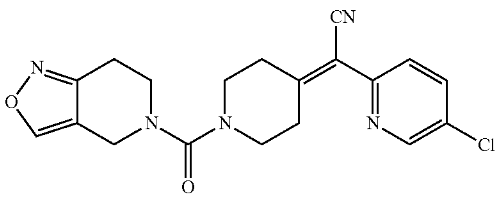 [SMILES: N#CC(=C1CCN(C(=O)N2CCc3nocc3C2)CC1)c1ccc(Cl)cn1]
Compound 162
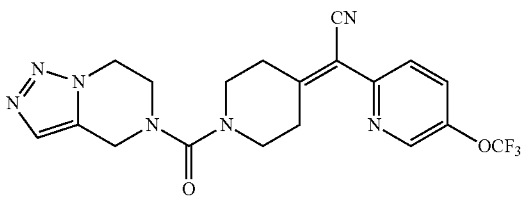

TABLE 1-continued

Compound 163

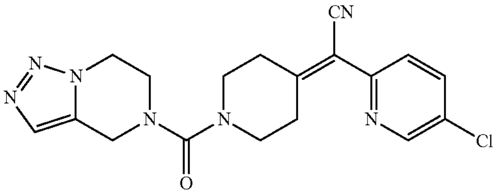 [SMILES: N#CC(=C1CCN(C(=O)N2CCn3nncc3C2)CC1)c1ccc(Cl)cn1]

Compound 164

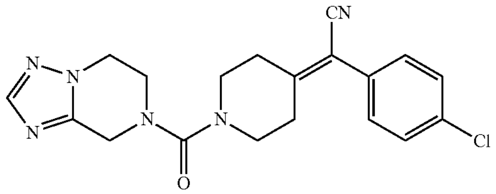 [SMILES: N#CC(=C1CCN(C(=O)N2CCn3ncnc3C2)CC1)c1ccc(Cl)cc1]

Compound 165

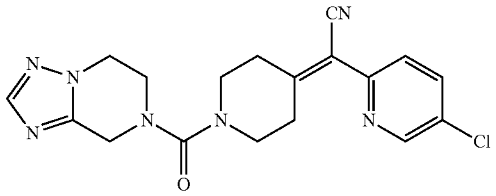 [SMILES: N#CC(=C1CCN(C(=O)N2CCn3ncnc3C2)CC1)c1ccc(Cl)cn1]

Compound 166

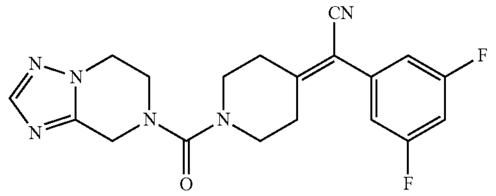 [SMILES: N#CC(=C1CCN(C(=O)N2CCn3ncnc3C2)CC1)c1cc(F)cc(F)c1]

Compound 167

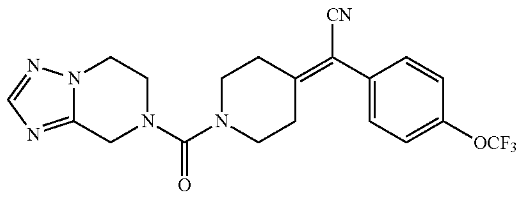 [SMILES: N#CC(=C1CCN(C(=O)N2CCn3ncnc3C2)CC1)c1ccc(OC(F)(F)F)cc1]

Compound 168

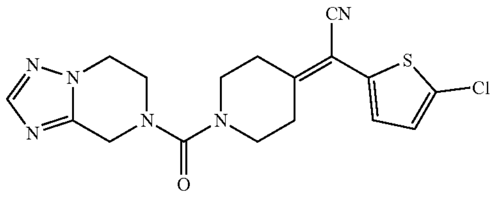 [SMILES: N#CC(=C1CCN(C(=O)N2CCn3ncnc3C2)CC1)c1ccc(Cl)s1]

TABLE 1-continued

Compound 169

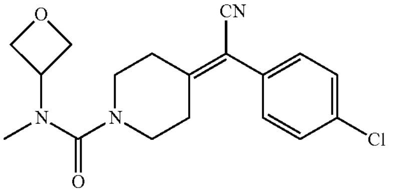 [SMILES: CN(C(=O)N1CCC(=C(C#N)c2ccc(Cl)cc2)CC1)C1COC1]

Compound 170

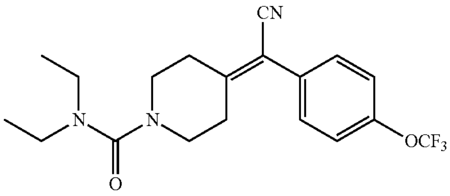 [SMILES: CCN(CC)C(=O)N1CCC(=C(C#N)c2ccc(OC(F)(F)F)cc2)CC1]

Compound 171

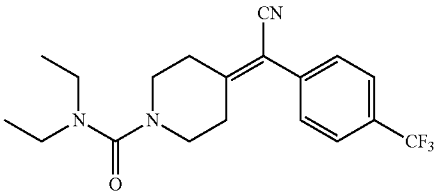 [SMILES: CCN(CC)C(=O)N1CCC(=C(C#N)c2ccc(C(F)(F)F)cc2)CC1]

Compound 172

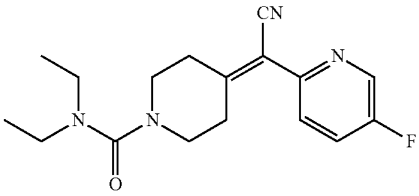 [SMILES: CCN(CC)C(=O)N1CCC(=C(C#N)c2ccc(F)cn2)CC1]

Compound 173

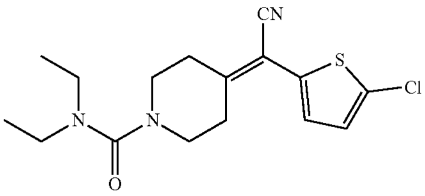 [SMILES: CCN(CC)C(=O)N1CCC(=C(C#N)c2ccc(Cl)s2)CC1]

EXPERIMENTAL

General Preparation Methods

Compounds of the present invention may be prepared by methods known in the art.

General Information

Commercial grade reagents and solvents were used without further purification. Thin-layer chromatography (TLC) was performed on Merck-plates; pre-coated aluminium sheets. Visualization of plates was done by the following techniques: 1) ultraviolet illumination (254 nm), 2) dipping the plate into ninhydrin solution followed by heating.

$^1$H-NMR spectra were measured with a Bruker Avance III 400 (400 MHz) spectrometer with the solvent as indicated.

Example compounds of the invention may be prepared starting from 1-Boc-4-piperidone and a substituted acetonitrile in a Knoevenagel reaction (Scheme 1). After Boc-deprotection in acidic conditions, the hydrochloride derivative may be treated with carbonyldiimidazole (CDI) to produce imidazole derivative, which was methylated with methyl iodide (MeI) to produce the iodide salt of the methylated imidazole derivative. The formed iodide salt may be used as an intermediate for the compound (I) preparation.

Scheme 1. General synthesis route that may be used for the preparation of compounds of formula (I) of the invention.

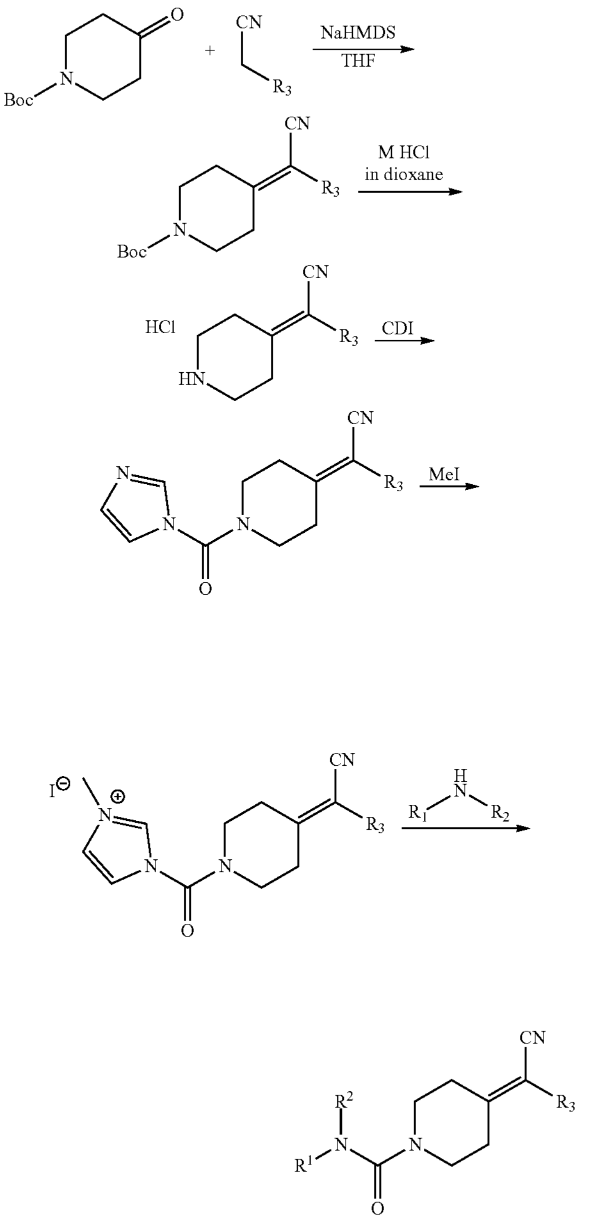

(I)

TABLE 2

| Intermediates that may be used in a method for the preparation of a compound of formula (I). |
|---|
| INT-2 |
| 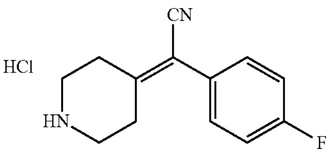 [SMILES: Cl ; N#CC(=C1CCNCC1)c1ccc(F)cc1] |
| INT-4 |
| 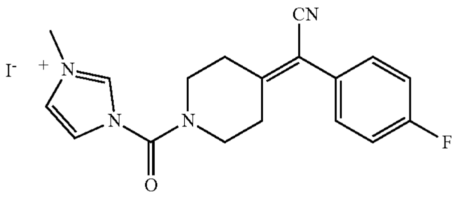 |
| INT-6 |
| 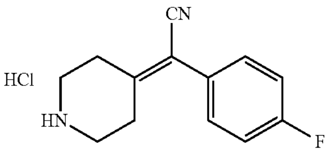 [SMILES: Cl ; N#CC(=C1CCNCC1)c1ccc(F)cc1] |
| INT-8 |
| 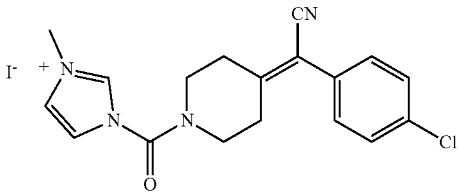 |
| INT-10 |
| 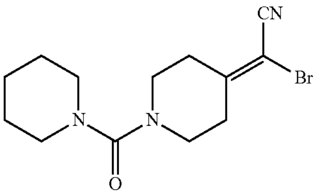 [SMILES: N#CC(Br)=C1CCN(C(=O)N2CCCCC2)CC1] |
| INT-12 |
| 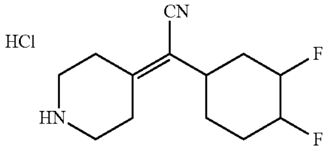 [SMILES: Cl ; N#CC(=C1CCNCC1)C1CCC(F)C(F)C1] |
| INT-14 |
| 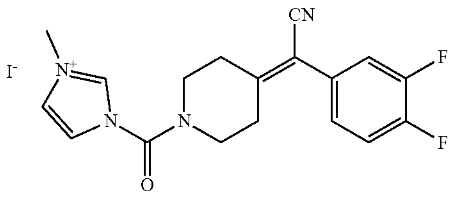 [SMILES: [I-] ; C[n+]1ccn(C(=O)N2CCC(=C(C#N)c3ccc(F)c(F)c3)CC2)c1] |

TABLE 2-continued
Intermediates that may be used in a method for the preparation of a compound of formula (I).
INT-16
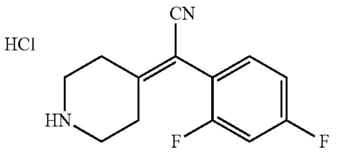 [SMILES: Cl ; N#CC(=C1CCNCC1)c1ccc(F)cc1F]
INT-18
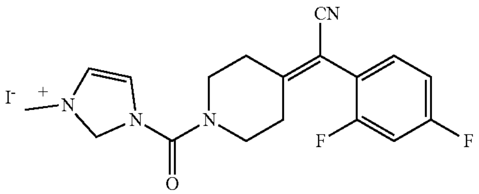 [SMILES: [I-] ; CN1C=CN(C(=O)N2CCC(=C(C#N)c3ccc(F)cc3F)CC2)C1]
INT-20
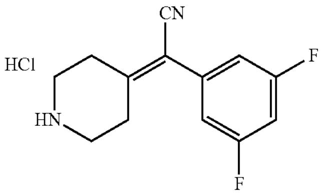 [SMILES: Cl ; N#CC(=C1CCNCC1)c1cc(F)cc(F)c1]
INT.22
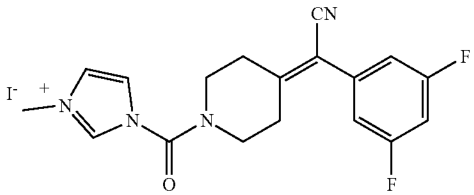
INT-24
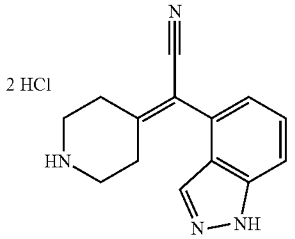 [SMILES: "2 HCl" ; N#CC(=C1CCNCC1)c1cccc2[nH]ncc12]
INT-26
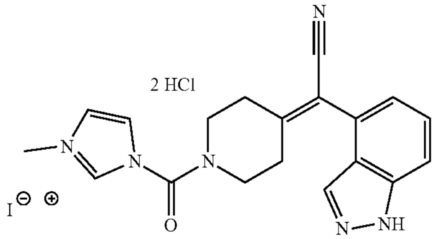
TABLE 2-continued
Intermediates that may be used in a method for the preparation of a compound of formula (I).
INT-28
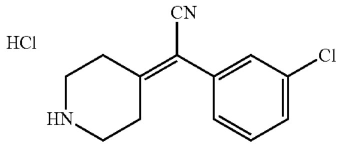 [SMILES: Cl ; N#CC(=C1CCNCC1)c1cccc(Cl)c1]
INT-30
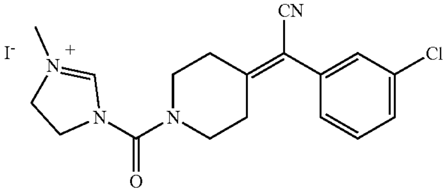
INT-32
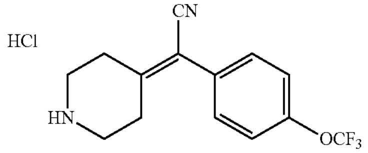 [SMILES: Cl ; N#CC(=C1CCNCC1)c1ccc(OC(F)(F)F)cc1]
INT-34
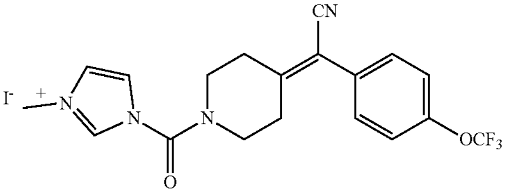
INT-36
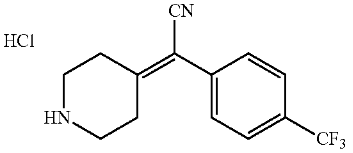 [SMILES: Cl ; N#CC(=C1CCNCC1)c1ccc(C(F)(F)F)cc1]
INT-38
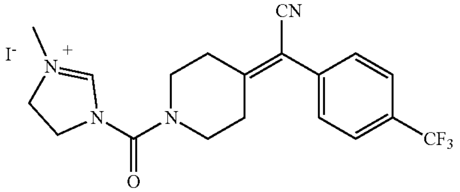
INT.40
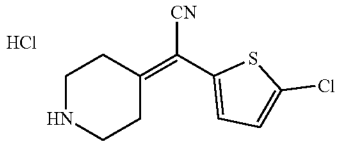 [SMILES: Cl ; N#CC(=C1CCNCC1)c1ccc(Cl)s1]

TABLE 2-continued

Intermediates that may be used in a method for the preparation of a compound of formula (I).

INT-42

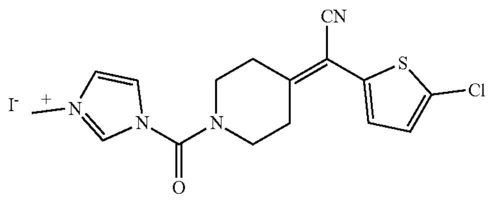

INT-44

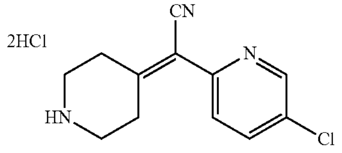 [SMILES: "2HCl" ; N#CC(=C1CCNCC1)c1ccc(Cl)cn1]

INT-46

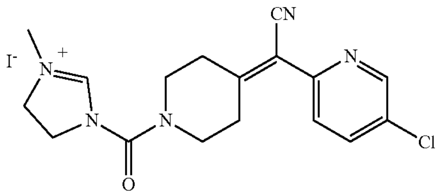

INT-48

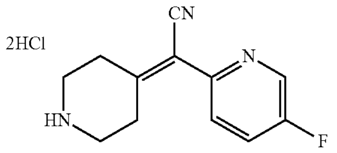 [SMILES: "2HCl" ; N#CC(=C1CCNCC1)c1ccc(F)cn1]

INT-50

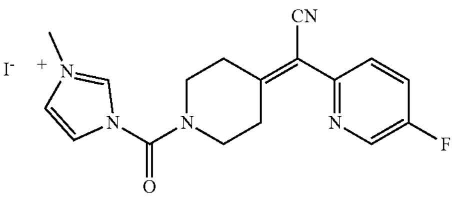

INT-53

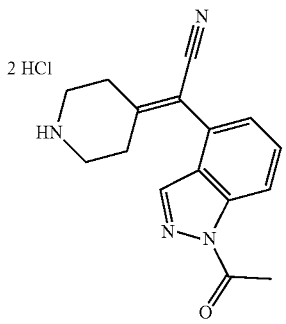 [SMILES: "2 HCl" ; CC(=O)n1ncc2c(C(C#N)=C3CCNCC3)cccc21]

TABLE 2-continued

Intermediates that may be used in a method for the preparation of a compound of formula (I).

INT-55

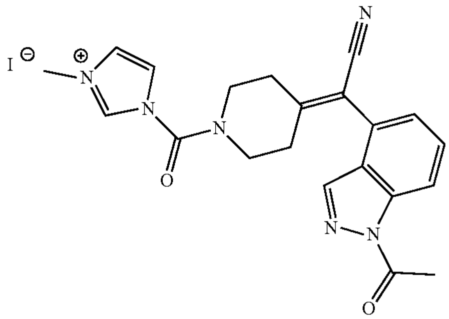 [SMILES: [I-] ; CC(=O)n1ncc2c(C(C#N)=C3CCN(C(=O)n4cc[n+](C)c4)CC3)cccc21]

INT-59

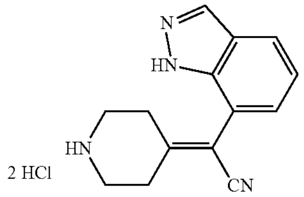 [SMILES: "2 HCl" ; N#CC(=C1CCNCC1)c1cccc2cn[nH]c12]

INT-61

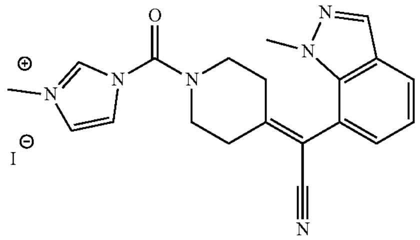

INT-63

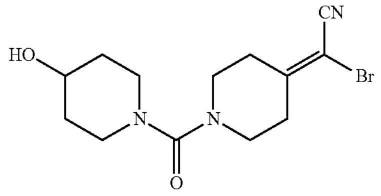 [SMILES: N#CC(Br)=C1CCN(C(=O)N2CCC(O)CC2)CC1]

INT-64

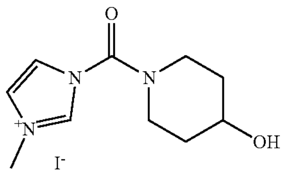

General Method A: Knoevenagel Reaction

To solution of 1-Boc-4-piperidone (100 mol-%) and substituted acetonitrile (100 mol-%) in MeOH (1.67 mL/mmol substituted acetonitrile) was added 25% NaOMe in MeOH solution (110 mol-%) and the reaction mixture heated at 70° C. for 2 h (or until complete). The reaction mixture was allowed to cool, then concentrated under reduced pressure. The residue was taken up water, and extracted twice with EtOAc. The combined organic layers were dried with sodium sulphate, concentrated under reduced pressure, and purified by column chromatography using EtOAc in hexanes as an eluent.

General Method B: Boc Deprotection

To the Boc-protected piperidine (100 mol-%) [either neat or as a solution in dichloromethane (DCM) or tert-butyl methyl ether (MTBE)] was added 4M HCl in dioxane (1000 mol-%) and the reaction stirred for 1 h, or until judged complete by TLC or LCMS. The reaction mixture was concentrated under reduced pressure and the residue suspended in EtOAc or MTBE, filtered and washed repeatedly with EtOAc and/or MTBE, then dried.

General Method C: Boc Deprotection

To the Boc-protected piperidine (100 mol-%) was added 4M HCl in dioxane (1000 mol-%) and the reaction stirred for 1 h, or until judged complete by TLC or LCMS. The reaction mixture was diluted with MTBE or EtOAc, filtered and washed repeatedly with MTBE or EtOAc, then dried.

General Method D: Suzuki coupling of tert-butyl 4-[bromo(cyano)methylidene]piperidine-1-carboxylate To a mixture of tert-butyl 4-[bromo(cyano)methylidene]piperidine-1-carboxylate (100 mol-%), boronic acid or ester (120 mol-%) and caesium carbonate (200 mol-%) in 1,4-dioxane (3.25 mL/mmol substrate) and water (0.37 mL/mmol substrate) was added [1,1'-Bis(di-tert-butylphosphino)ferrocene]-dichloropalladium(II) (2.5 mol-%) and the mixture sparged with nitrogen for 2 min. The reaction mixture was heated at 60° C. under nitrogen for 20 h, then allowed to cool. The reaction mixture was diluted with water and extracted trice with EtOAc. The combined extracts were dried with sodium sulphate, concentrated under reduced pressure and the precipitate was purified by column chromatography using EtOAc in hexanes as an eluent.

General Method E: Miyura Coupling for the Synthesis of Boronic Esters

To a solution of aryl bromide (100 mol-%) in 1,4-dioxane (4 mL/mmol substrate) was added bis(pinacolato)diboron (115 mol-%) and potassium acetate (460 mol-%) at 20° C. The reaction mixture was sparged with nitrogen for 5 min, then Pd(dppf)$Cl_2$·DCM (8 mol-%) was added and sparging repeated. The reaction was heated under reflux for 1.5 h, allowed to cool and concentrated under reduced pressure. The residue was partitioned between EtOAc and water, the organic layer was separated, washed successively with water and brine, dried with sodium sulphate and concentrated under reduced pressure. The crude material was purified by column chromatography.

Preparation of INT-2 and INT-4

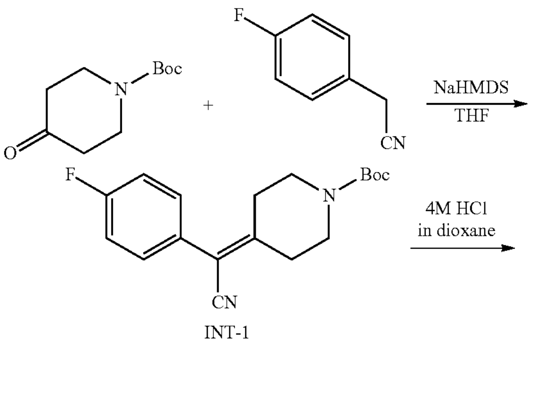

INT-1

-continued

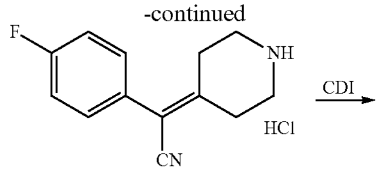

INT-2

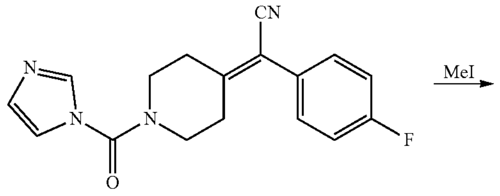

INT-3

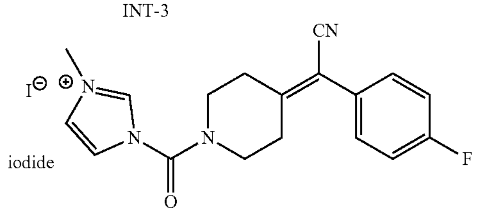

INT-4

INT-1: Synthesis of tert-butyl 4-[cyano(4-fluorophenyl)methylidene]piperidine-1-carboxylate To a solution of 2-(4-fluorophenyl)acetonitrile (4.07 g, 120 mol-%) in THE (100 mL) at 0° C. was added sodium hexamethyldisilazide (NaHMDS; 1M solution in THF, 30.1 mL, 120 mol-%) and the reaction mixture stirred at 0° C. for 30 min. A solution of 1-Boc-4-piperidone (5.0 g, 100 mol-%) in THE (20 mL) was added, and mixture stirred for 20 h, allowing to warm to room temperature. The reaction mixture was quenched with saturated ammonium chloride solution (50 mL), and extracted with EtOAc (3×100 mL). The combined organic layers were washed with brine (100 mL), then dried with sodium sulphate and concentrated, and the residue purified by column chromatography (0-20% EtOAc in iso-hexane) to give INT-1 (2.54 g, 32%) as a colourless oil which solidified on standing. $^1$H-NMR (400 MHz, $CDCl_3$) δ ppm 7.28-7.23 (m, 2H), 7.13-7.06 (m, 2H), 3.61 (t, 2H), 3.42 (t, 2H), 2.76 (t, 2H), 2.40 (t, 2H), 1.47 (s, 9H). m/z (ES+) 217.1 $(M-Boc+H)^+$.

INT-2: 2-(4-fluorophenyl)-2-(piperidin-4-ylidene)acetonitrile hydrochloride

Prepared according to General Method C from INT-1 to give INT-2 (1.54 g, 76%) as an off-white powder. $^1$H-NMR (400 MHz, DMSO-$d_6$) δ ppm 9.50 (s, 2H), 7.48-7.41 (m, 2H), 7.36-7.29 (m, 2H), 3.28 (t, 2H), 3.11 (t, 2H), 2.92 (t, 2H), 2.59 (t, 2H). m/z (ES+) 217.1 $(M+H)^+$.

INT-3: 2-(1-(1H-imidazole-1-carbonyl)piperidin-4-ylidene)-2-(4-fluorophenyl)acetonitrile INT-2 (3.00 g, 100 mol-%) was dissolved in dry THE (30 mL). Carbonyldiimidazole (CDI) (3.46 g, 180 mol-%) was added. Stirred at +60° C. for two hours. The solvent was evaporated and the residue was dissolved in ethyl acetate (30 ml). The reaction mixture is washed with water (5×10 mL) and brine (3×10 mL). Dried over sodium sulphate. The yield of INT-3 was 3.54 g; 96%. $^1$H-NMR (400 MHz, DMSO-$d_6$):

2.55 (m, 2H), 2.86 (m, 2H), 3.53 (m, 2H), 3.71 (m, 2H), 7.05 (s, 1H), 7.33 (dd, 2H), 7.43 (dd, 2H), 7.50 (s, 1H), 8.06 (s, 1H).

INT-4: 1-(4-(cyano(4-fluorophenyl)methylene)piperidine-1-carbonyl)-3-methyl-1H-imidazol-3-ium iodide INT-3 (3.5 g, 100 mol-%) was dissolved in dry acetonitrile (30 mL). Methyl iodide (7.1 mL, 1000 mol-%) was added under nitrogen atmosphere. Reaction mixture was stirred at +40° C. for three hours. Water (1 ml) was added and followed by co-evaporation with toluene (3x10 mL). The crude product was purified by trituration with heptane/DCM. The yield of INT-4 was 4.82 g; 94%. $^1$H-NMR (400 MHz, DMSO-$d_6$): 2.58 (m, 2H), 2.89 (m, 2H), 3.56 (m, 2H), 3.73 (m, 2H), 3.92 (s, 3H), 7.34 (dd, 2H), 7.44 (dd, 2H), 7.86 (s, 1H), 8.03 (s, 1H), 9.57 (s, 1H).

Preparation of INT-6 and INT-8

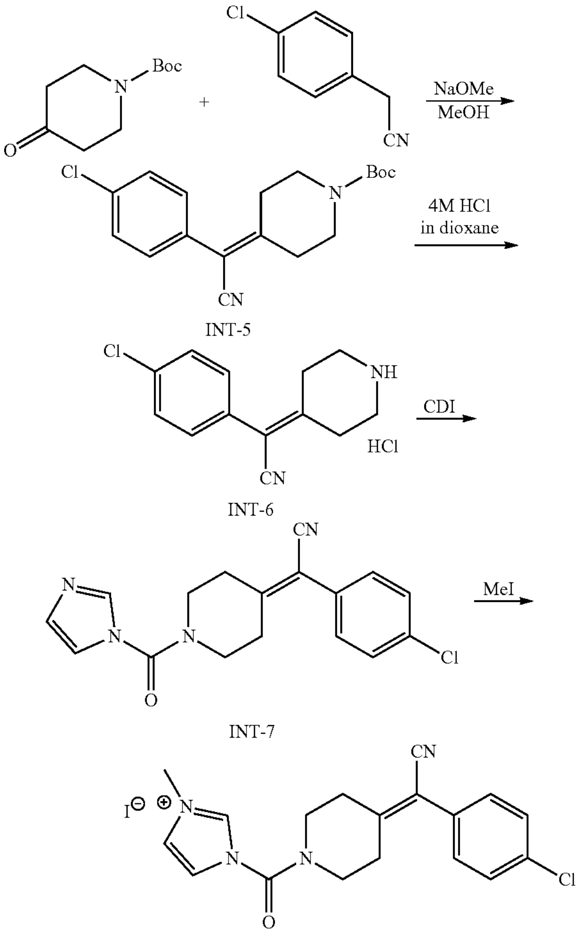

INT-5

INT-6

INT-7

INT-8

INT-5: Prepared according to General Method A to give tert-butyl 4-[cyano(4-chlorophenyl)methylidene]piperidine-1-carboxylate in 72% yield as an off-white solid. $^1$H-NMR (400 MHz, $CDCl_3$) δ ppm 7.39 (d, 2H), 7.22 (d, 2H), 3.61 (t, 2H), 3.42 (t, 2H), 2.76 (t, 2H), 2.40 (t, 2H), 1.43 (s, 9H).

INT-6: Prepared according to General Method B to give 2-(4-chlorophenyl)-2-(piperidin-4-ylidene)acetonitrile hydrochloride in 79% yield as an off-white powder. $^1$H-NMR (400 MHz, DMSO-$d_6$) δ ppm 9.31 (s, 2H), 7.60-7.52 (m, 2H), 7.46-7.38 (m, 2H), 3.31-3.27 (m, 2H), 3.14-3.10 (m, 2H), 2.91 (t, 2H), 2.59 (t, 2H). m/z (ES+) 233.1/235.1 $(M+H)^+$.

INT-7: 2-(1-(1H-imidazole-1-carbonyl)piperidin-4-ylidene)-2-(4-chlorophenyl)acetonitrile INT-6 (2.74 g, 100 mol-%) was dissolved in dry THE (30 mL). Carbonyldiimidazole CDI (2.48 g, 150 mol-%) was added. Stirred at +60° C. for three hours. The solvent was evaporated and the residue was dissolved in ethyl acetate (30 ml). The reaction mixture is washed with water (3x20 mL) and brine (3x10 mL). Dried over sodium sulphate. The yield of INT-7 was 3.14 g; 94%. $^1$H-NMR (400 MHz, DMSO-$d_6$): 2.56 (t, 2H), 2.86 (t, 2H), 3.53 (t, 2H), 3.71 (t, 2H), 7.05 (s, 1H), 7.41 (d, 2H), 7.50 (s, 1H), 7.56 (d, 2H), 8.06 (s, 1H).

INT-8: 1-(4-((4-chlorophenyl)(cyano)methylene)piperidine-1-carbonyl)-3-methyl-1H-imidazol-3-ium iodide INT-7 (2.4 g, 100 mol-%) was dissolved in dry acetonitrile (20 mL). Methyl iodide (2.3 mL, 500 mol-%) was added under nitrogen atmosphere. Additional amounts of methyl iodide (2x500 mol-%) were added during 7 hours at +40° C. Reaction mixture was stirred at room temperature overnight. Water (1 ml) was added and followed by co-evaporation with toluene (3x10 mL). The crude product was purified by trituration with heptane/DCM (v/v 5:0.5). The yield of INT-8 was 3.37 g; 87%. $^1$H-NMR (400 MHz, DMSO-$d_6$): 2.59 (t, 2H), 2.89 (t, 2H), 3.56 (m, 2H), 3.73 (m, 2H), 3.92 (s, 3H), 7.42 (d, 2H), 7.57 (d, 2H), 7.86 (s, 1H), 8.03 (s, 1H), 9.57 (s, 1H).

Preparation of INT-10

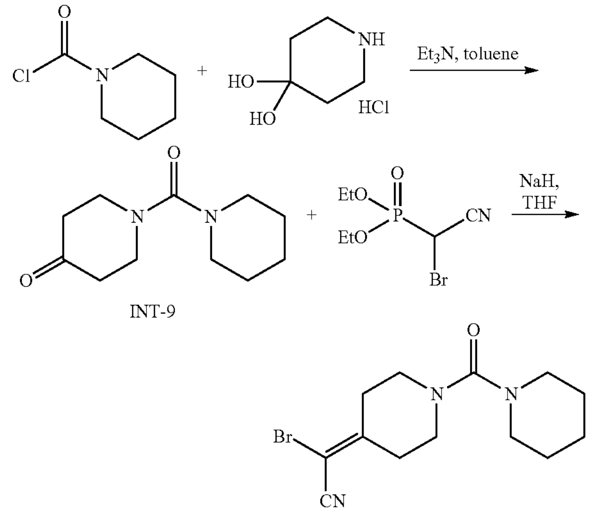

INT-9

INT-10

INT-9: To piperidine-4,4-diol hydrochloride (10.0 g, 100 mol-%) and triethylamine (18.1 mL, 200 mol-%) in toluene (288 mL) was added piperidine-1-carbonyl chloride (8.1 mL, 100 mol-%) and the suspension stirred at room temperature for 18 h. The reaction mixture was filtered and the filtrate concentrated under reduced pressure. The residue was purified by column chromatography (20-100% EtOAc in isohexane) to give 1-(piperidine-1-carbonyl)piperidin-4- one in 59% yield as an off-white crystalline solid. $^1$H-NMR (400 MHz, $CDCl_3$) δ ppm 3.51 (t, 4H), 3.26 (t, 4H), 2.48 (t, 4H), 1.65-1.55 (m, 6H). m/z (ES+) 211.2 $(M+H)^+$.

INT-10: To a suspension of sodium hydride (60% suspension in mineral oil, 203 mg, 512 mol-%) in THE (4 mL) at −78° C. was added a solution of diethyl bromo(cyano) methyl]phosphonate solution (1.08 g, 100 mol-%) in THE (5 mL). The dark grey-brown suspension was stirred for 15 min, then a solution of 1-(piperidine-1-carbonyl)piperidin-4-one (1.07 g, 120 mol-%) in THE (6 mL) was added. The mixture was allowed to warm to 20° C. over 1 h, then saturated aqueous ammonium chloride solution (20 mL) was added slowly and the mixture was extracted with EtOAc (3×20 mL). The combined extracts were dried with sodium sulphate, concentrated under reduced pressure and purified by column chromatography (20-70% EtOAc in hexanes) to give 2-bromo-2-[1-(piperidine-1-carbonyl)piperidin-4-ylidene]acetonitrile in 87% yield as a colourless solid. $^1$H-NMR (400 MHz, $CDCl_3$) δ ppm 3.32 (q, 4H), 3.22 (dd, 4H), 2.71-2.64 (m, 2H), 2.62-2.54 (m, 2H), 1.63-1.54 (m, 6H). m/z (ES+) 312.0/314.0 $(M+H)^+$.

Preparation of INT-12 and INT-14

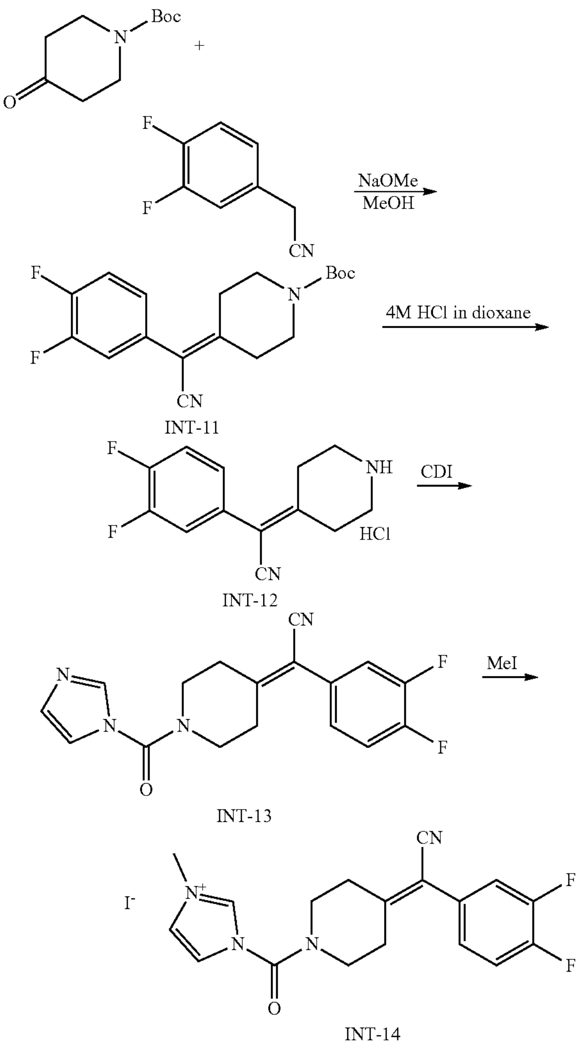

INT-11

INT-12

INT-13

INT-14

INT-11: Prepared according to General Method A to give tert-butyl 4-[cyano(3,4-difluorophenyl)methylidene]piperidine-1-carboxylate in 64% yield as a pale yellow solid. $^1$H-NMR (400 MHz, $CDCl_3$) δ ppm δ 7.25-7.17 (m, 1H), 7.16-7.08 (m, 1H), 7.02-6.98 (m, 1H), 3.61 (t, 2H), 3.43 (t, 2H), 2.76 (t, 2H), 2.40 (t, 2H), 1.47 (s, 9H). $^{19}$F NMR (376 MHz, $CDCl_3$) δ ppm −135.73 (dd, J=21.2, 6.2 Hz), −136.30 (d, J=21.2 Hz). m/z (ES+) 235.2 $(M-Boc+H)^+$.

INT-12: Prepared according to General Method B to give 2-(3,4-difluorophenyl)-2-(piperidin-4-ylidene)acetonitrile hydrochloride in 89% yield as an off-white solid. $^1$H-NMR (400 MHz, DMSO-$d_6$) δ ppm 9.50 (s, 2H), 7.61-7.51 (m, 2H), 7.30-7.24 (m, 1H), 3.27 (t, 2H), 3.12 (t, 2H), 2.94-2.88 (m, 2H), 2.59 (t, 2H). $^{19}$F NMR (376 MHz, DMSO-$d_6$) δ ppm −137.11 (d, J=22.6 Hz), −137.55 (d, J=22.5 Hz). m/z (ES+) 235.2 $(M+H)^+$.

INT-13: 2-(1-(1H-imidazole-1-carbonyl)piperidin-4-ylidene)-2-(3,4-difluorophenyl)acetonitrile Prepared in 92% yield according to method used in the preparation of INT-3. $^1$H-NMR (400 MHz, DMSO-$d_6$): 2.55 (m, 2H), 2.86 (m, 2H), 3.54 (m, 2H), 3.71 (m, 2H), 7.05 (s, 1H), 7.26 (m, 1H), 7.50-7.55 (m, 3H), 8.07 (s, 1H).

INT-14: 1-(4-(cyano(3,4-difluorophenyl)methylene) piperidine-1-carbonyl)-3-methyl-1H-imidazol-3-ium iodide Prepared in 79% yield according to method used in the preparation of INT-4. $^1$H-NMR (400 MHz, DMSO-$d_6$): 2.58 (m, 2H), 2.89 (m, 2H), 3.57 (m, 2H), 3.73 (m, 2H) 3.92 (s, 3H), 7.27 (m, 1H), 7.57 (m, 2H), 7.87 (s, 1H), 8.03 (s, 1H), 9.57 (s, 1H).

Preparation of INT-16 and INT-18

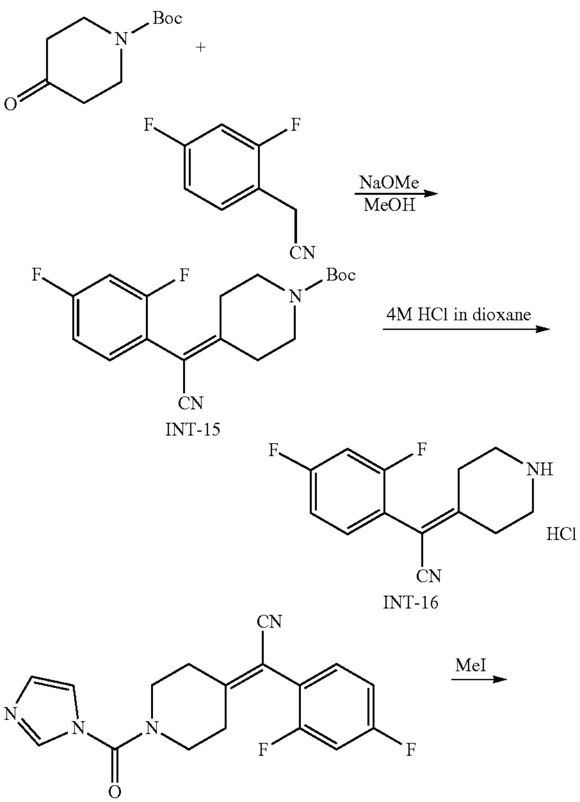

INT-15

INT-16

INT-17

-continued

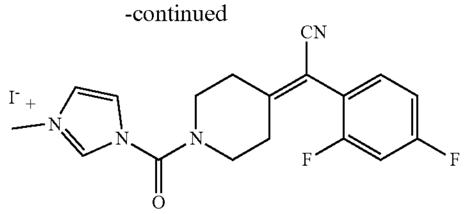

INT-18

INT-15: Prepared according to General Method A to give tert-butyl 4-[cyano(2,4-difluorophenyl)methylidene]piperidine-1-carboxylate in 65% yield as an off-white powder. $^1$H-NMR (400 MHz, $CDCl_3$) δ ppm 7.31-7.21 (m, 1H), 7.00-6.85 (m, 2H), 3.62 (t, 2H), 3.44 (t, 2H), 2.77 (t, 2H), 2.30-2.15 (m, 2H), 1.47 (s, 9H).

INT-16: Prepared according to General Method B to give 2-(2,4-difluorophenyl)-2-(piperidin-4-ylidene)acetonitrile hydrochloride in 81% yield as an off-white solid. $^1$H-NMR (400 MHz, DMSO-$d_6$) δ ppm 9.13 (s, 2H), 7.53 (td, 1H), 7.50-7.41 (m, 1H), 7.25 (td, 1H), 3.31 (s, 2H), 3.17-3.07 (m, 2H), 2.97-2.86 (m, 2H), 2.48-2.44 (m, 2H). $^{19}F$ NMR (376 MHz, DMSO-$d_6$) δ ppm −107.43 (dd, J=9.7, 4.1 Hz), −108.98 (dd, J=9.0, 4.3 Hz). m/z (ES+) 235.2 $(M+H)^+$.

INT-17: 2-(1-(1H-imidazole-1-carbonyl)piperidin-4-ylidene)-2-(2,4-difluorophenyl)acetonitrile Prepared in 93% yield according to method used in the preparation of INT-3 in three hours reaction time. $^1$H-NMR (400 MHz, DMSO-$d_6$): 2.41 (t, 2H), 2.88 (t, 2H), 3.53 (t, 2H), 3.71 (t, 2H), 7.05 (s, 1H), 7.24 (m, 1H), 7.45 (m, 1H), 7.50 (m, 2H), 8.06 (s, 1H).

INT-18: 2-(2,4-difluorophenyl)-2-(1-(3-methyl-1H-3λ$^4$-imidazole-1-carbonyl)piperidin-4-ylidene)acetonitrile iodide Prepared in 81% yield according to method used in the preparation of INT-4 in 5.5 hours reaction time at +40° C. The crude product was purified by trituration with ethyl acetate. $^1$H-NMR (400 MHz, DMSO-$d_6$): 2.45 (t, 2H), 2.92 (t, 2H), 3.56 (t, 2H), 3.74 (t, 2H), 3.92 (s, 3H), 7.26 (m, 1H), 7.44-7.54 (m, 2H), 7.87 (m, 1H), 8.04 (s, 1H), 9.57 (s, 1H).

Preparation of INT-20 and INT-22

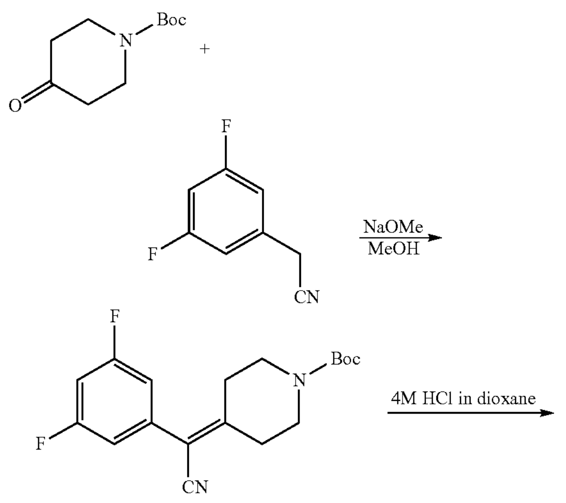

INT-19

-continued

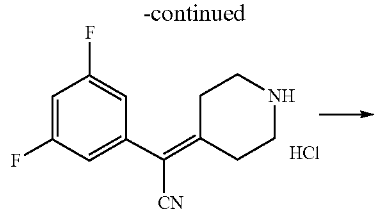

INT-20

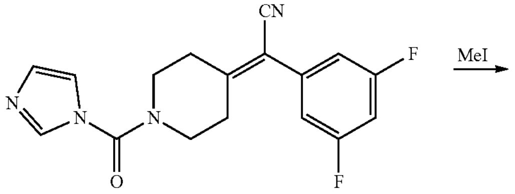

INT-21

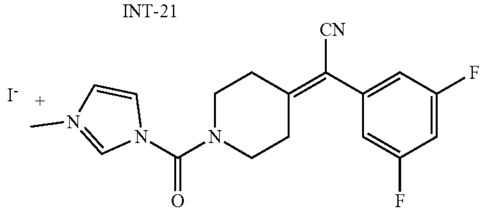

INT-22

INT-19: Prepared according to General Method A to give tert-butyl 4-[cyano(3,5-difluorophenyl)methylidene]piperidine-1-carboxylate in 35% yield as a pale yellow solid. $^1$H-NMR (400 MHz, $CDCl_3$) δ ppm 6.91-6.79 (m, 3H), 3.62 (t, 2H), 3.45 (t, 2H), 2.76 (t, 2H), 2.43 (t, 2H), 1.48 (s, 9H). $^{19}F$ NMR (376 MHz, $CDCl_3$) δ ppm −107.95. m/z (ES+) 235.2 $(M-Boc+H)^+$.

INT-20: Prepared according to General Method B to give 2-(3,5-difluorophenyl)-2-(piperidin-4-ylidene)acetonitrile hydrochloride in 93% yield as an off-white solid. $^1$H-NMR (400 MHz, DMSO-$d_6$) δ ppm 9.47 (s, 2H), 7.41-7.33 (m, 1H), 7.24-7.16 (m, 2H), 3.27 (t, 2H), 3.14 (t, 2H), 2.95-2.88 (m, 2H), 2.60 (t, 2H). $^{19}F$ NMR (376 MHz, DMSO-$d_6$) δ ppm −108.37. m/z (ES+) 235.2 $(M+H)^+$.

INT-21: 2-(1-(1H-imidazole-1-carbonyl)piperidin-4-ylidene)-2-(3,5-difluorophenyl)acetonitrile Prepared according to method used in the preparation of INT-3 in 95% yield in 3 hours reaction time. $^1$H-NMR (400 MHz, DMSO-$d_6$): 2.57 (t, 2H), 2.85 (t, 2H), 3.55 (t, 2H), 3.70 (t, 2H), 7.05 (s, 1H), 7.16-7.19 (m, 2H), 7.37 (m, 1H), 7.50 (s, 1H), 8.06 (s, 1H).

INT-22: 2-(3,5-difluorophenyl)-2-(1-(3-methyl-1H-3λ$^4$-imidazole-1-carbonyl)piperidin-4-ylidene)acetonitrile iodide Prepared according to method used in the preparation of INT-4 in 99% yield in 5 hours reaction time at +40° C. and overnight at room temperature. $^1$H-NMR (400 MHz, DMSO-$d_6$): 2.59 (m, 2H), 2.89 (m, 2H), 3.57 (m, 2H), 3.73 (m, 2H), 3.92 (s, 3H), 7.19 (m, 2H), 7.38 (m, 1H), 7.86 (s, 1H), 8.03 (s, 1H), 9.57 (s, 1H).

Preparation of INT-24 and INT-26

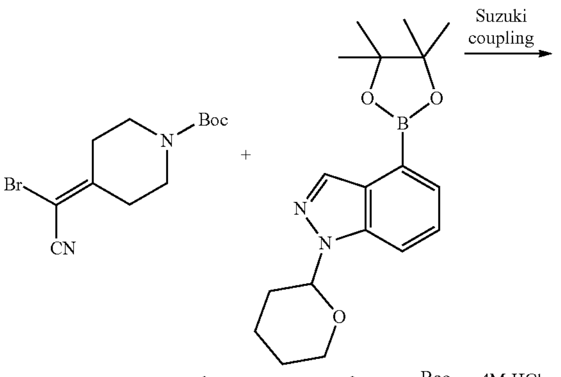

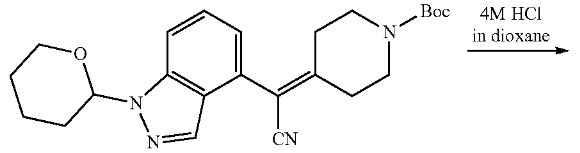

INT-23

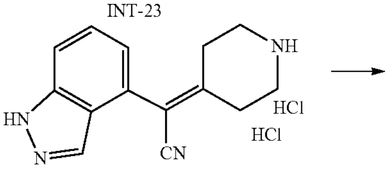

INT-24

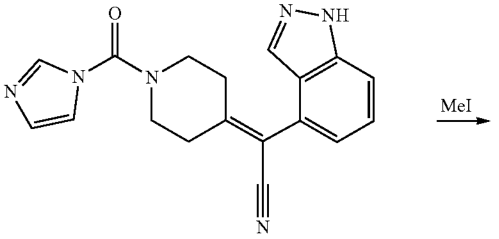

INT-25

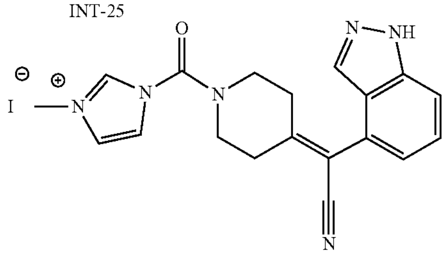

INT-26

INT-23: The reaction was carried out according to General Method D to give tert-butyl 4-{cyano[1-(tetrahydro-2H-pyran-2-yl)-1H-indazol-4-yl]methylene}piperidine-1-carboxylate in 93% yield as a pale yellow gum. $^{1}$H-NMR (400 MHz, $CDCl_3$) δ ppm 7.99 (d, 1H), 7.64 (dt, 1H), 7.41 (dd, 1H), 7.05 (dd, 1H), 5.75 (dd, 1H), 4.04 (d, 1H), 3.81-3.71 (m, 1H), 3.66 (t, 2H), 3.38 (t, 2H), 2.85 (t, 2H), 2.66-2.51 (m, 1H), 2.31 (t, 2H), 2.23-2.06 (m, 2H), 1.86-1.60 (m, 3H), 1.47 (s, 9H). m/z (ES+) 423.3 $(M+H)^+$.

INT-24: To a solution of INT-23 (2.86 g, 100 mol-%) in MTBE (0.5 mL) at 0° C. was added 4M HCl in dioxane (5.9 mL, 380 mol-%) After 10 min, MeOH (3 mL) was added and the mixture was stirred for 16 h. MTBE was added and the solid was filtered and triturated with EtOAc to give 2-(1H-indazol-4-yl)-2-(piperidin-4-ylidene)acetonitrile dihydrochloride in 85% as a pale pink solid. $^{1}$H-NMR (400 MHz, DMSO-$d_6$) δ ppm 9.53 (s, 2H), 8.13 (d, 1H), 7.64 (d, 1H), 7.42 (dd, 1H), 7.10 (d, 1H), 5.88-4.46 (m, 2H), 3.43-3.28 (m, 2H), 3.14-3.05 (m, 2H), 3.01 (t, 2H), 2.56-2.50 (m, 2H). m/z (ES+) 239.2 $(M+H)^+$.

INT-25: 2-(1-(1H-imidazole-1-carbonyl)piperidin-4-ylidene)-2-(1H-indazol-4-yl)acetonitrile Prepared in quantitative yield according to method used in the preparation of INT-3 in 6 hours reaction time. $^{1}$H-NMR (400 MHz, DMSO-$d_6$): 2.47 (t, 2H), 2.95 (t, 2H), 3.51 (t, 2H), 3.78 (t, 2H), 7.04 (s, 1H), 7.10 (d, 1H), 7.44 (t, 1H), 7.50 (s, 1H), 7.63 (d, 1H), 8.06 (s, 1H), 8.10 (s, 1H), 13.37 (s, 1H).

INT-26: 1-(4-(cyano(1H-indazol-4-yl)methylene) piperidine-1-carbonyl)-3-methyl-1H-imidazol-3-ium iodide Prepared according to method used in the preparation of INT-4 in overnight reaction time. $^{1}$H-NMR (400 MHz, DMSO-$d_6$): 2.99 (m, 2H), 3.35 (m, 2H), 3.53 (m, 2H), 3.81 (m, 2H), 3.91 (s, 3H), 7.11 (d, 1H), 7.45 (d, 1H), 7.65 (d, 1H), 7.86 (s, 1H), 8.03 (s, 1H), 8.10 (s, 1H), 9.57 (s, 1H), 13.39 (s, 1H).

Preparation of INT-28 and INT-30

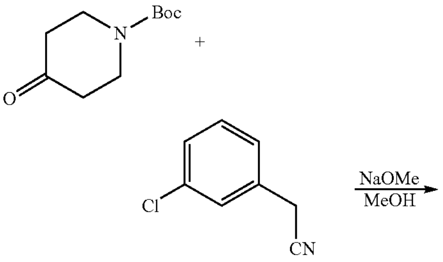

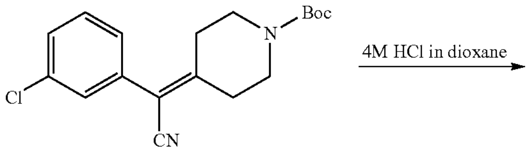

INT-27

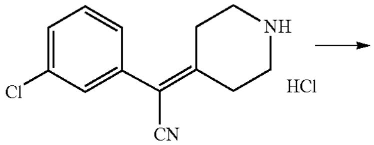

INT-28

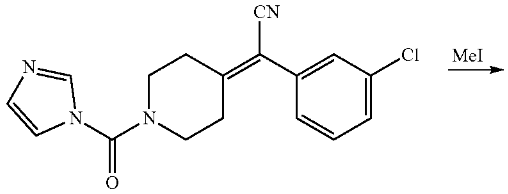

INT-29

-continued

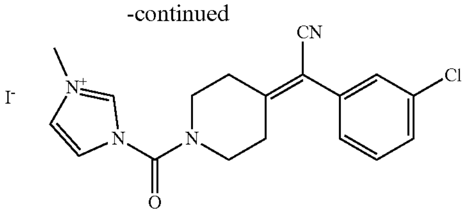

INT-30

INT-27: Prepared according to General Method A to give tert-butyl 4-[(3-chlorophenyl)(cyano) methylene]piperidine-1-carboxylate in 45% yield as an off-white solid. $^1$H-NMR (400 MHz, $CDCl_3$) δ ppm 7.38-7.27 (m, 3H), 7.20-7.13 (m, 1H), 3.61 (t, 2H), 3.43 (t, 2H), 2.76 (t, 2H), 2.41 (t, 2H), 1.48 (s, 9H). m/z (ES+) 277.2/279.2, $(M-t-Bu+H)^+$.

INT-28: Prepared according to General Method B to give 2-(3-chlorophenyl)-2-(piperidin-4-ylidene)acetonitrile hydrochloride in 83% yield as an off-white powder. $^1$H-NMR (400 MHz, DMSO-$d_6$) δ ppm 9.46 (s, 2H), 7.52 (d, 2H), 7.49 (s, 1H), 7.38-7.35 (m, 1H), 3.28 (t, 2H), 3.12 (t, 2H), 2.92 (t, 2H), 2.60 (t, 2H). m/z (ES+) 233.2/255.2 ($C_1$ isotope pattern) $(M+H)^+$.

INT-29: 2-(1-(1H-imidazole-1-carbonyl)piperidin-4-ylidene)-2-(3-chlorophenyl)acetonitrile Prepared in 98% yield according to method used in the preparation of INT-3 in seven hours reaction time. $^1$H-NMR (400 MHz, DMSO-$d_6$): 2.56 (t, 2H), 2.86 (t, 2H), 3.54 (t, 2H), 3.71 (t, 2H), 7.05 (s, 1H), 7.36 (m, 1H), 7.46 (m, 1H), 7.49-7.52 (m, 3H), 8.07 (s, 1H).

INT-30: 2-(3-chlorophenyl)-2-(1-(3-methyl-1H-3λ$^4$-imidazole-1-carbonyl)piperidin-4-ylidene)acetonitrile iodide Prepared in 95% yield according to method used in the preparation of INT-4 in 3 hours reaction time at +40° C. and overnight at room temperature. The crude product was purified by trituration with heptane:ethyl acetate. $^1$H-NMR (400 MHz, DMSO-$d_6$): 2.59 (t, 2H), 2.89 (t, 2H), 3.57 (t, 2H), 3.73 (t, 2H), 3.92 (s, 3H), 7.37 (m, 1H), 7.47 (s, 1H), 7.50-7.54 (m, 2H), 7.86 (m, 1H), 8.03 (s, 1H), 9.57 (s, 1H).

Preparation of INT-32 and INT-34

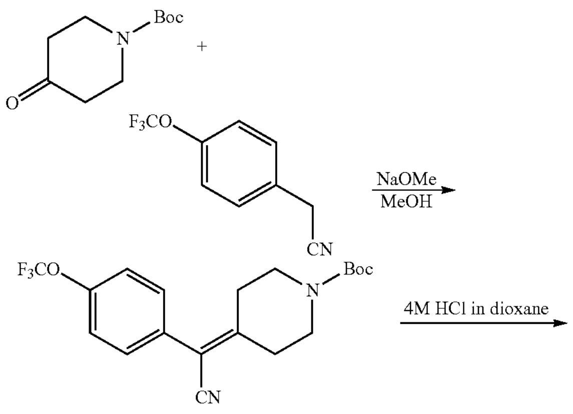

INT-31

-continued

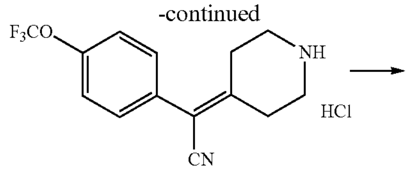

INT-32

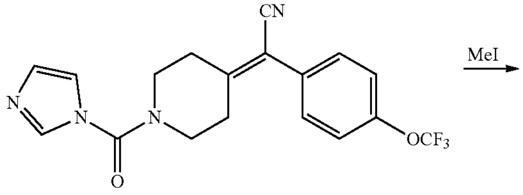

INT-33

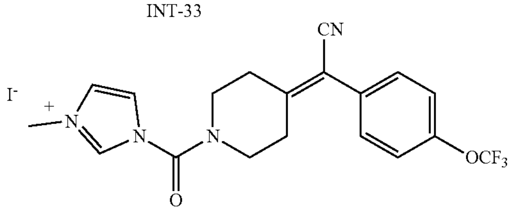

INT-34

INT-31: Prepared according to General Method A to give tert-butyl 4-{cyano[4-(trifluoromethoxy)phenyl] methylene}piperidine-1-carboxylate in 77% yield as a yellow oil. $^1$H-NMR (400 MHz, $CDCl_3$) δ ppm 7.35-7.29 (m, 2H), 7.29-7.22 (m, 2H), 3.62 (t, 2H), 3.44 (t, 2H), 2.77 (t, 2H), 2.41 (t, 2H), 1.48 (s, 9H).

INT-32: Prepared according to General Method B to give 2-(piperidin-4-ylidene)-2-[4-(trifluoromethoxy)phenyl]acetonitrile hydrochloride in 82% yield as an off-white solid. $^1$H-NMR (400 MHz, DMSO-$d_6$) δ ppm 9.21 (s, 2H), 7.72-7.31 (m, 4H), 3.33-3.24 (m, 2H), 3.18-3.08 (m, 2H), 2.91 (t, 2H), 2.59 (t, 2H). $^{19}$F NMR (400 MHz, DMSO-$d_6$) δ ppm−56.74. m/z (ES+) 283.1 $(M+H)^+$.

INT-33: 2-(1-(1H-imidazole-1-carbonyl)piperidin-4-ylidene)-2-(4-(trifluoromethoxy)phenyl)acetonitrile Prepared in quantitative yield according to method used in the preparation of INT-3. $^1$H-NMR (400 MHz, DMSO-$d_6$): 2.57 (t, 2H), 2.87 (t, 2H), 3.54 (t, 2H), 3.72 (t, 2H), 7.05 (s, 1H), 7.46-7.55 (m, 5H), 8.06 (s, 1H).

INT-34: 2-(1-(3-methyl-1H-3λ$^4$-imidazole-1-carbonyl)piperidin-4-ylidene)-2-(4-(trifluoromethoxy)phenyl)acetonitrile iodide Prepared in 94% yield according to method used in the preparation of INT-4. $^1$H-NMR (400 MHz, DMSO-$d_6$): 2.59 (t, 2H), 2.91 (t, 2H), 3.57 (t, 2H), 3.74 (t, 2H), 3.92 (s, 3H), 7.49-7.55 (m, 4H), 7.87 (s, 1H), 8.03 (s, 1H), 9.57 (s, 1H).

Preparation of INT-36 and INT-38

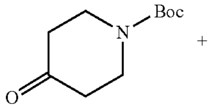

-continued

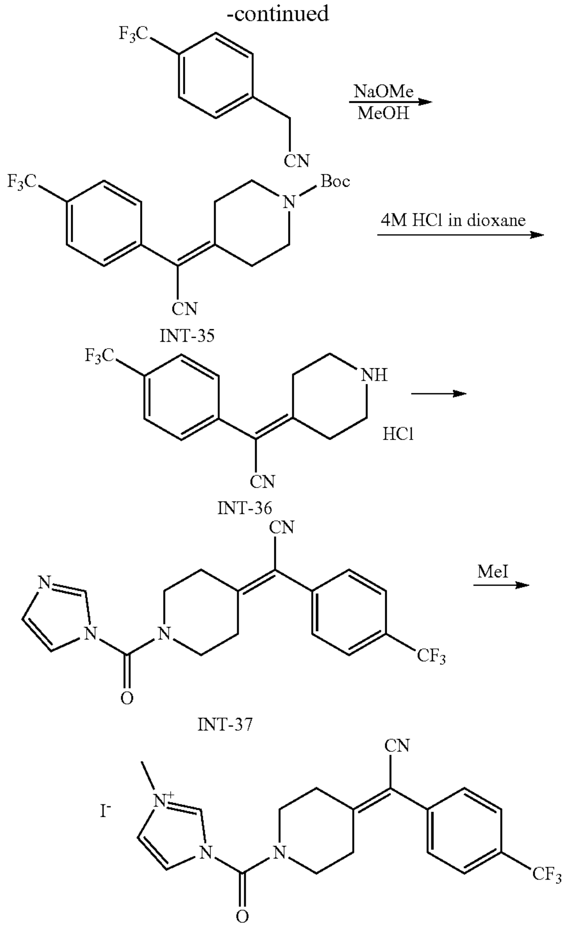

INT-35

INT-36

INT-37

INT-38

INT-35: Prepared according to General Method A to give tert-butyl 4-{cyano[4-(trifluoromethyl)phenyl]methylene}piperidine-1-carboxylate in 52% yield as a cream solid. $^1$H-NMR (400 MHz, $CDCl_3$) δ ppm 7.73-7.62 (m, 2H), 7.52-7.37 (m, 2H), 3.71-3.54 (m, 2H), 3.50-3.37 (m, 2H), 2.84-2.73 (m, 2H), 2.47-2.36 (m, 2H), 1.48 (s, 9H). $^{19}$F NMR (376 MHz, $CDCl_3$) δ ppm −62.86-−62.76 (m) (rotamers). m/z (ES+) 365.3 $(M-H)^-$.

INT-36: Prepared according to General Method B to give 2-(piperidin-4-ylidene)-2-[4-(trifluoromethyl)phenyl]acetonitrile hydrochloride in 83% yield as an off-white powder. $^1$H-NMR (400 MHz, DMSO-$d_6$) δ ppm 9.50 (s, 2H), 7.86 (d, 2H), 7.64 (d, 2H), 3.32-3.26 (m, 2H), 3.12 (t, 2H), 2.95 (t, 2H), 2.62 (t, 2H). $^{19}$F NMR (376 MHz, DMSO-$d_6$) δ ppm −61.28. m/z (ES+) 267.3 $(M+H)^+$.

INT-37: 2-(1-(1H-imidazole-1-carbonyl)piperidin-4-ylidene)-2-(4-(trifluoromethyl)phenyl)acetonitrile Prepared in 97% yield according to method used in the preparation of INT-3 in three hours reaction time. $^1$H-NMR (400 MHz, DMSO-$d_6$): 2.59 (m, 2H), 2.90 (m, 2H), 3.54 (m, 2H), 3.73 (m, 2H), 7.05 (s, 1H), 7.50 (s, 1H), 7.63 (d, 2H), 7.86 (d, 2H), 8.07 (s, 1H).

INT-38: 1-(4-(cyano(4-(trifluoromethyl)phenyl)methylene)piperidine-1-carbonyl)-3-methyl-1H-imidazol-3-ium iodide Prepared in 94% yield according to method used in the preparation of INT-4. $^1$H-NMR (400 MHz, DMSO-$d_6$): 2.62 (m, 2H), 2.93 (m, 2H), 3.57 (m, 2H), 3.75 (m, 2H), 3.92 (s, 3H), 7.64 (d, 2H), 7.87 (m, 3H), 8.03 (s, 1H), 9.57 (s, 1H).

Preparation of INT-40 and INT-42

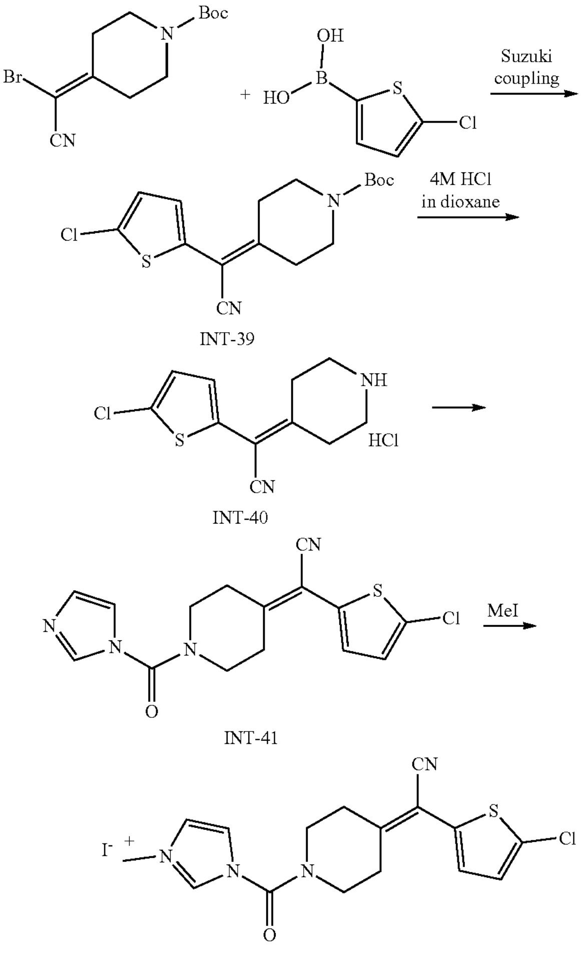

INT-39

INT-40

INT-41

INT-42

INT-39: Prepared according to General Method D to give tert-butyl 4-[(5-chlorothiophen-2-yl)(cyano)methylene]piperidine-1-carboxylate in 81% yield as an orange gum. $^1$H-NMR (400 MHz, $CDCl_3$) δ ppm 6.92 (d, 1H), 6.88 (d, 1H), 3.59 (t, 2H), 3.49 (t, 2H), 2.85-2.71 (m, 2H), 2.61 (t, 2H), 1.48 (s, 9H). m/z (ES+) 239.1/241.1 $(M-Boc+H)^+$.

INT-40: Prepared according to General Method B to give 2-(5-chlorothiophen-2-yl)-2-(piperidin-4-ylidene)acetonitrile hydrochloride in 89% yield as a fawn solid. 1H (400 MHz, DMSO-$d_6$) δ ppm 9.37 (s, 2H), 7.21 (d, 1H), 7.15 (d, 1H), 3.33-3.24 (m, 3H), 3.20-3.10 (m, 2H), 2.91 (t, 2H), 2.78 (t, 2H). m/z (ES+) 239.1/241.1 $(M+H)^+$.

INT-41: 2-(1-(1H-imidazole-1-carbonyl)piperidin-4-ylidene)-2-(5-chlorothiophen-2-yl)acetonitrile Prepared in quantitative yield according to method used in the preparation of INT-3 in four hours reaction time. $^1$H-NMR (400 MHz, DMSO-$d_6$): 2.76 (t, 2H), 2.88 (t, 2H), 3.59 (t, 2H), 3.69 (t, 2H), 7.05 (s, 1H), 7.13 (d, 1H), 7.21 (d, 1H), 7.50 (s, 1H), 8.06 (s, 1H).

INT-42: 2-(5-chlorothiophen-2-yl)-2-(1-(3-methyl-1H-3λ$^4$-imidazole-1-carbonyl)piperidin-4-ylidene) acetonitrile iodide Prepared in 90% yield according to method used in the preparation of INT-4 in 5 hours reaction time at +40° C. and overnight at room temperature. $^1$H-NMR (400 MHz, DMSO-$d_6$): 2.80 (t, 2H), 2.92 (t, 2H), 3.62 (t, 2H), 3.72 (t, 2H), 3.92 (s, 3H), 7.14 (d, 1H), 7.22 (d, 1H), 7.87 (s, 1H), 8.04 (s, 1H), 9.57 (s, 1H).

Preparation of INT-44 and INT-46

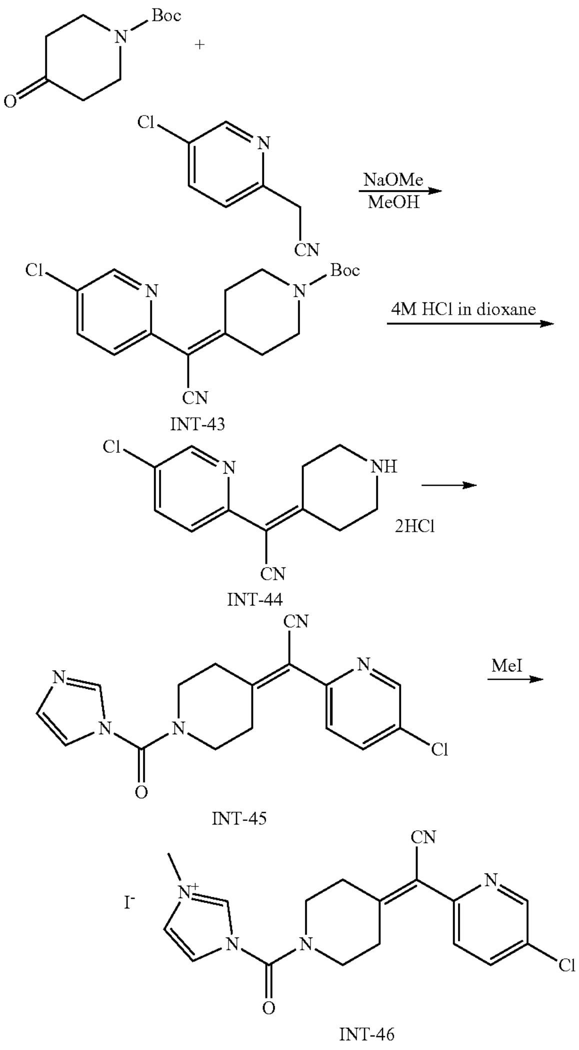

INT-43

INT-44

INT-45

INT-46

INT-43: Prepared according to General Method A to give tert-butyl 4-[(5-chloropyridin-2-yl)(cyano)methylene]piperidine-1-carboxylate in 36% yield as an orange oil. $^1$H-NMR (400 MHz, $CDCl_3$) δ ppm 8.58 (d, 1H), 7.77-7.70 (m, 1H), 7.45 (d, 1H), 3.63 (t, 2H), 3.49 (t, 2H), 2.85-2.76 (m, 4H), 1.48 (s, 9H). m/z (ES+) 334.2 $(M+H)^+$.

INT-44: Prepared according to General Method B to give 2-(5-chloropyridin-2-yl)-2-(piperidin-4-ylidene)acetonitrile dihydrochloride 84% yield as a beige solid. $^1$H-NMR (400 MHz, DMSO-$d_6$) δ ppm 9.52 (s, 2H), 8.73 (d, 1H), 8.08 (dd, 1H), 7.62 (d, 1H), 6.44 (s, 1H), 3.36-3.27 (m, 2H), 3.18-3.09 (m, 2H), 2.98 (t, 2H), 2.89 (t, 2H). m/z (ES+) 234.1 $(M+H)^+$.

INT-45: 2-(1-(1H-imidazole-1-carbonyl)piperidin-4-ylidene)-2-(5-chloropyridin-2-yl)acetonitrile Prepared in 87% yield according to method used in the preparation of INT-3. $^1$H-NMR (400 MHz, DMSO-$d_6$): 2.83 (t, 2H), 2.92 (t, 2H), 3.56 (t, 2H), 3.73 (t, 2H), 7.05 (s, 1H), 7.51 (s, 1H), 7.59 (d, 1H), 8.07 (m, 2H), 8.74 (d, 1H).

INT-46: 1-(4-((5-chloropyridin-2-yl)(cyano)methylene)piperidine-1-carbonyl)-3-methyl-1H-imidazol-3-ium iodide Prepared in 93% yield according to method used in the preparation of INT-4. $^1$H-NMR (400 MHz, DMSO-$d_6$): 2.90 (t, 2H), 2.96 (t, 2H), 3.59 (m, 2H), 3.76 (m, 2H), 3.92 (s, 3H), 7.61 (d, 1H), 7.87 (s, 1H), 8.04 (s, 1H), 8.10 (dd, 1H), 8.74 (d, 1H), 9.58 (s, 1H).

Preparation of INT-48 and INT-50

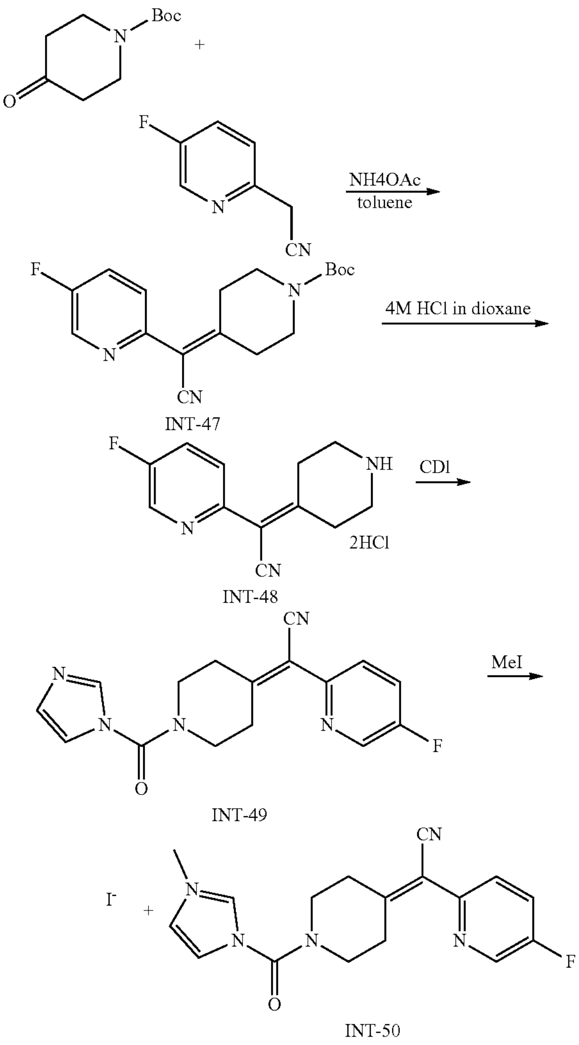

INT-47

INT-48

INT-49

INT-50

INT-47: A mixture of 2-(5-fluoropyridin-2-yl)acetonitrile (2.48 g, 100 mol-%), tert-butyl 4-oxopiperidine-1-carboxylate (3.71 g, 102 mol-%) and ammonium acetate (2.89 g, 205 mol-%) in toluene (17 mL) was heated at 100° C. for 8 h. The reaction mixture was allowed to cool, concentrated under reduced pressure and purified by column chromatography (10-50% EtOAc in hexane) to give tert-butyl 4-[cyano(5-fluoropyridin-2-yl)methylene]piperidine-1-carboxylate (3.34 g, 58%) as a yellow solid. $^{1}$H-NMR (400 MHz, $CDCl_3$) δ ppm 8.49 (d, 1H), 7.54-7.42 (m, 2H), 3.63 (t, 2H), 3.49 (t, 2H), 2.81 (t, 2H), 2.79-2.72 (m, 2H), 1.48 (s, 9H). $^{19}$F NMR (376 MHz, $CDCl_3$) δ ppm −126.18. m/z (ES+) 318.2 $(M+H)^+$.

INT-48: To a solution of INT-47 (3.63 g, 100 mol-%) in DCM (8 mL) was added 4M HCl in dioxane (11 mL), then stirred at room temperature for 1 h. Further 4M HCl in dioxane (6 mL) was added followed by DCM (5 mL) and MeOH (3 mL), and the reaction mixture stirred overnight. The solvent was removed under reduced pressure, the residue dissolved in a small quantity of MeOH and diluted with MTBE. The precipitate formed was collected and dried to give 2-(5-fluoropyridin-2-yl)-2-(piperidin-4-ylidene)acetonitrile dihydrochloride (2.96 g, 89%) as a pale orange solid. $^{1}$H-NMR (400 MHz, DMSO-$d_6$) δ ppm 9.55 (s, 1H), 8.69 (d, 1H), 7.88 (td, 1H), 7.66 (dd, 1H), 7.35 (s, 1H), 3.35-3.26 (m, 2H), 3.15-3.11 (m, 2H), 2.97 (t, 2H), 2.86 (t, 2H). $^{19}$F NMR (376 MHz, DMSO) δ ppm −126.38. m/z (ES+) 218.2 $(M+H)^+$.

INT-49: 2-(1-(1H-imidazole-1-carbonyl)piperidin-4-ylidene)-2-(5-fluoropyridin-2-yl)acetonitrile Prepared in 71% yield according to method used in the preparation of INT-3. $^{1}$H-NMR (400 MHz, DMSO-$d_6$): δ ppm 2.80 (m, 2H), 2.92 (m, 2H), 3.56 (m, 2H), 3.73 (m, 2H), 7.05 (s, 1H), 7.51 (s, 1H), 7.63 (d, 1H), 7.87 (d, 1H), 8.07 (s, 1H), 8.69 (s, 1H).

INT-50: 2-(5-fluoropyridin-2-yl)-2-(1-(3-methyl-1H-3λ$^4$-imidazole-1-carbonyl)piperidin-4-ylidene)acetonitrile iodide Prepared in 86% yield according to method used in the preparation of INT-4 in three hours reaction time. $^{1}$H-NMR (400 MHz, DMSO-$d_6$): δ ppm 2.86 (m, 2H), 2.95 (m, 2H), 3.59 (m, 2H), 3.76 (m, 2H), 3.92 (s, 3H), 7.76 (m, 1H), 7.90 (m, 2H), 8.04 (s, 1H), 8.70 (d, 1H), 9.58 (s, 1H).

Preparation of INT-53 and INT-55

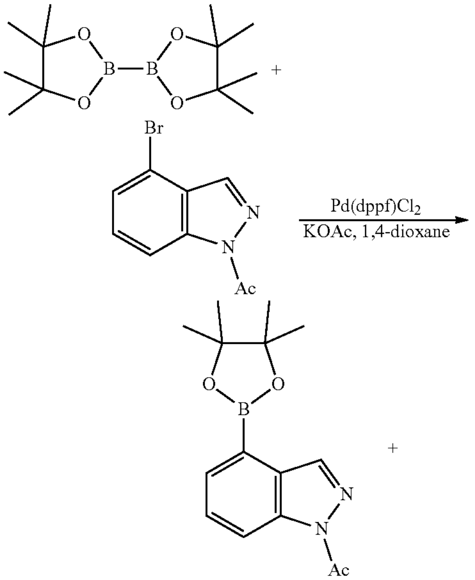

INT-51

-continued

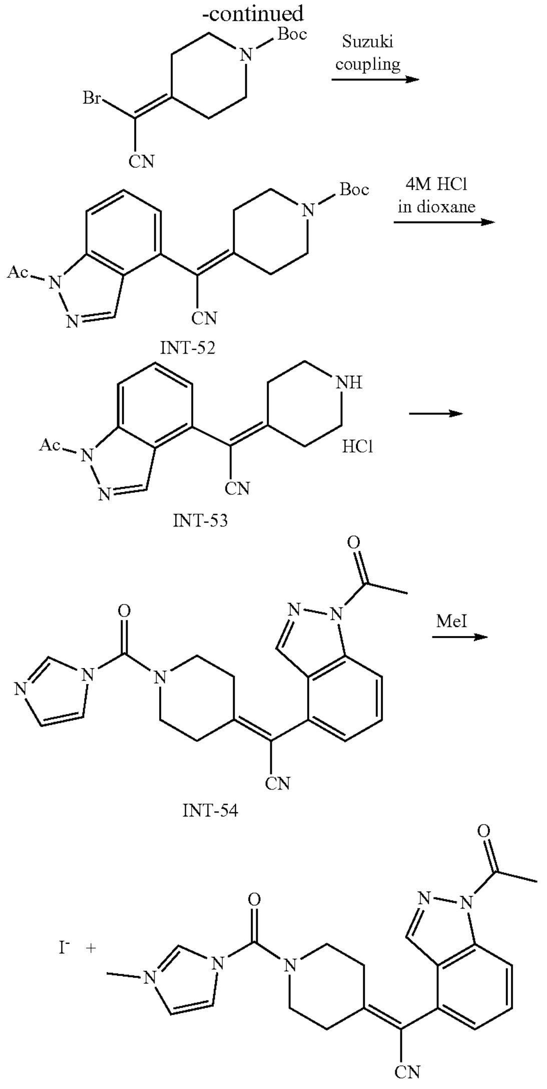

INT-52

INT-53

INT-54

INT-55

INT-51: Prepared according to General Method E to give 1-[4-(4,4,5,5-tetramethyl-1,3,2-dioxaborolan-2-yl)-1H-indazol-1-yl]ethan-1-one in 57% yield as an off-white powder. $^{1}$H-NMR (400 MHz, $CDCl_3$): δ ppm 8.59-8.51 (m, 2H), 7.82 (d, 1H), 7.53 (t, 1H), 2.78 (s, 3H), 1.43 (s, 12H).

INT-52: Prepared according to General Method D to give tert-butyl 4-[(1-acetyl-1H-indazol-4-yl)(cyano)methylene]piperidine-1-carboxylate in 84% yield as an off-white foam. $^{1}$H-NMR (400 MHz, $CDCl_3$): δ ppm 8.50 (d, 1H), 8.14 (s, 1H), 7.59 (dd, 1H), 7.22 (d, 1H), 3.68 (t, 2H), 3.41 (t, 2H), 2.87 (t, 2H), 2.81 (s, 3H), 2.33 (t, 2H), 1.48 (s, 9H). m/z (ES+) 281.2 $(M-Boc+H)^+$.

INT-53: Prepared according to General Method B to give 2-(1-acetyl-1H-indazol-4-yl)-2-(piperidin-4-ylidene)acetonitrile hydrochloride in 93% yield as a colourless solid. $^{1}$H-NMR (400 MHz, DMSO-$d_6$) δ ppm 9.25 (s, 2H), 8.57 (d, 1H), 8.40 (d, 1H), 7.73 (dd, 1H), 7.43 (dd, 1H), 3.39 (t, 2H), 3.09 (t, 2H), 3.01 (t, 2H), 2.75 (s, 3H), 2.46 (t, 2H). m/z (ES+) 281.1 $(M+H)^+$.

INT-54: 2-(1-(1H-imidazole-1-carbonyl)piperidin-4-ylidene)-2-(1-acetyl-1H-indazol-4-yl)acetonitrile Prepared in 83% yield according to method used in the preparation of INT-3 in three hours reaction time. $^{1}$H-NMR (400 MHz, DMSO-$d_6$): 2.43 (t, 2H), 2.75 (s, 3H), 2.96 (t, 2H), 3.50 (t, 2H), 3.80 (t, 2H), 7.05 (s, 1H), 7.42 (d, 1H), 7.50 (s, 1H), 7.70-7.76 (m, 1H), 8.06 (s, 1H), 8.39 (d, 1H), 8.53 (s, 1H).

INT-55: 2-(1-acetyl-1H-indazol-4-yl)-2-(1-(3-methyl-1H-3λ$^4$-imidazole-1-carbonyl)piperidin-4-ylidene)acetonitrile iodide Prepared in 91% yield according to method used in the preparation of INT-4 in seven hours reaction time at +40° C. and overnight at room temperature. $^1$H-NMR (400 MHz, DMSO-$d_6$): 2.46 (t, 2H), 2.75 (s, 3H), 3.00 (t, 2H), 3.53 (t, 2H), 3.83 (t, 2H), 3.92 (s, 3H), 7.43 (d, 1H), 7.70-7.80 (m, 1H), 7.86 (s, 1H), 8.03 (s, 1H), 8.40 (d, 1H), 8.54 (s, 1H), 9.58 (s, 1H).

Preparation of INT-59 and INT-61

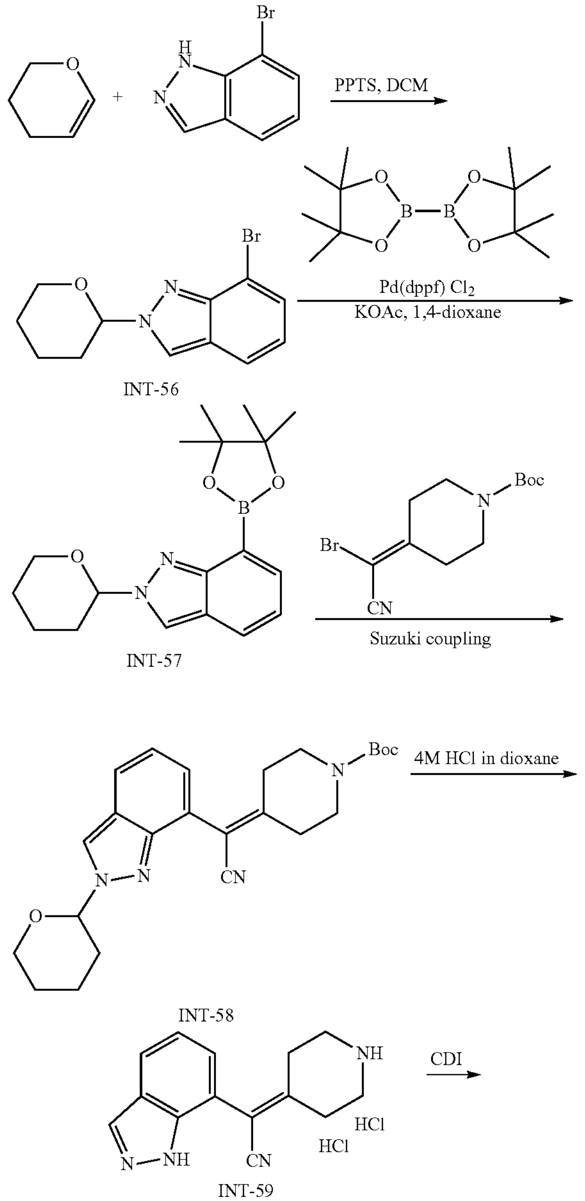

INT-56

INT-57

INT-58

INT-59

-continued

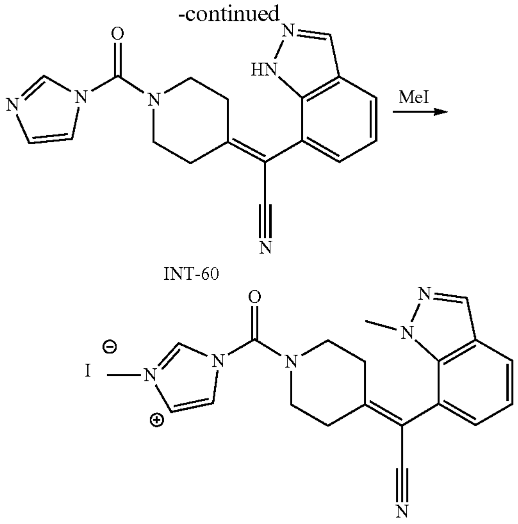

INT-60

INT-61

INT-56: A solution of 7-bromo-1H-indazole (1.31 g, 100 mol-%), 3,4-dihydro-2H-pyran (1.2 mL, 200 mol-%) and pyridinium p-toluenesulfonate (0.17 g, 100 mol-%) in DCM (5 ml) was stirred for 16 h at room temperature. The reaction mixture was concentrated under reduced pressure, water was added (50 mL) and the mixture was extracted with EtOAc (3×50 mL). The combined organic layers were dried with sodium sulphate, concentrated under reduced pressure and purified by column chromatography (3-40% EtOAc in hexanes) to give 7-bromo-1-(tetrahydro-2H-pyran-2-yl)-1H-indazole (27%) as an off-white solid and 7-bromo-2-(tetrahydro-2H-pyran-2-yl)-2H-indazole (71%) as a colourless oil, both of which were used in the subsequent step without purification.

7-bromo-1-(tetrahydro-2H-pyran-2-yl)-1H-indazole: $^1$H-NMR (400 MHz, $CDCl_3$) δ ppm 8.05 (s, 1H), 7.68 (dd, 1H), 7.59 (dd, 1H), 7.02 (t, 1H), 6.53 (dd, 1H), 4.11-3.98 (m, 1H), 3.90-3.74 (m, 1H), 2.80-2.58 (m, 1H), 2.25-2.07 (m, 2H), 1.90-1.57 (m, 3H). m/z (ES+) 281.1/283.1 $(M+H)^+$.

7-bromo-2-(tetrahydro-2H-pyran-2-yl)-2H-indazole: $^1$H-NMR (400 MHz, $CDCl_3$) δ ppm 8.27 (s, 1H), 7.63 (dd, 1H), 7.50 (dd, 1H), 6.93 (dd, 1H), 5.77 (dd, 1H), 4.23-4.07 (m, 1H), 3.84-3.70 (m, 1H), 2.36-2.24 (m, 1H), 2.14-1.94 (m, 2H), 1.95-1.38 (m, 3H). m/z (ES+) 281.1/283.1 $(M+H)^+$.

INT-57: Prepared according to General Method E to give 2-(tetrahydro-2H-pyran-2-yl)-7-(4,4,5,5-tetramethyl-1,3,2-dioxaborolan-2-yl)-2H-indazole) in 76% yield as a yellow solid which was used in the subsequent step without purification. $^1$H-NMR (400 MHz, $CDCl_3$) δ ppm 8.18 (s, 1H), 7.82 (dd, 1H), 7.77 (dd, 1H), 7.07 (dd, 1H), 5.82 (dd, 1H), 4.21-4.07 (m, 1H), 3.83-3.72 (m, 1H), 2.32-2.19 (m, 1H), 2.12-2.01 (m, 2H), 1.86-1.57 (m, 3H), 1.41 (s, 12H).

INT-58: Prepared according to General Method D to give tert-butyl 4-{cyano[2-(tetrahydro-2H-pyran-2-yl)-2H-indazol-7-yl]methylene}piperidine-1-carboxylate) in 74% yield as an orange gum. $^1$H-NMR (400 MHz, $CDCl_3$) δ ppm 8.22 (s, 1H), 7.70 (dd, 1H), 7.21 (d, 1H), 7.09 (dd, 1H), 5.70 (dd, 1H), 4.16-4.08 (m, 1H), 3.82-3.72 (m, 1H), 3.71-3.63 (m, 2H), 3.46 (t, 2H), 2.85 (t, 2H), 2.32 (t, 2H), 2.26-2.20 (m, 1H), 2.15-2.05 (m, 2H), 1.82-1.63 (m, 3H), 1.23 (s, 9H). m/z (ES+) 423.4 $(M+H)^+$.

INT-59: To a stirred solution of INT-58 (623 mg, 100 mol-%) in DCM (2 mL) at 0° C. was added 4M HCl in dioxane (1.3 mL, 384 mol-%) After 10 min, MeOH (1.5 mL)

was added and the mixture was stirred at 20° C. for 18 h. MTBE was added and the solid was filtered and dried to give 2-(1H-indazol-7-yl)-2-(piperidin-4-ylidene)acetonitrile dihydrochloride (284 mg, 69%) as an off-white powder. $^1$H-NMR (400 MHz, DMSO-$d_6$) δ ppm 9.49 (s, 2H), 8.20 (s, 1H), 7.87 (dd, 1H), 7.33 (dd, 1H), 7.21 (dd, 1H), 7.13-6.04 (bs, 2H), 3.43-3.30 (m, 2H), 3.11-3.03 (m, 2H), 3.03-2.96 (m, 2H), 2.34 (t, 2H). m/z (ES+) 239.2 $(M+H)^+$.

INT-60: 2-(1-(1H-imidazole-1-carbonyl)piperidin-4-ylidene)-2-(1H-indazol-7-yl)acetonitrile Prepared in 96% yield according to method used in the preparation of INT-3. $^1$H-NMR (400 MHz, DMSO-$d_6$): 2.30 (t, 2H), 2.93 (t, 2H), 3.49 (t, 2H), 3.79 (t, 2H), 7.04 (s, 1H), 7.21 (t, 1H), 7.31 (d, 1H), 7.49 (s, 1H), 7.86 (d, 1H), 8.06 (s, 1H), 8.20 (s, 1H), 13.29 (s, 1H).

INT-61: 1-(4-(cyano(1-methyl-1H-indazol-7-yl)methylene)piperidine-1-carbonyl)-3-methyl-1H-3λ$^4$-imidazol-1-ium iodide Prepared in 98% yield according to method used in the preparation of INT-4. $^1$H-NMR (400 MHz, DMSO-$d_6$): 2.46 (t, 2H), 2.97 (t, 2H), 3.57 (m, 2H), 3.77 (m, 2H), 3.92 (s, 3H), 4.20 (s, 3H), 7.12 (t, 1H), 7.22 (m, 1H), 7.81 (d, 1H), 7.86 (m, 1H), 8.04 (m, 1H), 8.47 (s, 1H), 9.57 (s, 1H).

Preparation of INT-63

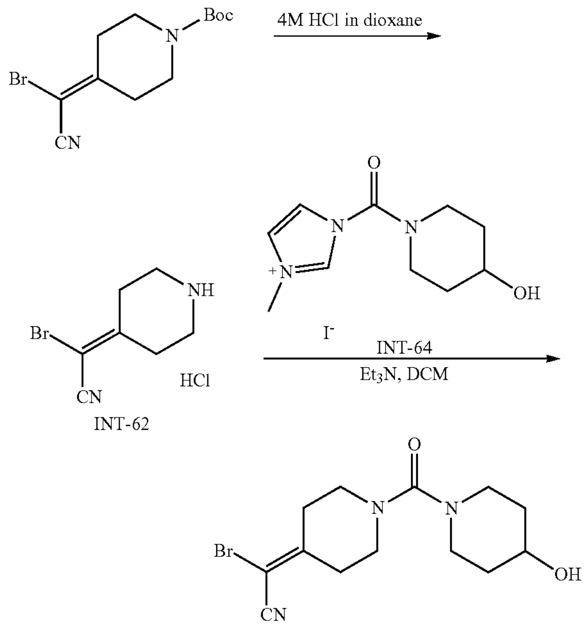

INT-62

INT-63

INT-62: Prepared according to General Method C to give 2-bromo-2-(piperidin-4-ylidene)acetonitrile hydrochloride in 87% yield as a colourless powder. $^1$H-NMR (400 MHz, DMSO-$d_6$) δ ppm 9.40 (s, 2H), 3.20 (dt, 4H), 2.82 (t, 2H), 2.74 (t, 2H). m/z (ES+) 203.0/205.0 $(M+H)^+$.

INT-63: Prepared from INT-62 and INT-64 according to method used in the preparation of compound 3 to give 2-bromo-2-[1-(4-hydroxypiperidine-1-carbonyl)piperidin-4-ylidene]acetonitrile in 50% yield as a brown solid. $^1$H-NMR (400 MHz, $CDCl_3$) δ ppm 3.93-3.83 (m, 1H), 3.59 (dt, 2H), 3.38-3.30 (m, 4H), 3.02 (ddd, 2H), 2.72-2.65 (m, 2H), 2.63-2.55 (m, 2H), 1.95-1.85 (m, 2H), 1.57-1.47 (m, 2H). m/z (ES+) 328.0/330.0 $(M+H)^+$.

INT-64: 1-(4-hydroxypiperidine-1-carbonyl)-3-methyl-1H-imidazol-3-ium iodide

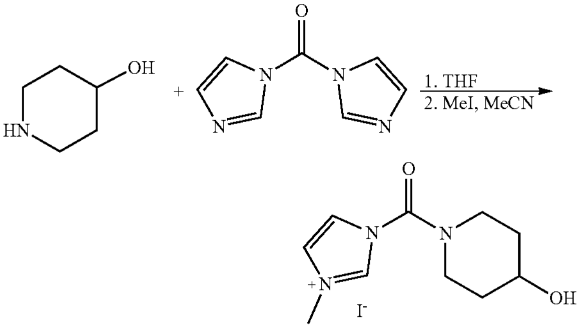

INT-64

A stirred solution of piperidin-4-ol (2.00 g, 100 mol-%) and carbonyl diimidazole (3.21 g, 100 mol-%) in THE (25 mL) was heated under reflux for 18 h, then allowed to cool. The solvent was concentrated under reduced pressure to give 1-(1H-imidazole-1-carbonyl)piperidin-4-ol as a colourless, viscous oil (5.23 g). This intermediate was dissolved in MeCN (20 mL), iodomethane (2.5 mL, 400 mol-%) was added and the reaction mixture stirred in a sealed vessel for 24 h. The volatiles were concentrated under reduced pressure to give 1-(4-hydroxypiperidine-1-carbonyl)-3-methyl-1H-imidazol-3-ium iodide (5.40 g) as an orange oil which was used in the subsequent step without purification. m/z (ES+) 210 $M^+$.

Compound 1

2-(4-fluorophenyl)-2-(1-(morpholine-4-carbonyl)piperidin-4-ylidene)acetonitrile

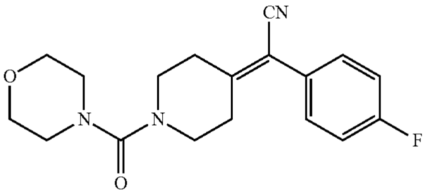 [SMILES: N#CC(=C1CCN(C(=O)N2CCOCC2)CC1)c1ccc(F)cc1]

INT-2 (50.0 mg, 100 mol-%) was dissolved in dry dichloromethane (DCM) (2 ml). 4-Morpholinecarbonyl chloride (26 μl, 110 mol-%) and triethylamine (83 μl, 300 mol-%) were added. Stirred at room temperature under nitrogen for 3 hours. The reaction mixture was diluted with DCM (5 mL) and washed with 0.25 N HCl (3x5 mL), 0.1 N NaOH (3x5 mL), water (3x5 mL) and brine (3x5 mL). Dried over sodium sulphate. The crude product was purified by trituration with heptane. The yield was 80%. $^1$H-NMR (400 MHz, DMSO-$d_6$): 2.38 (t, 2H), 2.70 (t, 2H), 3.16 (m, 4H), 3.21 (t, 2H), 3.38 (t, 2H), 3.57 (m, 4H), 7.29-7.33 (m, 2H), 7.39-7.43 (m, 2H).

Compound 2

2-(4-chlorophenyl)-2-(1-(morpholine-4-carbonyl) piperidin-4-ylidene)acetonitrile

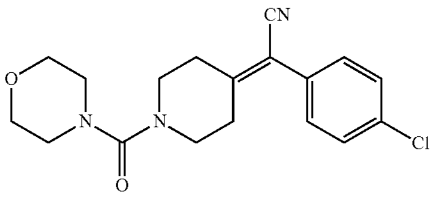 [SMILES: N#CC(=C1CCN(C(=O)N2CCOCC2)CC1)c1ccc(Cl)cc1]

Compound 2 was synthesized in 81% yield by the method used in the preparation of the compound 1 by using INT-6 and 4-morpholinecarbonyl chloride as starting materials in four hours reaction time. $^1$H-NMR (400 MHz, DMSO-$d_6$): 2.40 (t, 2H), 2.70 (t, 2H), 3.16 (m, 4H), 3.22 (t, 2H), 3.39 (t, 2H), 3.57 (m, 4H), 7.38-7.40 (m, 2H), 7.53-7.55 (m, 2H).

Compound 3

2-(4-fluorophenyl)-2-(1-(piperidine-1-carbonyl)piperidin-4-ylidene)acetonitrile

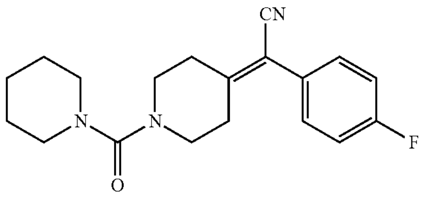 [SMILES: N#CC(=C1CCN(C(=O)N2CCCCC2)CC1)c1ccc(F)cc1]

INT-4 (70 mg, 100 mol-%) was dissolved in dry DCM (2 mL). Piperidine (19 µl, 120 mol-%) and triethylamine (43 µl, 200 mol-%) were added. Stirred at room temperature under nitrogen for 3 hours. The reaction mixture was diluted with DCM (8 mL) and washed with water (1×5 mL), 0.5 N HCl (2×5 mL), water (1×5 mL), and brine (1×10 mL). Dried over sodium sulphate followed by purification by chromatography yielding the product 19 mg. $^1$H-NMR (400 MHz, DMSO-$d_6$): 1.47 (m, 6H), 2.38 (m, 2H), 2.68 (m, 2H), 3.13 (m, 6H), 3.35 (m, 2H), 7.30 (m, 2H), 7.40 (m, 2H).

Compound 4

2-(4-fluorophenyl)-2-(1-(4-hydroxypiperidine-1-carbonyl)piperidin-4-ylidene)acetonitrile

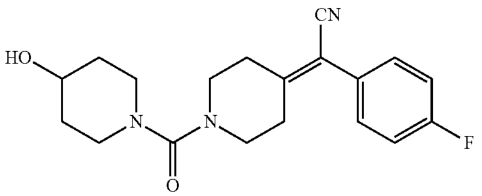 [SMILES: N#CC(=C1CCN(C(=O)N2CCC(O)CC2)CC1)c1ccc(F)cc1]

Compound 4 was synthesized by the method used in the preparation of the compound 3 in 59% yield by using INT-4 and piperidin-4-ol as starting materials in 3 hours reaction time. $^1$H-NMR (400 MHz, DMSO-$d_6$): 1.33 (m, 2H), 1.72 (m, 2H), 2.38 (s, 2H), 2.69 (s, 2H), 2.88 (m, 2H), 3.18 (s, 2H), 3.45 (m, 4H), 3.62 (s, 1H), 4.70 (s, 1H), 7.30 (m, 2H), 7.41 (m, 2H).

Compound 5

4-(cyano(4-fluorophenyl)methylene)-N,N-diethylpiperidine-1-carboxamide

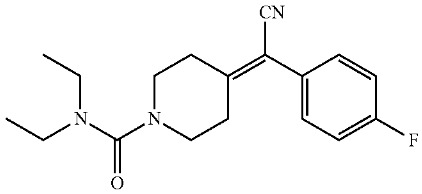 [SMILES: CCN(CC)C(=O)N1CCC(=C(C#N)c2ccc(F)cc2)CC1]

Compound 5 was synthesized in 59% yield by the method used in the preparation of the compound 3 by using INT-4 and diethylamine as starting materials in 3 hours reaction time. $^1$H-NMR (400 MHz, DMSO-$d_6$): 1.05 (m, 6H), 2.37 (m, 2H), 2.70 (m, 2H), 3.14 (m, 6H), 3.30 (m, 2H), 7.31 (m, 2H), 7.41 (m, 2H).

Compound 6

2-(4-fluorophenyl)-2-(1-(pyrrolidine-1-carbonyl) piperidin-4-ylidene)acetonitrile

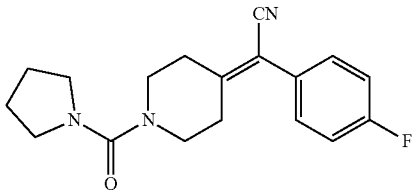 [SMILES: N#CC(=C1CCN(C(=O)N2CCCC2)CC1)c1ccc(F)cc1]

Compound 6 was synthesized by the method used in the preparation of the compound 3 in quantitative yield by using INT-4 and pyrrolidine as starting materials in one hours reaction time. $^1$H-NMR (400 MHz, DMSO-$d_6$): 1.75 (m, 4H), 2.38 (m, 2H), 2.69 (m, 2H), 3.22 (m, 2H), 3.28 (m, 4H), 3.39 (m, 2H), 7.31 (m, 2H), 7.41 (m, 2H).

Compound 7

(R)-2-(4-fluorophenyl)-2-(1-(3-methoxypyrrolidine-1-carbonyl)piperidin-4-ylidene)acetonitrile

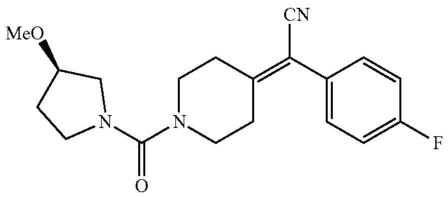 [SMILES: CO[C@@H]1CCN(C(=O)N2CCC(=C(C#N)c3ccc(F)cc3)CC2)C1]

Compound 7 was synthesized by the method used in the preparation of the compound 3 in 64% yield by using INT-4 and (3R)-3-methoxypyrrolidine hydrochloride as starting materials. $^1$H-NMR (400 MHz, DMSO-$d_6$): 1.78-1.93 (m, 2H), 2.37 (s, 2H), 2.67 (s, 2H), 3.18-3.49 (m, 11H), 3.90 (m, 1H), 7.31 (m, 2H), 7.41 (m, 2H).

Compound 8

(S)-2-(4-fluorophenyl)-2-(1-(2-(methoxymethyl) pyrrolidine-1-carbonyl)piperidin-4-ylidene)acetonitrile

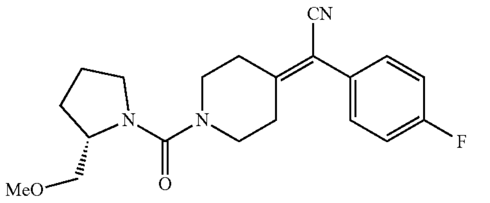 [SMILES: COC[C@@H]1CCCN1C(=O)N1CCC(=C(C#N)c2ccc(F)cc2)CC1]

Compound 8 was synthesized by the method used in the preparation of the compound 3 in 73% yield by using INT-4 and (S)-(+)-2-(methoxymethyl)pyrrolidine as starting materials. $^1$H-NMR (400 MHz, DMSO-$d_6$): 1.61-1.68 (m, 2H), 1.85 (m, 1H), 1.99 (m, 1H), 2.30 (m, 1H), 2.46 (m, 1H), 2.59 (m, 1H), 2.76 (m, 1H), 3.16 (m, 2H), 3.23 (s, 3H), 3.28-3.46 (m, 6H), 4.06 (m, 1H), 7.30 (dd, 2H), 7.41 (dd, 2H).

Compound 9

(S)-2-(4-fluorophenyl)-2-(1-(3-hydroxypyrrolidine-1-carbonyl)piperidin-4-ylidene)acetonitrile

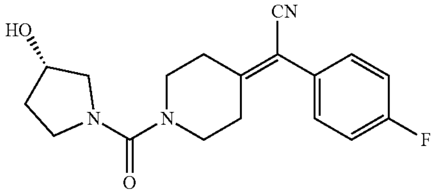 [SMILES: N#CC(=C1CCN(C(=O)N2CC[C@H](O)C2)CC1)c1ccc(F)cc1]

Compound 9 was synthesized by the method used in the preparation of the compound 3 in 79% yield by using INT-4 and (S)-3-hydroxypyrrolidine as starting materials. $^1$H-NMR (400 MHz, DMSO-$d_6$): 1.72 (m, 1H), 1.82 (m, 1H), 2.37 (m, 2H), 2.69 (m, 2H), 3.08 (d, 1H), 3.19-3.28 (m, 3H), 3.38-3.51 (m, 5H), 4.21 (d, 1H), 7.30 (dd, 2H), 7.41 (dd, 2H).

Compound 10

2-(3,5-difluorophenyl)-2-(1-(piperidine-1-carbonyl) piperidin-4-ylidene)acetonitrile

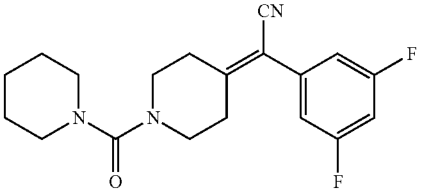 [SMILES: N#CC(=C1CCN(C(=O)N2CCCCC2)CC1)c1cc(F)cc(F)c1]

INT-10 (50 mg, 100 mol-%) was dissolved in tetrahydrofuran (THF) (3 ml) and water (1 ml). 3,5-Difluorophenylboronic acid (40 mg, 150 mol-%), $Cs_2CO_3$ (157 mg, 300 mol-%) ja Pd(dppf)$Cl_2$ (12 mg, 10 mol-%) were added. Stirred at 90° C. under nitrogen for 1.5 hours. The solvent was evaporated and ethyl acetate (10 ml) added. The reaction mixture was washed with water (2×5 ml) and brine (1×5 ml) and dried over sodium sulphate. The yield was 35% after chromatographic purification and trituration with heptane. $^1$H-NMR (400 MHz, DMSO-$d_6$): 1.47 (m, 4H), 1.53 (m, 2H), 2.40 (t, 2H), 2.69 (t, 2H), 3.13 (m, 4H), 3.19 (t, 2H), 3.33 (m, 2H), 7.13-7.19 (m, 2H), 7.30-7.38 (m, 1H).

Compound 11

2-(4-fluorophenyl)-2-(1-(isoindoline-2-carbonyl) piperidin-4-ylidene)acetonitrile

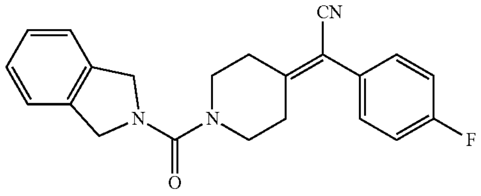 [SMILES: N#CC(=C1CCN(C(=O)N2Cc3ccccc3C2)CC1)c1ccc(F)cc1]

Compound 11 was synthesized by the method used in the preparation of the compound 3 in 80% yield by using INT-4 and isoindoline as starting materials, the crude product was purified by trituration with methanol. $^1$H-NMR (400 MHz, $CDCl_3$): 2.54 (m, 2H), 2.88 (m, 2H), 3.36 (m, 2H), 3.56 (m, 2H), 4.81 (s, 4H), 7.12 (dd, 2H), 7.26 (m, 6H). $^1$H-NMR (400 MHz, DMSO-$d_6$): 2.40 (s, 2H), 2.77 (s, 2H), 3.30 (s, 2H), 3.49 (s, 2H), 4.74 (s, 4H), 7.32 (br s, 6H), 7.43 (s, 2H).

Compound 12

2-(4-fluorophenyl)-2-(1-(4,5,6,7-tetrahydroisoxazolo [4,3-c]pyridine-5-carbonyl)piperidin-4-ylidene)acetonitrile

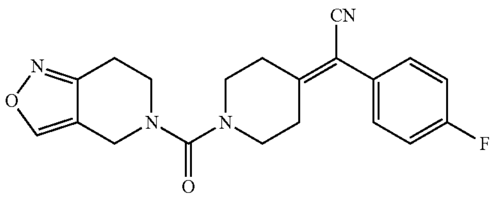 [SMILES: N#CC(=C1CCN(C(=O)N2CCc3nocc3C2)CC1)c1ccc(F)cc1]

Compound 12 was synthesized by the method used in the preparation of the compound 3 in 71% yield by using INT-4 and 4,5,6,7-tetrahydroisoxazolo[4,3-c]pyridine×HCl (150 mol-%) as starting materials, the crude product was purified by trituration with a mixture of DCM and heptane. $^1$H-NMR (400 MHz, DMSO-$d_6$): 2.41 (s, 2H), 2.72 (s, 2H), 2.86 (s, 2H), 3.25 (s, 2H), 3.44 (s, 4H), 4.30 (s, 2H), 7.31 (m, 2H), 7.41 (s, 2H), 8.67 (s, 1H).

Compound 13

2-(4-fluorophenyl)-2-(1-(4,5,6,7-tetrahydro-[1,2,3]triazolo[1,5-a]pyrazine-5-carbonyl)piperidin-4-ylidene)acetonitrile

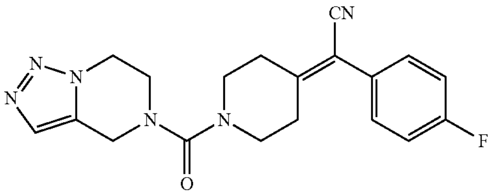 [SMILES: N#CC(=C1CCN(C(=O)N2CCn3nncc3C2)CC1)c1ccc(F)cc1]

Compound 13 was synthesized by the method used in the preparation of the compound 3 in 59% yield by using INT-4 and 4,5,6,7-tetrahydro-1,2,3-triazolo[1,5-a]pyrazine (150 mol-%) as starting materials in 3 hours reaction time, the crude product was purified by trituration with a mixture of DCM and heptane. $^{1}$H-NMR (400 MHz, DMSO-$d_6$): 2.43 (s, 3H), 2.73 (s, 2H), 3.47 (s, 3H), 3.67 (s, 2H), 4.43 (s, 2H), 4.53 (s, 2H), 7.32 (s, 2H), 7.41 (s, 2H), 7.59 (s, 1H).

Compound 14

4-(cyano(4-fluorophenyl)methylene)-N-methyl-N-(tetrahydro-2H-pyran-4-yl)piperidine-1-carboxamide

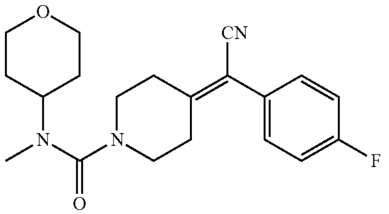 [SMILES: CN(C(=O)N1CCC(=C(C#N)c2ccc(F)cc2)CC1)C1CCOCC1]

Compound 14 was synthesized by the method used in the preparation of the compound 3 in 44% yield by using INT-4 and methyl-(tetrahydro-pyran-4-yl)-amine HCl (150 mol-%) as starting materials in 3 hours reaction time, the crude product was purified by chromatography. $^{1}$H-NMR (400 MHz, DMSO-$d_6$): 0.86 (t, 1H), 1.24 (m, 2H), 1.53 (d, 2H), 1.73 (m, 2H), 2.39 (t, 2H), 2.69 (s, 3H), 2.72 (s, 1H), 3.15 (t, 2H), 3.31 (m, 1H), 3.36 (s, 1H), 3.73 (m, 1H), 3.90 (m, 2H), 7.30 (dd, 2H), 7.40 (m, 2H).

Compound 15

2-(1-(3-oxa-8-azabicyclo[3.2.1]octane-8-carbonyl)piperidin-4-ylidene)-2-(4-fluorophenyl)acetonitrile

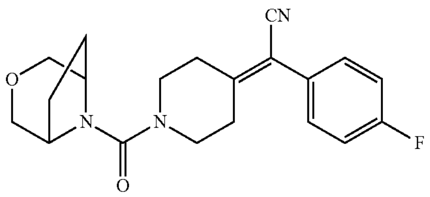 [SMILES: N#CC(=C1CCN(C(=O)N2C3CCC2COC3)CC1)c1ccc(F)cc1]

Compound 15 was synthesized by the method used in the preparation of the compound 3 in 83% yield by using INT-4 and 3-oxa-8-azabicyclo[3.2.1]octane, HCl (150 mol-%) as starting materials in 1.5 hours reaction time, the crude product was purified by trituration with heptane. $^{1}$H-NMR (400 MHz, DMSO-$d_6$): 1.72-1.80 (m, 4H), 2.39 (t, 2H), 2.70 (t, 2H), 3.33 (m, 2H), 3.48-3.51 (m, 4H), 3.60 (s, 1H), 3.63 (s, 1H), 3.84 (br s, 2H), 7.31 (m, 2H), 7.41 (m, 2H).

Compound 16

4-(cyano(4-fluorophenyl)methylene)-N,N-dimethylpiperidine-1-carboxamide

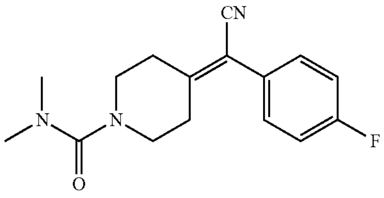 [SMILES: CN(C)C(=O)N1CCC(=C(C#N)c2ccc(F)cc2)CC1]

Compound 16 was synthesized by the method used in the preparation of the compound 3 in 97% yield by using INT-4 and dimethylamine hydrochloride (200 mol-%) as starting materials in 1.5 hours reaction time, the crude product was purified by trituration with heptane. $^{1}$H-NMR (400 MHz, DMSO-$d_6$): 2.38 (t, 2H), 2.69 (t, 2H), 3.16 (t, 2H), 3.33 (s, 2H), 2.75 (s, 6H), 7.30 (m, 2H), 7.40 (m, 2H).

Compound 17

2-(3-chlorophenyl)-2-(1-(4-methoxypiperidine-1-carbonyl)piperidin-4-ylidene)acetonitrile

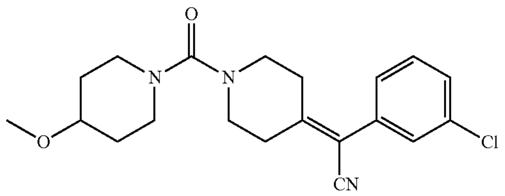 [SMILES: COC1CCN(C(=O)N2CCC(=C(C#N)c3cccc(Cl)c3)CC2)CC1]

Compound 17 was synthesized as clear oil by the method used in the preparation of the compound 3 in 99% yield by using INT-30 and 4-methoxypiperidine (150 mol-%) as starting materials in two hours reaction time. $^{1}$H-NMR (400 MHz, DMSO-$d_6$): 1.38 (t, 2H), 1.82 (m, 2H), 2.39 (t, 2H), 2.69 (t, 2H), 2.93 (t, 2H), 3.19 (t, 2H), 3.24 (s, 3H), 3.31-3.42 (m, 5H), 7.33 (m, 1H), 7.44 (s, 1H), 7.50 (m, 2H).

Compound 18

2-(4-chlorophenyl)-2-(1-(4-hydroxypiperidine-1-carbonyl)piperidin-4-ylidene)acetonitrile

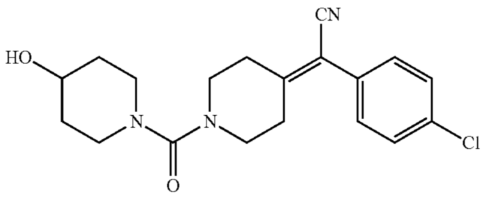 [SMILES: N#CC(=C1CCN(C(=O)N2CCC(O)CC2)CC1)c1ccc(Cl)cc1]

Compound 18 was synthesized in 96% yield as a white solid by the method used in the preparation of the compound 3 with 400 mol-% of triethylamine, by using INT-8 and piperidin-4-ol (150 mol-%) as starting materials in 90 minutes reaction time at room temperature, the crude product was purified by trituration with heptane:DCM (v/v 5:0.5). $^1$H-NMR (400 MHz, DMSO-$d_6$): 1.33 (m, 2H), 1.71 (m, 2H), 2.39 (dd, 2H), 2.69 (dd, 2H), 2.88 (dd, 2H), 3.18 (dd, 2H), 3.35 (s, 2H), 3.44 (m, 2H), 3.61 (m, 1H), 4.69 (d, 1H), 7.39 (d, 2H), 7.54 (d, 2H).

Compound 19

2-(4-fluorophenyl)-2-(1-(4-(hydroxymethyl)piperidine-1-carbonyl)piperidin-4-ylidene)acetonitrile

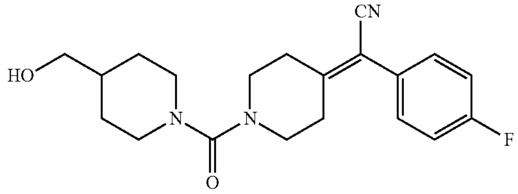 [SMILES: N#CC(=C1CCN(C(=O)N2CCC(CO)CC2)CC1)c1ccc(F)cc1]

Compound 19 was synthesized by the method used in the preparation of the compound 3 in 75% yield by using INT-4 and piperidin-4-ylmethanol as starting materials in 3 hours reaction time. $^1$H-NMR (400 MHz, DMSO-$d_6$): 1.03-1.11 (m, 2H), 1.52 (m, 1H), 1.60-1.66 (m, 2H), 2.38 (t, 2H), 2.69-2.74 (m, 4H), 3.17 (t, 2H), 3.25 (t, 2H), 3.33 (m, 2H), 3.59-3.63 (m, 2H), 4.47 (s, 1H), 7.30 (m, 2H), 7.41 (m, 2H).

Compound 20

2-(1-(4-ethoxypiperidine-1-carbonyl)piperidin-4-ylidene)-2-(4-fluorophenyl)acetonitrile

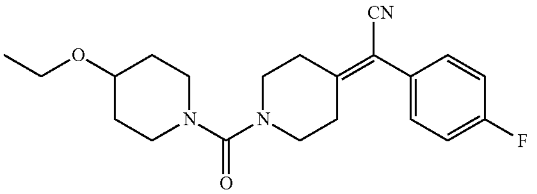 [SMILES: CCOC1CCN(C(=O)N2CCC(=C(C#N)c3ccc(F)cc3)CC2)CC1]

Compound 20 was synthesized by the method used in the preparation of the compound 3 in 56% yield by using INT-4 and 4-ethoxypiperidine as starting materials in two hours reaction time. $^1$H-NMR (400 MHz, DMSO-$d_6$): 1.10 (t, 3H), 1.33-1.40 (m, 2H), 1.80-1.82 (m, 2H), 2.37 (t, 2H), 2.68 (t, 2H), 2.88-2.93 (m, 2H), 3.18 (t, 2H), 3.33 (t, 2H), 3.40-3.49 (m, 5H), 7.28-7.33 (m, 2H), 7.39-7.43 (m, 2H).

Compound 21

2-(4-fluorophenyl)-2-(1-(4-(1-hydroxyethyl)piperidine-1-carbonyl)piperidin-4-ylidene)acetonitrile

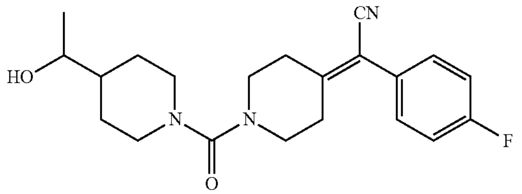 [SMILES: CC(O)C1CCN(C(=O)N2CCC(=C(C#N)c3ccc(F)cc3)CC2)CC1]

Compound 21 was synthesized as clear oil by the method used in the preparation of the compound 3 in 87% yield by using INT-4 and 1-(piperidin-4-yl)ethan-1-ol (150 mol-%) as starting materials in one hour reaction time. $^1$H-NMR (400 MHz, DMSO-$d_6$): 1.03 (s, 3H), 1.12-1.31 (m, 4H), 1.52 (d, 1H), 1.74 (d, 1H), 2.38 (s, 2H), 2.69 (s, 4H), 3.18 (s, 2H), 3.35 (s, 2H), 3.63 (d, 2H), 4.39 (s, 1H), 7.30 (br s, 2H), 7.41 (br s, 2H).

Compound 22

2-(4-fluorophenyl)-2-(1-(3-methoxyazetidine-1-carbonyl)piperidin-4-ylidene)acetonitrile

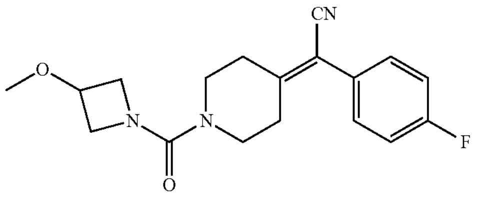 [SMILES: COC1CN(C(=O)N2CCC(=C(C#N)c3ccc(F)cc3)CC2)C1]

Compound 22 was synthesized as clear oil by the method used in the preparation of the compound 3 in 84% yield by using INT-4 and 3-hydroxy-3-methylazetidine, HCl (150 mol-%) as starting materials in 90 minutes reaction time. $^1$H-NMR (400 MHz, DMSO-$d_6$): 2.35 (m, 2H), 2.66 (m, 2H), 3.19 (s, 3H), 3.26 (m, 2H), 3.43 (m, 2H), 3.74 (m, 2H), 4.08 (m, 3H), 7.31 (m, 2H), 7.40 (m, 2H).

Compound 23

1-(4-(cyano(4-fluorophenyl)methylene)piperidine-1-carbonyl)azetidine-3-carbonitrile

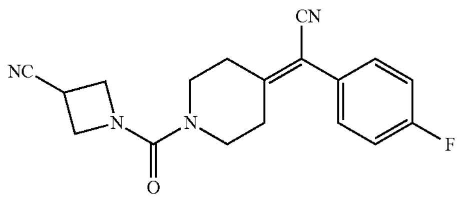 [SMILES: N#CC(=C1CCN(C(=O)N2CC(C#N)C2)CC1)c1ccc(F)cc1]

Compound 23 was synthesized as clear oil by the method used in the preparation of the compound 3 in 82% yield by using INT-4 and azetidine-3-carbonitrile, HCl (150 mol-%) as starting materials in 60 minutes reaction time. $^1$H-NMR (400 MHz, DMSO-$d_6$): 2.35 (m, 2H), 2.67 (m, 2H), 3.27 (m, 2H), 3.44 (m, 2H), 3.74 (m, 1H), 4.07 (dd, 2H), 4.18 (dd, 2H), 7.31 (dd, 2H), 7.40 (m, 2H).

Compound 24

2-(4-fluorophenyl)-2-(1-(4,5,6,7-tetrahydro-1H-imidazo[4,5-c]pyridine-5-carbonyl)piperidin-4-ylidene) acetonitrile

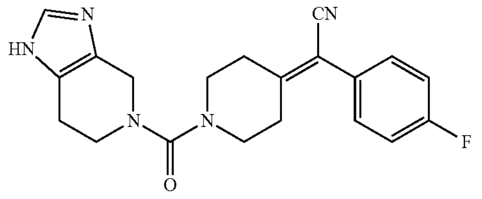 [SMILES: N#CC(=C1CCN(C(=O)N2CCc3[nH]cnc3C2)CC1)c1ccc(F)cc1]

Compound 24 was synthesized by the method used in the preparation of the compound 3 in 34% yield by using INT-4 and 4,5,6,7-tetrahydro-1H-imidazol[4,5-c]-pyridine diHCl (150 mol-%) as starting materials stirring 7 hours at +50° C. and then overnight at room temperature. Crude oily product was purified by chromatography followed by co-evaporation with DCM and heptane producing a white solid. $^1$H-NMR (400 MHz, DMSO-$d_6$): 2.41 (m, 2H), 2.66 (m, 2H), 2.72 (m, 2H), 3.23 (m, 2H), 3.44-3.46 (m, 4H), 4.18 (br s, 2H), 7.31 (dd, 2H), 7.42 (m, 2H), 7.48 (s, 1H), 11.84 (br s, 1H).

Compound 25

2-(4-fluorophenyl)-2-(1-(4,5,6,7-tetrahydro-1H-pyrazolo[4,3-c]pyridine-5-carbonyl) piperidin-4-ylidene)acetonitrile

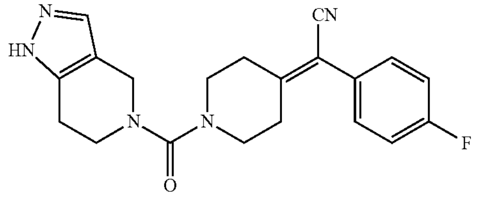 [SMILES: N#CC(=C1CCN(C(=O)N2CCc3[nH]ncc3C2)CC1)c1ccc(F)cc1]

Compound 25 was synthesized as clear oil by the method used in the preparation of the compound 3 in 70% yield by using INT-4 and 4,5,6,7-tetrahydro-1H-pyrazolo[4,3-c]pyridine (150 mol-%) as starting materials stirring overnight at room temperature. $^1$H-NMR (400 MHz, DMSO-$d_6$): 2.41 (s, 2H), 2.72 (s, 4H), 3.23 (s, 2H), 3.42 (m, 4H), 4.24 (s, 2H), 7.31 (s, 2H), 7.41 (br s, 3H), 12.48 (s, 1H).

Compound 26

2-(4-fluorophenyl)-2-(1-(5,6,7,8-tetrahydro-[1,2,4]triazolo[1,5-a]pyrazine-7-carbonyl)piperidin-4-ylidene)acetonitrile

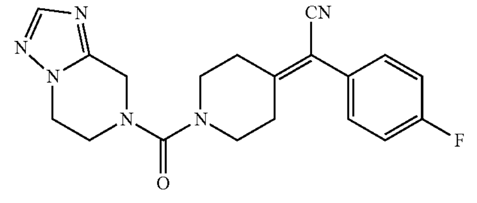 [SMILES: N#CC(=C1CCN(C(=O)N2CCn3ncnc3C2)CC1)c1ccc(F)cc1]

Compound 26 was synthesized by the method used in the preparation of the compound 3 using THE as a solvent in 37% yield by using INT-4 and 5,6,7,8-tetrahydro[1,2,4]triazolo[1,5-a]pyrazine (150 mol-%) as starting materials stirring 6 hours at room temperature. $^1$H-NMR (400 MHz, DMSO-$d_6$): 2.41 (dd, 2H), 2.74 (dd, 2H), 3.30 (m, 2H), 3.48 (dd, 2H), 3.70 (dd, 2H), 4.21 (dd, 2H), 4.50 (s, 2H), 7.32 (dd, 2H), 7.42 (m, 2H), 7.96 (s, 1H).

Compound 27

2-(4-fluorophenyl)-2-(1-(5,6,7,8-tetrahydroimidazo[1,5-a]pyrazine-7-carbonyl)piperidin-4-ylidene)acetonitrile

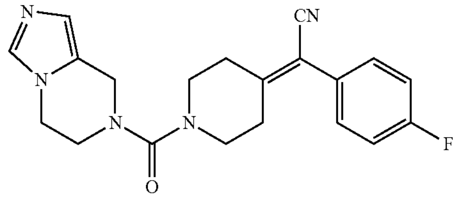 [SMILES: N#CC(=C1CCN(C(=O)N2CCn3cncc3C2)CC1)c1ccc(F)cc1]

Compound 27 was synthesized by the method used in the preparation of the compound 3 using THE as a solvent in 62% yield by using INT-4 and 5,6,7,8-tetrahydroimidazo[1,5-a]pyrazine (150 mol-%) as starting materials stirring 3.5 hours at room temperature. $^1$H-NMR (400 MHz, DMSO-$d_6$): 2.43 (m, 2H), 2.74 (m, 2H), 3.35 (m, 2H), 3.47 (m, 2H), 3.65 (m, 2H), 4.30 (m, 2H), 4.51 (m, 2H), 7.32 (m, 2H), 7.45 (m, 3H), 9.05 (s, 1H).

Compound 28

2-(4-fluorophenyl)-2-(1-(1,2,3,4-tetrahydropyrrolo[1,2-a]pyrazine-2-carbonyl)piperidin-4-ylidene)acetonitrile

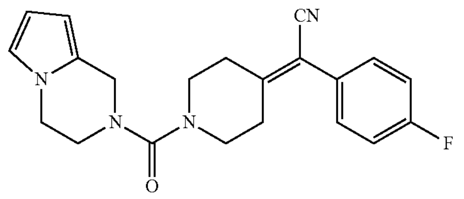 [SMILES: N#CC(=C1CCN(C(=O)N2CCn3cccc3C2)CC1)c1ccc(F)cc1]

Compound 28 was synthesized by the method used in the preparation of the compound 3 using THE as a solvent in 28% yield by using INT-4 and 1,2,3,4-tetrahydropyrrolo[1,2-a]pyrazine (150 mol-%) as starting materials stirring 4 hours at room temperature. $^1$H-NMR (400 MHz, DMSO-$d_6$): 2.41 (m, 2H), 2.72 (m, 2H), 3.26 (m, 2H), 3.43 (m, 2H), 3.56 (m, 2H), 3.98 (m, 2H), 4.37 (m, 2H), 5.80 (d, 1H), 5.99 (d, 1H), 6.65 (d, 1H), 7.31 (m, 2H), 7.41 (m, 2H).

Compound 29

2-(1-((1R,4R)-2-azabicyclo[2.2.1]heptane-2-carbonyl)piperidin-4-ylidene)-2-(4-fluorophenyl)acetonitrile

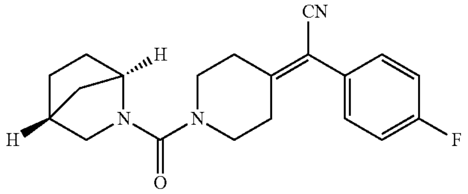 [SMILES: N#CC(=C1CCN(C(=O)N2C[C@@H]3CC[C@@H]2C3)CC1)c1ccc(F)cc1]

Compound 29 was synthesized as an oil by the method used in the preparation of the compound 3 using DCM as a solvent in 99% yield by using INT-4 and 2-azabicyclo[2.2.1]heptane (150 mol-%) as starting materials stirring two hours at room temperature. $^1$H-NMR (400 MHz, DMSO-$d_6$): 1.24-1.34 (m, 3H), 1.46 (d, 1H), 1.58 (s, 2H), 1.72 (d, 1H), 2.37 (m, 2H), 2.68 (m, 2H), 2.83 (d, 1H), 3.18-3.40 (m, 5H), 4.00 (s, 1H), 7.20 (m, 2H), 7.40 (m, 2H).

Compound 30

2-(1-(2,3-dihydro-1H-pyrrolo[2,3-b]pyridine-1-carbonyl)piperidin-4-ylidene)-2-(4-fluorophenyl)acetonitrile

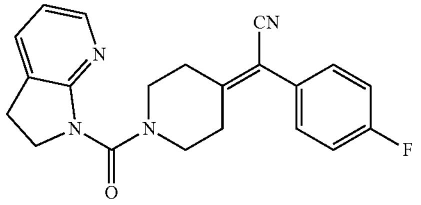 [SMILES: N#CC(=C1CCN(C(=O)N2CCc3cccnc32)CC1)c1ccc(F)cc1]

Compound 30 was synthesized in 14% yield after chromatographic purification by the method used in the preparation of the compound 3 by using INT-4 and 2,3-dihydro-1H-pyrrolo[2,3-b]pyridine as starting materials in six hours reaction time. $^1$H-NMR (400 MHz, $CDCl_3$): 2.58 (t, 2H), 2.95 (t, 2H), 3.02 (t, 2H), 3.52 (t, 2H), 3.68 (t, 2H), 3.98 (t, 2H), 6.76 (m, 1H), 7.11 (m, 2H), 7.26 (m, 2H), 7.40 (m, 1H), 8.02 (m, 1H).

Compound 31

2-(1-(3-oxa-8-azabicyclo[3.2.1]octane-8-carbonyl)piperidin-4-ylidene)-2-(3,4-difluorophenyl)acetonitrile

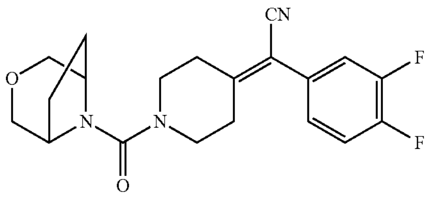 [SMILES: N#CC(=C1CCN(C(=O)N2C3CCC2COC3)CC1)c1ccc(F)c(F)c1]

Compound 31 was synthesized by the method used in the preparation of the compound 3 in 75% yield by using INT-14 and 3-oxa-8-azabicyclo[3.2.1]octane, HCl (150 mol-%) as starting materials stirring two hours at room temperature. $^1$H-NMR (400 MHz, DMSO-$d_6$): 1.76 (m, 4H), 2.39 (m, 2H), 2.69 (m, 2H), 3.33 (m, 2H), 3.50 (m, 4H), 3.61 (m, 2H), 3.83 (s, 2H), 7.24 (br s, 1H), 7.53 (m, 2H).

Compound 32

2-(3,4-difluorophenyl)-2-(1-(4,5,6,7-tetrahydroisoxazolo[4,3-c]pyridine-5-carbonyl)piperidin-4-ylidene)acetonitrile

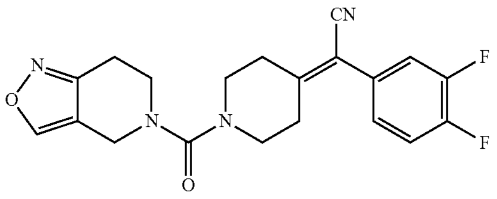 [SMILES: N#CC(=C1CCN(C(=O)N2CCc3nocc3C2)CC1)c1ccc(F)c(F)c1]

Compound 32 was synthesized by the method used in the preparation of the compound 3 in 71% yield by using INT-14 and 4,5,6,7-tetrahydroisoxazolo[4,3-c]pyridine, HCl (150 mol-%) as starting materials stirring 2.5 hours at room temperature. $^1$H-NMR (400 MHz, DMSO-$d_6$): 2.41 (m, 2H), 2.72 (m, 2H), 2.86 (m, 2H), 3.26 (m, 2H), 3.45 (m, 4H), 4.30 (s, 2H), 7.24 (br s, 1H), 7.53 (m, 2H), 8.67 (s, 1H).

Compound 33

2-(3,4-difluorophenyl)-2-(1-(4-(hydroxymethyl)piperidine-1-carbonyl)piperidin-4-ylidene)acetonitrile

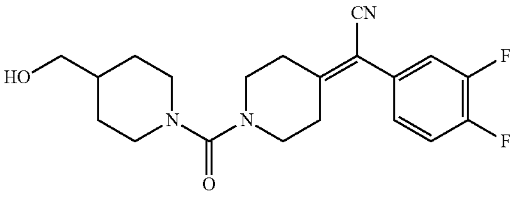 [SMILES: N#CC(=C1CCN(C(=O)N2CCC(CO)CC2)CC1)c1ccc(F)c(F)c1]

Compound 33 was synthesized by the method used in the preparation of the compound 3 in 67% yield by using INT-14 and piperidin-4-ylmethanol (150 mol-%) as starting materials stirring at room temperature. $^1$H-NMR (400 MHz, DMSO-$d_6$): 1.08 (m, 2H), 1.51-1.64 (m, 3H), 2.37 (m, 2H), 2.71 (m, 4H), 3.20 (m, 5H), 3.33 (m, 1H), 3.61 (d, 2H), 4.48 (s, 1H), 7.23 (s, 1H), 7.52 (m, 2H).

Compound 34

2-(1-((1R,4R)-2-azabicyclo[2.2.1]heptane-2-carbonyl)piperidin-4-ylidene)-2-(3,4-difluorophenyl)acetonitrile

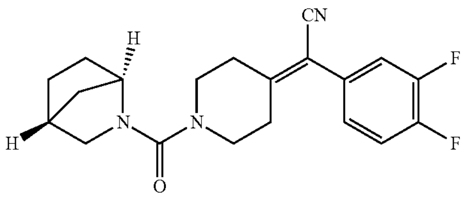 [SMILES: N#CC(=C1CCN(C(=O)N2C[C@@H]3CC[C@@H]2C3)CC1)c1ccc(F)c(F)c1]

Compound 34 was synthesized by the method used in the preparation of the compound 3 in 99% yield as an oil by using INT-14 and 2-azabicyclo[2.2.1]heptane (150 mol-%) as starting materials stirring for two hours at room temperature. $^1$H-NMR (400 MHz, DMSO-$d_6$): 1.33 (d, 2H), 1.47 (d, 1H), 1.59 (m, 2H), 1.73 (d, 1H), 2.30-2.43 (m, 3H), 2.60-2.74 (m, 2H), 2.83 (d, 1H), 3.14-3.29 (m, 2H), 3.36-3.45 (m, 4H), 7.23 (m, 1H), 7.48-7.58 (m, 2H).

Compound 35

2-(3,4-difluorophenyl)-2-(1-(4,5,6,7-tetrahydrothieno[3,2-c]pyridine-5-carbonyl)piperidin-4-ylidene) acetonitrile

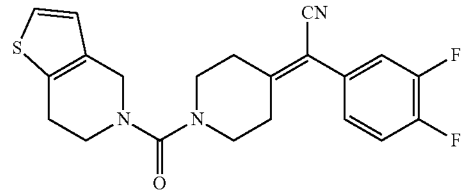 [SMILES: N#CC(=C1CCN(C(=O)N2CCc3sccc3C2)CC1)c1ccc(F)c(F)c1]

Compound 35 was synthesized by the method used in the preparation of the compound 3 using in 81% yield by using INT-14 and 4,5,6,7-tetrahydrothieno[3,2-c]pyridine, HCl (150 mol-%) as starting materials stirring for two hours at room temperature. $^1$H-NMR (400 MHz, DMSO-$d_6$): 2.42 (m, 2H), 2.72 (m, 2H), 2.86 (m, 2H), 3.25 (m, 2H), 3.41-3.48 (m, 4H), 4.31 (s, 2H), 6.87 (d, 1H), 7.25 (m, 1H), 7.33 (d, 1H), 7.54 (m, 2H).

Compound 36

1-(4-(cyano(3,4-difluorophenyl)methylene)piperidine-1-carbonyl)azetidine-3-carbonitrile

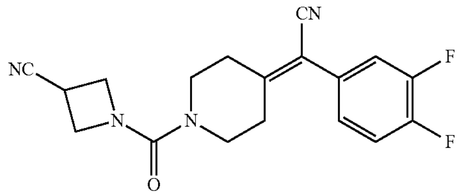 [SMILES: N#CC(=C1CCN(C(=O)N2CC(C#N)C2)CC1)c1ccc(F)c(F)c1]

Compound 36 was synthesized by the method used in the preparation of the compound 3 in 84% yield by using INT-14 and azetidine-3-carbonitrile, HCl (150 mol-%) as starting materials stirring for two hours at room temperature. $^1$H-NMR (400 MHz, DMSO-$d_6$): 2.36 (m, 2H), 2.67 (m, 2H), 3.27 (m, 2H), 3.43 (m, 2H), 3.74 (m, 1H), 4.07 (t, 2H), 4.19 (t, 2H), 7.24 (m, 1H), 7.49-7.59 (m, 2H).

Compound 37

2-(1-(3-oxa-8-azabicyclo[3.2.1]octane-8-carbonyl)piperidin-4-ylidene)-2-(2,4-difluorophenyl)acetonitrile

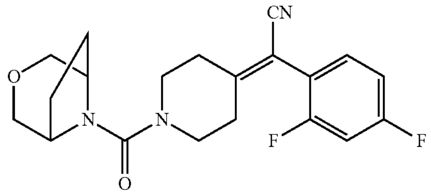 [SMILES: N#CC(=C1CCN(C(=O)N2C3CCC2COC3)CC1)c1ccc(F)cc1F]

Compound 37 was synthesized by the method used in the preparation of the compound 3 in 47% yield by using INT-18 and 3-oxa-8-azabicyclo[3.2.1]octane as starting materials in five hours reaction time. $^1$H-NMR (400 MHz, DMSO-$d_6$): 1.70-1.80 (m, 4H), 2.55 (t, 2H), 2.72 (t, 2H), 3.30-3.40 (m, 2H), 3.50 (m, 4H), 3.59-3.63 (m, 2H), 3.84 (m, 2H), 7.22 (m, 1H), 7.40-7.50 (m, 2H).

Compound 38

2-(2,4-difluorophenyl)-2-(1-(4,5,6,7-tetrahydroisoxazolo[4,3-c]pyridine-5-carbonyl)piperidin-4-ylidene) acetonitrile

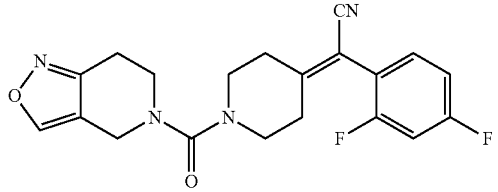 [SMILES: N#CC(=C1CCN(C(=O)N2CCc3nocc3C2)CC1)c1ccc(F)cc1F]

Compound 38 was synthesized by the method used in the preparation of the compound 3 in 92% yield by using INT-18 and 4,5,6,7-tetrahydroisoxazolo[4,3-c]pyridine as starting materials in 4 hours reaction time. $^1$H-NMR (400 MHz, DMSO-$d_6$): 2.27 (t, 2H), 2.75 (t, 2H), 2.86 (t, 2H), 3.24 (t, 2H), 3.40-3.50 (m, 4H), 4.31 (s, 2H), 7.22 (m, 1H), 7.40-7.55 (m, 2H), 8.67 (s, 1H).

Compound 39

2-(2,4-difluorophenyl)-2-(1-(4-(hydroxymethyl)piperidine-1-carbonyl)piperidin-4-ylidene)acetonitrile

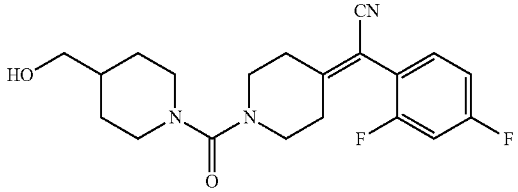 [SMILES: N#CC(=C1CCN(C(=O)N2CCC(CO)CC2)CC1)c1ccc(F)cc1F]

Compound 39 was synthesized by the method used in the preparation of the compound 3 in 77% yield by using INT-18 and piperidin-4-ylmethanol as starting materials in 3 hours reaction time.

$^1$H-NMR (400 MHz, DMSO-$d_6$): 1.02-1.10 (m, 2H), 1.51 (m, 1H), 1.60-1.65 (m, 2H), 2.23 (t, 2H), 2.65-2.75 (m, 4H), 3.16 (t, 2H), 3.24 (t, 2H), 3.35 (m, 2H), 3.58-3.63 (m, 2H), 4.47 (s, 1H), 7.22 (m, 1H), 7.38-7.52 (m, 2H).

Compound 40

1-(4-(cyano(2,4-difluorophenyl)methylene)piperidine-1-carbonyl)azetidine-3-carbonitrile

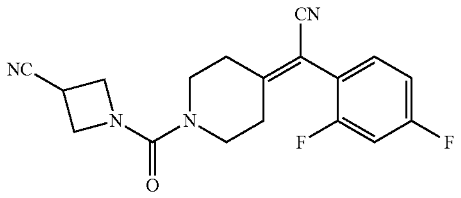 [SMILES: N#CC(=C1CCN(C(=O)N2CC(C#N)C2)CC1)c1ccc(F)cc1F]

Compound 40 was synthesized by the method used in the preparation of the compound 3 in 58% yield by using INT-18 and azetidine-3-carbonitrile as starting materials in 3 hours reaction time. $^1$H-NMR (400 MHz, DMSO-$d_6$): 2.21 (t, 2H), 2.69 (t, 2H), 3.26 (t, 2H), 3.44 (t, 2H), 3.69-3.77 (m, 1H), 4.05-4.08 (m, 2H), 4.16-4.20 (m, 2H), 7.22 (m, 1H), 7.40-7.52 (m, 2H).

Compound 41

2-(3,4-difluorophenyl)-2-(1-(4-hydroxypiperidine-1-carbonyl)piperidin-4-ylidene)acetonitrile

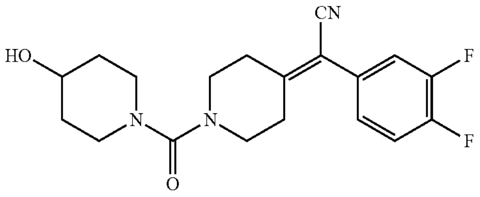 [SMILES: N#CC(=C1CCN(C(=O)N2CCC(O)CC2)CC1)c1ccc(F)c(F)c1]

Compound 41 was prepared from INT-12 and INT-64 (140 mol-%) in the presence of triethylamine (300 mol-%) in DCM by stirring at room temperature overnight, then diluted with DCM and washed sequentially with 1M HCl solution, saturated aqueous sodium bicarbonate solution and brine, then dried (sodium sulphate) and concentrated under reduced pressure. The resultant residue was purified by column chromatography (EtOAc in hexanes). The yield of product was 49% as an off-white solid. $^1$H-NMR (400 MHz, $CDCl_3$) δ ppm 7.25-7.17 (m, 1H), 7.15-7.09 (m, 1H), 7.05-6.98 (m, 1H), 3.91-3.84 (m, 1H), 3.63-3.56 (m, 2H), 3.45-3.40 (m, 2H), 3.25 (t, 2H), 3.05-2.97 (m, 2H), 2.82-2.76 (m, 2H), 2.48-2.43 (m, 2H), 1.94-1.87 (m, 2H), 1.56-1.46 (m, 3H). $^{19}$F NMR (376 MHz, $CDCl_3$) δ ppm −135.77 (d, J=21.2 Hz), −136.34 (d, J=21.1 Hz). m/z (ES+) 362.2 $(M+H)^+$.

Compound 42

2-(2,4-difluorophenyl)-2-(1-(4-hydroxypiperidine-1-carbonyl)piperidin-4-ylidene)acetonitrile

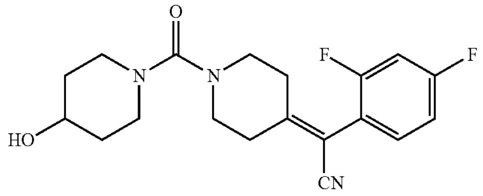 [SMILES: N#CC(=C1CCN(C(=O)N2CCC(O)CC2)CC1)c1ccc(F)cc1F]

Compound 42 was synthesized in 52% yield by the method used in the preparation of the compound 41 by using INT-18 and INT-64 as starting materials. $^1$H-NMR (400 MHz, $CDCl_3$) δ ppm 7.35-7.18 (m, 1H), 7.01-6.85 (m, 2H), 3.93-3.83 (m, 1H), 3.65-3.54 (m, 2H), 3.44 (t, 2H), 3.27 (t, 2H), 3.01 (ddd, 2H), 2.85-2.78 (m, 2H), 2.33-2.25 (m, 2H), 1.95-1.86 (m, 2H), 1.56-1.46 (m, 3H). $^{19}$F NMR (376 MHz, $CDCl_3$) δ ppm −107.36 (d, J=8.8 Hz), −108.21 (d, J=8.8 Hz). m/z (ES+) 362.2 $(M+H)^+$.

Compound 43

2-(3,4-difluorophenyl)-2-(1-(4,5,6,7-tetrahydro-1H-pyrazolo[4,3-c]pyridine-5-carbonyl)piperidin-4-ylidene)acetonitrile

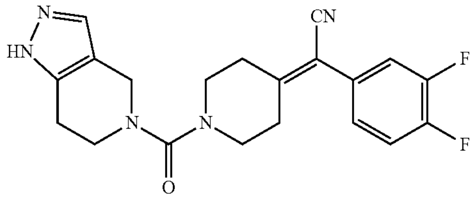 [SMILES: N#CC(=C1CCN(C(=O)N2CCc3[nH]ncc3C2)CC1)c1ccc(F)c(F)c1]

Compound 43 was synthesized by the method used in the preparation of the compound 3 in 63% yield by using INT-14 and 4,5,6,7-tetrahydro-1H-pyrazolo[4,3-c]pyridine (150 mol-%) as starting materials stirring overnight at room temperature. $^1$H-NMR (400 MHz, DMSO-$d_6$): 2.41 (t, 2H), 2.72 (m, 4H), 3.24 (t, 2H), 3.39-3.45 (m, 5H), 4.24 (s, 2H), 7.23 (m, 1H), 7.39 (br s, 1H), 7.50-7.59 (m, 2H).

Compound 44

2-(3,4-difluorophenyl)-2-(1-(5,6,7,8-tetrahydroimidazo[1,5-a]pyrazine-7-carbonyl)piperidin-4-ylidene)acetonitrile

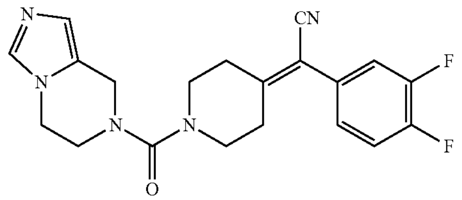 [SMILES: N#CC(=C1CCN(C(=O)N2CCn3cncc3C2)CC1)c1ccc(F)c(F)c1]

Compound 44 was synthesized by the method used in the preparation of the compound 3 in 77% yield by using INT-14 and 5,6,7,8-tetrahydroimidazo[1,5-a]pyrazine (150 mol-%) as starting materials stirring 4 hours at room temperature. $^1$H NMR (400 MHz, DMSO-$d_6$): 2.40 (m, 2H), 2.72 (m, 2H), 3.27 (m, 2H), 3.44 (m, 2H), 3.56 (m, 2H), 4.08 (t, 2H), 4.42 (s, 2H), 6.72 (s, 1H), 7.25 (m, 1H), 7.49-7.59 (m, 3H).

Compound 45

2-(1H-indazol-4-yl)-2-(1-(morpholine-4-carbonyl)piperidin-4-ylidene)acetonitrile

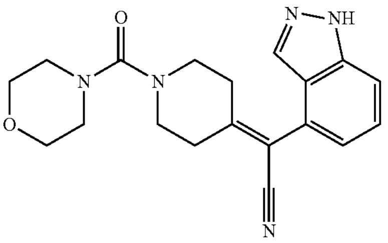 [SMILES: N#CC(=C1CCN(C(=O)N2CCOCC2)CC1)c1cccc2[nH]ncc12]

Compound 45 was synthesized by the method used in the preparation of the compound 1 in 52% yield by using INT-24 and dropwise added morpholine-4-carbonyl chloride (110 mol-%) as starting materials stirring 3 hours at room temperature. The product was triturated with heptane-EtOAc (v/v 10:1) and methanol. $^1$H-NMR (400 MHz, DMSO-$d_6$): 2.30 (t, 2H), 2.79 (t, 2H), 3.17 (m, 6H), 3.45 (t, 2H), 3.56 (m, 4H), 7.08 (d, 1H), 7.42 (t, 1H), 7.62 (d, 1H), 8.08 (s, 1H), 13.35 (s, 1H).

Compound 46

2-(4-chlorophenyl)-2-(1-(5,6,7,8-tetrahydroimidazo[1,5-a]pyrazine-7-carbonyl) piperidin-4-ylidene) acetonitrile

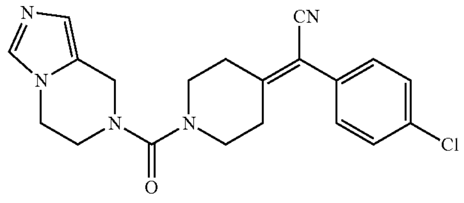 [SMILES: N#CC(=C1CCN(C(=O)N2CCn3cncc3C2)CC1)c1ccc(Cl)cc1]

Compound 46 was synthesized by the method used in the preparation of the compound 3 in 62% yield by using INT-8 and 5,6,7,8-tetrahydroimidazo[1,5-a]pyrazine (150 mol-%) as starting materials stirring four hours at room temperature. $^1$H NMR (400 MHz, DMSO-$d_6$): 2.42 (t, 2H), 2.73 (t, 2H), 3.27 (m, 2H), 3.44 (m, 2H), 3.55 (t, 2H), 4.08 (t, 2H), 4.42 (s, 2H), 6.72 (s, 1H), 7.38 (d, 2H), 7.54 (d, 2H), 7.59 (s, 1H).

Compound 47

2-(4-chlorophenyl)-2-(1-(4,5,6,7-tetrahydrothieno[3,2-c]pyridine-5-carbonyl)piperidin-4-ylidene acetonitrile

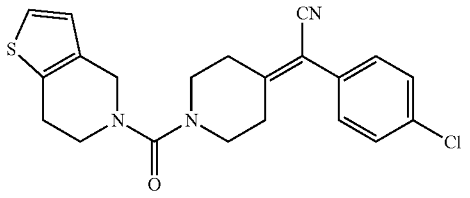 [SMILES: N#CC(=C1CCN(C(=O)N2CCc3sccc3C2)CC1)c1ccc(Cl)cc1]

Compound 47 was synthesized by the method used in the preparation of the compound 3 in 67% yield by using INT-8 and 4,5,6,7-tetrahydrothieno[3,2-c]pyridine, HCl (150 mol-%) as starting materials stirring two hours at room temperature. $^1$H NMR (400 MHz, DMSO-$d_6$): 2.43 (m, 2H), 2.73 (m, 2H), 2.86 (m, 2H), 3.25 (m, 2H), 3.42 (m, 2H), 3.48 (m, 2H), 4.31 (s, 2H), 6.87 (d, 1H), 7.33 (d, 1H), 7.40 (d, 2H), 7.54 (d, 2H).

Compound 48

2-(1-(4-hydroxypiperidine-1-carbonyl)piperidin-4-ylidene)-2-(1H-indazol-4-yl)acetonitrile

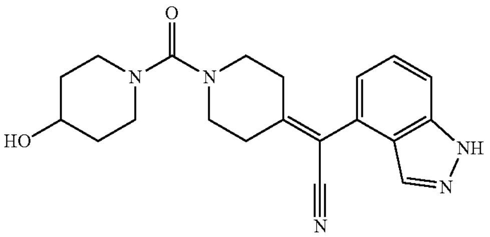 [SMILES: N#CC(=C1CCN(C(=O)N2CCC(O)CC2)CC1)c1cccc2[nH]ncc12]

Compound 4 was synthesized in 16% yield by the method used in the preparation of the compound 41 by using INT-24 and INT-64 as starting materials. $^1$H-NMR (400 MHz, DMSO-$d_6$) δ ppm 13.33 (s, 1H), 8.07 (t, 1H), 7.61 (d, 1H), 7.42 (dd, 1H), 7.07 (d, 1H), 4.67 (d, 1H), 3.61 (dq, 1H), 3.51-3.36 (m, 4H), 3.14 (t, 2H), 2.93-2.82 (m, 2H), 2.78 (t, 2H), 2.29 (t, 2H), 1.70 (d, 2H), 1.39-1.23 (m, 1H). m/z (ES+) 366.2 $(M+H)^+$.

Compound 49

2-(1-(4-(hydroxymethyl)piperidine-1-carbonyl)piperidin-4-ylidene)-2-(1H-indazol-4-yl)acetonitrile

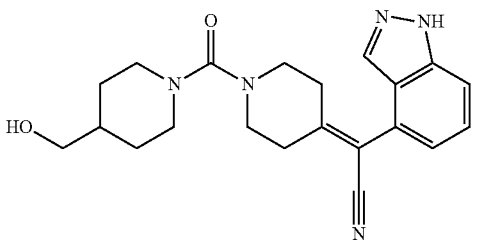 [SMILES: N#CC(=C1CCN(C(=O)N2CCC(CO)CC2)CC1)c1cccc2[nH]ncc12]

Compound 49 was synthesized by the method used in the preparation of the compound 3 in 11% yield by using INT-26 and piperidin-4-ylmethanol (150 mol-%) as starting materials stirring two hours at room temperature. $^1$H-NMR (400 MHz, DMSO-$d_6$): 1.08 (m 2H), 1.62 (d, 2H), 2.29 (m, 2H), 2.71 (m, 3H), 2.77 (t, 2H), 3.14 (t, 2H), 3.24 (t, 2H), 3.42 (t, 2H), 3.61 (d, 2H), 4.44 (t, 1H), 7.07 (d, 1H), 7.42 (t, 1H), 7.61 (d, 1H), 8.07 (s, 1H), 13.33 (s, 1H).

Compound 50

2-(3,5-difluorophenyl)-2-(1-(4-(hydroxymethyl)piperidine-1-carbonyl)piperidin-4-ylidene)acetonitrile

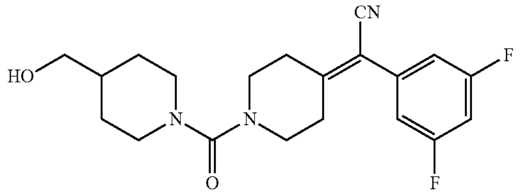 [SMILES: N#CC(=C1CCN(C(=O)N2CCC(CO)CC2)CC1)c1cc(F)cc(F)c1]

Compound 50 was synthesized by the method used in the preparation of the compound 3 in 57% yield by using INT-22 and piperidin-4-ylmethanol as starting materials in 3 hours reaction time. $^1$H-NMR (400 MHz, DMSO-$d_6$): 1.01-1.12 (m, 2H), 1.52 (m, 1H), 1.60-1.65 (m, 2H), 2.39 (t, 2H), 2.65-2.75 (m, 4H), 3.18 (t, 2H), 3.24 (t, 2H), 3.33 (m, 2H), 3.58-3.63 (m, 2H), 4.46 (t, 1H), 7.12-7.17 (m, 2H), 7.34 (m, 1H).

Compound 51

2-(3,5-difluorophenyl)-2-(1-(4,5,6,7-tetrahydrothieno[3,2-c]pyridine-5-carbonyl)piperidin-4-ylidene)acetonitrile

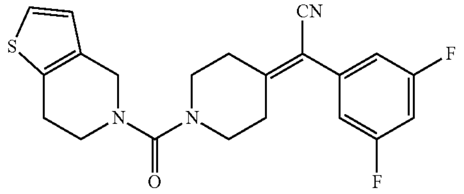 [SMILES: N#CC(=C1CCN(C(=O)N2CCc3sccc3C2)CC1)c1cc(F)cc(F)c1]

Compound 51 was synthesized by the method used in the preparation of the compound 3 in THE in 75% yield by using INT-22 and 4,5,6,7-tetrahydrothieno[3,2-c]pyridine as starting materials in 3 hours reaction time. $^1$H-NMR (400 MHz, DMSO-$d_6$): 2.44 (t, 2H), 2.73 (t, 2H), 2.86 (t, 2H), 3.26 (t, 2H), 3.42 (t, 2H), 3.48 (t, 2H), 4.31 (s, 2H), 6.87 (d, 1H), 7.14-7.19 (m, 2H), 7.32 (d, 1H), 7.35-7.38 (m, 1H).

Compound 52

2-(3,5-difluorophenyl)-2-(1-(5,6,7,8-tetrahydroimidazo[1,5-a]pyrazine-7-carbonyl)piperidin-4-ylidene)acetonitrile

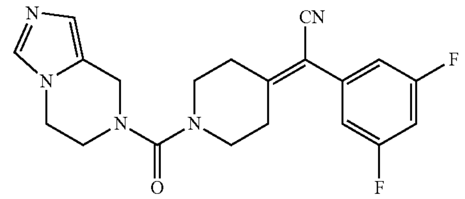 [SMILES: N#CC(=C1CCN(C(=O)N2CCn3cncc3C2)CC1)c1cc(F)cc(F)c1]

Compound 52 was synthesized by the method used in the preparation of the compound 3 in 39% yield after chromatographic purification by using INT-22 and 5,6,7,8-tetrahydroimidazo[1,5-a]pyrazine as starting materials in 4 hours reaction time. $^1$H-NMR (400 MHz, DMSO-$d_6$): 2.43 (t, 2H), 2.73 (t, 2H), 3.28 (t, 2H), 3.44 (t, 2H), 3.55 (t, 2H), 4.08 (t, 2H), 4.42 (s, 2H), 6.71 (s, 1H), 7.14-7.19 (m, 2H), 7.35 (m, 1H), 7.57 (s, 1H).

Compound 53

2-(1-(4-(hydroxymethyl)piperidine-1-carbonyl)piperidin-4-ylidene)-2-(4-(trifluoromethoxy)phenyl)acetonitrile

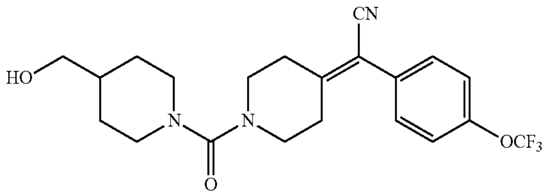 [SMILES: N#CC(=C1CCN(C(=O)N2CCC(CO)CC2)CC1)c1ccc(OC(F)(F)F)cc1]

Compound 53 was synthesized by the method used in the preparation of the compound 3 in 75% yield by using INT-34 and piperidin-4-ylmethanol as starting materials in 4 hours reaction time. $^1$H-NMR (400 MHz, DMSO-$d_6$): 1.02-1.13 (m, 2H), 1.52 (m, 1H), 1.60-1.65 (m, 2H), 2.39 (t, 2H), 2.65-2.75 (m, 4H), 3.18 (t, 2H), 3.25 (t, 2H), 3.35 (m, 2H), 3.58-3.64 (m, 2H), 4.47 (t, 1H), 7.44-7.53 (m, 4H).

Compound 54

2-(1-(4,5,6,7-tetrahydro-1H-pyrazolo[4,3-c]pyridine-5-carbonyl)piperidin-4-ylidene)-2-(4-(trifluoromethoxy)phenyl)acetonitrile

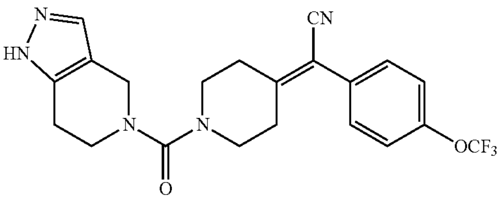 [SMILES: N#CC(=C1CCN(C(=O)N2CCc3[nH]ncc3C2)CC1)c1ccc(OC(F)(F)F)cc1]

Compound 54 was synthesized by the method used in the preparation of the compound 3 in 67% yield after chromatographic purification by using INT-34 and 4,5,6,7-tetrahydro-1H-pyrazolo[4,3-c]pyridine as starting materials in 5 hours reaction time. $^1$H-NMR (400 MHz, DMSO-$d_6$): 2.42 (t, 2H), 2.70-2.74 (m, 4H), 3.24 (t, 2H), 3.40-3.45 (m, 4H), 4.25 (br s, 2H), 7.20-7.50 (m, 1H, isomers), 7.45-7.53 (m, 4H), 12.48 (s, 1H).

Compound 55

2-(1-(5,6,7,8-tetrahydroimidazo[1,5-a]pyrazine-7-carbonyl)piperidin-4-ylidene)-2-(4-(trifluoromethoxy)phenyl)acetonitrile

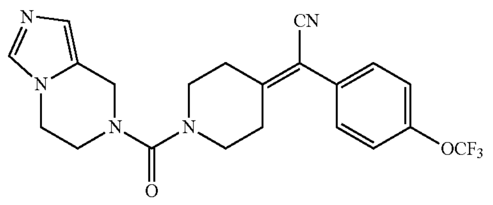 [SMILES: N#CC(=C1CCN(C(=O)N2CCn3cncc3C2)CC1)c1ccc(OC(F)(F)F)cc1]

Compound 55 was synthesized by the method used in the preparation of the compound 3 in 41% yield by using INT-34 and 5,6,7,8-tetrahydroimidazo[1,5-a]pyrazine as starting materials in 6 hours reaction time. $^1$H-NMR (400 MHz, DMSO-$d_6$): 2.43 (t, 2H), 2.74 (t, 2H), 3.27 (t, 2H), 3.45 (t, 2H), 3.55 (t, 2H), 4.08 (t, 2H), 4.42 (s, 2H), 6.71 (s, 1H), 7.44-7.53 (m, 4H), 7.57 (s, 1H).

Compound 56

2-(1-(4-hydroxypiperidine-1-carbonyl)piperidin-4-ylidene)-2-(1H-indazol-7-yl)acetonitrile

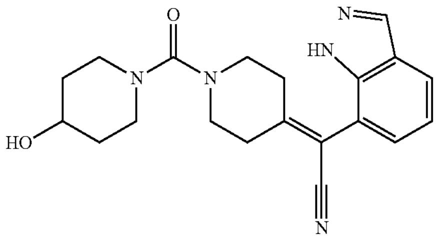 [SMILES: N#CC(=C1CCN(C(=O)N2CCC(O)CC2)CC1)c1cccc(C=N)c1N]

Compound 56 was synthesized in 35% yield by the method used in the preparation of the compound 41 by using INT-59 and INT-64 as starting materials. $^1$H-NMR (400 MHz, $CDCl_3$) δ ppm 8.08 (s, 1H), 7.77 (dd, 1H), 7.24 (dd, 1H), 7.17 (dd, 1H), 3.86-3.75 (m, 1H), 3.61-3.51 (m, 2H), 3.47 (t, 2H), 3.18 (dd, 2H), 2.98 (ddd, 2H), 2.88 (t, 2H), 2.30 (t, 2H), 1.91-1.79 (m, 2H), 1.56-1.41 (m, 2H). $^1$H-NMR (400 MHz, DMSO-$d_6$) δ ppm 13.20 (s, 1H), 8.18 (s, 1H), 7.84 (dd, 1H), 7.29 (dd, 1H), 7.19 (dd, 1H), 4.67 (d, 1H), 3.66-3.56 (m, 1H), 3.50-3.38 (m, 4H), 3.17-3.05 (m, 2H), 2.87 (td, 2H), 2.77 (t, 2H), 2.18-2.10 (m, 2H), 1.75-1.64 (m, 2H), 1.38-1.23 (m, 2H). m/z (ES+) 366.2 $(M+H)^+$.

Compound 57

2-(5-chlorothiophen-2-yl)-2-(1-(4-hydroxypiperidine-1-carbonyl)piperidin-4-ylidene)acetonitrile

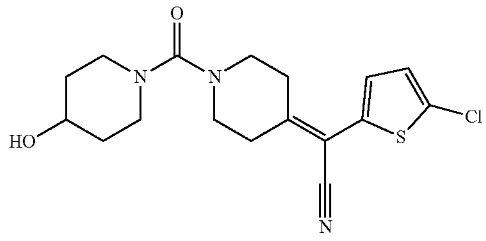 [SMILES: N#CC(=C1CCN(C(=O)N2CCC(O)CC2)CC1)c1ccc(Cl)s1]

Compound 57 was synthesized as a yellow gum in 12% yield by the method used in the preparation of the compound 41 by using INT-40 and INT-64 as starting materials. $^1$H-NMR (400 MHz, $CDCl_3$) δ ppm 6.91 (d, 1H), 6.88 (d, 1H), 3.88 (dt, 1H), 3.60 (dt, 2H), 3.42 (t, 2H), 3.31 (t, 2H), 3.02 (ddd, 2H), 2.83-2.77 (m, 2H), 2.67 (dd, 2H), 1.96-1.85 (m, 2H), 1.56-1.47 (m, 2H). m/z (ES+) 366.2/368.2 $(M+H)^+$.

Compound 58

2-(3,5-difluorophenyl)-2-(1-(4-hydroxypiperidine-1-carbonyl)piperidin-4-ylidene)acetonitrile

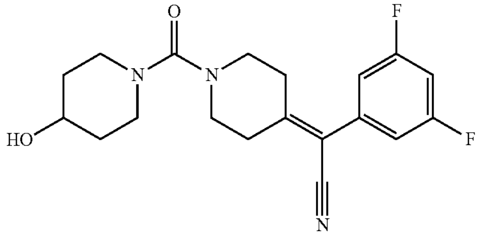 [SMILES: N#CC(=C1CCN(C(=O)N2CCC(O)CC2)CC1)c1cc(F)cc(F)c1]

Compound 58 was synthesized as an off-white solid in 44% yield by the method used in the preparation of the compound 41 by using INT-20 and INT-64 as starting materials. $^1$H-NMR (400 MHz, $CDCl_3$) δ ppm 6.86-6.79 (m, 3H), 3.93-3.83 (m, 1H), 3.64-3.55 (m, 2H), 3.43 (t, 2H), 3.26 (t, 2H), 3.06-2.97 (m, 2H), 2.82-2.77 (m, 2H), 2.51-2.46 (m, 2H), 1.96-1.86 (m, 2H), 1.58-1.47 (m, 3H). $^{19}$F NMR (376 MHz, $CDCl_3$) δ ppm −107.99. m/z (ES+) 362.2 $(M+H)^+$.

Compound 59

2-(1-methyl-1H-indazol-7-yl)-2-(1-(5,6,7,8-tetrahydroimidazo[1,5-a]pyrazine-7-carbonyl)piperidin-4-ylidene)acetonitrile

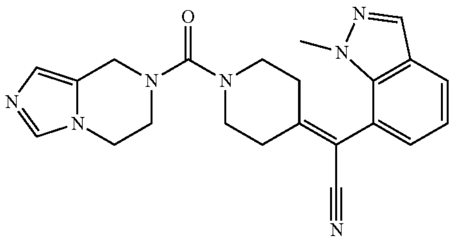 [SMILES: Cn1ncc2cccc(C(C#N)=C3CCN(C(=O)N4CCn5cncc5C4)CC3)c21]

Compound 59 was synthesized by the method used in the preparation of the compound 3 in 12% yield by using INT-61 and 5,6,7,8-tetrahydroimidazo[1,5-a]pyrazine (150 mol-%) as starting materials stirring 3 hours at +50° C. $^1$H-NMR (400 MHz, $CDCl_3$): 2.41 (t, 2H), 2.94 (t, 2H), 3.34 (t, 2H), 3.57 (t, 2H), 3.67 (t, 2H), 4.12 (t, 2H), 4.24 (s, 3H), 4.54 (s, 2H), 6.85 (s, 1H), 7.10 (t, 1H), 7.20 (d, 1H), 7.45 (s, 1H), 7.69 (d, 1H), 7.96 (s, 1H).

Compound 60

2-(1H-indazol-4-yl)-2-(1-(4,5,6,7-tetrahydro-1H-pyrazolo[4,3-c]pyridine-5-carbonyl)piperidin-4-ylidene)acetonitrile

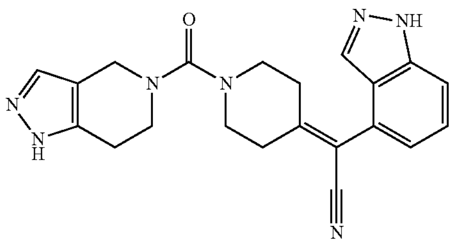 [SMILES: N#CC(=C1CCN(C(=O)N2CCc3[nH]ncc3C2)CC1)c1cccc2[nH]ncc12]

Compound 6 was synthesized by the method used in the preparation of the compound 3 in 13% yield by using INT-24 and 4,5,6,7-tetrahydro-1H-pyrazolo[4,3-c]pyridine (150 mol-%) as starting materials stirring 4 hours at +50° C. $^1$H-NMR (400 MHz, DMSO-$d_6$): 2.32 (m, 2H), 2.71 (m, 2H), 2.81 (m, 2H), 3.20 (m, 2H), 3.45 (m, 4H), 4.24 (s, 2H), 7.08 (d, 1H), 7.42 (t, 2H), 7.62 (d, 1H), 8.09 (s, 1H), 12.47 (s, 1H), 13.27 (s, 1H).

Compound 61

2-(1H-indazol-4-yl)-2-(1-(5,6,7,8-tetrahydroimidazo[1,5-a]pyrazine-7-carbonyl)piperidin-4-ylidene)acetonitrile

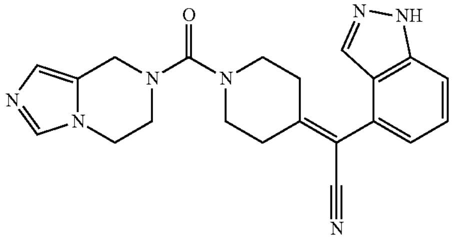 [SMILES: N#CC(=C1CCN(C(=O)N2CCn3cncc3C2)CC1)c1cccc2[nH]ncc12]

Compound 61 was synthesized by the method used in the preparation of the compound 3 in 31% yield by using INT-24 and 5,6,7,8-tetrahydroimidazo[1,5-a]pyrazine (150 mol-%) as starting materials stirring 6 hours at +50° C. $^1$H-NMR (400 MHz, DMSO-$d_6$): 2.33 (m, 2H), 2.82 (m, 2H), 3.24 (m, 2H), 3.53 (m, 4H), 4.08 (m, 2H), 4.42 (s, 2H), 6.71 (s, 1H), 7.09 (d, 1H), 7.43 (m, 1H), 7.57-7.63 (m, 2H), 8.09 (s, 1H), 13.36 (s, 1H).

Compound 62

2-(5-chloropyridin-2-yl)-2-(1-(4-hydroxypiperidine-1-carbonyl)piperidin-4-ylidene)acetonitrile

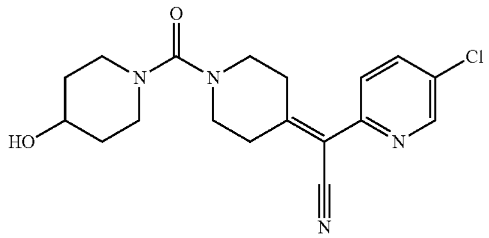 [SMILES: N#CC(=C1CCN(C(=O)N2CCC(O)CC2)CC1)c1ccc(Cl)cn1]

Compound 62 was synthesized as a pale yellow solid in 52% yield by the method used in the preparation of the compound 41 by using INT-44 and INT-64 as starting materials. $^1$H-NMR (400 MHz, $CDCl_3$) δ ppm 8.58 (d, 1H), 7.74 (dd, 1H), 7.45 (d, 1H), 3.92-3.83 (m, 1H), 3.64-3.56 (m, 2H), 3.47 (t, 2H), 3.33 (t, 2H), 3.05-2.97 (m, 2H), 2.87-2.80 (m, 4H), 1.95-1.87 (m, 2H), 1.58-1.48 (m, 3H). m/z (ES+) 361.2 $(M+H)^+$.

Compound 63

2-(5-chlorothiophen-2-yl)-2-(1-(4-(hydroxymethyl)piperidine-1-carbonyl)piperidin-4-ylidene)acetonitrile

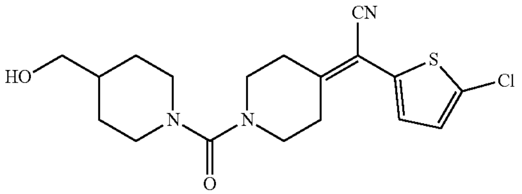 [SMILES: N#CC(=C1CCN(C(=O)N2CCC(CO)CC2)CC1)c1ccc(Cl)s1]

Compound 63 was synthesized by the method used in the preparation of the compound 3 in 88% yield by using INT-42 and piperidin-4-ylmethanol as starting materials in 5 hours reaction time. $^1$H-NMR (400 MHz, DMSO-$d_6$): 1.02-1.14 (m, 2H), 1.52 (m, 1H), 1.60-1.65 (m, 2H), 2.57 (t, 2H), 2.65-2.75 (m, 4H), 3.20-3.27 (m, 4H), 3.33 (m, 2H), 3.58-3.63 (m, 2H), 4.47 (s, 1H), 7.09 (d, 1H), 7.18 (d, 1H).

Compound 64

2-(5-chlorothiophen-2-yl)-2-(1-(4,5,6,7-tetrahydrothieno[3,2-c]pyridine-5-carbonyl)piperidin-4-ylidene)acetonitrile

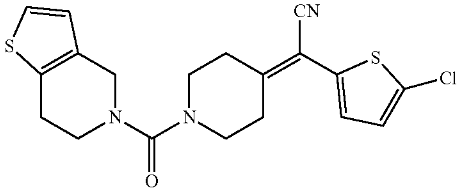 [SMILES: N#CC(=C1CCN(C(=O)N2CCc3sccc3C2)CC1)c1ccc(Cl)s1]

Compound 64 was synthesized by the method used in the preparation of the compound 3 in 48% yield after chromatographic purification by using INT-42 and 4,5,6,7-tetrahydrothieno[3,2-c]pyridine as starting materials in 5 hours reaction time. $^1$H-NMR (400 MHz, DMSO-$d_6$): 2.61 (t, 2H), 2.74 (t, 2H), 2.86 (t, 2H), 3.33 (m, 2H), 3.41 (t, 2H), 3.48 (t, 2H), 4.31 (s, 2H), 6.87 (d, 1H), 7.10 (d, 1H), 7.18 (d, 1H), 7.32 (d, 1H).

Compound 65

2-(5-chloropyridin-2-yl)-2-(1-(4-(hydroxymethyl) piperidine-1-carbonyl)piperidin-4-ylidene)acetonitrile

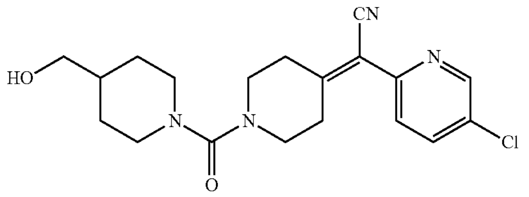 [SMILES: N#CC(=C1CCN(C(=O)N2CCC(CO)CC2)CC1)c1ccc(Cl)cn1]

Compound 65 was synthesized by the method used in the preparation of the compound 3 using THE as a solvent in 44% yield by using INT-46 and piperidin-4-ylmethanol (150 mol-%) as starting materials stirring 3 hours at +50° C. $^1$H-NMR (400 MHz, DMSO-$d_6$): 1.06 (m, 2H), 1.53 (m, 1H), 1.64 (d, 2H), 2.63 (t, 2H), 2.74 (m, 4H), 3.19-3.27 (m, 4H), 3.38 (t, 2H), 3.62 (d, 2H), 4.47 (t, 1H), 7.56 (d, 1H), 8.06 (dd, 1H), 8.72 (d, 1H).

Compound 66

2-(5-chloropyridin-2-yl)-2-(1-(4,5,6,7-tetrahydrothieno[3,2-c]pyridine-5-carbonyl)piperidin-4-ylidene) acetonitrile

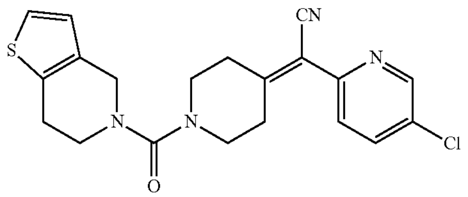 [SMILES: N#CC(=C1CCN(C(=O)N2CCc3sccc3C2)CC1)c1ccc(Cl)cn1]

Compound 66 was synthesized by the method used in the preparation of the compound 3 using THE as a solvent in 55% yield by using INT-46 and 4,5,6,7-tetrahydrothieno[3,2-c]pyridine, HCl (150 mol-%) as starting materials stirring 3 hours at +50° C. $^1$H-NMR (400 MHz, DMSO-$d_6$): 2.68 (t, 2H), 2.78 (t, 2H), 2.86 (t, 2H), 3.28 (t, 2H), 3.44 (t, 2H), 3.49 (t, 2H), 4.32 (s, 2H), 6.88 (d, 1H), 7.33 (d, 1H), 7.57 (d, 1H), 8.06 (dd, 1H), 8.73 (d, 1H).

Compound 67

2-(5-chloropyridin-2-yl)-2-(1-(4,5,6,7-tetrahydro-1H-pyrazolo[4,3-c]pyridine-5-carbonyl)piperidin-4-ylidene)acetonitrile

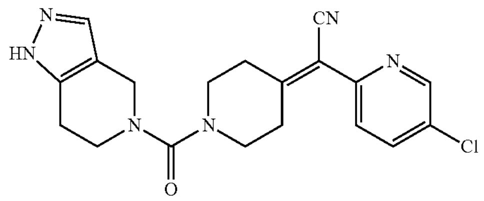 [SMILES: N#CC(=C1CCN(C(=O)N2CCc3[nH]ncc3C2)CC1)c1ccc(Cl)cn1]

Compound 67 was synthesized by the method used in the preparation of the compound 3 using THE as a solvent in 38% yield by using INT-46 and 4,5,6,7-tetrahydro-1H-pyrazolo[4,3-c]pyridine (150 mol-%) as starting materials stirring 3 hours at +50° C. $^1$H-NMR (400 MHz, DMSO-$d_6$): 2.66 (t, 2H), 2.72 (t, 2H), 2.77 (t, 2H), 3.26 (t, 2H), 3.44 (m, 4H), 4.25 (s, 2H), 7.28-7.49 (m, 1H), 7.57 (d, 1H), 8.06 (dd, 1H), 8.73 (d, 1H), 12.48 (s, 1H).

Compound 68

2-(5-chloropyridin-2-yl)-2-(1-(5,6,7,8-tetrahydroimidazo[1,5-a]pyrazine-7-carbonyl)piperidin-4-ylidene) acetonitrile

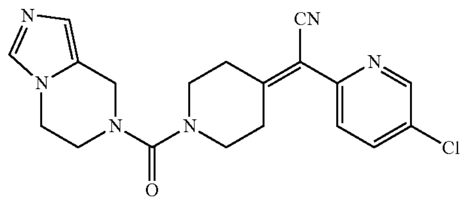 [SMILES: N#CC(=C1CCN(C(=O)N2CCn3cncc3C2)CC1)c1ccc(Cl)cn1]

Compound 68 was synthesized by the method used in the preparation of the compound 3 using THE as a solvent in 57% yield by using INT-46 and 5,6,7,8-tetrahydroimidazo[1,5-a]pyrazine (150 mol-%) as starting materials stirring 3 hours at +50° C. $^1$H-NMR (400 MHz, DMSO-$d_6$): 2.68 (t, 2H), 2.78 (t, 2H), 3.30 (t, 2H), 3.47 (t, 2H), 3.56 (t, 2H), 4.09 (t, 2H), 4.43 (s, 2H), 6.72 (s, 1H), 7.57 (m, 2H), 8.06 (dd, 1H), 8.73 (d, 1H).

Compound 69

4-((4-chlorophenyl)(cyano)methylene)-N-methyl-N-(tetrahydro-2H-pyran-4-yl)piperidine-1-carboxamide

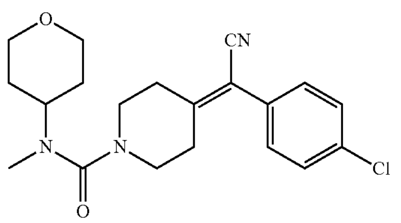 [SMILES: CN(C(=O)N1CCC(=C(C#N)c2ccc(Cl)cc2)CC1)C1CCOCC1]

Compound 69 was synthesized in 17% yield after chromatographic purification by the method used in the preparation of the compound 3 by using INT-8 and methyl (tetrahydro-pyran-4-yl)-amine as starting materials in 6 hours reaction time. $^1$H-NMR (400 MHz, $CDCl_3$): 1.60-1.70 (m, 2H), 1.78-1.90 (m, 2H), 2.48 (t, 2H), 2.79 (s, 3H), 2.81 (t, 2H), 3.22 (t, 2H), 3.40 (t, 2H), 3.46 (t, 2H), 3.93 (m, 1H), 4.01-4.06 (m, 2H), 7.21-7.25 (m, 2H), 7.37-7.41 (m, 2H).

Compound 70

2-(1-(4-hydroxypiperidine-1-carbonyl)piperidin-4-ylidene)-2-(1H-indazol-3-yl)acetonitrile

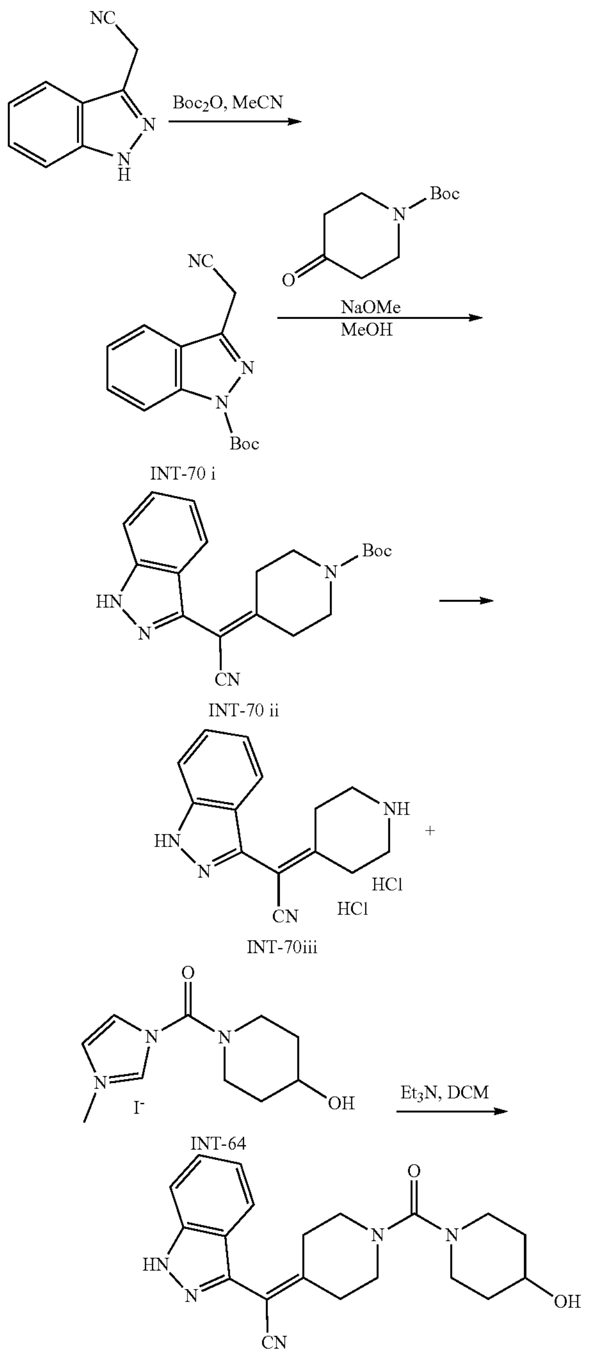

INT-70 i

INT-70 ii

INT-70iii

INT-64

Compound 70

INT-70i: To a solution of 2-(1H-indazol-3-yl)acetonitrile (250 mg, 100 mol-%.) in MeCN (6.3 mL) was added di-tert-butyl dicarbonate (417 mg, 120 mol-%) and DMAP (3.9 mg, 2 mol-%), and the reaction stirred for 3 h. The reaction mixture was concentrated under reduced pressure to give a residue which was taken up in water (20 mL) and extracted with EtOAc (3×30 mL). The organic layers were combined and washed with saturated aqueous sodium bicarbonate solution (30 mL), brine (30 mL), dried (sodium sulphate) and concentrated under reduced pressure. The residue was purified by column chromatography (0-25% EtOAc in hexanes) to give tert-butyl 3-(cyanomethyl)-1H-indazole-1-carboxylate (400 mg, 98%) as a yellow oil. $^1$H-NMR (400 MHz, $CDCl_3$) δ ppm 8.17 (d, 1H), 7.86 (dt, 1H), 7.59 (ddd, 1H), 7.40 (ddd, 1H), 4.12 (s, 2H), 1.73 (s, 9H). m/z (ES+) 202.1 (M−t−Bu+H)

INT-70ii: Prepared according to General Method A to give tert-butyl-4-[cyano(1H-indazol-3-yl)methylidene]piperidine-1-carboxylate in 58% yield as an off-white solid. $^1$H-NMR (400 MHz, $CDCl_3$) δ ppm 7.99 (dq, 1H), 7.65-7.50 (m, 2H), 3.77 (t, 2H), 3.60 (s, 1H), 2.98 (t, 2H), 2.89-2.77 (m, 2H), 1.58 (s, 9H). m/z (ES+) 239.2 $(M\text{-}Boc+H)^+$.

INT-70iii: Prepared according to General Method B to give 2-(1H-indazol-3-yl)-2-(piperidin-4-ylidene)acetonitrile dihydrochloride in 62% yield as a pale yellow solid. $^1$H-NMR (400 MHz, DMSO-$d_6$) δ ppm 13.65 (s, 1H), 9.38 (s, 2H), 7.82 (dt, 1H), 7.63 (dd, 1H), 7.44 (ddd, 1H), 7.25 (ddd, 1H), 3.42-3.28 (m, 2H), 3.21-3.10 (m, 2H), 3.03 (t, 2H), 2.91 (t, 2H). m/z (ES+) 239.2 $(M+H)^+$.

Compound 70 was synthesized as an off-white powder in 20% yield by the method used in the preparation of the compound 41 by using INT-70iii and INT-64 as starting materials. $^1$H-NMR (400 MHz, $CDCl_3$) δ ppm 10.26 (s, 1H), 7.89 (d, 1H), 7.56-7.50 (m, 1H), 7.50-7.41 (m, 1H), 7.30-7.22 (m, 1H), 3.99-3.83 (m, 1H), 3.66-3.56 (m, 2H), 3.51 (t, 2H), 3.33 (t, 2H), 3.02 (ddd, 2H), 2.96-2.89 (m, 2H), 2.78 (t, 2H), 1.96-1.88 (m, 2H), 1.66-1.39 (m, 3H). m/z (ES+) 366.2 $(M+H)^+$.

Compound 71

2-(1H-indazol-7-yl)-2-(1-(4,5,6,7-tetrahydro-1H-pyrazolo[4,3-c]pyridine-5-carbonyl)piperidin-4-ylidene)acetonitrile

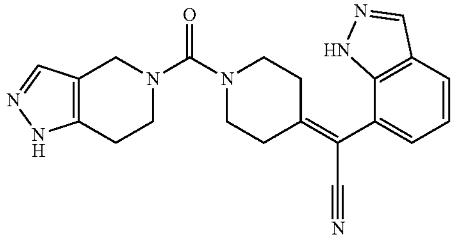 [SMILES: N#CC(=C1CCN(C(=O)N2CCc3[nH]ncc3C2)CC1)c1cccc2cn[nH]c12]

Compound 71 was synthesized by the method used in the preparation of the compound 3 using THE as a solvent in 9% yield by using a mixture of non-methylated and methylated INT-61 and 4,5,6,7-tetrahydro-1H-pyrazolo[4,3-c]pyridine (150 mol-%) as starting materials stirring 3 hours at +50° C. $^1$H-NMR (400 MHz, $CDCl_3$): 2.43 (t, 2H), 2.85 & 2.86 (2×t, 4H), 3.28 (t, 2H), 3.51 (t, 2H), 3.57 (t, 2H), 4.36 (s, 2H), 7.22 (t, 1H), 7.29 (d, 1H), 7.37 (s, 1H), 7.81 (d, 1H), 8.14 (s, 1H), 10.51 (br s, 1H), 11.55 (br s, 1H).

Compound 72

2-(1H-indazol-7-yl)-2-(1-(5,6,7,8-tetrahydroimidazo[1,5-a]pyrazine-7-carbonyl)piperidin-4-ylidene)acetonitrile

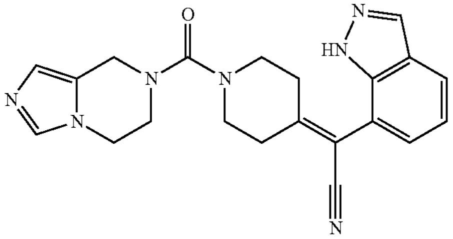 [SMILES: N#CC(=C1CCN(C(=O)N2CCn3cncc3C2)CC1)c1cccc2cn[nH]c12]

Compound 72 was synthesized by the method used in the preparation of the compound 3 in 9% yield by using a mixture of methylated and non-methylated INT-61 and 5,6,7,8-tetrahydroimidazo[1,5-a]pyrazine (150 mol-%) as starting materials stirring 3 hours at +50° C. $^1$H-NMR (400 MHz, $CDCl_3$): 2.45 (t, 2H), 2.88 (t, 2H), 3.29 (t, 2H), 3.51 (t, 2H), 3.68 (t, 2H), 4.12 (t, 2H), 4.54 (s, 2H), 6.85 (s, 1H), 7.22 (t, 1H), 7.28 (m, 1H), 7.51 (s, 1H), 7.82 (d, 1H), 8.15 (s, 1H), 11.68 (br s, 1H).

Compound 73

2-(2,4-difluorophenyl)-2-(1-(4-(methoxymethyl)piperidine-1-carbonyl)piperidin-4-ylidene)acetonitrile

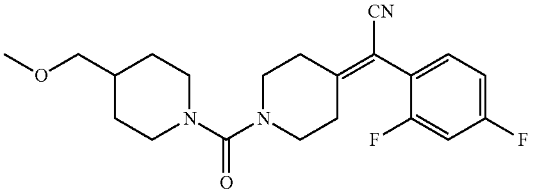 [SMILES: COCC1CCN(C(=O)N2CCC(=C(C#N)c3ccc(F)cc3F)CC2)CC1]

Compound 73 was synthesized by the method used in the preparation of the compound 3 in 88% yield by using INT-18 and 4-(methoxymethyl)piperidine (150 mol-%) as starting materials stirring two hours at room temperature. $^1$H-NMR (400 MHz, DMSO-$d_6$): 1.06-1.16 (m, 2H), 1.25 (m, 1H), 1.62 (d, 2H), 1.69 (br s, 1H), 2.23 (t, 2H), 2.69-2.75 (m, 4H), 3.17 (d, 4H), 3.18 (s, 3H), 3.36 (m, 1H), 3.61 (d, 2H), 7.22 (t, 1H), 7.40-7.51 (m, 2H).

Compound 74

2-(4-chlorophenyl)-2-(1-(4-(hydroxymethyl)piperidine-1-carbonyl)piperidin-4-ylidene)acetonitrile

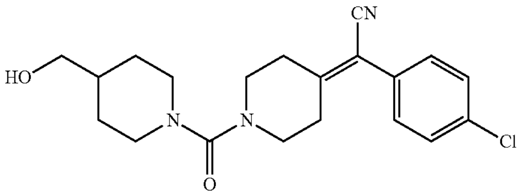 [SMILES: N#CC(=C1CCN(C(=O)N2CCC(CO)CC2)CC1)c1ccc(Cl)cc1]

Compound 74 was synthesized in 84% yield by the method used in the preparation of the compound 3 by using INT-8 and piperidin-4-ylmethanol as starting materials in 5 hours reaction time. $^1$H-NMR (400 MHz, DMSO-$d_6$): 1.03-1.11 (m, 2H), 1.52 (m, 1H), 1.60-1.66 (m, 2H), 2.39 (t, 2H), 2.68-2.75 (m, 4H), 3.17 (t, 2H), 3.25 (t, 2H), 3.33 (m, 2H), 3.59-3.63 (m, 2H), 4.47 (s, 1H), 7.37-7.40 (m, 2H), 7.52-7.55 (m, 2H).

Compound 75

2-(5-chlorothiophen-2-yl)-2-(1-(4-(methoxymethyl)piperidine-1-carbonyl)piperidin-4-ylidene)acetonitrile

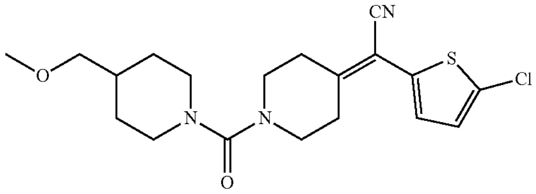 [SMILES: COCC1CCN(C(=O)N2CCC(=C(C#N)c3ccc(Cl)s3)CC2)CC1]

Compound 75 was synthesized in 71% yield after chromatographic purification by the method used in the preparation of the compound 3 by using INT-42 and 4-(methoxymethyl)piperidine as starting materials in 3 hours reaction time. $^1$H-NMR (400 MHz, DMSO-$d_6$): 1.05-1.17 (m, 2H), 1.59-1.65 (m, 2H), 1.70 (m, 1H), 2.57 (t, 2H), 2.65-2.76 (m, 4H), 3.16-3.19 (m, 2H), 3.20-3.25 (m, 2H), 3.23 (s, 3H), 3.33 (m, 2H), 3.57-3.63 (m, 2H), 7.09 (d, 1H), 7.18 (d, 1H).

Compound 76

2-(1-(4-(hydroxymethyl)piperidine-1-carbonyl)piperidin-4-ylidene)-2-(4-(trifluoromethyl)phenyl)acetonitrile

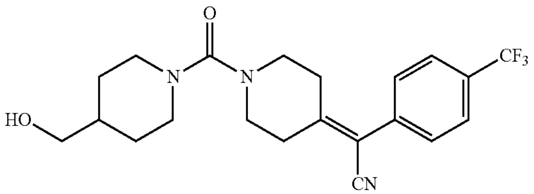 [SMILES: N#CC(=C1CCN(C(=O)N2CCC(CO)CC2)CC1)c1ccc(C(F)(F)F)cc1]

Compound 76 was synthesized by the method used in the preparation of the compound 3 in 94% yield by using INT-38 and piperidin-4-ylmethanol (150 mol-%) as starting materials stirring two hours at room temperature. $^1$H-NMR (400 MHz, DMSO-$d_6$): 1.08 (m, 2H), 1.24 (s, 1H), 1.52 (br s 1H), 1.63 (d, 2H), 2.41 (s, 2H), 2.72 (m, 4H), 3.19 (m, 2H), 3.25 (m, 2H)), 3.36 (m, 1H), 3.62 (d, 2H), 4.47 (s, 1H), 7.61 (d, 2H), 7.84 (d, 2H).

Compound 77

1-(4-((5-chlorothiophen-2-yl)(cyano)methylene) piperidine-1-carbonyl)piperidine-4-sulfonamide

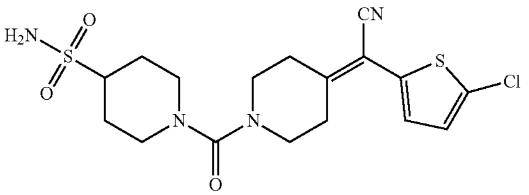 [SMILES: N#CC(=C1CCN(C(=O)N2CCC(S(N)(=O)=O)CC2)CC1)c1ccc(Cl)s1]

Compound 77 was synthesized by the method used in the preparation of the compound 3 in 51% yield after chromatographic purification by using INT-42 and piperidine-4-sulfonamide as starting materials in 4 hours reaction time. $^1$H-NMR (400 MHz, DMSO-$d_6$): 1.55 (m, 2H), 1.98 (m, 2H), 2.59 (m, 2H), 2.71 (m, 2H), 2.81 (m, 2H), 3.02 (m, 1H), 3.26 (m, 2H), 3.33 (m, 2H), 3.70 (m, 2H), 6.76 (br s, 2H), 7.09 (d, 1H), 7.18 (d, 1H).

Compound 78

2-(5-chlorothiophen-2-yl)-2-(1-(4-methoxypiperidine-1-carbonyl)piperidin-4-ylidene)acetonitrile

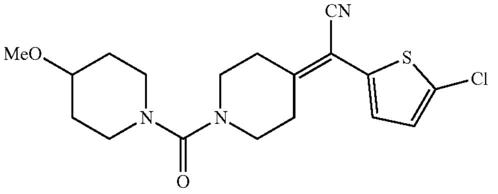 [SMILES: COC1CCN(C(=O)N2CCC(=C(C#N)c3ccc(Cl)s3)CC2)CC1]

Compound 78 was synthesized by the method used in the preparation of the compound 3 in 85% yield by using INT-42 and 4-metoksipiperidiini (150 mol-%) as starting materials stirring two hours at room temperature. $^1$H-NMR (400 MHz, DMSO-$d_6$): 1.38 (m, 2H), 1.82 (m, 2H), 2.57 (m, 2H), 2.69 (m, 2H), 2.93 (t, 2H), 3.25 (m, 5H), 3.30-3.42 (m, 5H), 7.09 (d, 1H), 7.18 (d, 1H).

Compound 79

2-(4-chlorophenyl)-2-(1-(4-methoxypiperidine-1-carbonyl)piperidin-4-ylidene)acetonitrile

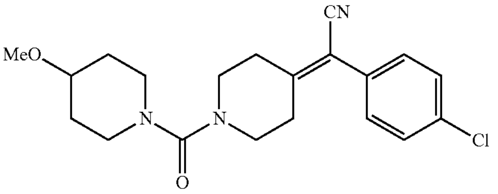 [SMILES: COC1CCN(C(=O)N2CCC(=C(C#N)c3ccc(Cl)cc3)CC2)CC1]

Compound 79 was synthesized by the method used in the preparation of the compound 3 in 85% yield by using INT-8 and 4-metoksipiperidiini (150 mol-%) as starting materials stirring two hours at room temperature. $^1$H-NMR (400 MHz, DMSO-$d_6$): 1.38 (m, 2H), 1.82 (m, 2H), 2.39 (m, 2H), 2.69 (m, 2H), 2.92 (t, 2H), 3.18 (m, 2H), 3.24 (s, 3H), 3.35-3.42 (m, 5H), 7.39 (d, 2H), 7.54 (d, 2H).

Compound 80

2-(3-chlorophenyl)-2-(1-(4-hydroxypiperidine-1-carbonyl)piperidin-4-ylidene)acetonitrile

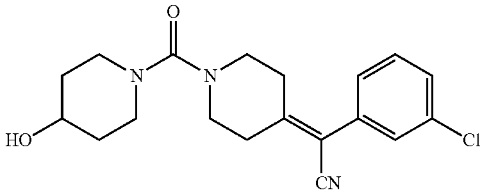 [SMILES: N#CC(=C1CCN(C(=O)N2CCC(O)CC2)CC1)c1cccc(Cl)c1]

Compound 80 was synthesized as a colourless foam in 63% yield by the method used in the preparation of the compound 41 by using INT-28 and INT-64 as starting materials. $^1$H-NMR (400 MHz, DMSO-$d_6$) δ ppm 7.53-7.47 (m, 2H), 7.43 (s, 1H), 7.36-7.30 (m, 1H), 3.65-3.58 (m, 1H), 3.48-3.38 (m, 2H), 3.34 (t, 2H), 3.18 (t, 2H), 2.88 (ddd, 2H), 2.69 (t, 2H), 2.39 (t, 2H), 1.76-1.66 (m, 2H), 1.38-1.26 (m, 2H). m/z (ES+) 360.2/362.2 $(M+H)^+$.

Compound 81

2-(5-chloropyridin-2-yl)-2-(1-(4-methoxypiperidine-1-carbonyl)piperidin-4-ylidene)acetonitrile

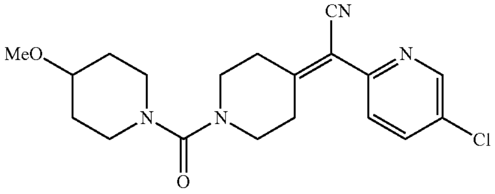 [SMILES: COC1CCN(C(=O)N2CCC(=C(C#N)c3ccc(Cl)cn3)CC2)CC1]

Compound 82 was synthesized by the method used in the preparation of the compound 3 in 86% yield by using INT-46 and 4-metoksipiperidiini (150 mol-%) as starting materials stirring 4 hours at room temperature. $^1$H-NMR (400 MHz, DMSO-$d_6$): 1.38 (m, 2H), 1.82 (m, 2H), 2.64 (m, 2H), 2.74 (m, 2H), 2.93 (t, 2H), 3.22 (m, 2H), 3.25 (s, 3H), 3.30-3.42 (m, 5H), 7.56 (d, 1H), 8.05 (d, 1H), 8.72 (s, 1H).

Compound 82

(S)-2-(4-chlorophenyl)-2-(1-(2-(methoxymethyl) pyrrolidine-1-carbonyl)piperidin-4-ylidene)acetonitrile

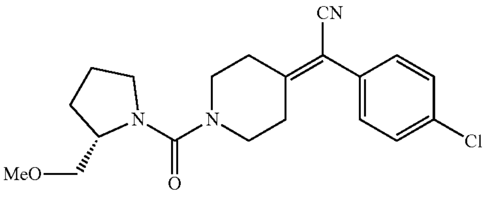 [SMILES: COC[C@@H]1CCCN1C(=O)N1CCC(=C(C#N)c2ccc(Cl)cc2)CC1]

Compound 82 was synthesized as a oil by the method used in the preparation of the compound 3 in 77% yield by using INT-8 and (S)-(+)-2-(methoxymethyl)pyrrolidine (150 mol-%) as starting materials stirring 1.5 hours at room temperature. $^{1}$H-NMR (400 MHz, DMSO-$d_6$): 1.61 (m, 2H), 1.82 (m, 1H), 1.98 (m, 1H), 2.32 (m, 1H), 2.44 (m, 1H), 2.62 (m, 1H), 2.76 (m, 1H), 3.17 (t, 2H), 3.24 (s, 3H), 3.41 (m, 6H), 4.06 (br s, 1H), 7.39 (d, 2H), 7.54 (d, 2H).

Compound 83

2-(5-fluoropyridin-2-yl)-2-(1-(morpholine-4-carbonyl)piperidin-4-ylidene)acetonitrile

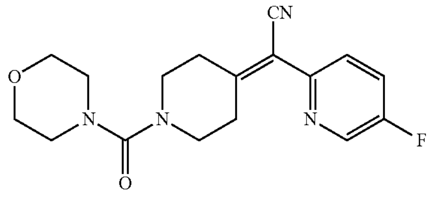

Compound 83 was synthesized by the method used in the preparation of the compound 1 in 86% yield by using INT-48 and 4-morpholinecarbonyl chloride (150 mol-%) as starting materials stirring two hours at room temperature. $^{1}$H-NMR (400 MHz, DMSO-$d_6$): 2.83 (m, 4H), 3.30 (t, 4H), 3.35 (t, 2H), 3.49 (t, 2H), 3.70 (t, 4H), 7.46-7.53 (m, 2H), 8.49 (d, 1H).

Compound 84

2-(5-fluoropyridin-2-yl)-2-(1-(4,5,6,7-tetrahydroisoxazolo[4,3-c]pyridine-5-carbonyl)piperidin-4-ylidene)acetonitrile

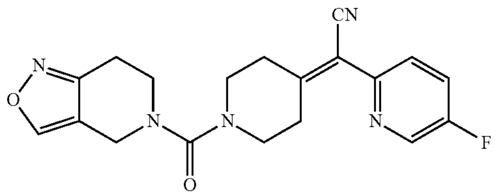 [SMILES: N#CC(=C1CCN(C(=O)N2CCc3nocc3C2)CC1)c1ccc(F)cn1]

Compound 84 was synthesized by the method used in the preparation of the compound 3 in 68% yield by using INT-50 and 4,5,6,7-tetrahydroisoxazolo[4,3-c]pyridine× HCl (150 mol-%) as starting materials stirring 5 hours at room temperature. $^{1}$H-NMR (400 MHz, DMSO-$d_6$): 2.64 (m, 2H), 2.77 (m, 2H), 2.87 (m, 2H), 3.29 (m, 2H), 3.46 (m, 4H), 4.31 (s, 2H), 7.61 (s, 1H), 7.86 (s, 1H), 8.68 (s, 2H).

Compound 85

2-(4-fluorophenyl)-2-(1-(3-(hydroxymethyl)azetidine-1-carbonyl)piperidin-4-ylidene)acetonitrile

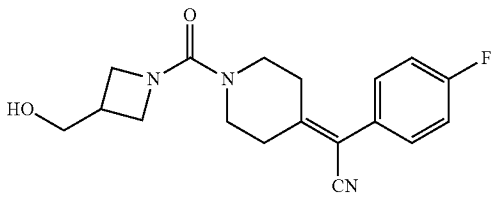 [SMILES: N#CC(=C1CCN(C(=O)N2CC(CO)C2)CC1)c1ccc(F)cc1]

Compound 85 was synthesized by the method used in the preparation of the compound 3 in 62% yield by using INT-4 and azetidin-3-ylmethanol, HCl (150 mol-%) as starting materials stirring 5 hours at room temperature. $^{1}$H-NMR (400 MHz, DMSO-$d_6$): 2.34 (t, 2H), 2.59 (m, 1H), 2.65 (t, 2H), 3.25 (t, 2H), 3.42 (t, 2H), 3.49 (t, 2H), 3.64 (t, 2H), 3.90 (t, 2H), 4.75 (t, 1H), 7.31 (dd, 2H), 7.40 (dd, 2H).

Compound 86

2-(5-chloropyridin-3-yl)-2-(1-(4-hydroxypiperidine-1-carbonyl)piperidin-4-ylidene)acetonitrile

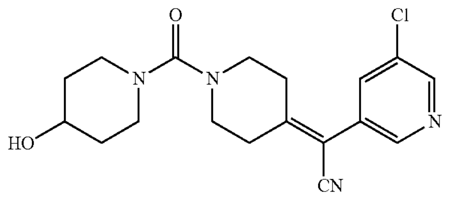 [SMILES: N#CC(=C1CCN(C(=O)N2CCC(O)CC2)CC1)c1cncc(Cl)c1]

Compound 86 was prepared starting from tert-butyl 4-oxopiperidine-1-carboxylate and 2-(5-chloropyridin-3-yl) acetonitrile according to General method A in 38% yield, followed by General method B yielding dihydrochloride intermediate as an off-white powder in 77% yield. Finally compound 86 was synthesized as a cream solid in 62% yield by the method used in the preparation of the compound 41 by using 2-(5-chloropyridin-3-yl)-2-(piperidin-4-ylidene) acetonitrile dihydrochloride and INT-64 as starting materials. $^{1}$H-NMR (400 MHz, $CDCl_3$) δ ppm 8.58 (d, 1H), 8.40 (d, 1H), 7.65 (t, 1H), 3.98-3.82 (m, 1H), 3.60 (dt, 2H), 3.45 (t, 2H), 3.28 (t, 2H), 3.03 (ddd, 2H), 2.84 (t, 2H), 2.48 (t, 2H), 1.90 (dt, 2H), 1.58-1.44 (m, 3H). m/z (ES+) 361.2/363.2 $(M+H)^+$.

Compound 87

2-(1-(4,5,6,7-tetrahydroisoxazolo[4,3-c]pyridine-5-carbonyl)piperidin-4-ylidene)-2-(4-(trifluoromethyl)phenyl)acetonitrile

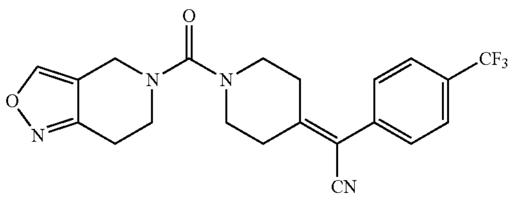 [SMILES: N#CC(=C1CCN(C(=O)N2CCc3nocc3C2)CC1)c1ccc(C(F)(F)F)cc1]

Compound 87 was synthesized by the method used in the preparation of the compound 3 in 93% yield by using INT-38 and 4,5,6,7-tetrahydroisoxazolo[4,3-c]pyridine, HCl (150 mol-%) as starting materials stirring two hours at room temperature. $^{1}$H-NMR (400 MHz, DMSO-$d_6$): 2.44 (t, 2H), 2.76 (t, 2H), 2.87 (t, 2H), 3.27 (t, 2H), 3.46 (m, 4H), 4.31 (s, 2H), 7.61 (d, 2H), 7.85 (d, 2H), 8.68 (s, 1H).

Compound 88

2-(3-chlorophenyl)-2-(1-(4-(hydroxymethyl)piperidine-1-carbonyl)piperidin-4-ylidene)acetonitrile

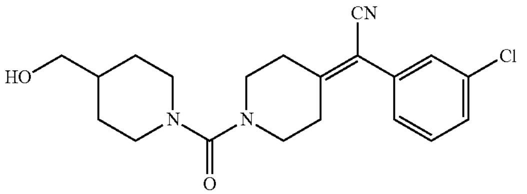 [SMILES: N#CC(=C1CCN(C(=O)N2CCC(CO)CC2)CC1)c1cccc(Cl)c1]

Compound 88 was synthesized by the method used in the preparation of the compound 3 in 64% yield by using INT-30 and piperidin-4-ylmethanol as starting materials in two hours reaction time. $^{1}$H-NMR (400 MHz, DMSO-$d_6$): 1.02-1.10 (m, 2H), 1.51 (m, 1H), 1.60-1.65 (m, 2H), 2.39 (t, 2H), 2.65-2.75 (m, 4H), 3.18 (t, 2H), 3.24 (t, 2H), 3.30-3.40 (m, 2H), 3.58-3.63 (m, 2H), 4.46 (s, 1H), 7.33 (m, 1H), 7.44 (m, 1H), 7.46-7.54 (m, 2H).

Compound 89

2-(3-chlorophenyl)-2-(1-(4,5,6,7-tetrahydroisoxazolo[4,3-c]pyridine-5-carbonyl)piperidin-4-ylidene)acetonitrile

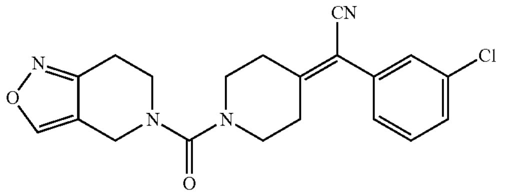 [SMILES: N#CC(=C1CCN(C(=O)N2CCc3nocc3C2)CC1)c1cccc(Cl)c1]

Compound 89 was synthesized by the method used in the preparation of the compound 3 in 74% yield by using INT-30 and 4,5,6,7-tetrahydroisoxazolo[4,3-c]pyridine×HCl as starting materials in 6 hours reaction time. $^{1}$H-NMR (400 MHz, DMSO-$d_6$): 2.42 (t, 2H), 2.73 (t, 2H), 2.87 (t, 2H), 3.26 (t, 2H), 3.40-3.50 (m, 4H), 4.31 (s, 2H), 7.34 (m, 1H), 7.45 (m, 1H), 7.48-7.52 (m, 2H), 8.68 (s, 1H).

Compound 90

2-(4-chlorophenyl)-2-(1-(4-(trifluoromethyl)piperidine-1-carbonyl)piperidin-4-ylidene)acetonitrile

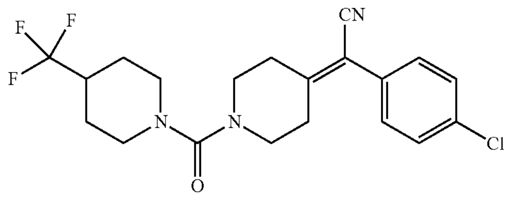 [SMILES: N#CC(=C1CCN(C(=O)N2CCC(C(F)(F)F)CC2)CC1)c1ccc(Cl)cc1]

Compound 90 was synthesized by the method used in the preparation of the compound 3 in 82% yield by using INT-8 and 4-(trifluoromethyl)piperidine as starting materials in 6 hours reaction time. $^{1}$H-NMR (400 MHz, DMSO-$d_6$): 1.33-1.46 (m, 2H), 1.75-1.80 (m, 2H), 2.39 (t, 2H), 2.50-2.55 (m, 1H), 2.70 (t, 2H), 2.73-2.83 (m, 2H), 3.20 (t, 2H), 3.37 (t, 2H), 3.60-3.70 (m, 2H), 7.37-7.41 (m, 2H), 7.52-7.56 (m, 2H).

Compound 91

2-(2,4-difluorophenyl)-2-(1-(4-methoxypiperidine-1-carbonyl)piperidin-4-ylidene)acetonitrile

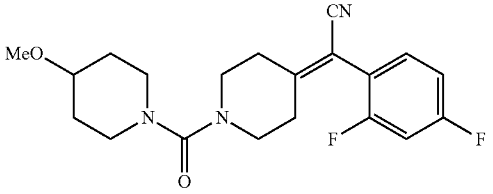 [SMILES: COC1CCN(C(=O)N2CCC(=C(C#N)c3ccc(F)cc3F)CC2)CC1]

Compound 91 was synthesized by the method used in the preparation of the compound 3 in 63% yield by using INT-18 and 4-methoxypiperidine as starting materials in two hours reaction time. $^{1}$H-NMR (400 MHz, DMSO-$d_6$): 1.33-1.42 (m, 2H), 1.75-1.85 (m, 2H), 2.23 (t, 2H), 2.71 (t, 2H), 2.88-3.00 (m, 2H), 3.17 (t, 2H), 3.24 (t, 3H), 3.25-3.45 (m, 5H), 7.18-7.25 (m, 1H), 7.38-7.52 (m, 2H).

Compound 92

2-(1-(4-ethoxypiperidine-1-carbonyl)piperidin-4-ylidene)-2-(1H-indazol-4-yl)acetonitrile

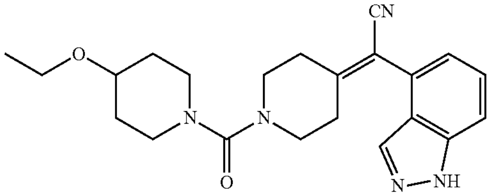 [SMILES: CCOC1CCN(C(=O)N2CCC(=C(C#N)c3cccc4[nH]ncc34)CC2)CC1]

Compound 92 was synthesized by the method used in the preparation of the compound 3 by using INT-55 and 4-ethoxypiperidine as starting materials in four hours reaction time. The product was purified chromatographically, followed by acetate removal with 2 N HCl in methanol in 6 hours reaction time at room temperature. The total yield was 50%. $^{1}$H-NMR (400 MHz, DMSO-$d_6$): 1.10 (t, 3H), 1.30-1.42 (m, 2H), 1.75-1.85 (m, 2H), 2.29 (t, 2H), 2.78 (t, 2H), 2.85-2.95 (m, 2H), 3.15 (t, 2H), 3.35-3.50 (m, 7H), 7.08 (d, 1H), 7.39-7.45 (m, 1H), 7.61 (d, 1H), 8.08 (s, 1H), 13.35 (br s, 1H).

Compound 93

2-(1-acetyl-1H-indazol-4-yl)-2-(1-(4,5,6,7-tetrahydroisoxazolo[4,3-c]pyridine-5-carbonyl)piperidin-4-ylidene)acetonitrile

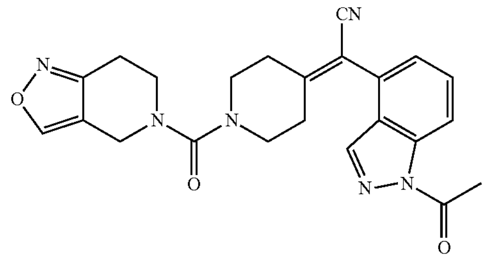 [SMILES: CC(=O)n1ncc2c(C(C#N)=C3CCN(C(=O)N4CCc5nocc5C4)CC3)cccc21]

Compound 93 was synthesized by the method used in the preparation of the compound 3 in 46% yield after chromatographic purification by using INT-55 and 4,5,6,7-tetrahydroisoxazolo[4,3-c]pyridine×HCl as starting materials in 7 hours reaction time. $^{1}$H-NMR (400 MHz, DMSO-$d_6$): 2.29 (t, 2H), 2.75 (s, 3H), 2.80-2.90 (m, 4H), 3.22 (t, 2H), 3.46 (t, 2H), 3.51 (t, 2H), 4.31 (s, 2H), 7.41 (d, 1H), 7.69-7.75 (m, 1H), 8.38 (d, 1H), 8.53 (s, 1H), 8.68 (s, 1H).

Compound 94

2-(5-fluoro-1H-indazol-3-yl)-2-(1-(4-hydroxypiperidine-1-carbonyl)piperidin-4-ylidene)acetonitrile

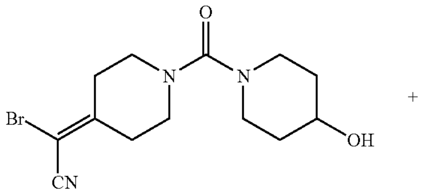

INT-63

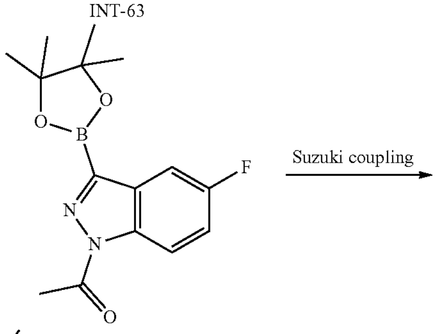

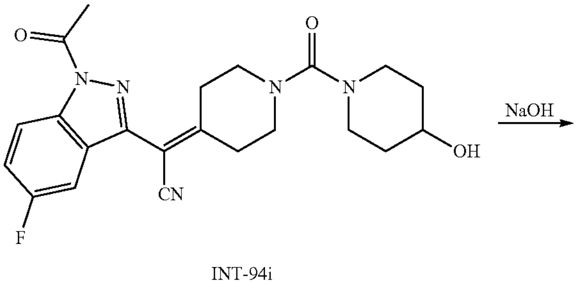

INT-94i

-continued

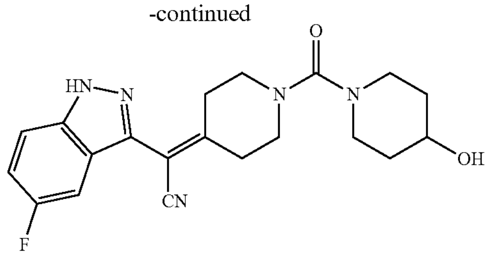

Compound 94

INT-94i: To a mixture of INT-63 (120 mg, 100 mol-%), 1-[5-fluoro-3-(4,4,5,5-tetramethyl-1,3,2-dioxaborolan-2-yl)-1H-indazol-1-yl]ethan-1-one (133 mg, 120 mol-%) and caesium carbonate (238 mg, 200 mol-%) in 1,4-dioxane (1.4 mL) and water (0.2 mL) was added [1,1'-bis(di-tert-butylphosphino)ferrocene]dichloropalladium(II) (6 mg, 0.025 mol-%) and the mixture sparged with nitrogen for 2 min. The reaction mixture was heated at 60° C. under nitrogen for 18 h, then allowed to cool. The reaction mixture was diluted with water (10 mL), and extracted with EtOAc (3×10 mL). The combined extracts were dried (sodium sulphate), and concentrated under reduced pressure to give to give 2-(1-acetyl-5-fluoro-1H-indazol-3-yl)-2-[1-(4-hydroxypiperidine-1-carbonyl)piperidin-4-ylidene]acetonitrile as a brown gum, which was used without purification. m/z (ES+) 426.3 $(M+H)^+$.

Compound 94 was prepared from INT-94i by addition of 1M NaOH solution (0.40 mL, 0.40 mmol), and the mixture was stirred at 20° C. for 1 h. The reaction mixture was quenched with saturated aqueous ammonium chloride solution (10 mL) and the mixture was extracted with EtOAc (3×10 mL). The combined organics layers were washed with brine (10 mL), dried (sodium sulphate), concentrated under reduced pressure, and purified by column chromatography (1-10% MeOH in DCM) in 14% yield as a pale brown solid. $^{1}$H-NMR (400 MHz, $CD_3OD$+10% $CDCl_3$) δ ppm 7.57 (dd, 1H), 7.44 (dd, 1H), 7.25 (td, 1H), 3.83-3.72 (m, 1H), 3.68-3.57 (m, 1H), 3.52 (t, 2H), 3.38-3.32 (m, 2H), 3.02 (ddd, 2H), 2.91 (t, 2H), 2.70 (t, 2H), 1.91-1.80 (m, 2H), 1.56-1.41 (m, 2H). $^{19}$F NMR (376 MHz, $CD_3OD$+10% $CDCl_3$) δ ppm −122.86. m/z (ES+) 382.2, $(M+H)^+$.

Compound 95

2-(3-chlorophenyl)-2-(1-(4-(3-hydroxypropyl)piperidine-1-carbonyl)piperidin-4-ylidene)acetonitrile

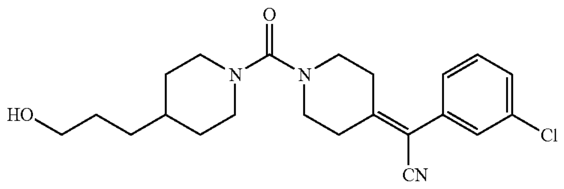 [SMILES: N#CC(=C1CCN(C(=O)N2CCC(CCCO)CC2)CC1)c1cccc(Cl)c1]

Compound 95 was synthesized by the method used in the preparation of the compound 3 in 73% yield by using INT-28 and 4-piperidinepropanol (150 mol-%) as starting materials stirring two hours at room temperature. $^{1}$H-NMR (400 MHz, DMSO-$d_6$): 1.05 (m, 2H), 1.22 (m, 2H), 1.42 (m, 3H), 1.63 (m, 2H), 2.35 (s, 3H), 2.70 (m, 4H), 3.18 (m, 2H), 3.30 (m, 3H), 3.59 (m, 2H), 4.37 (s, 1H), 7.33 (br s, 1H), 7.44 (s, 1H), 7.50 (m, 2H).

Compound 96

2-(1-(4-acetylpiperazine-1-carbonyl)piperidin-4-ylidene)-2-(3-chlorophenyl)acetonitrile

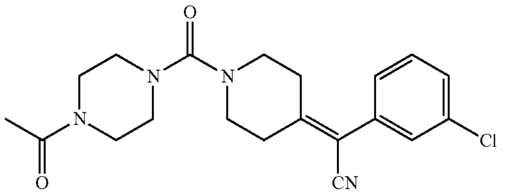 [SMILES: CC(=O)N1CCN(C(=O)N2CCC(=C(C#N)c3cccc(Cl)c3)CC2)CC1]

Compound 96 was synthesized by the method used in the preparation of the compound 3 in 67% yield by using INT-28 and 1-acetylpiperazine (150 mol-%) as starting materials stirring two hours at room temperature. $^{1}$H-NMR (400 MHz, DMSO-$d_6$): 2.01 (s, 3H), 2.40 (m, 2H), 2.71 (m, 2H), 3.13 (m, 2H), 3.19 (m, 2H), 3.24 (m, 2H), 3.44 (m, 6H), 7.34 (m, 1H), 7.45 (s, 1H), 7.50 (m, 2H).

Compound 97

2-(4-fluorophenyl)-2-(1-(4-(2-hydroxyethyl)piperidine-1-carbonyl)piperidin-4-ylidene)acetonitrile

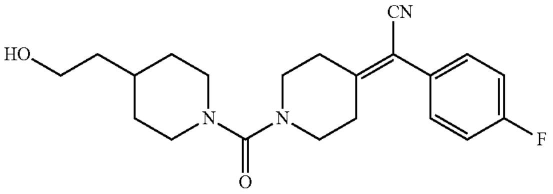 [SMILES: N#CC(=C1CCN(C(=O)N2CCC(CCO)CC2)CC1)c1ccc(F)cc1]

Compound 97 was synthesized by the method used in the preparation of the compound 3 in 61% yield after chromatographic purification by using INT-4 and 4-piperidineethanol as starting materials in 4 hours reaction time. $^{1}$H-NMR (400 MHz, DMSO-$d_6$): 1.00-1.12 (m, 2H), 1.32-1.40 (m, 2H), 1.50-1.59 (m, 1H), 1.59-1.65 (m, 2H), 2.37 (t, 2H), 2.65-2.75 (m, 4H), 3.17 (t, 2H), 3.30-3.37 (m, 2H), 3.40-3.49 (m, 2H), 3.55-3.62 (m, 2H), 4.36 (t, 1H), 7.28-7.34 (m, 2H), 7.37-7.43 (m, 2H).

Compound 98

2-(4-fluorophenyl)-2-(1-(4-(trifluoromethyl)piperidine-1-carbonyl)piperidin-4-ylidene)acetonitrile

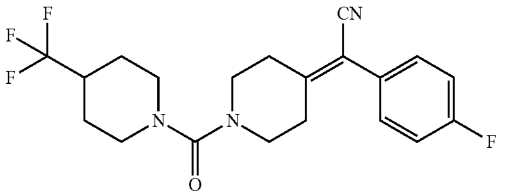 [SMILES: N#CC(=C1CCN(C(=O)N2CCC(C(F)(F)F)CC2)CC1)c1ccc(F)cc1]

Compound 98 was synthesized by the method used in the preparation of the compound 3 in 74% yield by using INT-4 and 4-(trifluoromethyl)piperidine as starting materials in 4 hours reaction time. $^{1}$H-NMR (400 MHz, DMSO-$d_6$): 1.33-1.47 (m, 2H), 1.75-1.82 (m, 2H), 2.39 (t, 2H), 2.45-2.55 (m, 1H), 2.70 (t, 2H), 2.79 (t, 2H), 3.21 (t, 2H), 3.30-3.40 (m, 2H), 3.62-3.70 (m, 2H), 7.28-7.34 (m, 2H), 7.39-7.45 (m, 2H).

Compound 99

1-(4-((3-chlorophenyl)(cyano)methylene)piperidine-1-carbonyl)piperidine-4-sulfonamide

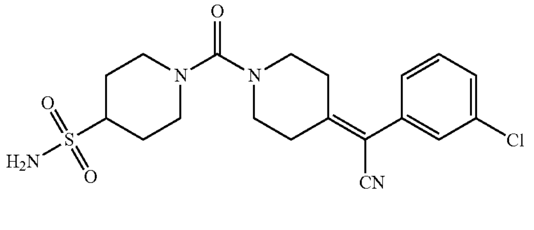 [SMILES: N#CC(=C1CCN(C(=O)N2CCC(S(N)(=O)=O)CC2)CC1)c1cccc(Cl)c1]

Compound 99 was synthesized by the method used in the preparation of the compound 3 in 64% yield by using INT-28 and 4-piperidinesulfonamide HCl (150 mol-%) as starting materials stirring two hours at room temperature. $^{1}$H-NMR (400 MHz, DMSO-$d_6$): 1.53 (m, 2H), 1.97 (m, 2H), 2.40 (m, 2H), 2.70 (t, 2H), 2.81 (t, 2H), 3.02 (t, 1H), 3.21 (t, 2H), 3.37 (m, 2H), 3.70 (m, 2H), 6.76 (s, 2H), 7.33 (m, 1H), 7.44 (s, 1H), 7.50 (m, 2H).

Compound 100

2-(4-fluorophenyl)-2-(1-(thiomorpholine-4-carbonyl)piperidin-4-ylidene)acetonitrile

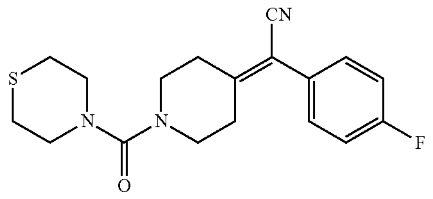 [SMILES: N#CC(=C1CCN(C(=O)N2CCSCC2)CC1)c1ccc(F)cc1]

Compound 100 was synthesized by the method used in the preparation of the compound 3 in 48% yield by using INT-4 and thiomorpholine as starting materials in 3 hours reaction time. $^{1}$H-NMR (400 MHz, DMSO-$d_6$): 2.38 (m, 2H), 2.40-2.60 (m, 6H), 2.69 (m, 2H), 3.19 (m, 2H), 3.41 (s, 4H), 7.31 (m, 2H), 7.41 (m, 2H).

Compound 101

2-(4-fluorophenyl)-2-(1-(octahydrocyclopenta[c]pyrrole-2-carbonyl)piperidin-4-ylidene)acetonitrile

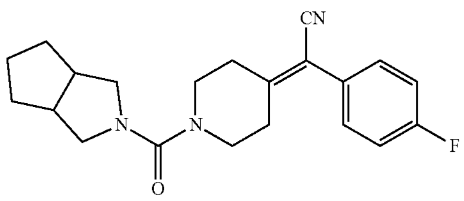 [SMILES: N#CC(=C1CCN(C(=O)N2CC3CCCC3C2)CC1)c1ccc(F)cc1]

Compound 101 was synthesized by the method used in the preparation of the compound 3 in 70% yield by using INT-4 and octahydrocyclopenta[c]pyrrole as starting materials in 1 hour reaction time. $^1$H-NMR (400 MHz, DMSO-$d_6$): 1.37 (t, 2H), 1.52 (m, 1H), 1.62-1.73 (m, 3H), 2.37 (m, 2H), 2.54 (m, 2H), 2.68 (m, 2H), 3.05 (d, 2H), 3.21 (m, 2H), 3.38 (m, 2H), 3.47 (t, 2H), 7.30 (t, 2H), 7.41 (t, 2H).

Compound 102

2-(4-fluorophenyl)-2-(1-(indoline-1-carbonyl)piperidin-4-ylidene)acetonitrile

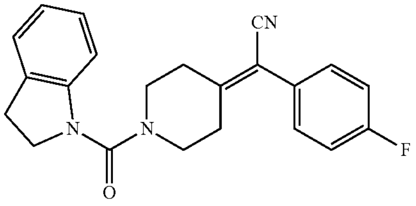 [SMILES: N#CC(=C1CCN(C(=O)N2CCc3ccccc32)CC1)c1ccc(F)cc1]

Compound 102 was synthesized by the method used in the preparation of the compound 3 in 17% yield by using INT-4 and indoline as starting materials in overnight reaction time. Purified by heptane trituration as an oil. $^1$H-NMR (400 MHz, $CDCl_3$): 2.53 (t, 2H), 2.86 (t, 2H), 3.05 (t, 2H), 3.40 (t, 2H), 3.57 (t, 2H), 3.95 (t, 2H), 6.92 (t, 1H), 7.01 (d, 1H), 7.11 (m, 3H), 7.19 (d, 1H), 7.29 (m, 2H).

Compound 103

4-((5-chlorothiophen-2-yl)(cyano)methylene)-N-methyl-N-(oxetan-3-yl)piperidine-1-carboxamide

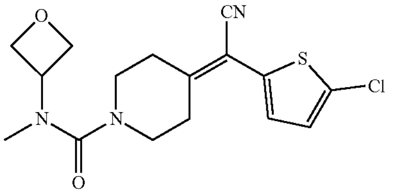 [SMILES: CN(C(=O)N1CCC(=C(C#N)c2ccc(Cl)s2)CC1)C1COC1]

Compound 103 was synthesized by the method used in the preparation of the compound 3 in 94% yield by using INT-42 and N-methyl-3-oxetanamine as starting materials in 4.5 hours reaction time. $^1$H-NMR (400 MHz, DMSO-$d_6$): 2.59 (t, 2H), 2.71 (t, 2H), 2.80 (s, 3H), 3.26 (t, 2H), 3.38 (t, 2H), 4.50-4.65 (m, 5H), 7.11 (d, 1H), 7.19 (d, 1H).

Compound 104

2-(4-chlorophenyl)-2-(1-(piperidine-1-carbonyl)piperidin-4-ylidene)acetonitrile

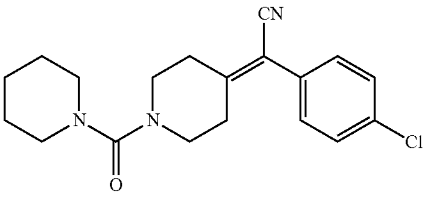 [SMILES: N#CC(=C1CCN(C(=O)N2CCCCC2)CC1)c1ccc(Cl)cc1]

Compound 104 was synthesized by the method used in the preparation of the compound 3 in 59% yield by using INT-8 and piperidine as starting materials in 1.5 hours reaction time. $^1$H-NMR (400 MHz, DMSO-$d_6$): 1.40-1.60 (m, 6H), 2.39 (m, 2H), 2.69 (m, 2H), 3.10-3.20 (m, 6H), 3.30-3.40 (m, 2H), 7.38 (d, 2H), 7.53 (d, 2H).

Compound 105

4-((4-chlorophenyl)(cyano)methylene)-N,N-diethylpiperidine-1-carboxamide

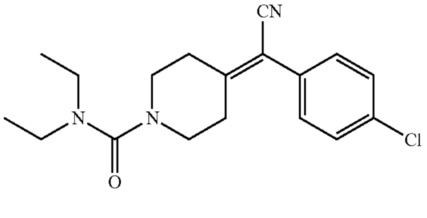 [SMILES: CCN(CC)C(=O)N1CCC(=C(C#N)c2ccc(Cl)cc2)CC1]

Compound 105 was synthesized by the method used in the preparation of the compound 3 in 81% yield by using INT-8 and diethylamine as starting materials in 4 hours reaction time. $^1$H-NMR (400 MHz, DMSO-$d_6$): 1.05 (t, 6H), 2.40 (t, 2H), 2.70 (t, 2H), 3.10-3.17 (m, 6H), 3.28-3.30 (m, 2H), 7.39 (d, 2H), 7.54 (d, 2H).

Compound 106

2-(4-fluorophenyl)-2-(1-(4-(methoxymethyl)piperidine-1-carbonyl)piperidin-4-ylidene)acetonitrile

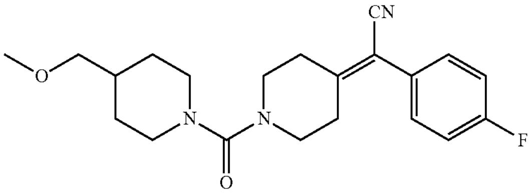 [SMILES: COCC1CCN(C(=O)N2CCC(=C(C#N)c3ccc(F)cc3)CC2)CC1]

Compound 106 was synthesized by the method used in the preparation of the compound 3 in 58% yield by using INT-4 and 4-(methoxymethyl)piperidine as starting materials in 4 hours reaction time. $^1$H-NMR (400 MHz, DMSO-$d_6$): 1.05-1.18 (m, 2H), 1.58-1.68 (m, 2H), 1.69-1.75 (m, 1H), 2.37 (t, 2H), 2.65-2.76 (m, 4H), 3.17 (m, 4H), 3.22 (s, 3H), 3.30-3.40 (m, 2H), 3.56-3.63 (m, 2H), 7.30 (m, 2H), 7.41 (m, 2H).

Compound 107

2-(4-fluorophenyl)-2-(1-(4-hydroxyazepane-1-carbonyl)piperidin-4-ylidene)acetonitrile

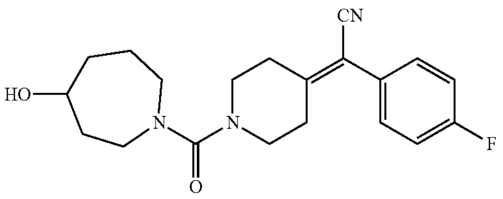 [SMILES: N#CC(=C1CCN(C(=O)N2CCCC(O)CC2)CC1)c1ccc(F)cc1]

Compound 107 was synthesized by the method used in the preparation of the compound 3 in 71% yield by using INT-4 and azepan-4-ol as starting materials in 2 hours reaction time. $^1$H-NMR (400 MHz, DMSO-$d_6$): 1.40-1.58 (m, 2H), 1.60-1.72 (m, 2H), 1.75-1.90 (m, 2H), 2.39 (t, 2H), 2.70 (t, 2H), 3.08-3.17 (m, 3H), 3.20-3.30 (m, 3H), 3.30-3.35 (m, 2H), 3.63 (m, 1H), 4.50 (d, 1H), 7.30 (m, 2H), 7.40 (m, 2H).

Compound 108

2-(4-fluorophenyl)-2-(1-(4,5,6,7-tetrahydrothieno[3,2-c]pyridine-5-carbonyl)piperidin-4-ylidene)acetonitrile

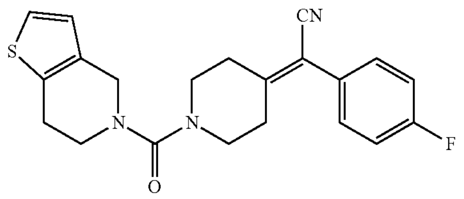 [SMILES: N#CC(=C1CCN(C(=O)N2CCc3sccc3C2)CC1)c1ccc(F)cc1]

Compound 108 was synthesized by the method used in the preparation of the compound 3 in 87% yield by using INT-4 and 4,5,6,7-tetrahydrothieno[3,2-c]pyridine (150 mol-%) as starting materials in 90 minutes reaction time. The crude product was purified by trituration with heptane: methanol (v/v 1:1) producing a white solid. $^1$H-NMR (400 MHz, DMSO-$d_6$): 2.41 (t, 2H), 2.72 (t, 2H), 2.85 (m, 2H), 3.24 (t, 2H), 3.41 (t, 2H), 3.48 (t, 2H), 4.31 (s, 2H), 6.86 (d, 1H), 7.28-7.34 (m, 3H), 7.41 (m, 2H).

Compound 109

2-(1-(5-fluoroindoline-1-carbonyl)piperidin-4-ylidene)-2-(4-fluorophenyl)acetonitrile

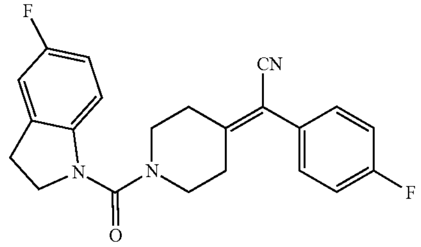 [SMILES: N#CC(=C1CCN(C(=O)N2CCc3cc(F)ccc32)CC1)c1ccc(F)cc1]

Compound 109 was synthesized by the method used in the preparation of the compound 3 at 50-66° C. for 6 hours, then overnight at room temperature in THE in 9% yield after chromatographic purification by using INT-4 and 5-fluoroindoline (300 mol-%) as starting materials. $^1$H-NMR (400 MHz, $CDCl_3$): 2.53 (t, 2H), 2.86 (t, 2H), 3.04 (t, 2H), 3.38 (t, 2H), 3.56 (t, 2H), 3.97 (t, 2H), 6.83 (m, 1H), 6.90 (m, 1H), 6.95-7.01 (m, 1H), 7.11 (m, 2H), 7.25-7.30 (m, 2H).

Compound 110

(R)-2-(4-fluorophenyl)-2-(1-(2-methylpiperidine-1-carbonyl)piperidin-4-ylidene)acetonitrile

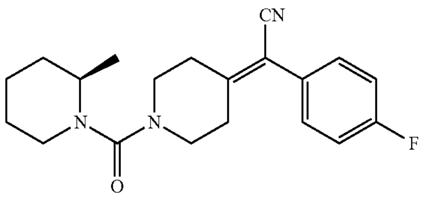 [SMILES: C[C@@H]1CCCCN1C(=O)N1CCC(=C(C#N)c2ccc(F)cc2)CC1]

Compound 110 was synthesized by the method used in the preparation of the compound 3 in 6% yield by using INT-4 and (R)-2-methylpiperidine as starting materials in overnight reaction time. $^1$H-NMR (400 MHz, $CDCl_3$): 1.19/1.20 (2×s, isom, 3H), 1.40-1.53 (m, 2H), 1.61-1.73 (m, 5H), 2.46 (m, 2H), 2.80 (m, 2H), 2.98-3.05 (m, 1H), 3.21 (m, 2H), 3.39 (m, 2H), 4.03 (m, 1H), 7.07-7.14 (m, 2H), 7.24-7.30 (m, 2H).

Compound 111

2-(1-((1R,4R)-2-azabicyclo[2.2.1]heptane-2-carbonyl)piperidin-4-ylidene)-2-(2,4-difluorophenyl)acetonitrile

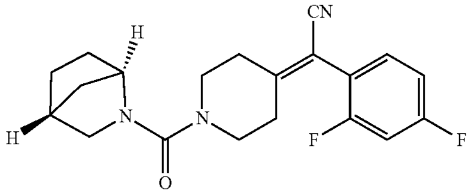 [SMILES: N#CC(=C1CCN(C(=O)N2C[C@@H]3CC[C@@H]2C3)CC1)c1ccc(F)cc1F]

Compound 111 was synthesized by the method used in the preparation of the compound 3 in 46% yield by using INT-18 and 2-azabicyclo[2.2.1]heptane as starting materials in 2.5 hours reaction time. $^1$H-NMR (400 MHz, DMSO-$d_6$): 1.30-1.35 (m, 2H), 1.44-1.48 (m, 1H), 1.58 (m, 2H), 1.69-1.74 (m, 1H), 2.14-2.30 (m, 2H), 2.60-2.78 (m, 2H), 2.83 (m, 1H), 3.10-3.30 (m, 2H), 3.31-3.46 (m, 4H), 4.00 (s, 1H), 7.22 (m, 1H), 7.40-7.52 (m, 2H).

Compound 112

2-(2,4-difluorophenyl)-2-(1-(4,5,6,7-tetrahydrothieno[3,2-c]pyridine-5-carbonyl)piperidin-4-ylidene)acetonitrile

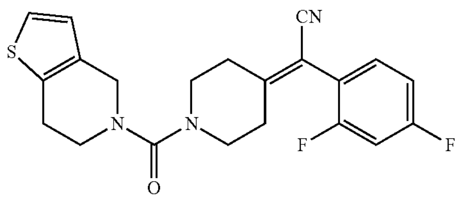 [SMILES: N#CC(=C1CCN(C(=O)N2CCc3sccc3C2)CC1)c1ccc(F)cc1F]

Compound 112 was synthesized by the method used in the preparation of the compound 3 in 78% yield by using INT-18 and 4,5,6,7-tetrahydrothieno[3,2-c]pyridine×HCl as starting materials in 3 hours reaction time. $^1$H-NMR (400

MHz, DMSO-$d_6$): 2.27 (t, 2H), 2.75 (t, 2H), 2.85 (m, 2H), 3.10-3.50 (m, 6H), 4.31 (s, 2H), 6.87 (m, 1H), 7.23 (m, 1H), 7.32 (m, 1H), 7.47 (m, 2H).

Compound 113

2-(4-chlorophenyl)-2-(1-(4,5,6,7-tetrahydro-1H-pyrazolo[4,3-c]pyridine-5-carbonyl)piperidin-4-ylidene)acetonitrile

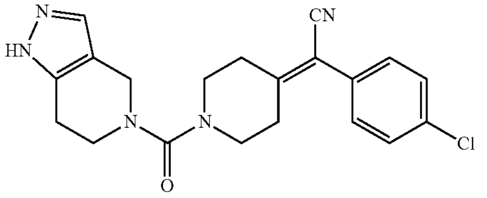 [SMILES: N#CC(=C1CCN(C(=O)N2CCc3[nH]ncc3C2)CC1)c1ccc(Cl)cc1]

Compound 113 was synthesized by the method used in the preparation of the compound 3 in 68% yield after chromatographic purification by using INT-8 and 4,5,6,7-tetrahydro-1H-pyrazolo[4,3-c]pyridine as starting materials in 3.5 hours reaction time. $^1$H-NMR (400 MHz, DMSO-$d_6$): 2.41 (t, 2H), 2.70-2.74 (m, 4H), 3.23 (t, 2H), 3.34-3.50 (m, 4H), 4.24 (s, 2H), 7.37-7.41 (m, 3H), 7.54 (d, 2H), 12.48 (br s, 1H).

Compound 114

2-(1H-indazol-4-yl)-2-(1-(4,5,6,7-tetrahydrothieno[3,2-c]pyridine-5-carbonyl)piperidin-4-ylidene)acetonitrile

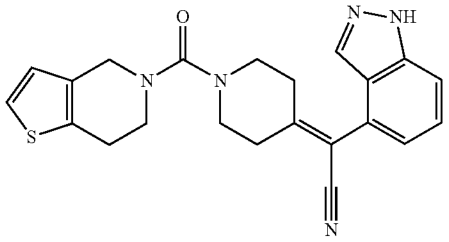 [SMILES: N#CC(=C1CCN(C(=O)N2CCc3sccc3C2)CC1)c1cccc2[nH]ncc12]

Compound 114 was synthesized by the method used in the preparation of the compound 3 in THE at 50° C. in 19% yield after chromatographic purification by using INT-26 and 4,5,6,7-tetrahydrothieno[3,2-c]pyridine as starting materials in 6.5 hours reaction time. $^1$H-NMR (400 MHz, DMSO-$d_6$): 2.33 (m, 2H), 2.80-2.87 (m, 4H), 3.21 (t, 2H), 3.48 (m, 4H), 4.31 (s, 2H), 6.87 (d, 1H), 7.08 (d, 1H), 7.32 (d, 1H), 7.43 (m, 1H), 7.62 (d, 1H), 8.09 (s, 1H), 13.35 (s, 1H).

Compound 115

2-(1-(4-hydroxypiperidine-1-carbonyl)piperidin-4-ylidene)-2-(4-(trifluoromethoxy)phenyl)acetonitrile

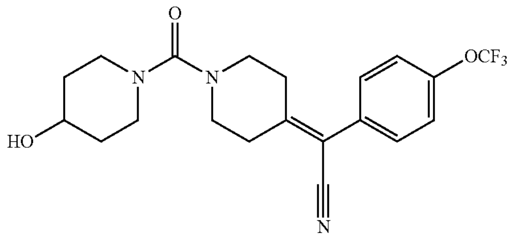 [SMILES: N#CC(=C1CCN(C(=O)N2CCC(O)CC2)CC1)c1ccc(OC(F)(F)F)cc1]

Compound 115 was synthesized by the method used in the preparation of the compound 41 in 24% yield by using INT-32 and INT-64 as starting materials. $^1$H NMR (400 MHz, $CDCl_3$) δ ppm 7.36-7.29 (m, 2H), 7.29-7.22 (m, 2H), 3.93-3.82 (m, 1H), 3.65-3.55 (m, 2H), 3.44 (t, J=5.8 Hz, 2H), 3.26 (t, J=5.8 Hz, 2H), 3.02 (ddd, J=13.1, 9.5, 3.2 Hz, 2H), 2.85-2.77 (m, 2H), 2.51-2.44 (m, 2H), 1.96-1.85 (m, 2H), 1.56-1.47 (m, 2H). $^{19}$F NMR (376 MHz, $CDCl_3$) δ ppm −57.82.

Compound 116

2-(3,5-difluorophenyl)-2-(1-(4,5,6,7-tetrahydro-1H-pyrazolo[4,3-c]pyridine-5-carbonyl)piperidin-4-ylidene)acetonitrile

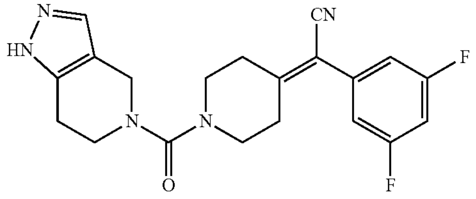 [SMILES: N#CC(=C1CCN(C(=O)N2CCc3[nH]ncc3C2)CC1)c1cc(F)cc(F)c1]

Compound 116 was synthesized by the method used in the preparation of the compound 3 in 75% yield after chromatographic purification by using INT-22 and 4,5,6,7-tetrahydro-1H-pyrazolo[4,3-c]pyridine as starting materials in 5 hours reaction time. $^1$H-NMR (400 MHz, DMSO-$d_6$): 2.43 (t, 2H), 2.72 (m, 4H), 3.25 (t, 2H), 3.35-3.50 (m, 4H), 4.25 (s, 2H), 7.14-7.19 (m, 2H), 7.35 (m, 1H), 7.26/7.47 (br m, 1H, isomers), 12.48 (s, 1H).

Compound 117

2-(1-(4,5,6,7-tetrahydrothieno[3,2-c]pyridine-5-carbonyl)piperidin-4-ylidene)-2-(4-(trifluoromethoxy)phenyl)acetonitrile

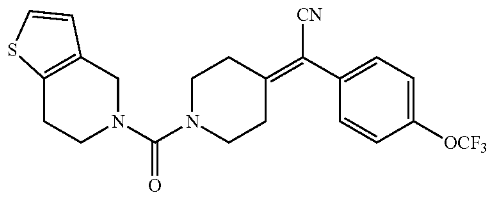 [SMILES: N#CC(=C1CCN(C(=O)N2CCc3sccc3C2)CC1)c1ccc(OC(F)(F)F)cc1]

Compound 117 was synthesized by the method used in the preparation of the compound 3 in 80% yield by using INT-34 and 4,5,6,7-tetrahydrothieno[3,2-c]pyridinexHCl as starting materials in 5 hours reaction time. $^1$H-NMR (400 MHz, DMSO-$d_6$): 2.43 (t, 2H), 2.75 (t, 2H), 2.86 (t, 2H), 3.25 (t, 2H), 3.43 (m, 2H), 3.48 (m, 2H), 4.31 (s, 2H), 6.87 (m, 1H), 7.32 (m, 1H), 7.44-7.55 (m, 4H).

Compound 118

2-(1-(4-(hydroxymethyl)piperidine-1-carbonyl)piperidin-4-ylidene)-2-(1-methyl-1H-indazol-7-yl)acetonitrile

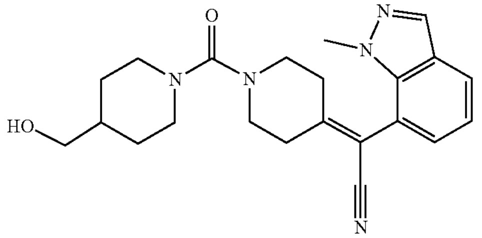 [SMILES: Cn1ncc2cccc(C(C#N)=C3CCN(C(=O)N4CCC(CO)CC4)CC3)c21]

Compound 118 was synthesized by the method used in the preparation of the compound 3 in THE in 17% yield after chromatographic purification using INT-61 and piperidin-4-ylmethanol as starting materials in 1 hour reaction time at +50° C. $^1$H-NMR (400 MHz, $CDCl_3$): 1.20-1.30 (m, 2H), 1.63-1.80 (m, 3H), 2.38 (t, 2H), 2.81 (m, 2H), 2.90 (m, 2H), 3.28 (t, 2H), 3.48-3.55 (m, 4H), 3.72-3.79 (m, 2H), 4.24 (s, 3H), 7.09 (m, 1H), 7.18 (d, 1H), 7.68 (d, 1H), 7.95 (s, 1H).

Compound 119

2-(1-methyl-1H-indazol-7-yl)-2-(1-(4,5,6,7-tetrahydro-1H-pyrazolo[4,3-c]pyridine-5-carbonyl)piperidin-4-ylidene)acetonitrile

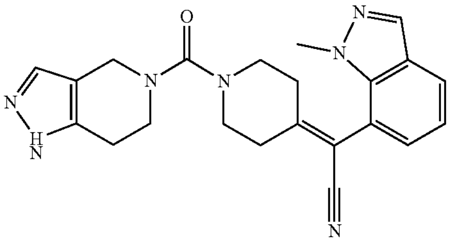

Compound 119 was synthesized by the method used in the preparation of the compound 3 in THE in 15% yield after chromatographic purification using INT-61 and 4,5,6,7-tetrahydro-1H-pyrazolo[4,3-c]pyridine as starting materials in 3 hours reaction time at +50° C. $^1$H-NMR (400 MHz, $CDCl_3$): 2.41 (t, 2H), 2.87 (t, 2H), 2.93 (t, 2H), 3.33 (t, 2H), 3.52-3.60 (m, 4H), 4.24 (s, 3H), 4.37 (s, 2H), 7.07-7.13 (m, 1H), 7.19 (d, 1H), 7.37 (s, 1H), 7.68 (d, 1H), 7.96 (s, 1H).

Compound 120

2-(5-chlorothiophen-2-yl)-2-(1-(4,5,6,7-tetrahydro-1H-pyrazolo[4,3-c]pyridine-5-carbonyl)piperidin-4-ylidene)acetonitrile

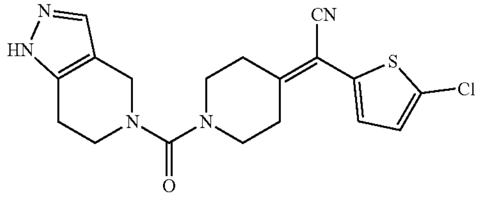 [SMILES: N#CC(=C1CCN(C(=O)N2CCc3[nH]ncc3C2)CC1)c1ccc(Cl)s1]

Compound 120 was synthesized by the method used in the preparation of the compound 3 in 39% yield by using INT-42 and 4,5,6,7-tetrahydro-1H-pyrazolo[4,3-c]pyridine as starting materials in 3 hours reaction time. $^1$H-NMR (400 MHz, DMSO-$d_6$): 2.60 (t, 2H), 2.72 (m, 4H), 3.28 (t, 2H), 3.35-3.49 (m, 4H), 4.26 (s, 2H), 7.09 (d, 1H), 7.18 (d, 1H), 7.26/7.48 (br m, 1H, isomers), 12.48 (s, 1H).

Compound 121

2-(5-chlorothiophen-2-yl)-2-(1-(5,6,7,8-tetrahydroimidazo[1,5-a]pyrazine-7-carbonyl)piperidin-4-ylidene)acetonitrile

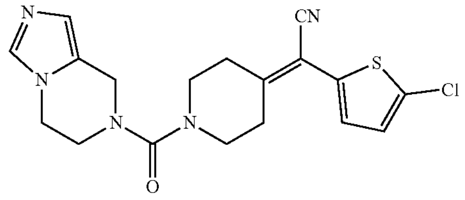 [SMILES: N#CC(=C1CCN(C(=O)N2CCn3cncc3C2)CC1)c1ccc(Cl)s1]

Compound 121 was synthesized by the method used in the preparation of the compound 3 in 47% yield by using INT-42 and 5,6,7,8-tetrahydroimidazo[1,5-a]pyrazine as starting materials in 5.5 hours reaction time. $^1$H-NMR (400 MHz, DMSO-$d_6$): 2.61 (t, 2H), 2.74 (t, 2H), 3.25-3.40 (m, 2H), 3.43 (t, 2H), 3.55 (t, 2H), 4.08 (t, 2H), 4.42 (s, 2H), 6.71 (s, 1H), 7.09 (d, 1H), 7.19 (d, 1H), 7.57 (s, 1H).

Compound 122

2-(2,4-difluorophenyl)-2-(1-(4,5,6,7-tetrahydro-1H-pyrazolo[4,3-c]pyridine-5-carbonyl)piperidin-4-ylidene)acetonitrile

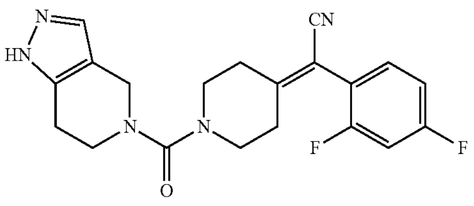 [SMILES: N#CC(=C1CCN(C(=O)N2CCc3[nH]ncc3C2)CC1)c1ccc(F)cc1F]

Compound 122 was synthesized by the method used in the preparation of the compound 3 in 66% yield after chromatographic purification by using INT-18 and 4,5,6,7-tetrahydro-1H-pyrazolo[4,3-c]pyridine as starting materials in 4 hours reaction time. $^1$H-NMR (400 MHz, DMSO-$d_6$):

2.27 (t, 2H), 2.73 (m, 4H), 3.23 (t, 2H), 3.35-3.50 (m, 4H), 4.25 (s, 2H), 7.18-7.25 (m, 1H), 7.39-7.53 (m, 2H), 7.20-7.53 (m, 1H, isomers), 12.47 (s, 1H).

Compound 123

2-(2,4-difluorophenyl)-2-(1-(5,6,7,8-tetrahydroimidazo[1,5-a]pyrazine-7-carbonyl)piperidin-4-ylidene) acetonitrile

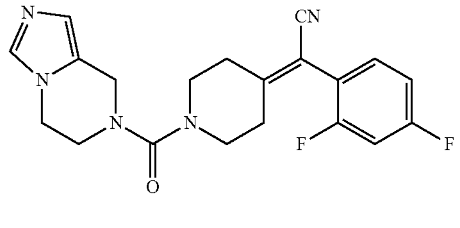 [SMILES: N#CC(=C1CCN(C(=O)N2CCn3cncc3C2)CC1)c1ccc(F)cc1F]

Compound 123 was synthesized by the method used in the preparation of the compound 3 in 58% yield by using INT-18 and 5,6,7,8-tetrahydroimidazo[1,5-a]pyrazine as starting materials in 5 hours reaction time. $^1$H-NMR (400 MHz, DMSO-$d_6$): 2.28 (t, 2H), 2.75 (t, 2H), 3.26 (t, 2H), 3.44 (t, 2H), 3.55 (t, 2H), 4.08 (t, 2H), 4.42 (s, 2H), 6.71 (s, 1H), 7.23 (m, 1H), 7.40-7.55 (m, 2H), 7.57 (s, 1H).

Compound 124

2-(1-(4-(1-hydroxyethyl)piperidine-1-carbonyl)piperidin-4-ylidene)-2-(4-(trifluoromethoxy)phenyl) acetonitrile

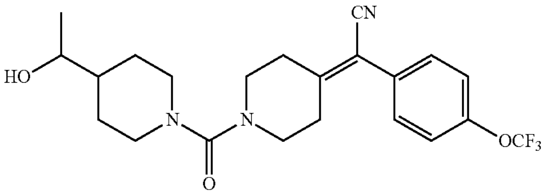 [SMILES: CC(O)C1CCN(C(=O)N2CCC(=C(C#N)c3ccc(OC(F)(F)F)cc3)CC2)CC1]

Compound 124 was synthesized by the method used in the preparation of the compound 3 in 49% yield by using INT-34 and 1-(piperidin-4-yl)ethan-1-ol as starting materials in 2.5 hours reaction time. $^1$H-NMR (400 MHz, DMSO-$d_6$): 1.02 (d, 3H), 1.05-1.22 (m, 2H), 1.31 (m, 1H), 1.50-1.53 (m, 1H), 1.72-1.75 (m, 1H), 2.39 (t, 2H), 2.60-2.75 (m, 4H), 3.18 (t, 2H), 3.28-3.40 (m, 3H), 3.60-3.66 (m, 2H), 4.39 (d, 1H), 7.44-7.53 (m, 4H).

Compound 125

2-(5-chlorothiophen-2-yl)-2-(1-(4-ethoxypiperidine-1-carbonyl)piperidin-4-ylidene)acetonitrile

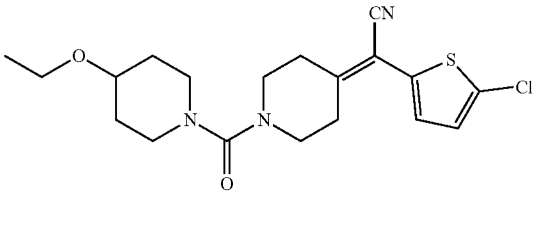 [SMILES: CCOC1CCN(C(=O)N2CCC(=C(C#N)c3ccc(Cl)s3)CC2)CC1]

Compound 125 was synthesized by the method used in the preparation of the compound 3 in 64% yield by using INT-42 and 4-ethoxypiperidine as starting materials in 4 hours reaction time. $^1$H-NMR (400 MHz, DMSO-$d_6$): 1.10 (t, 3H), 1.30-1.40 (m, 2H), 1.75-1.85 (m, 2H), 2.57 (t, 2H), 2.69 (t, 2H), 2.91 (t, 2H), 3.23 (m, 2H), 3.30-3.40 (m, 2H), 3.41-3.50 (m, 5H), 7.09 (m, 1H), 7.18 (m, 1H).

Compound 126

1-(4-((4-chlorophenyl)(cyano)methylene)piperidine-1-carbonyl)piperidine-4-sulfonamide

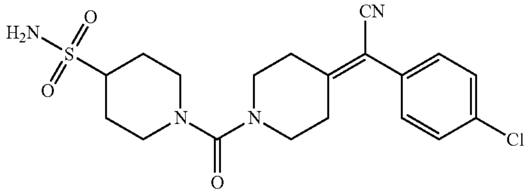 [SMILES: N#CC(=C1CCN(C(=O)N2CCC(S(N)(=O)=O)CC2)CC1)c1ccc(Cl)cc1]

Compound 126 was synthesized by the method used in the preparation of the compound 3 in 52% yield after chromatographic purification by using INT-8 and 4-piperidinesulfonamide as starting materials in 5.5 hours reaction time. $^1$H-NMR (400 MHz, DMSO-$d_6$): 1.50-1.60 (m, 2H), 1.96 (m, 2H), 2.40 (t, 2H), 2.70 (t, 2H), 2.81 (m, 2H), 3.02 (m, 1H), 3.20 (m, 2H), 3.37 (m, 2H), 3.65-3.72 (m, 2H), 6.76 (s, 2H), 7.39 (d, 2H), 7.54 (d, 2H).

Compound 127

2-(1-(4-hydroxypiperidine-1-carbonyl)piperidin-4-ylidene)-2-(4-(trifluoromethyl)phenyl)acetonitrile

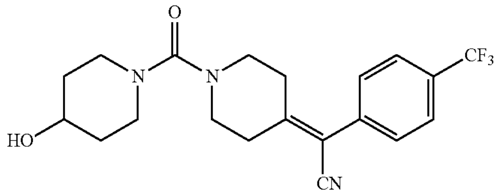 [SMILES: N#CC(=C1CCN(C(=O)N2CCC(O)CC2)CC1)c1ccc(C(F)(F)F)cc1]

Compound 127 was synthesized by the method used in the preparation of the compound 41 in 62% yield by using INT-36 and INT-64 as starting materials. 1H NMR (400 MHz, $CDCl_3$) δ ppm 7.68 (d, J=7.7 Hz, 2H), 7.44-7.39 (m, 2H), 3.91-3.85 (m, 1H), 3.63-3.56 (m, 2H), 3.45 (t, J=5.8 Hz, 2H), 3.26 (t, J=5.8 Hz, 2H), 3.06-2.98 (m, 2H), 2.86-2.81 (m, 2H), 2.48 (dd, J=6.4, 5.1 Hz, 2H), 1.94-1.87 (m, 2H), 1.57-1.48 (m, 3H). $^{19}$F NMR (376 MHz, $CDCl_3$) δ −62.83. m/z (ES+) 394.2 $(M+H)^+$.

Compound 128

2-(1-(4-ethoxypiperidine-1-carbonyl)piperidin-4-ylidene)-2-(4-(trifluoromethyl)phenyl) acetonitrile

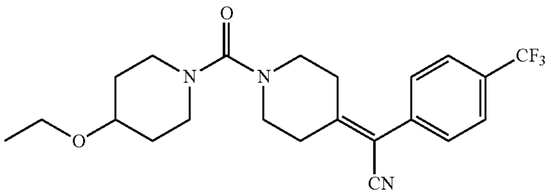 [SMILES: CCOC1CCN(C(=O)N2CCC(=C(C#N)c3ccc(C(F)(F)F)cc3)CC2)CC1]

Compound 128 was synthesized by the method used in the preparation of the compound 3 in 89% yield by using INT-38 and 4-ethoxypiperidine as starting materials in 2 hours reaction time. $^1$H-NMR (400 MHz, DMSO-$d_6$): 1.10 (t, 3H), 1.34-1.40 (m, 2H), 1.75-1.85 (m, 2H), 2.41 (t, 2H), 2.72 (t, 2H), 2.91 (m, 2H), 3.19 (m, 2H), 3.30-3.50 (m, 7H), 7.61 (d, 2H), 7.84 (d, 2H).

Compound 129

2-(3-chlorophenyl)-2-(1-(4-ethoxypiperidine-1-carbonyl)piperidin-4-ylidene)acetonitrile

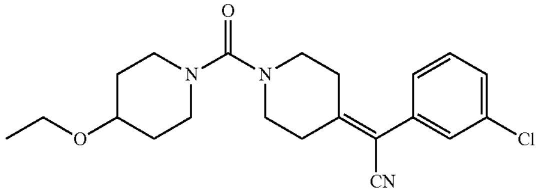 [SMILES: CCOC1CCN(C(=O)N2CCC(=C(C#N)c3cccc(Cl)c3)CC2)CC1]

Compound 129 was synthesized by the method used in the preparation of the compound 3 in 53% yield by using INT-30 and 4-ethoxypiperidine (150 mol-%) as starting materials in 3.5 hours reaction time. $^1$H-NMR (400 MHz, DMSO-$d_6$): 1.10 (t, 3H), 1.33-1.45 (m, 2H), 1.76-1.85 (m, 2H), 2.39 (t, 2H), 2.69 (t, 2H), 2.91 (t, 2H), 3.19 (t, 2H), 3.35 (m, 2H), 3.40-3.50 (m, 5H), 7.33 (m, 1H), 7.44 (s, 1H), 7.50 (m, 2H).

Compound 130

2-(1-(4-acetylpiperazine-1-carbonyl)piperidin-4-ylidene)-2-(4-chlorophenyl)acetonitrile

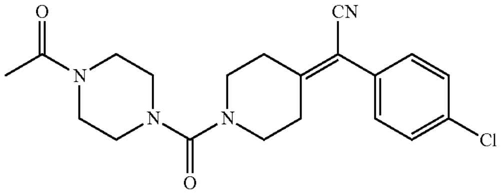 [SMILES: CC(=O)N1CCN(C(=O)N2CCC(=C(C#N)c3ccc(Cl)cc3)CC2)CC1]

Compound 130 was synthesized by the method used in the preparation of the compound 3 in 93% yield by using INT-8 and 1-acetylpiperazine (150 mol-%) as starting materials in 3 hours reaction time. $^1$H-NMR (400 MHz, DMSO-$d_6$): 2.01 (s, 3H), 2.40 (t, 2H), 2.70 (t, 2H), 3.13 (m, 2H), 3.15-3.25 (m, 4H), 3.35-3.45 (m, 6H), 7.39 (d, 2H), 7.54 (d, 2H).

Compound 131

2-(4-chlorophenyl)-2-(1-(4-(2-hydroxyethyl)piperidine-1-carbonyl)piperidin-4-ylidene) acetonitrile

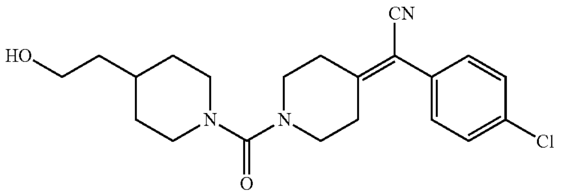 [SMILES: N#CC(=C1CCN(C(=O)N2CCC(CCO)CC2)CC1)c1ccc(Cl)cc1]

Compound 131 was synthesized by the method used in the preparation of the compound 3 in 83% yield by using INT-8 and 4-piperidineethanol as starting materials in 3 hours reaction time. $^1$H-NMR (400 MHz, DMSO-$d_6$): 1.00-1.10 (m, 2H), 1.35 (m, 2H), 1.54 (m, 1H), 1.60-1.65 (m, 2H), 2.39 (t, 2H), 2.65-2.75 (m, 4H), 3.17 (t, 2H), 3.30-3.40 (m, 2H), 3.43 (t, 2H), 3.53-3.62 (m, 2H), 4.36 (s, 1H), 7.39 (d, 2H), 7.53 (d, 2H).

Compound 132

2-(4-chlorophenyl)-2-(1-(4-(3-hydroxypropyl)piperidine-1-carbonyl)piperidin-4-ylidene)acetonitrile

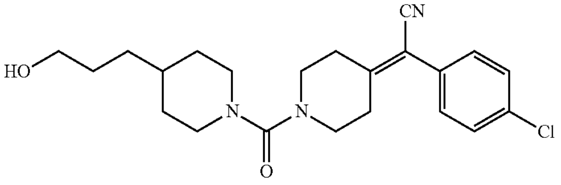 [SMILES: N#CC(=C1CCN(C(=O)N2CCC(CCCO)CC2)CC1)c1ccc(Cl)cc1]

Compound 132 was synthesized by the method used in the preparation of the compound 3 in 75% yield by using INT-8 and 4-piperidinepropanol as starting materials in 6 hours reaction time. $^1$H-NMR (400 MHz, DMSO-$d_6$): 1.00-1.10 (m, 2H), 1.20 (m, 2H), 1.30-1.45 (m, 3H), 1.60-1.65 (m, 2H), 2.39 (t, 2H), 2.65-2.75 (m, 4H), 3.17 (t, 2H), 3.30-3.40 (m, 4H), 3.55-3.63 (m, 2H), 4.35 (m, 1H), 7.39 (d, 2H), 7.53 (d, 2H).

Compound 133

2-(4-chlorophenyl)-2-(1-(4-isopropoxypiperidine-1-carbonyl)piperidin-4-ylidene)acetonitrile

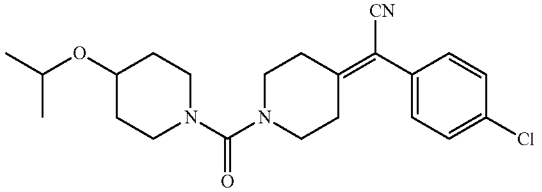 [SMILES: CC(C)OC1CCN(C(=O)N2CCC(=C(C#N)c3ccc(Cl)cc3)CC2)CC1]

Compound 133 was synthesized by the method used in the preparation of the compound 3 in 98% yield by using INT-8 and 4-isopropoxypiperidine as starting materials in 6 hours reaction time. $^1$H-NMR (400 MHz, DMSO-$d_6$): 1.05-

1.08 (m, 6H), 1.30-1.38 (m, 2H), 1.70-1.80 (m, 2H), 2.38 (t, 2H), 2.68 (t, 2H), 2.85-2.95 (m, 2H), 3.18 (m, 2H), 3.30-3.37 (m, 2H), 3.38-3.45 (m, 2H), 3.52 (m, 1H), 3.69 (m, 1H), 7.39 (d, 2H), 7.53 (d, 2H).

Compound 134

2-(4-chlorophenyl)-2-(1-(4-propoxypiperidine-1-carbonyl)piperidin-4-ylidene)acetonitrile

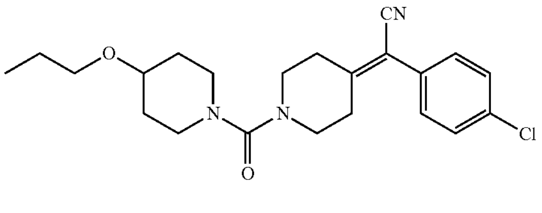 [SMILES: CCCOC1CCN(C(=O)N2CCC(=C(C#N)c3ccc(Cl)cc3)CC2)CC1]

Compound 134 was synthesized by the method used in the preparation of the compound 3 in 70% yield by using INT-8 and 4-propoxypiperidine as starting materials in 4 hours reaction time. $^{1}$H-NMR (400 MHz, DMSO-$d_6$): 0.87 (t, 3H), 1.36-1.44 (m, 2H), 1.45-1.54 (m, 2H), 1.75-1.85 (m, 2H), 2.39 (t, 2H), 2.70 (t, 2H), 2.93 (t, 2H), 3.19 (m, 2H), 3.30-3.39 (m, 4H), 3.39-3.45 (m, 3H), 7.39 (d, 2H), 7.54 (d, 2H).

Compound 135

2-(5-chloropyridin-2-yl)-2-(1-(4-(trifluoromethyl)piperidine-1-carbonyl)piperidin-4-ylidene)acetonitrile

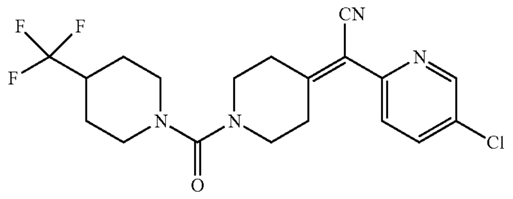 [SMILES: N#CC(=C1CCN(C(=O)N2CCC(C(F)(F)F)CC2)CC1)c1ccc(Cl)cn1]

Compound 135 was synthesized by the method used in the preparation of the compound 3 in quantitative yield by using INT-46 and 4-(trifluoromethyl)piperidine (150 mol-%) as starting materials in 5 hours reaction time. $^{1}$H-NMR (400 MHz, DMSO-$d_6$): 1.35-1.46 (m, 2H), 1.75-1.82 (m, 2H), 2.64 (t, 2H), 2.70-2.85 (m, 4H), 3.24 (t, 2H), 3.30-3.35 (m, 1H), 3.40 (t, 2H), 3.63-3.71 (m, 2H), 7.56 (d, 1H), 8.05 (dd, 1H), 8.72 (d, 1H).

Compound 136

2-(1-methyl-1H-indazol-7-yl)-2-(1-(4,5,6,7-tetrahydroisoxazolo[4,3-c]pyridine-5-carbonyl)piperidin-4-ylidene)acetonitrile

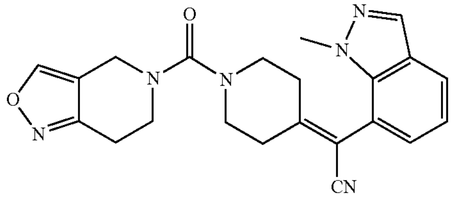 [SMILES: Cn1ncc2cccc(C(C#N)=C3CCN(C(=O)N4CCc5nocc5C4)CC3)c21]

Compound 136 was synthesized by the method used in the preparation of the compound 3 in 12% yield using INT-61 and 4,5,6,7-tetrahydroisoxazolo[4,3-c]pyridine (150 mol-%) as starting materials in 2 hours reaction time. $^{1}$H-NMR (400 MHz, $CDCl_3$): 2.41 (t, 2H), 2.90-3.00 (m, 4H), 3.34 (t, 2H), 3.50-3.60 (m, 4H), 4.24 (s, 3H), 4.38 (s, 2H), 7.10 (m, 1H), 7.19 (d, 1H), 7.69 (d, 1H), 7.96 (s, 1H), 8.21 (s, 1H).

Compound 137

2-(2,4-difluorophenyl)-2-(1-(4-ethoxypiperidine-1-carbonyl)piperidin-4-ylidene)acetonitrile

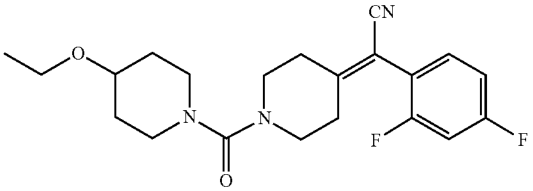 [SMILES: CCOC1CCN(C(=O)N2CCC(=C(C#N)c3ccc(F)cc3F)CC2)CC1]

Compound 137 was synthesized by the method used in the preparation of the compound 3 in 85% yield by using INT-18 and 4-ethoxypiperidine as starting materials in 4 hours reaction time. $^{1}$H-NMR (400 MHz, DMSO-$d_6$): 1.10 (t, 3H), 1.30-1.40 (m, 2H), 1.75-1.85 (m, 2H), 2.23 (t, 2H), 2.70 (t, 2H), 2.91 (m, 2H), 3.17 (t, 2H), 3.35-3-50 (m, 7H), 7.21 (m, 1H), 7.39-7.53 (m, 2H).

Compound 138

2-(1H-indazol-4-yl)-2-(1-(4,5,6,7-tetrahydroisoxazolo[4,3-c]pyridine-5-carbonyl)piperidin-4-ylidene)acetonitrile

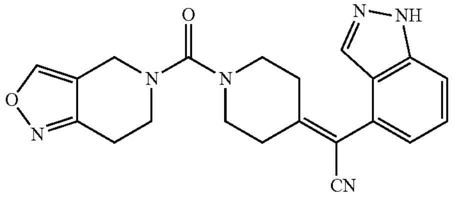 [SMILES: N#CC(=C1CCN(C(=O)N2CCc3nocc3C2)CC1)c1cccc2[nH]ncc12]

Compound 138 was synthesized in 87% yield from the compound 93 by the acetate removal with 2 N HCl in methanol in overnight reaction time at room temperature. $^{1}$H-NMR (400 MHz, DMSO-$d_6$): 2.33 (t, 2H), 2.80-2.90 (m, 4H), 3.22 (t, 2H), 3.40-3.52 (m, 4H), 4.30 (s, 2H), 7.08 (d, 1H), 7.43 (m, 1H), 7.62 (d, 1H), 8.09 (s, 1H), 8.67 (s, 1H), 13.35 (br s, 1H).

Compound 139

2-(3-chlorophenyl)-2-(1-(4-isopropoxypiperidine-1-carbonyl)piperidin-4-ylidene)acetonitrile

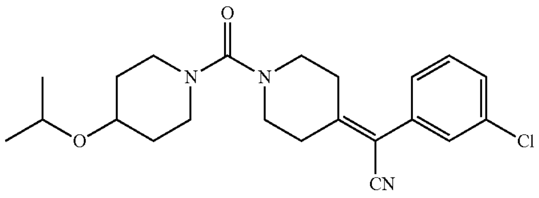 [SMILES: CC(C)OC1CCN(C(=O)N2CCC(=C(C#N)c3cccc(Cl)c3)CC2)CC1]

Compound 139 was synthesized by the method used in the preparation of the compound 3 in 96% yield using INT-30 and 4-isopropoxypiperidine as starting materials in 2 hours reaction time. $^1$H-NMR (400 MHz, DMSO-$d_6$): 1.07 (d, 6H), 1.30-1.40 (m, 2H), 1.71-1.80 (m, 2H), 2.39 (t, 2H), 2.69 (t, 2H), 2.85-2.97 (m, 2H), 3.19 (t, 2H), 3.30-3.45 (m, 4H), 3.52 (m, 1H), 3.69 (m, 1H), 7.33 (m, 1H), 7.44 (s, 1H), 7.49 (m, 2H).

Compound 140

2-(3-chlorophenyl)-2-(1-(4-(2-hydroxyethyl)piperidine-1-carbonyl)piperidin-4-ylidene)acetonitrile

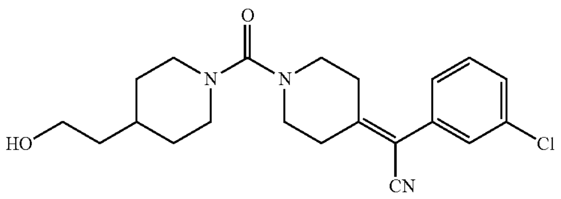 [SMILES: N#CC(=C1CCN(C(=O)N2CCC(CCO)CC2)CC1)c1cccc(Cl)c1]

Compound 140 was synthesized by the method used in the preparation of the compound 3 in 93% yield using INT-30 and 4-piperidineethanol as starting materials in 2 hours reaction time. $^1$H-NMR (400 MHz, DMSO-$d_6$): 1.00-1.12 (m, 2H), 1.30-1.40 (m, 2H), 1.50-1.58 (m, 1H), 1.60-1.66 (m, 2H), 2.39 (t, 2H), 2.65-2.75 (m, 4H), 3.18 (t, 2H), 3.30-3.40 (m, 2H), 3.40-3.47 (m, 2H), 3.55-3.65 (m, 2H), 4.36 (s, 1H), 7.33 (m, 1H), 7.44 (s, 1H), 7.47-7.54 (m, 2H).

Compound 141

2-(4-chlorophenyl)-2-(1-(4,5,6,7-tetrahydroisoxazolo[4,3-c]pyridine-5-carbonyl)piperidin-4-ylidene)acetonitrile

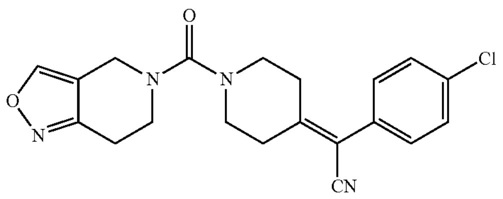 [SMILES: N#CC(=C1CCN(C(=O)N2CCc3nocc3C2)CC1)c1ccc(Cl)cc1]

Compound 141 was synthesized by the method used in the preparation of the compound 3 in 82% yield by using INT-8 and 4,5,6,7-tetrahydroisoxazolo[4,3-c]pyridine as starting materials in 5 hours reaction time. $^1$H-NMR (400 MHz, DMSO-$d_6$): 2.42 (t, 2H), 2.73 (t, 2H), 2.86 (t, 2H), 3.25 (t, 2H), 3.40-3.50 (m, 4H), 4.30 (s, 2H), 7.39 (d, 2H), 7.54 (d, 2H), 8.68 (s, 1H).

Compound 142

2-(4-fluorophenyl)-2-(1-(4-(3-hydroxypropyl)piperidine-1-carbonyl)piperidin-4-ylidene)acetonitrile

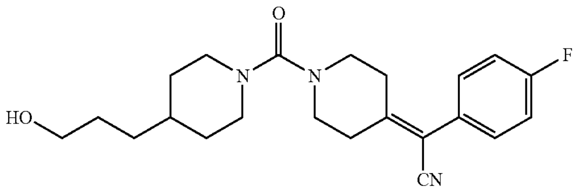 [SMILES: N#CC(=C1CCN(C(=O)N2CCC(CCCO)CC2)CC1)c1ccc(F)cc1]

Compound 142 was synthesized by the method used in the preparation of the compound 3 in 78% yield by using INT-4 and 4-piperidinepropanol as starting materials in 5 hours reaction time. $^1$H-NMR (400 MHz, DMSO-$d_6$): 0.98-1.10 (m, 2H), 1.22 (m, 2H), 1.30-1.50 (m, 3H), 1.60-1.66 (m, 2H), 2.38 (t, 2H), 2.65-2.75 (m, 4H), 3.17 (t, 2H), 3.30-3.40 (m, 4H), 3.55-3.65 (m, 2H), 4.37 (s, 1H), 7.30 (m, 2H), 7.41 (m, 2H).

Compound 143

2-(1-(4-acetylpiperazine-1-carbonyl)piperidin-4-ylidene)-2-(4-fluorophenyl)acetonitrile

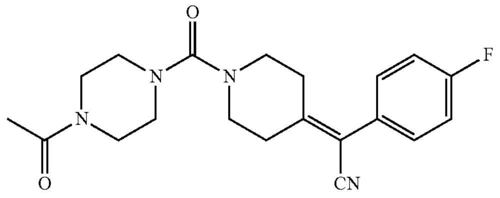 [SMILES: CC(=O)N1CCN(C(=O)N2CCC(=C(C#N)c3ccc(F)cc3)CC2)CC1]

Compound 143 was synthesized by the method used in the preparation of the compound 3 in 91% yield by using INT-4 and 1-acetylpiperazine as starting materials in 4.5 hours reaction time. $^1$H-NMR (400 MHz, DMSO-$d_6$): 2.01 (s, 3H), 2.39 (t, 2H), 2.70 (t, 2H), 3.13 (t, 2H), 3.15-3.25 (m, 4H), 3.35-3.50 (m, 6H), 7.31 (m, 2H), 7.42 (m, 2H).

Compound 144

2-(1H-indazol-4-yl)-2-(1-(4-methoxypiperidine-1-carbonyl)piperidin-4-ylidene)acetonitrile

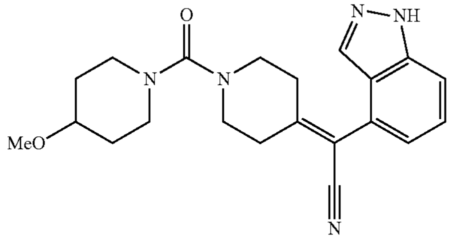 [SMILES: COC1CCN(C(=O)N2CCC(=C(C#N)c3cccc4[nH]ncc34)CC2)CC1]

Compound 144 was synthesized as a by-product by the method used in the preparation of the compound 3 by using INT-55 and 4-methoxypiperidine as starting materials in 6 hours reaction time. The yield was 43% after chromatographic purification. $^1$H-NMR (400 MHz, DMSO-$d_6$): 1.37

(m, 2H), 1.81 (m, 2H), 2.29 (t, 2H), 2.78 (t, 2H), 2.85-2.98 (m, 2H), 3.14 (m, 2H), 3.24 (s, 3H), 3.30-3.45 (m, 5H), 7.08 (m, 1H), 7.43 (m, 1H), 7.61 (m, 1H), 8.08 (s, 1H), 13.34 (br s, 1H).

Compound 145

2-(1H-indazol-4-yl)-2-(1-(4-(trifluoromethyl)piperidine-1-carbonyl)piperidin-4-ylidene) acetonitrile

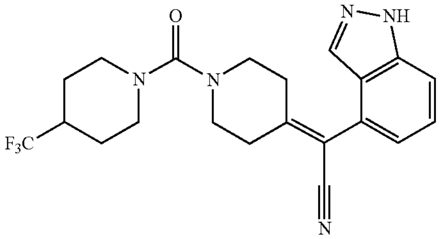 [SMILES: N#CC(=C1CCN(C(=O)N2CCC(C(F)(F)F)CC2)CC1)c1cccc2[nH]ncc12]

Compound 145 was synthesized by the method used in the preparation of the compound 3 by using INT-55 and 4-(trifluoromethyl)piperidine as starting materials in 6 hours reaction time. The product was received in 36% yield by acetate removal with 2 N HCl in methanol in 6 hours reaction time at room temperature. $^{1}$H-NMR (400 MHz, DMSO-$d_6$): 1.32-1.46 (m, 2H), 1.75-1.80 (m, 2H), 2.30 (t, 2H), 2.75-2.85 (m, 4H), 3.17 (t, 2H), 3.30-3.35 (m, 1H), 3.44 (t, 2H), 3.63-3.69 (m, 2H), 7.08 (d, 1H), 7.39-7.45 (m, 1H), 7.62 (d, 1H), 8.08 (s, 1H), 13.35 (br s, 1H).

Compound 146

2-(1-(4-methoxypiperidine-1-carbonyl)piperidin-4-ylidene)-2-(4-(trifluoromethyl)phenyl)acetonitrile

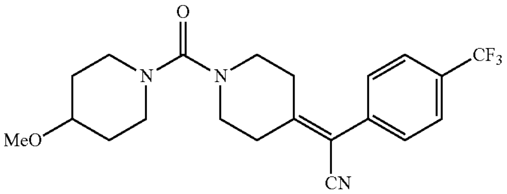 [SMILES: COC1CCN(C(=O)N2CCC(=C(C#N)c3ccc(C(F)(F)F)cc3)CC2)CC1]

Compound 146 was synthesized by the method used in the preparation of the compound 3 in 84% yield by using INT-38 and 4-methoxypiperidine as starting materials in 1.5 hours reaction time. $^{1}$H-NMR (400 MHz, DMSO-$d_6$): 1.35-1.45 (m, 2H), 1.75-1.90 (m, 2H), 2.41 (t, 2H), 2.73 (t, 2H), 2.93 (m, 2H), 3.19 (m, 2H), 3.24 (s, 3H), 3.30-3.45 (m, 5H), 7.61 (d, 2H), 7.84 (d, 2H).

Compound 147

2-(1-(morpholine-4-carbonyl)piperidin-4-ylidene)-2-(4-(trifluoromethyl)phenyl)acetonitrile

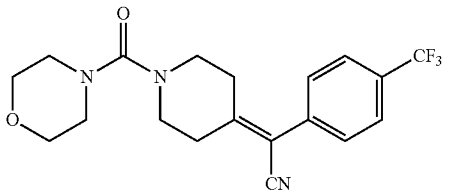 [SMILES: N#CC(=C1CCN(C(=O)N2CCOCC2)CC1)c1ccc(C(F)(F)F)cc1]

Compound 147 was synthesized in 95% yield by the method used in the preparation of the compound 1 by using INT-36 and 4-morpholinecarbonyl chloride as starting materials in 1.5 hours reaction time. $^{1}$H-NMR (400 MHz, DMSO-$d_6$): 2.41 (t, 2H), 2.73 (t, 2H), 3.10-3.20 (m, 4H), 3.22 (t, 2H), 3.41 (t, 2H), 3.57 (m, 4H), 7.61 (d, 2H), 7.84 (d, 2H).

Compound 148

1-(4-(cyano(4-(trifluoromethyl)phenyl)methylene) piperidine-1-carbonyl)piperidine-4-sulfonamide

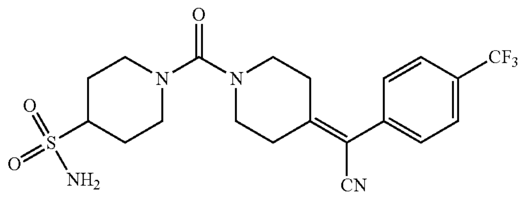 [SMILES: N#CC(=C1CCN(C(=O)N2CCC(S(N)(=O)=O)CC2)CC1)c1ccc(C(F)(F)F)cc1]

Compound 148 was synthesized by the method used in the preparation of the compound 3 in 65% yield by using INT-38 and 4-piperidinesulfonamide as starting materials in 3 hours reaction time. $^{1}$H-NMR (400 MHz, DMSO-$d_6$): 1.48-1.62 (m, 2H), 1.94-2.00 (m, 2H), 2.42 (t, 2H), 2.74 (t, 2H), 2.82 (m, 2H), 3.02 (m, 1H), 3.21 (t, 2H), 3.39 (t, 2H), 3.67-3.72 (m, 2H), 6.77 (s, 2H), 7.61 (d, 2H), 7.84 (d, 2H).

Compound 149

2-(1-(4-(2-hydroxyethyl)piperidine-1-carbonyl)piperidin-4-ylidene)-2-(4-(trifluoromethyl)phenyl)acetonitrile

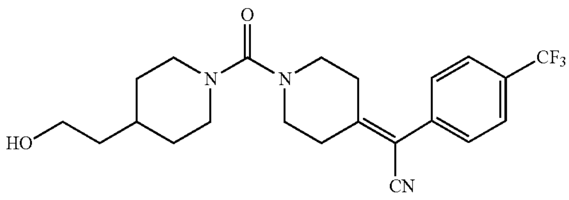 [SMILES: N#CC(=C1CCN(C(=O)N2CCC(CCO)CC2)CC1)c1ccc(C(F)(F)F)cc1]

Compound 149 was synthesized by the method used in the preparation of the compound 3 in 87% yield by using INT-38 and 4-piperidineethanol as starting materials in 2 hours reaction time. $^{1}$H-NMR (400 MHz, DMSO-$d_6$): 1.00-1.14 (m, 2H), 1.30-1.40 (m, 2H), 1.50-1.59 (m, 1H), 1.60-1.65 (m, 2H), 2.41 (t, 2H), 2.65-2.80 (m, 4H), 3.18 (m, 2H), 3.30-3.38 (m, 2H), 3.40-3.48 (m, 2H), 3.55-3.65 (m, 2H), 4.36 (t, 1H), 7.61 (d, 2H), 7.84 (d, 2H).

Compound 150

2-(1-(4,5,6,7-tetrahydro-[1,2,3]triazolo[1,5-a]pyrazine-5-carbonyl)piperidin-4-ylidene)-2-(4-(trifluoromethyl)phenyl)acetonitrile

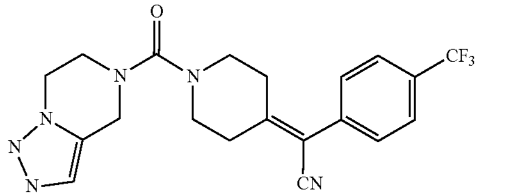

Compound 150 was synthesized by the method used in the preparation of the compound 3 in 53% yield after chromatographic purification by using INT-38 and 4,5,6,7-tetrahydro-1,2,3-triazolo[1,5-a]pyrazine as starting materials in overnight reaction time. $^1$H-NMR (400 MHz, DMSO-$d_6$): 2.45 (t, 2H), 2.77 (t, 2H), 3.25-3.40 (m, 2H), 3.49 (t, 2H), 3.69 (t, 2H), 4.43 (M, 2H), 4.54 (s, 2H), 7.58-7.65 (m, 3H), 7.85 (d, 2H).

Compound 151

2-(1-(4-(1-hydroxyethyl)piperidine-1-carbonyl)piperidin-4-ylidene)-2-(4-(trifluoromethyl)phenyl)acetonitrile

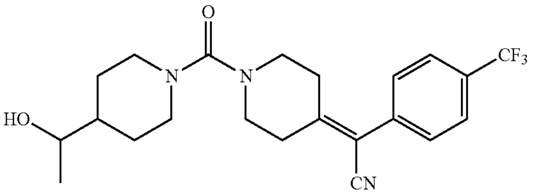 [SMILES: CC(O)C1CCN(C(=O)N2CCC(=C(C#N)c3ccc(C(F)(F)F)cc3)CC2)CC1]

Compound 151 was synthesized by the method used in the preparation of the compound 3 in 69% yield by using INT-38 and 1-(piperidin-4-yl)ethan-1-ol as starting materials in 1.5 hours reaction time. $^1$H-NMR (400 MHz, DMSO-$d_6$): 1.02 (d, 3H), 1.05-1.35 (m, 2H), 1.50-1.55 (m, 1H), 1.70-1.78 (m, 1H), 2.41 (t, 2H), 2.60-2.80 (m, 4H), 3.19 (m, 2H), 3.30-3.40 (m, 4H), 3.60-3.68 (m, 2H), 4.39 (d, 1H), 7.61 (d, 2H), 7.84 (d, 2H).

Compound 152

2-(1-(5,6,7,8-tetrahydro-[1,2,4]triazolo[1,5-a]pyrazine-7-carbonyl)piperidin-4-ylidene)-2-(4-(trifluoromethyl)phenyl)acetonitrile

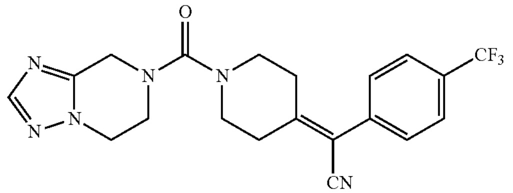 [SMILES: N#CC(=C1CCN(C(=O)N2CCn3ncnc3C2)CC1)c1ccc(C(F)(F)F)cc1]

Compound 152 was synthesized by the method used in the preparation of the compound 3 in 66% yield by using INT-38 and 5,6,7,8-tetrahydro-[1,2,4]triazolo[1,5-a]pyrazine as starting materials in overnight reaction time. $^1$H-NMR (400 MHz, DMSO-$d_6$): 2.46 (m, 2H), 2.77 (m, 2H), 3.30-3.36 (m, 2H), 3.50 (m, 2H), 3.71 (m, 2H), 4.21 (m, 2H), 4.50 (s, 2H), 7.62 (d, 2H), 7.85 (d, 2H), 7.96 (s, 1H).

Compound 153

2-(3-chlorophenyl)-2-(1-(4-(methoxymethyl)piperidine-1-carbonyl)piperidin-4-ylidene)acetonitrile

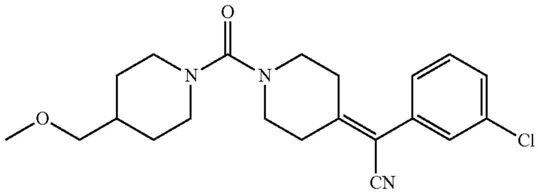 [SMILES: COCC1CCN(C(=O)N2CCC(=C(C#N)c3cccc(Cl)c3)CC2)CC1]

Compound 153 was synthesized by the method used in the preparation of the compound 3 in 91% yield by using INT-30 and 4-(methoxymethyl)piperidine as starting materials in 6 hours reaction time. $^1$H-NMR (400 MHz, DMSO-$d_6$): 1.05-1.16 (m, 2H), 1.58-1.65 (m, 2H), 1.65-1.75 (m, 1H), 2.38 (t, 2H), 2.69 (t, 2H), 2.69-2.76 (m, 2H), 3.15-3.20 (m, 4H), 3.22 (s, 3H), 3.30-3.40 (m, 2H), 3.56-3.64 (m, 2H), 7.33 (m, 1H), 7.44 (s, 1H), 7.48-7.52 (m, 2H).

Compound 154

2-(3-chlorophenyl)-2-(1-(4-(1-hydroxyethyl)piperidine-1-carbonyl)piperidin-4-ylidene)acetonitrile

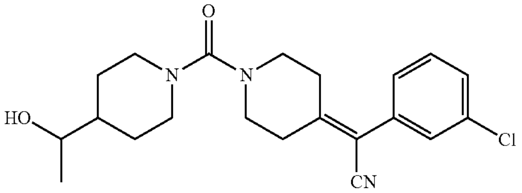 [SMILES: CC(O)C1CCN(C(=O)N2CCC(=C(C#N)c3cccc(Cl)c3)CC2)CC1]

Compound 154 was synthesized by the method used in the preparation of the compound 3 in quantitative yield by using INT-30 and 1-(piperidin-4-yl)ethan-1-ol as starting materials in 5 hours reaction time. $^1$H-NMR (400 MHz, DMSO-$d_6$): 1.02 (d, 3H), 1.06-1.24 (m, 2H), 1.25-1.37 (m, 1H), 1.50-1.55 (m, 1H), 1.70-1.78 (m, 1H), 2.39 (t, 2H), 2.60-2.75 (m, 4H), 3.18 (t, 2H), 3.30-3.40 (m, 3H), 3.60-3.68 (m, 2H), 4.39 (d, 1H), 7.33 (m, 1H), 7.44 (s, 1H), 7.48-7.52 (m, 2H).

Compound 155

2-(3-chlorophenyl)-2-(1-(4,5,6,7-tetrahydro-[1,2,3]triazolo[1,5-a]pyrazine-5-carbonyl)piperidin-4-ylidene)acetonitrile

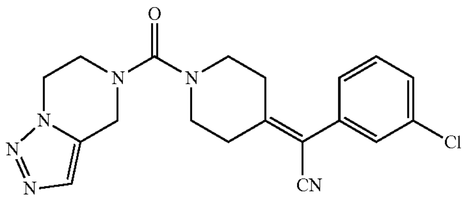 [SMILES: N#CC(=C1CCN(C(=O)N2CCn3nncc3C2)CC1)c1cccc(Cl)c1]

Compound 155 was synthesized by the method used in the preparation of the compound 3 in 57% yield after chromatographic purification using INT-30 and 4,5,6,7-tetrahydro-1,2,3-triazolo[1,5-a]pyrazine as starting materials in 4 hours reaction time. $^{1}$H-NMR (400 MHz, DMSO-$d_6$): 2.43 (t, 2H), 2.74 (t, 2H), 3.25-3.35 (m, 2H), 3.47 (t, 2H), 3.67 (t, 2H), 4.43 (t, 2H), 4.53 (s, 2H), 7.34 (m, 1H), 7.45 (s, 1H), 7.48-7.53 (m, 2H), 7.60 (s, 1H).

Compound 156

2-(1-(3-oxa-8-azabicyclo[3.2.1]octane-8-carbonyl)piperidin-4-ylidene)-2-(3-chlorophenyl)acetonitrile

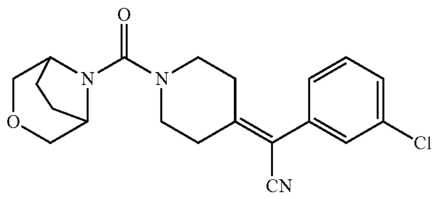 [SMILES: N#CC(=C1CCN(C(=O)N2C3CCC2COC3)CC1)c1cccc(Cl)c1]

Compound 156 was synthesized by the method used in the preparation of the compound 3 in 55% yield after chromatographic purification using INT-30 and 3-oxa-8-azabicyclo[3.2.1]octane as starting materials in 5 hours reaction time. $^{1}$H-NMR (400 MHz, DMSO-$d_6$): 1.70-1.85 (m, 4H), 2.40 (t, 2H), 2.70 (t, 2H), 3.30-3.40 (m, 2H), 3.45-3.55 (m, 4H), 3.58-3.65 (m, 2H), 3.84 (m, 2H), 7.34 (m, 1H), 7.45 (s, 1H), 7.51 (m, 2H).

Compound 157

2-(3-chlorophenyl)-2-(1-(5,6,7,8-tetrahydro-[1,2,4]triazolo[1,5-a]pyrazine-7-carbonyl)piperidin-4-ylidene)acetonitrile

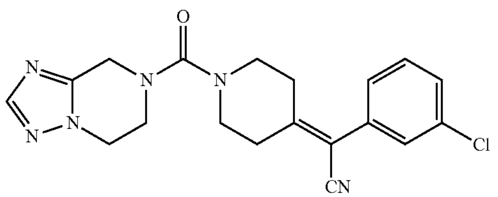 [SMILES: N#CC(=C1CCN(C(=O)N2CCn3ncnc3C2)CC1)c1cccc(Cl)c1]

Compound 157 was synthesized by the method used in the preparation of the compound 3 in 53% yield after chromatographic purification using INT-30 and 5,6,7,8-tetrahydro-[1,2,4]triazolo[1,5-a]pyrazine as starting materials in 6 hours reaction time. $^{1}$H-NMR (400 MHz, DMSO-$d_6$): 2.44 (t, 2H), 2.74 (t, 2H), 3.28-3.35 (m, 2H), 3.48 (t, 2H), 3.70 (t, 2H), 4.21 (t, 2H), 4.50 (s, 2H), 7.34 (m, 1H), 7.45 (s, 1H), 7.49-7.53 (m, 2H), 7.95 (s, 1H).

Compound 158

2-(3,5-difluorophenyl)-2-(1-(4,5,6,7-tetrahydroisoxazolo[4,3-c]pyridine-5-carbonyl)piperidin-4-ylidene)acetonitrile

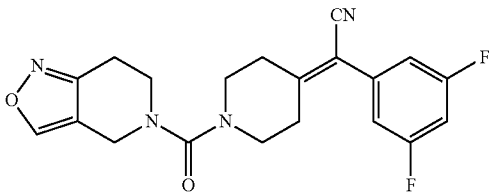 [SMILES: N#CC(=C1CCN(C(=O)N2CCc3nocc3C2)CC1)c1cc(F)cc(F)c1]

Compound 158 was synthesized by the method used in the preparation of the compound 3 in 67% yield after chromatographic purification by using INT-22 and 4,5,6,7-tetrahydroisoxazolo[4,3-c]pyridine as starting materials in 2 hours reaction time. $^{1}$H-NMR (400 MHz, DMSO-$d_6$): 2.43 (t, 2H), 2.73 (t, 2H), 2.87 (t, 2H), 3.27 (t, 2H), 3.35-3.50 (m, 4H), 4.31 (s, 2H), 7.14-7.19 (m, 2H), 7.35 (m, 1H), 8.68 (s, 1H).

Compound 159

2-(1-(4,5,6,7-tetrahydroisoxazolo[4,3-c]pyridine-5-carbonyl)piperidin-4-ylidene)-2-(4-(trifluoromethoxy)phenyl)acetonitrile

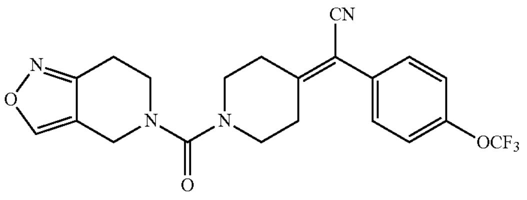 [SMILES: N#CC(=C1CCN(C(=O)N2CCc3nocc3C2)CC1)c1ccc(OC(F)(F)F)cc1]

Compound 159 was synthesized by the method used in the preparation of the compound 3 in 63% yield by using INT-34 and 4,5,6,7-tetrahydroisoxazolo[4,3-c]pyridine as starting materials in 2 hours reaction time. $^{1}$H-NMR (400 MHz, DMSO-$d_6$): 2.43 (t, 2H), 2.75 (t, 2H), 2.87 (t, 2H), 3.27 (t, 2H), 3.35-3.50 (m, 4H), 4.31 (s, 2H), 7.44-7.54 (m, 4H), 8.68 (s, 1H).

Compound 160

2-(5-chlorothiophen-2-yl)-2-(1-(4,5,6,7-tetrahydroisoxazolo[4,3-c]pyridine-5-carbonyl)piperidin-4-ylidene)acetonitrile

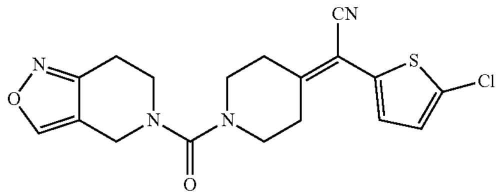 [SMILES: N#CC(=C1CCN(C(=O)N2CCc3nocc3C2)CC1)c1ccc(Cl)s1]

Compound 160 was synthesized by the method used in the preparation of the compound 3 in 67% yield by using INT-42 and 4,5,6,7-tetrahydroisoxazolo[4,3-c]pyridine as starting materials in 2 hours reaction time. $^1$H-NMR (400 MHz, DMSO-$d_6$): 2.61 (t, 2H), 2.73 (t, 2H), 2.87 (t, 2H), 3.31 (m, 2H), 3.35-3.50 (m, 4H), 4.31 (s, 2H), 7.10 (d, 1H), 7.19 (d, 1H), 8.68 (s, 1H).

Compound 161

2-(5-chloropyridin-2-yl)-2-(1-(4,5,6,7-tetrahydroisoxazolo[4,3-c]pyridine-5-carbonyl)piperidin-4-ylidene)acetonitrile

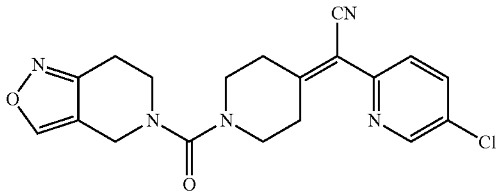 [SMILES: N#CC(=C1CCN(C(=O)N2CCc3nocc3C2)CC1)c1ccc(Cl)cn1]

Compound 161 was synthesized by the method used in the preparation of the compound 3 in 20% yield by using INT-46 and 4,5,6,7-tetrahydroisoxazolo[4,3-c]pyridine as starting materials in 3 hours reaction time. $^1$H-NMR (400 MHz, $CDCl_3$): 2.85-2.93 (m, 4H), 2.99 (t, 2H), 3.39 (t, 2H), 3.50-3.60 (m, 4H), 4.39 (s, 2H), 7.47 (d, 1H), 7.75 (dd, 1H), 8.22 (s, 1H), 8.58 (d, 1H).

Compound 162

2-(1-(4,5,6,7-tetrahydro-[1,2,3]triazolo[1,5-a]pyrazine-5-carbonyl)piperidin-4-ylidene)-2-(4-(trifluoromethoxy)phenyl)acetonitrile

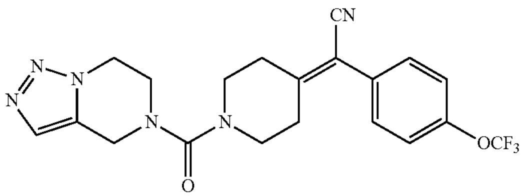 [SMILES: N#CC(=C1CCN(C(=O)N2CCn3nncc3C2)CC1)c1ccc(OC(F)(F)F)cc1]

Compound 162 was synthesized by the method used in the preparation of the compound 3 in 63% yield by using INT-34 and 4,5,6,7-tetrahydro-1,2,3-triazolo[1,5-a]pyrazine as starting materials in overnight reaction time. $^1$H-NMR (400 MHz, DMSO-$d_6$): 2.44 (t, 2H), 2.75 (t, 2H), 3.30 (t, 2H), 3.48 (t, 2H), 3.68 (t, 2H), 4.43 (t, 2H), 4.53 (s, 2H), 7.44-7.55 (m, 4H), 7.60 (s, 1H).

Compound 163

2-(5-chloropyridin-2-yl)-2-(1-(4,5,6,7-tetrahydro-[1,2,3]triazolo[1,5-a]pyrazine-5-carbonyl)piperidin-4-ylidene)acetonitrile

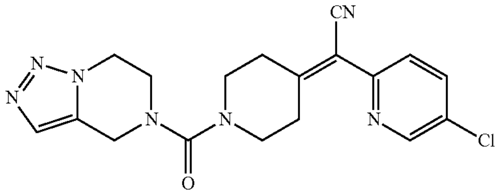 [SMILES: N#CC(=C1CCN(C(=O)N2CCn3nncc3C2)CC1)c1ccc(Cl)cn1]

Compound 163 was synthesized by the method used in the preparation of the compound 3 in 20% yield by using INT-46 and 4,5,6,7-tetrahydro-1,2,3-triazolo[1,5-a]pyrazine as starting materials in 3 hours reaction time. $^1$H-NMR (400 MHz, $CDCl_3$): 2.85-2.96 (m, 4H), 3.42 (t, 2H), 3.57 (t, 2H), 3.76 (t, 2H), 4.53 (t, 2H), 4.62 (s, 2H), 7.48 (d, 1H), 7.55 (s, 1H), 7.76 (dd, 1H), 8.59 (d, 1H).

Compound 164

2-(4-chlorophenyl)-2-(1-(5,6,7,8-tetrahydro-[1,2,4]triazolo[1,5-a]pyrazine-7-carbonyl)piperidin-4-ylidene)acetonitrile

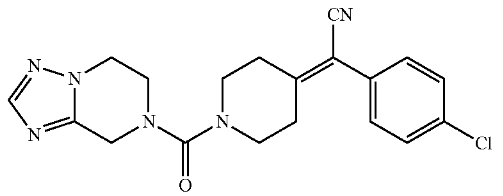 [SMILES: N#CC(=C1CCN(C(=O)N2CCn3ncnc3C2)CC1)c1ccc(Cl)cc1]

Compound 164 was synthesized by the method used in the preparation of the compound 3 in 60% yield using INT-8 and 5,6,7,8-tetrahydro-[1,2,4]triazolo[1,5-a]pyrazine as starting materials in overnight reaction time. $^1$H-NMR (400 MHz, DMSO-$d_6$): 2.44 (t, 2H), 2.74 (t, 2H), 3.28-3.35 (m, 2H), 3.48 (t, 2H), 3.70 (t, 2H), 4.21 (t, 2H), 4.50 (s, 2H), 7.40 (d, 2H), 7.55 (d, 2H), 7.95 (m, 1H).

Compound 165

2-(5-chloropyridin-2-yl)-2-(1-(5,6,7,8-tetrahydro-[1,2,4]triazolo[1,5-a]pyrazine-7-carbonyl)piperidin-4-ylidene)acetonitrile

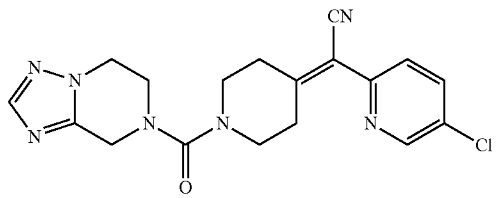 [SMILES: N#CC(=C1CCN(C(=O)N2CCn3ncnc3C2)CC1)c1ccc(Cl)cn1]

Compound 165 was synthesized by the method used in the preparation of the compound 3 in 25% yield after chromatographic purification by using INT-46 and 5,6,7,8-tetrahydro-[1,2,4]triazolo[1,5-a]pyrazine as starting materials in 5 hours reaction time. $^1$H-NMR (400 MHz, DMSO-d$_6$): 2.69 (t, 2H), 2.79 (t, 2H), 3.28-3.35 (m, 2H), 3.51 (t, 2H), 3.71 (t, 2H), 4.21 (t, 2H), 4.51 (s, 2H), 7.57 (d, 1H), 7.96 (s, 1H), 8.06 (dd, 1H), 8.73 (d, 1H).

Compound 166

2-(3,5-difluorophenyl)-2-(1-(5,6,7,8-tetrahydro-[1,2,4]triazolo[1,5-a]pyrazine-7-carbonyl)piperidin-4-ylidene)acetonitrile

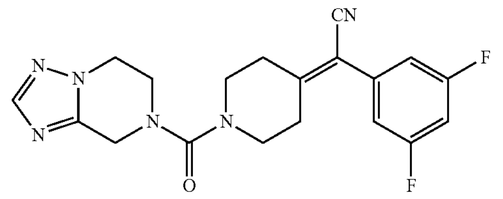 [SMILES: N#CC(=C1CCN(C(=O)N2CCn3ncnc3C2)CC1)c1cc(F)cc(F)c1]

Compound 166 was synthesized by the method used in the preparation of the compound 3 in 26% yield after chromatographic purification by using INT-22 and 5,6,7,8-tetrahydro-[1,2,4]triazolo[1,5-a]pyrazine as starting materials in 6.5 hours reaction time. $^1$H-NMR (400 MHz, DMSO-d$_6$): 2.45 (t, 2H), 2.74 (t, 2H), 3.28-3.40 (m, 2H), 3.48 (t, 2H), 3.70 (t, 2H), 4.21 (t, 2H), 4.50 (s, 2H), 7.10-7.20 (m, 2H), 7.30-7.40 (m, 1H), 7.96 (s, 1H).

Compound 167

2-(1-(5,6,7,8-tetrahydro-[1,2,4]triazolo[1,5-a]pyrazine-7-carbonyl)piperidin-4-ylidene)-2-(4-(trifluoromethoxy)phenyl)acetonitrile

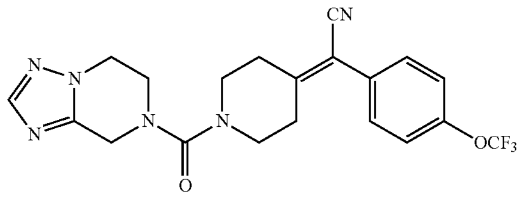 [SMILES: N#CC(=C1CCN(C(=O)N2CCn3ncnc3C2)CC1)c1ccc(OC(F)(F)F)cc1]

Compound 167 was synthesized by the method used in the preparation of the compound 3 in 60% yield by using INT-34 and 5,6,7,8-tetrahydro-[1,2,4]triazolo[1,5-a]pyrazine as starting materials in overnight reaction time. $^1$H-NMR (400 MHz, DMSO-d$_6$): 2.44 (t, 2H), 2.75 (t, 2H), 3.28-3.35 (m, 2H), 3.49 (t, 2H), 3.70 (t, 2H), 4.21 (t, 2H), 4.50 (s, 2H), 7.44-7.54 (m, 4H), 7.96 (s, 1H).

Compound 168

2-(5-chlorothiophen-2-yl)-2-(1-(5,6,7,8-tetrahydro-[1,2,4]triazolo[1,5-a]pyrazine-7-carbonyl)piperidin-4-ylidene)acetonitrile

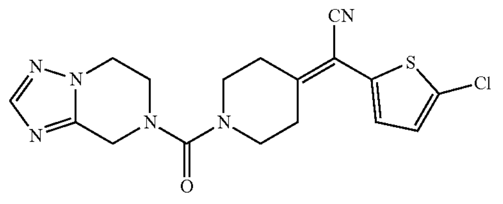 [SMILES: N#CC(=C1CCN(C(=O)N2CCn3ncnc3C2)CC1)c1ccc(Cl)s1]

Compound 168 was synthesized by the method used in the preparation of the compound 3 in 54% yield by using INT-42 and 5,6,7,8-tetrahydro-[1,2,4]triazolo[1,5-a]pyrazine as starting materials in overnight reaction time. $^1$H-NMR (400 MHz, DMSO-d$_6$): 2.63 (t, 2H), 2.75 (t, 2H), 3.28-3.35 (m, 2H), 3.47 (t, 2H), 3.70 (t, 2H), 4.21 (t, 2H), 4.50 (s, 2H), 7.10 (d, 1H), 7.19 (d, 1H), 7.96 (s, 1H).

Compound 169

4-((4-chlorophenyl)(cyano)methylene)-N-methyl-N-(oxetan-3-yl)piperidine-1-carboxamide

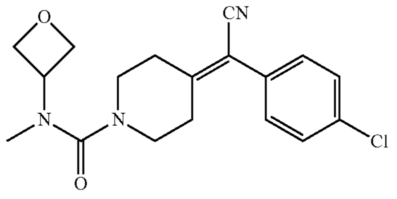 [SMILES: CN(C(=O)N1CCC(=C(C#N)c2ccc(Cl)cc2)CC1)C1COC1]

Compound 169 was synthesized by the method used in the preparation of the compound 3 in 90% yield using INT-8 and N-methyl-3-oxetanamine as starting materials in overnight reaction time. $^1$H-NMR (400 MHz, DMSO-d$_6$): 2.40 (t, 2H), 2.71 (t, 2H), 2.80 (s, 3H), 3.21 (t, 2H), 3.39 (t, 2H), 4.48-4.65 (m, 5H), 7.39 (d, 2H), 7.54 (d, 2H).

Compound 170

4-(cyano(4-(trifluoromethoxy)phenyl)methylene)-N,N-diethylpiperidine-1-carboxamide

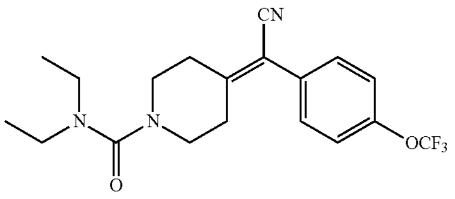 [SMILES: CCN(CC)C(=O)N1CCC(=C(C#N)c2ccc(OC(F)(F)F)cc2)CC1]

Compound 170 was synthesized by the method used in the preparation of the compound 3 in 56% yield by using INT-34 and diethylamine as starting materials in overnight reaction time. $^1$H-NMR (400 MHz, DMSO-d$_6$): 1.06 (t, 6H), 2.40 (t, 2H), 2.71 (t, 2H), 3.10-3.17 (m, 6H), 3.30-3.35 (m, 2H), 7.44-7.53 (m, 4H).

Compound 171

4-(cyano(4-(trifluoromethyl)phenyl)methylene)-N,N-diethylpiperidine-1-carboxamide

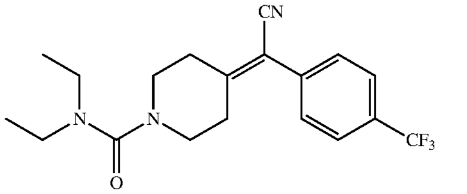 [SMILES: CCN(CC)C(=O)N1CCC(=C(C#N)c2ccc(C(F)(F)F)cc2)CC1]

Compound 171 was synthesized by the method used in the preparation of the compound 3 in 47% yield by using INT-38 and diethylamine as starting materials in overnight reaction time. $^1$H-NMR (400 MHz, DMSO-$d_6$): 1.06 (t, 6H), 2.42 (t, 2H), 2.73 (t, 2H), 3.10-3.18 (m, 6H), 3.30-3.36 (m, 2H), 7.61 (d, 2H), 7.84 (d, 2H).

Compound 172

4-(cyano(5-fluoropyridin-2-yl)methylene)-N,N-diethylpiperidine-1-carboxamide

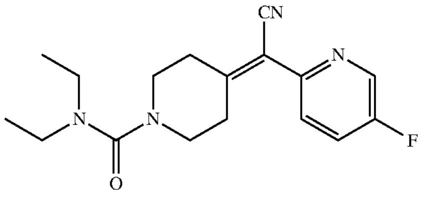 [SMILES: CCN(CC)C(=O)N1CCC(=C(C#N)c2ccc(F)cn2)CC1]

Compound 172 was synthesized by the method used in the preparation of the compound 3 in 25% yield by using INT-50 and diethylamine as starting materials by stirring overnight at room temperature. $^1$H-NMR (400 MHz, DMSO-$d_6$): 1.06 (t, 6H), 2.60 (m, 2H), 2.74 (m, 2H), 3.08-3.20 (m, 6H), 3.29-3.36 (m, 2H), 7.61 (m, 1H), 7.86 (m, 1H), 8.67 (m, 1H).

Compound 173

4-((5-chlorothiophen-2-yl)(cyano)methylene)-N,N-diethylpiperidine-1-carboxamide

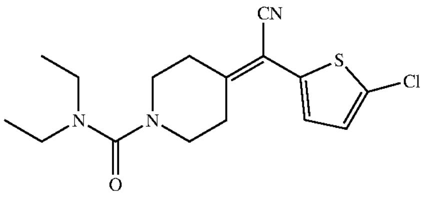 [SMILES: CCN(CC)C(=O)N1CCC(=C(C#N)c2ccc(Cl)s2)CC1]

Compound 173 was synthesized by the method used in the preparation of the compound 3 in 54% yield by using INT-42 and diethylamine as starting materials stirring overnight at room temperature. $^1$H-NMR (400 MHz, DMSO-$d_6$): 1.06 (t, 6H), 2.58 (t, 2H), 2.70 (t, 2H), 3.09-3.17 (m, 4H), 3.19 (t, 2H), 3.29-3.33 (m, 2H), 7.09 (d, 1H), 7.18 (d, 1H).

Pharmacological Tests

The following tests are provided to demonstrate the present invention in illustrative way and should not be considered as limiting in the scope of invention. Further, the concentrations of the compound in the assays are exemplary and should not be taken as limiting. A person skilled in the art may define pharmaceutically relevant concentrations with method known in the art.

Inhibition of AKR1C3 (17β-Hydroxysteroid Dehydrogenase Type 5) Enzyme

Recombinant human AKR1C3 (17β-HSD5) protein (GenBank Accession No. NM_003739.6) produced in *E. coli* was used for screening. Recombinant protein (27 nM/1 μg/ml) was incubated in 20 mM $KH_2PO_4$, 1 mM EDTA, complete protease inhibitor cocktail, pH 7.4 with 1 μM 9-acetyl-2,3,6,7-tetrahydro-1H,5H,11H-pyrano[2,3-f]pyrido[3,2,1-ij]quinolin-11-one and 1 mM NADPH for 60 to 120 min at RT, in the presence of the potential inhibitor at 500 nM concentration. Inhibitor stock solutions were prepared in DMSO. Final concentration of DMSO was adjusted to 1% in all samples. The samples were analysed by fluorescent measurement with Tecan Spark microplate reader at wavelengths 420 nm for excitation and 510 nm for emission. Samples were evaluated against standards of 9-(1-hydroxyethyl)-2,3,6,7-tetrahydro-1H,5H,11H-pyrano[2,3-f]pyrido[3,2,1-ij]quinolin-11-one at concentrations 1 μM-10 nM. Background fluorescence was reduced from all the samples and standards. The concentrations of formed product were calculated from the standard curve with Tecan Spark Magellan software. The formed product concentrations were used to calculate conversion percentages. The inhibition percentages for the samples were calculated from the conversion percentages.

Inhibition percentages of samples were calculated using following formula:

$$\frac{(\text{Control conversion }\%) - (\text{sample conversion }\%)}{(\text{Control conversion }\%)} * 100$$

The inhibition % values were determined for exemplified compounds and the results are summarized in Table 3.

Inhibition of the 17β-Hydroxysteroid Dehydrogenase Type 2 Enzyme

Recombinant human 173-HSD2 protein (GenBank Accession No. NM_002153.3) produced in Sf-9 insect cells with baculovirus was used for screening.

Recombinant protein (105 nM/4.5 μg/ml) was incubated in 20 mM $KH_2PO_4$ pH 8.5, 1 mM EDTA, complete protease inhibitor cocktail, 1 mM NAD with 56.25 nM testosterone (including $^3$H-labelled testosterone) for 30 min at RT, in the presence of the potential inhibitor at 10 μM concentration. Inhibitor stock solutions were prepared in DMSO. Final concentration of DMSO was adjusted to 1% in all samples. The enzyme reaction was stopped by addition of 10% trichloroacetic acid (final concentration 1%). Samples were filtrated through 0.22 m filtration plate. Analyses of samples was done with Waters Acquity UPLC H-class equipped with XBridge C18 column and XBridge VanGuard C18 guard column. Acetonitrile: 0.1% formic acid in water (42/58 v/v) with flow of 1.2 ml/min was used for mobile phase. The eluent was mixed with scintillant and the radioactivity was monitored in the eluate by a Scintillation Analyser. The conversion percentage of tritiated substrate (testosterone) to product tritiated (androstenedione) for each sample was determined by the relative percentages of substrate and product in the chromatogram. The inhibition percentages of samples were calculated using following formula:

$$\frac{(DMSO\ \text{control product conversion}\,\%) - (\text{sample product conversion}\ \%)}{(DMSO\ \text{control product conversion}\,\%)} * 100$$

The inhibition % values were determined for exemplified compounds and the results are summarized in Table 3.

Inhibition of the Aldo-Keto Reductase Family 1 Member C2

Recombinant human aldo-keto reductase family 1 member C2 (AKR1C2) protein (GenBank Accession No. NM_001354.6) produced in Sf-9 insect cells with baculovirus was used for screening. Recombinant protein (13.6 nM/0.5 μg/ml) was incubated in 20 mM $KH_2PO_4$ pH 7.4, 1 mM EDTA, complete protease inhibitor tablet, 1 mM NADPH with 6.25 nM $^3$H-labelled dihydrotestosterone for 45 min at +37° C., in the presence of the potential inhibitor at 10 μM concentration. Inhibitor stock solutions were prepared in DMSO. Final concentration of DMSO was adjusted to 1% in all samples. The enzyme reaction was stopped by addition of 10% trichloroacetic acid (final concentration 1%). Samples were filtrated through 0.22 m filtration plate (Merck). Analyses of samples was done with Waters Acquity UPLC H-class equipped with XBridge C18 column and XBridge VanGuard C18 guard column. Acetonitrile: 0.1% formic acid in water (42/58 v/v) with flow of 1.2 ml/min was used for mobile phase. The eluent was mixed with scintillant and the radioactivity was monitored in the eluate by a Scintillation Analyser. The conversion percentage of triated substrate (dihydrotestosterone) to tritiated product (5α-androstane-3α,17β-diol) for each sample was determined by the relative percentages of substrate and product in the chromatogram. The inhibition percentages of samples were calculated using following formula:

$$\frac{(DMSO\ \text{control product conversion}\,\%) - (\text{sample product conversion}\ \%)}{(DMSO\ \text{control product conversion}\,\%)} * 100$$

The inhibition % values were determined for exemplified compounds and the results are summarized in Table 3.

Pharmacological Test Results

TABLE 3

| Compound no | AKR1C3 inhibition % at 500 nM | AKR1C2 inhibition % at 10 μM | 17β-HSD2 inhibition % at 10 μM |
|---|---|---|---|
| 1 | 99 | 5 | 2 |
| 2 | 99 | 4 | 3 |
| 3 | 95 | 18 | 28 |
| 4 | 99 | 0 | 8 |
| 5 | 99 | 15 | 15 |
| 6 | 95 | 8 | 10 |
| 7 | 95 | 9 | 1 |
| 8 | 98 | 7 | 8 |
| 9 | 89 | 4 | 13 |
| 10 | 89 | 10 | 4 |
| 11 | 96 | 17 | 24 |
| 12 | 99 | 19 | 8 |
| 13 | 99 | 19 | 7 |
| 14 | 94 | 11 | 3 |
| 15 | 97 | 6 | 11 |
| 16 | 97 | 8 | 14 |
| 17 | 98 | 8 | 31 |
| 18 | 99 | 7 | 11 |
| 19 | 99 | 12 | 19 |
| 20 | 97 | 2 | 9 |
| 21 | 95 | 9 | 20 |
| 22 | 88 | 9 | 7 |
| 23 | 96 | 13 | 1 |

TABLE 3-continued

| Compound no | AKR1C3 inhibition % at 500 nM | AKR1C2 inhibition % at 10 μM | 17β-HSD2 inhibition % at 10 μM |
|---|---|---|---|
| 24 | 96 | 8 | 11 |
| 25 | 98 | 28 | 27 |
| 26 | 97 | 6 | 13 |
| 27 | 98 | 16 | 7 |
| 28 | 97 | 8 | 27 |
| 29 | 96 | 5 | 30 |
| 30 | 95 | 15 | 14 |
| 31 | 95 | 11 | 9 |
| 32 | 97 | 17 | 4 |
| 33 | 97 | 16 | 7 |
| 34 | 95 | 12 | 21 |
| 35 | 96 | 27 | 28 |
| 36 | 94 | 10 | −3 |
| 37 | 96 | 14 | 25 |
| 38 | 97 | 30 | 27 |
| 39 | 96 | 13 | 6 |
| 40 | 95 | 14 | 5 |
| 41 | 96 | 7 | 7 |
| 42 | 96 | 11 | 10 |
| 43 | 103 | 29 | 21 |
| 44 | 103 | 18 | 12 |
| 45 | 103 | 5 | 2 |
| 46 | 102 | 8 | 11 |
| 47 | 103 | 9 | 20 |
| 48 | 100 | 0 | 8 |
| 49 | 98 | 6 | 22 |
| 50 | 97 | 16 | 12 |
| 51 | 96 | 18 | 26 |
| 52 | 97 | 19 | 13 |
| 53 | 97 | 7 | 15 |
| 54 | 99 | 15 | 20 |
| 55 | 97 | 3 | 7 |
| 56 | 86 | −3 | 3 |
| 57 | 96 | 13 | 3 |
| 58 | 93 | 6 | 21 |
| 59 | 98 | 5 | 22 |
| 60 | 98 | 9 | 29 |
| 61 | 99 | 7 | 30 |
| 62 | 90 | −4 | 4 |
| 63 | 99 | 29 | 22 |
| 64 | 99 | 19 | 28 |
| 65 | 97 | 2 | 2 |
| 66 | 96 | 8 | 12 |
| 67 | 98 | 6 | 9 |
| 68 | 98 | 11 | 8 |
| 69 | 98 | 16 | 10 |
| 70 | 97 | 5 | 11 |
| 71 | 99 | 12 | 29 |
| 72 | 98 | 9 | 26 |
| 73 | 92 | 19 | 21 |
| 74 | 98 | 9 | 17 |
| 75 | 94 | 13 | 23 |
| 76 | 99 | 6 | 20 |
| 77 | 96 | 24 | 19 |
| 78 | 99 | 15 | 27 |
| 79 | 99 | 6 | 10 |
| 80 | 99 | 7 | 12 |
| 81 | 95 | −7 | 10 |
| 82 | 100 | 3 | 28 |
| 83 | 78 | 2 | 29 |
| 84 | 98 | 6 | 23 |
| 85 | 72 | 9 | 27 |
| 86 | 80 | 0 | 27 |
| 87 | 99 | 31 | 23 |
| 88 | 99 | 13 | 26 |
| 89 | 98 | 18 | 15 |
| 90 | 99 | 9 | 30 |
| 91 | 99 | 23 | 23 |
| 92 | 96 | 6 | 30 |
| 93 | 98 | 11 | 23 |
| 94 | 97 | 7 | 8 |
| 95 | 94 | 22 | 25 |
| 96 | 95 | 13 | 11 |
| 97 | 96 | 9 | 9 |
| 98 | 97 | 8 | 18 |
| 99 | 96 | 16 | 18 |

TABLE 3-continued

| Compound no | AKR1C3 inhibition % at 500 nM | AKR1C2 inhibition % at 10 μM | 17β-HSD2 inhibition % at 10 μM |
|---|---|---|---|
| 100 | 92 | 6 | −2 |
| 101 | 90 | 11 | 14 |
| 102 | 99 | 17 | 12 |
| 103 | 95 | 19 | −4 |
| 104 | 96 | 5 | 0 |
| 105 | 100 | 10 | 15 |
| 106 | 93 | 5 | 2 |
| 107 | 92 | 14 | −1 |
| 108 | 98 | 21 | −11 |
| 109 | 96 | 12 | 26 |
| 110 | 96 | 6 | 30 |
| 111 | 95 | 13 | 8 |
| 112 | 96 | 30 | 17 |
| 113 | 104 | 19 | 16 |
| 114 | 97 | 11 | 34 |
| 115 | 96 | 0 | −1 |
| 116 | 98 | 26 | 12 |
| 117 | 94 | 7 | 22 |
| 118 | 96 | 14 | 30 |
| 119 | 99 | 6 | 15 |
| 120 | 99 | 43 | 20 |
| 121 | 99 | 32 | −7 |
| 122 | 99 | 42 | 24 |
| 123 | 99 | 33 | 2 |
| 124 | 91 | 4 | 9 |
| 125 | 97 | 18 | 17 |
| 126 | 97 | 10 | 2 |
| 127 | 96 | −6 | 5 |
| 128 | 93 | 2 | 17 |
| 129 | 98 | 11 | 5 |
| 130 | 97 | 0 | 12 |
| 131 | 98 | 8 | 13 |
| 132 | 95 | 8 | 17 |
| 133 | 97 | 16 | 23 |
| 134 | 98 | 13 | 12 |
| 135 | 92 | 3 | 4 |
| 136 | 99 | 6 | 26 |
| 137 | 97 | 18 | 6 |
| 138 | 98 | 31 | 13 |
| 139 | 93 | 8 | 27 |
| 140 | 96 | 21 | 23 |
| 141 | 98 | 33 | 7 |
| 142 | 91 | 3 | 4 |
| 143 | 93 | 9 | 7 |
| 144 | 100 | 5 | 16 |
| 145 | 97 | 1 | 9 |
| 146 | 100 | 2 | 15 |
| 147 | 99 | 5 | 4 |
| 148 | 90 | 6 | 7 |
| 149 | 94 | 7 | 9 |
| 150 | 100 | 21 | 6 |
| 151 | 93 | 11 | 18 |
| 152 | 99 | 4 | 8 |
| 153 | 95 | 14 | 26 |
| 154 | 98 | 14 | 26 |
| 155 | 99 | 21 | 19 |
| 156 | 99 | 8 | 12 |
| 157 | 99 | 2 | 8 |
| 158 | 101 | 22 | −4 |
| 159 | 100 | 14 | 1 |
| 160 | 99 | 34 | 18 |
| 161 | 98 | 19 | 7 |
| 162 | 98 | 17 | 1 |
| 163 | 97 | 2 | 9 |
| 164 | 99 | 12 | 10 |
| 165 | 95 | 9 | 6 |
| 166 | 96 | 13 | 2 |
| 167 | 97 | 7 | −1 |
| 168 | 98 | 24 | −2 |
| 169 | 95 | 7 | −2 |
| 170 | 98 | 4 | 28 |
| 171 | 99 | 3 | 17 |
| 172 | 95 | −2 | 13 |
| 173 | 99 | 29 | 50 |

It will be obvious to a person skilled in the art that, as the technology advances, the inventive concept can be implemented in various ways. The invention and its embodiments are not limited to the examples described above but may vary within the scope of the claims.

The invention claimed is:

1. A compound of formula (I)

(I)

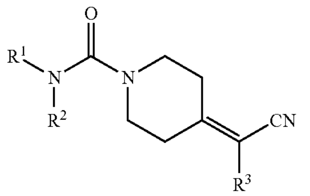

wherein $R^1$ is a group selected from $C_{1-6}$-alkyl, $C_{1-6}$-haloalkyl, $C_{1-6}$-perhaloalkyl, $(CH_2)_mOR'$, $(CH_2)_mN(R')_2$, 6- to 13-membered aryl, 5- to 11-membered heteroaryl, 3- to 12-membered cycloalkyl, and 3- to 10-membered heterocyclyl, and said group being optionally substituted with one to six substituent(s) each independently selected from $R^{11}$;

$R^2$ is a group selected from $C_{1-6}$-alkyl, $C_{1-6}$-haloalkyl, $C_{1-6}$-perhaloalkyl, $(CH_2)_mOR'$, $(CH_2)_mN(R')_2$, 6- to 13-membered aryl, 5- to 11-membered heteroaryl, 3- to 12-membered cycloalkyl, and 3- to 10-membered heterocyclyl, and said group being optionally substituted with one to six substituent(s) each independently selected from $R^{12}$;

or $R^1$ and $R^2$, together with the ring nitrogen atom they are attached to, form a 4- to 11-membered unsaturated or aromatic heterocycle or a 4- to 10-membered saturated or partially unsaturated heterocycle, and said heterocycle being optionally substituted with one to six substituent(s) each independently selected from $R^{13}$;

$R^3$ is a group selected from 6- to 13-membered aryl, 5- to 11-membered heteroaryl, 3- to 12-membered cycloalkyl, and 3- to 10-membered heterocyclyl, and said group being optionally substituted with one to six substituent(s) each independently selected from $R^{31}$;

$R^{11}$ is selected from halogen, CN, $C_{1-6}$-alkyl, $C_{1-6}$-alkoxy, $C_{1-6}$-(per)haloalkyl, $C_{1-6}$-(per)haloalkoxy, OR', oxo, $(OCH_2)_nOR'$, SR', $NO_2$, $N(R')_2$, $(CH_2)_nN(R')_2$, $(CH_2)_nOR'$, CH(XR')R', $CO_2R'$, $C(O)N(R')_2$, C(O)NR'C(O)R", NR'COR", C(=NH)R", C(=N—OR')R", C(O)R", NR'C(O)NR", $NR'SO_2R"$, $SO_2NHSO_2R"$, and $SO_2N(R')_2$ and being optionally substituted with one or more substituents each independently selected from the group consisting of R', OR', $N(R')_2$;

$R^{12}$ is selected from halogen, CN, $C_{1-6}$-alkyl, $C_{1-6}$-alkoxy, $C_{1-6}$-(per)haloalkyl, $C_{1-6}$-(per)haloalkoxy, OR', oxo, $(OCH_2)_nOR'$, SR', $NO_2$, $N(R')_2$, $(CH_2)_nN(R')_2$, $(CH_2)_nOR'$, CH(XR')R', $CO_2R'$, $C(O)N(R')_2$, NHCOR", C(=NH)R", C(=N—OR')R", C(O)R", and $SO_2N(R')_2$ and being optionally substituted with one or more substituents each independently selected from the group consisting of R', OR', $N(R')_2$;

$R^{13}$ is selected from halogen, CN, $C_{1-6}$-alkyl, $C_{1-6}$-alkoxy, $C_{1-6}$-(per)haloalkyl, $C_{1-6}$-(per)haloalkoxy, OR', oxo, $(OCH_2)_nOR'$, SR', $NO_2$, $N(R')_2$, $(CH_2)_nN(R')_2$, $(CH_2)_nOR'$, CH(XR')R', $CO_2R'$, $C(O)N(R')_2$, C(O)NR'C(O)R", NR'C(O)R", C(=NH)R", C(=N—OR')R", C(O)R", NR'C(O)NR", $NR'SO_2R"$, $SO_2NHSO_2R"$, and $SO_2N(R')_2$ and being optionally substituted with one or more substituents each independently selected from the group consisting of R', OR', $N(R')_2$;

$R^{31}$ is selected from halogen, CN, $C_{1-6}$-alkyl, $C_{1-6}$-alkoxy, $C_{1-6}$-(per)haloalkyl, $C_{1-6}$-(per)haloalkoxy, OR', oxo, $(OCH_2)_nOR'$, SR', $NO_2$, $N(R')_2$, $(CH_2)_nN(R')_2$, $(CH_2)_nOR'$, $CO_2R'$, $C(O)N(R')_2$, C(O)NR'C(O)R", NR'C(O)R", C(=NH)R", C(=N—OR'H)R", C(O)R", NR'C(O)NR", $NR'SO_2R"$, $SO_2NHSO_2R"$, and $SO_2N(R')_2$ and being optionally substituted with one or more substituents each independently selected from the group consisting of R', OR', $N(R')_2$;

each R' is independently selected from H, $C_{1-6}$-alkyl, $C_{1-6}$-haloalkyl, and $C_{1-6}$-perhaloalkyl, or when part of any $N(R')_2$ both R's, together with the nitrogen they are attached to, may form a 3- to 6-membered aliphatic or aromatic heterocyclic ring comprising 1 to 4 heteroatoms each independently selected from N, S, and O;

each R" is independently selected from $C_{1-6}$-alkyl, $C_{1-6}$-haloalkyl, and $C_{1-6}$-perhaloalkyl;

X is O or S;

m is 0-6; and n is 1-6; or a salt, solvate or solvate of a salt thereof.

2. A compound as claimed in any preceding claim, wherein $R^3$ is a group selected from 6-membered aryl and 5- to 9-membered heteroaryl, wherein the heteroaryl comprises 1 to 3 heteroatom(s) each independently selected from the group consisting of N, O, and S, and said group being optionally substituted with one to three substituent(s) each independently selected from $R^{31}$;

$R^{31}$ is as defined in claim 1; or a salt, solvate or solvate of a salt thereof.

3. A compound as claimed in claim 1, wherein $R^1$ is a group selected from $C_{1-6}$-alkyl, 5- to 9-membered heteroaryl, and 5- to 7-membered heterocyclyl, and said group being optionally substituted with one to three substituent(s) each independently selected from $R^{11}$; and $R^2$ is a group selected from $C_{1-6}$-alkyl, 5- to 9-membered heteroaryl, and 5- to 7-membered heterocyclyl, and said group being optionally substituted with one to three substituent(s) each independently selected from $R^{12}$;

$R^{11}$ and $R^{12}$ are as defined in claim 1; or a salt, solvate or solvate of a salt thereof.

4. A compound as claimed in claim 1, wherein $R^1$ and $R^2$, together with the ring nitrogen atom to which they are attached, form a 5- to 9-membered aromatic heterocycle or a 4- to 9-membered saturated heterocycle, wherein the heterocycle optionally comprises 1 to 4 further heteroatom(s) each independently selected from the group consisting of N, O, and S, and said heterocycle being optionally substituted with one to four substituent(s) each independently selected from $R^{13}$;

$R^{13}$ is as defined in claim 1; or a salt, solvate or solvate of a salt thereof.

5. A compound as claimed in claim 1, wherein $R^3$ is a group selected from phenyl, pyridinyl, thienyl, and 1H-indazolyl, and said group being optionally substituted with one or two substituent(s) each independently selected from $R^{31}$;

$R^{31}$ is as defined in claim 1; or a salt, solvate or solvate of a salt thereof.

6. A compound as claimed in claim 1, wherein $R^{31}$ is selected from halogen, $C_{1-3}$-alkyl, $C_{1-3}$-(per)haloalkyl, $C_{1-3}$-(per)haloalkoxy, and $C(O)C_{1-6}$-alkyl; or a salt, solvate or solvate of a salt thereof.

7. A compound as claimed in claim 1, wherein $R^1$ is a group selected from methyl, ethyl, and tetrahydropyranyl;

$R^2$ is a group selected from methyl, ethyl, and tetrahydropyranyl; or a salt, solvate or solvate of a salt thereof.

8. A compound as claimed in claim 1, wherein $R^1$ and $R^2$, together with the ring nitrogen atom to which they are attached, form an aromatic heterocycle or a saturated heterocycle selected from piperidinyl, piperazinyl, morpholinyl, pyrrolidinyl, indolinyl, isoindolinyl, 4,5-dihydro-7H-isoxazolo[3,4-c]pyridinyl, 6,7-dihydro-4H-isoxazolo[4,3-c]pyridinyl, 6,7-dihydro-4H-[1,2,3]triazolo[1,5-a]pyrazinyl, 3-oxa-8-azabicyclo[3.2.1]octanyl, azetidinyl, 1,4,6,7-tetrahydroimidazo[4,5-c]pyridinyl, 1,4,6,7-tetrahydropyrazolo[4,3-c]pyridinyl, 5,6-dihydro-8H-[1,2,4]triazolo[1,5-a]pyrazinyl, 5,6-dihydro-8H-imidazo[1,5-a]pyrazinyl, 3,4-dihydro-1H-pyrrolo[1,2-a]pyrazinyl, 2,3-dihydropyrrolo[2,3-b]pyridinyl, 2-azabicyclo[2.2.1]heptanyl, 6,7-dihydro-4H-thieno[3,2-c]pyridinyl, thiomorpholinyl, octahydrocyclopenta[c]pyrrolyl, N-methyl-N-(oxetan-3-yl), 4-hydroxyazepanyl, 5-fluoroindolinyl, 2-methylpiperidinyl, 4-isopropoxypiperidinyl, 4-propoxypiperidinyl, and 5,6-dihydro-8H-[1,2,4]triazolo[4,3-a]pyrazinyl, and said heterocycle being optionally substituted with one or two substituent(s) each independently selected from $R^{13}$;

$R^{13}$ is as defined in claim 1; or a salt, solvate or solvate of a salt thereof.

9. A compound as claimed in claim 1, wherein $R^{13}$ is selected from CN, $C_{1-3}$-(per)haloalkyl, OR', $(CH_2)_nOR'$, $CH(OH)C_{1-6}$-alkyl, C(O)R'', and $SO_2N(R')_2$;

each R' is independently selected from H, and $C_{1-6}$-alkyl;

each R'' is independently selected from $C_{1-6}$-alkyl;

n is 1-3; or a salt, solvate or solvate of a salt thereof.

10. A compound as claimed in claim 1, wherein the compound has formula (Ia)

(Ia)

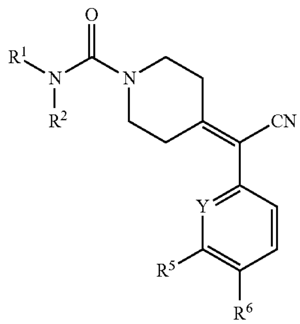

wherein

Y is N or C—$R^4$, wherein $R^4$ is H or F;

$R^5$ is H, Cl, or F;

or

Y is C—$R^4$, and $R^4$ and $R^5$, together with the carbon atoms they are attached to, form a 5-membered aromatic heterocycle;

$R^6$ is F, Cl, or H;

or

Y is N or C—$R^4$, wherein $R^4$ is H or F;

$R^5$ and $R^6$, together with the carbon atoms they are attached to, form a 5-membered aromatic heterocycle; and $R^1$ and $R^2$ are as defined in claim 1; or a salt, solvate or solvate of a salt thereof.

11. A compound as claimed in claim 1, wherein $R^1$ and $R^2$, together with the ring nitrogen atom to which they are attached, form an aromatic heterocycle or a saturated heterocycle selected from piperidin-1-yl, piperazin-1-yl, morpholin-4-yl, pyrrolidin-1-yl, indolin-1-yl, isoindolin-2-yl, 4,5-dihydro-7H-isoxazolo[3,4-c]pyridin-6-yl, 6,7-dihydro-4H-isoxazolo[4,3-c]pyridin-5-yl, 6,7-dihydro-4H-[1,2,3]triazolo[1,5-a]pyrazin-5-yl, 3-oxa-8-azabicyclo[3.2.1]octan-8-yl, azetidin-1-yl, 1,4,6,7-tetrahydroimidazo[4,5-c]pyridin-5-yl, 1,4,6,7-tetrahydropyrazolo[4,3-c]pyridin-5-yl, 5,6-dihydro-8H-[1,2,4]triazolo[1,5-a]pyrazin-7-yl, 5,6-dihydro-8H-imidazo[1,5-a]pyrazin-7-yl, 3,4-dihydro-1H-pyrrolo[1,2-a]pyrazin-2-yl, 2,3-dihydropyrrolo[2,3-b]pyridin-1-yl, 2-azabicyclo[2.2.1]heptan-2-yl, 6,7-dihydro-4H-thieno[3,2-c]pyridin-5-yl, and 5,6-dihydro-8H-[1,2,4]triazolo[4,3-a]pyrazin-7-yl, and said heterocycle being optionally substituted with one or two substituent(s) each independently selected from $R^{13}$;

$R^{13}$ is selected from CN, $C_{1-3}$-(per)haloalkyl, OR', $(CH_2)_nOR'$, $CH(OH)C_{1-6}$-alkyl, C(O)R'', and $SO_2N(R')_2$;

each R' is independently selected from H, and $C_{1-6}$-alkyl;

each R'' is independently selected from $C_{1-6}$-alkyl; or a salt, solvate or solvate of a salt thereof.

12. A compound as claimed in claim 1, wherein the compound has formula (Ib) or (Ic)

(Ib)

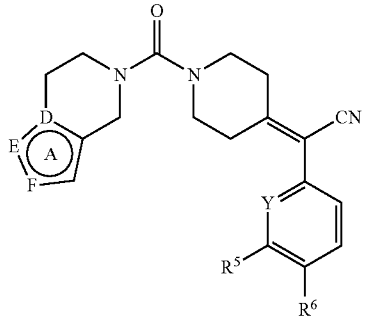

(Ic)

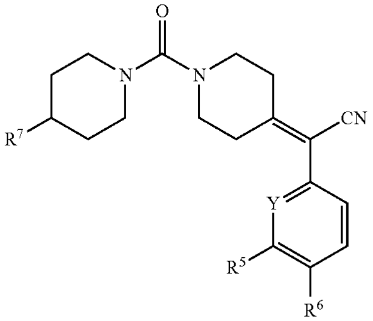

wherein

D is C or N;

E is N, NH, or CH;

F is O or N;

Y is N or C—$R^4$, wherein $R^4$ is H or F;

$R^5$ is H, Cl, or F;

or

Y is C—$R^4$, and $R^4$ and $R^5$, together with the carbon atoms they are attached to, form a 5-membered aromatic heterocycle;

$R^6$ is F, Cl, or H;

or

Y is N or C—$R^4$, wherein $R^4$ is H or F;

$R^5$ and $R^6$, together with the carbon atoms they are attached to, form a 5-membered aromatic heterocycle; and $R^7$ is OH or $CH_2OH$; or a salt, solvate or solvate of a salt thereof.

13. A compound, selected from the group consisting of:

2-(4-fluorophenyl)-2-(1-(4-hydroxypiperidine-1-carbonyl)piperidin-4-ylidene)acetonitrile (4);

2-(4-fluorophenyl)-2-(1-(4,5,6,7-tetrahydroisoxazolo[4,3-c]pyridine-5-carbonyl)piperidin-4-ylidene)acetonitrile (12);

2-(4-fluorophenyl)-2-(1-(4,5,6,7-tetrahydro-[1,2,3]triazolo[1,5-a]pyrazine-5-carbonyl)piperidin-4-ylidene)acetonitrile (13);

2-(4-chlorophenyl)-2-(1-(4-hydroxypiperidine-1-carbonyl)piperidin-4-ylidene)acetonitrile (18);

2-(4-fluorophenyl)-2-(1-(4,5,6,7-tetrahydro-1H-pyrazolo[4,3-c]pyridine-5-carbonyl)piperidin-4-ylidene)acetonitrile (25);

2-(3,4-difluorophenyl)-2-(1-(4-hydroxypiperidine-1-carbonyl)piperidin-4-ylidene)acetonitrile (41);

2-(2,4-difluorophenyl)-2-(1-(4-hydroxypiperidine-1-carbonyl)piperidin-4-ylidene)acetonitrile (42);

2-(3,4-difluorophenyl)-2-(1-(4,5,6,7-tetrahydro-1H-pyrazolo[4,3-c]pyridine-5-carbonyl)piperidin-4-ylidene)acetonitrile (43);

2-(3,4-difluorophenyl)-2-(1-(5,6,7,8-tetrahydroimidazo[1,5-a]pyrazine-7-carbonyl)piperidin-4-ylidene)acetonitrile (44);

2-(1-(4-hydroxypiperidine-1-carbonyl)piperidin-4-ylidene)-2-(1H-indazol-4-yl)acetonitrile (48);

2-(5-chloropyridin-2-yl)-2-(1-(4,5,6,7-tetrahydro-1H-pyrazolo[4,3-c]pyridine-5-carbonyl)piperidin-4-ylidene)acetonitrile (67);

2-(4-chlorophenyl)-2-(1-(4-(hydroxymethyl)piperidine-1-carbonyl)piperidin-4-ylidene)acetonitrile (74);

2-(3-chlorophenyl)-2-(1-(4-hydroxypiperidine-1-carbonyl)piperidin-4-ylidene)acetonitrile (80);

2-(5-fluoropyridin-2-yl)-2-(1-(4,5,6,7-tetrahydroisoxazolo[4,3-c]pyridine-5-carbonyl)piperidin-4-ylidene)acetonitrile (84);

1-(4-((3-chlorophenyl)(cyano)methylene)piperidine-1-carbonyl)piperidine-4-sulfonamide (99);

2-(4-chlorophenyl)-2-(1-(4,5,6,7-tetrahydro-1H-pyrazolo[4,3-c]pyridine-5-carbonyl)piperidin-4-ylidene)acetonitrile (113);

2-(1-(4-(hydroxymethyl)piperidine-1-carbonyl)piperidin-4-ylidene)-2-(1-methyl-1H-indazol-7-yl)acetonitrile (118);

2-(1H-indazol-4-yl)-2-(1-(4,5,6,7-tetrahydroisoxazolo[4,3-c]pyridine-5-carbonyl)piperidin-4-ylidene)acetonitrile (138);

2-(3-chlorophenyl)-2-(1-(4-(2-hydroxyethyl)piperidine-1-carbonyl)piperidin-4-ylidene)acetonitrile (140);

2-(4-chlorophenyl)-2-(1-(4,5,6,7-tetrahydroisoxazolo[4,3-c]pyridine-5-carbonyl)piperidin-4-ylidene)acetonitrile (141);

2-(1H-indazol-4-yl)-2-(1-(4-methoxypiperidine-1-carbonyl)piperidin-4-ylidene)acetonitrile (144);

2-(1H-indazol-4-yl)-2-(1-(4-(trifluoromethyl)piperidine-1-carbonyl)piperidin-4-ylidene)acetonitrile (145);

2-(1-(3-oxa-8-azabicyclo[3.2.1]octane-8-carbonyl)piperidin-4-ylidene)-2-(3-chlorophenyl)acetonitrile (156);

2-(5-chloropyridin-2-yl)-2-(1-(4,5,6,7-tetrahydroisoxazolo[4,3-c]pyridine-5-carbonyl)piperidin-4-ylidene)acetonitrile (161); or a salt, solvate or solvate of a salt thereof.

14. A method for the preparation of a compound of formula (I), or a salt, solvate or solvate of a salt thereof, as defined in claim 1, comprising the steps:

reacting a compound of formula (II)

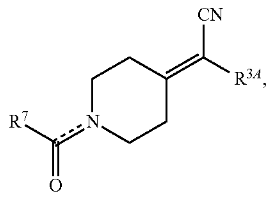

(II)

wherein the dotted line represents an optional bond, $R^7$ is a leaving group A or absent when the dotted line represents a bond, and $R^{3A}$ is $R^3$ as defined for compound of formula (I) or a leaving group B, with a compound of formula (III)

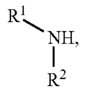

(III)

or hydrogen halide thereof, wherein $R^1$ and $R^2$ are as defined for compound of formula (I);

or reacting a compound of formula (IV)

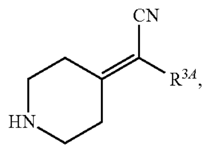

(IV)

or hydrogen halide thereof, wherein $R^{3A}$ is $R^3$ as defined for compound of formula (I) or a leaving group B, with a compound of formula (V)

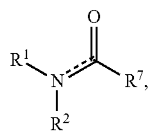

(V)

wherein the dotted line represents an optional bond, $R^7$ is a leaving group A or absent when the dotted line represents a bond, and $R^1$ and $R^2$ are as defined for compound of formula (I); optionally in the presence of a base, to obtain a compound of formula (I)

(I)

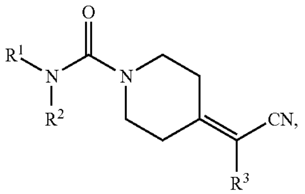

wherein $R^1$, $R^2$, and $R^3$ are as defined for compound of formula (I); or $R^1$ and $R^2$ are as defined for compound of formula (I), and $R^3$ is the leaving group B;

and optionally, provided that $R^3$ is the leaving group B, reacting the obtained compound of formula (I) with a compound of formula (VII)

(VII)

wherein $R^{3B}$ is $R^3$ as defined for compound of formula (I),

Z is a leaving group C or $B(R^8)_2$, wherein $R^8$ is OH, $OC_{1-6}$-alkyl, or both $R^8$, together with the ring boron atom they are attached to, form a cyclic boronic ester, in the presence of a base and a coupling agent, to obtain a compound of formula (I), wherein $R^1$, $R^2$, and $R^3$ are as defined in any preceding claim;

and optionally converting the compound of formula (I) to a salt, solvate or solvate of a salt thereof.

15. A pharmaceutical composition comprising an effective amount of one or more compounds of formula (I), or a salt, solvate, or solvate of a salt thereof, as claimed in claim 1, together with one or more pharmaceutically acceptable excipient(s).

16. The pharmaceutical composition as claimed in claim 14 comprising one or more compounds as claimed in claim 1 in combination with one or more further active ingredients.

17. A compound, or a salt, solvate or solvate of a salt thereof, as claimed in claim 1 for use as a medicament.

18. A method of treating a disease or disorder, comprising administering a compound, or a salt, or a solvate, or solvate of a salt thereof, as claimed in claim 1, wherein the disease or disorder is selected from the group consisting of polycystic ovary syndrome, endometriosis, uterine leiomyoma, uterine bleeding disorders, dysmenorrhoea, hyperandrogenism, chronic obstructive pulmonary disease (COPD), lung cancer, non-small-cell lung cancer, prostate cancer including castration-resistant prostate cancer, prostate hyperplasia, breast cancer, invasive breast ductal carcinoma, triple negative breast cancer, endometrial carcinoma, renal cell carcinoma, bladder carcinoma, pancreatic adenocarcinoma, acute myeloid leukemia, T-Cell acute lymphoblastic leukemia, melanoma, non-Hodgkins lymphoma, acne, seborrhoea, hair loss, premature sexual maturity, obesity, and inflammation-related pain.

19. A pharmaceutical composition comprising an effective amount of one or more compounds of claim 13, or a salt, solvate, or solvate of a salt thereof, together with one or more pharmaceutically acceptable excipient(s).

20. A method of treating a disease or disorder, comprising administering a pharmaceutical composition of claim 19, wherein the disease or disorder is selected from the group consisting of polycystic ovary syndrome, endometriosis, uterine leiomyoma, uterine bleeding disorders, dysmenorrhoea, hyperandrogenism, chronic obstructive pulmonary disease (COPD), lung cancer, non-small-cell lung cancer, prostate cancer including castration-resistant prostate cancer, prostate hyperplasia, breast cancer, invasive breast ductal carcinoma, triple negative breast cancer, endometrial carcinoma, renal cell carcinoma, bladder carcinoma, pancreatic adenocarcinoma, acute myeloid leukemia, T-Cell acute lymphoblastic leukemia, melanoma, non-Hodgkins lymphoma, acne, seborrhoea, hair loss, premature sexual maturity, obesity, and inflammation-related pain.

* * * * *